(12) United States Patent
Messerly et al.

(10) Patent No.: US 9,700,343 B2
(45) Date of Patent: Jul. 11, 2017

(54) DEVICES AND TECHNIQUES FOR CUTTING AND COAGULATING TISSUE

(71) Applicant: Ethicon Endo-Surgery, Inc., Cincinnati, OH (US)

(72) Inventors: Jeffrey D. Messerly, Cincinnati, OH (US); Brian D. Bertke, Ft. Thomas, KY (US); Karalyn R. Tellio, Cincinnati, OH (US); Eitan T. Wiener, Cincinnati, OH (US); David C. Yates, West Chester, OH (US); Jeffrey L. Aldridge, Lebanon, OH (US); Foster B. Stulen, Mason, OH (US); James R. Giordano, Milford, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 0 days.

(21) Appl. No.: 14/929,971

(22) Filed: Nov. 2, 2015

(65) Prior Publication Data
US 2016/0120563 A1 May 5, 2016

Related U.S. Application Data

(63) Continuation of application No. 13/839,014, filed on Mar. 15, 2013, now Pat. No. 9,237,921.
(Continued)

(51) Int. Cl.
*A61B 17/28* (2006.01)
*A61B 17/32* (2006.01)
(Continued)

(52) U.S. Cl.
CPC .............. *A61B 17/320068* (2013.01); *A61B 17/320092* (2013.01); *A61B 18/1206* (2013.01);
(Continued)

(58) Field of Classification Search
CPC .............. A61B 18/1206; A61B 18/128; A61B 18/1412; A61B 18/1452;
(Continued)

(56) References Cited

U.S. PATENT DOCUMENTS

| 969,528 A | 9/1910 | Disbrow |
|---|---|---|
| 1,570,025 A | 1/1926 | Young |

(Continued)

FOREIGN PATENT DOCUMENTS

| AU | 2003241752 A1 | 9/2003 |
|---|---|---|
| CA | 2535467 A1 | 4/1993 |

(Continued)

OTHER PUBLICATIONS

International Search Report for PCT/US2013/035368, dated Jun. 28, 2013 (4 pages).
(Continued)

*Primary Examiner* — Michael Carey

(57) ABSTRACT

Various forms are directed to systems and methods for driving an end effector coupled to an ultrasonic drive system of a surgical instrument. A generator may generate at least one electrical signal. The at least one electrical signal may be monitored against a first set of logic conditions. When an ultrasonic impedance of the surgical instrument exceeds a threshold impedance, a resonant frequency of the at least one electrical signal may be stored as a baseline frequency. A first response of the generator may be triggered upon the occurrence of either the first set of logic conditions being met or the resonant frequency of the at least one electrical signal differing from the baseline frequency by a baseline deviation threshold.

21 Claims, 117 Drawing Sheets

Related U.S. Application Data

(60) Provisional application No. 61/621,876, filed on Apr. 9, 2012.

(51) Int. Cl.
  *A61B 18/12* (2006.01)
  *A61B 18/14* (2006.01)
  *A61B 17/00* (2006.01)
  *A61B 18/00* (2006.01)

(52) U.S. Cl.
  CPC .. *A61B 18/1442* (2013.01); *A61B 2017/0003* (2013.01); *A61B 2017/00026* (2013.01); *A61B 2017/00115* (2013.01); *A61B 2017/00132* (2013.01); *A61B 2017/00176* (2013.01); *A61B 2018/00898* (2013.01); *A61B 2018/00994* (2013.01)

(58) Field of Classification Search
  CPC .... A61B 17/320068; A61B 17/320092; A61B 18/1442; A61B 201/0026; A61B 201/0003; A61B 201/00115; A61B 201/00132; A61B 201/0176; A61B 2018/00898; A61B 2018/00994
  USPC ............................................ 606/27, 39, 40
  See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,442,966 A | 6/1948 | Wallace |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,526,219 A | 9/1970 | Balamuth |
| 3,554,198 A | 1/1971 | Tatoian et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,776,238 A | 12/1973 | Peyman et al. |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,012,647 A | 3/1977 | Balamuth et al. |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,444 A | 5/1980 | Bonnell et al. |
| 4,300,083 A | 11/1981 | Heiges |
| 4,302,728 A | 11/1981 | Nakamura |
| 4,306,570 A | 12/1981 | Matthews |
| 4,445,063 A | 4/1984 | Smith |
| 4,491,132 A | 1/1985 | Aikins |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,545,374 A | 10/1985 | Jacobson |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,808,154 A | 2/1989 | Freeman |
| 4,819,635 A | 4/1989 | Shapiro |
| 4,827,911 A | 5/1989 | Broadwin et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,850,354 A | 7/1989 | McGurk-Burleson et al. |
| 4,852,578 A | 8/1989 | Companion et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,881,550 A | 11/1989 | Kothe |
| 4,896,009 A | 1/1990 | Pawlowski |
| 4,903,696 A | 2/1990 | Stasz et al. |
| 4,915,643 A | 4/1990 | Samejima et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,013,956 A | 5/1991 | Kurozumi et al. |
| 5,015,227 A | 5/1991 | Broadwin et al. |
| 5,026,370 A | 6/1991 | Lottick |
| 5,026,387 A | 6/1991 | Thomas |
| 5,042,707 A | 8/1991 | Taheri |
| 5,084,052 A | 1/1992 | Jacobs |
| 5,105,117 A | 4/1992 | Yamaguchi |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,162,044 A | 11/1992 | Gahn et al. |
| 5,163,421 A | 11/1992 | Bernstein et al. |
| 5,163,537 A | 11/1992 | Radev |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grezeszykowski |
| 5,188,102 A | 2/1993 | Idemoto et al. |
| D334,173 S | 3/1993 | Liu et al. |
| 5,209,719 A | 5/1993 | Baruch et al. |
| 5,213,569 A | 5/1993 | Davis |
| 5,214,339 A | 5/1993 | Naito |
| 5,218,529 A | 6/1993 | Meyer et al. |

(56) References Cited

U.S. PATENT DOCUMENTS

| | | |
|---|---|---|
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,312,023 A | 5/1994 | Green et al. |
| 5,312,425 A | 5/1994 | Evans et al. |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,387,215 A | 2/1995 | Fisher |
| 5,389,098 A | 2/1995 | Tsuruta et al. |
| 5,394,187 A | 2/1995 | Shipp |
| 5,396,266 A | 3/1995 | Brimhall |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,419,761 A | 5/1995 | Narayanan et al. |
| 5,421,829 A | 6/1995 | Olichney et al. |
| 5,423,844 A | 6/1995 | Miller |
| 5,438,997 A | 8/1995 | Sieben et al. |
| 5,445,639 A | 8/1995 | Kuslich et al. |
| 5,449,370 A | 9/1995 | Vaitekunas |
| 5,451,220 A | 9/1995 | Ciervo |
| 5,456,684 A | 10/1995 | Schmidt et al. |
| 5,471,988 A | 12/1995 | Fujio et al. |
| 5,472,443 A | 12/1995 | Cordis et al. |
| 5,478,003 A | 12/1995 | Green et al. |
| 5,483,501 A | 1/1996 | Park et al. |
| 5,486,162 A | 1/1996 | Brumbach |
| 5,490,860 A | 2/1996 | Middle et al. |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,540,693 A | 7/1996 | Fisher |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,573,424 A | 11/1996 | Poppe |
| 5,577,654 A | 11/1996 | Bishop |
| 5,591,187 A | 1/1997 | Dekel |
| 5,593,414 A | 1/1997 | Shipp et al. |
| 5,601,601 A | 2/1997 | Tal et al. |
| 5,603,773 A | 2/1997 | Campbell |
| 5,607,436 A | 3/1997 | Pratt et al. |
| 5,618,304 A | 4/1997 | Hart et al. |
| 5,618,492 A | 4/1997 | Auten et al. |
| 5,620,447 A | 4/1997 | Smith et al. |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,717 A | 5/1997 | Yoon |
| 5,640,741 A | 6/1997 | Yano |
| D381,077 S | 7/1997 | Hunt |
| 5,651,780 A | 7/1997 | Jackson et al. |
| 5,653,713 A | 8/1997 | Michelson |
| 5,662,662 A | 9/1997 | Bishop et al. |
| 5,669,922 A | 9/1997 | Hood |
| 5,674,235 A | 10/1997 | Parisi |
| 5,678,568 A | 10/1997 | Uchikubo et al. |
| 5,690,269 A | 11/1997 | Bolanos et al. |
| 5,694,936 A | 12/1997 | Fujimoto et al. |
| 5,700,261 A | 12/1997 | Brinkerhoff |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,717,306 A | 2/1998 | Shipp |
| 5,728,130 A | 3/1998 | Ishikawa et al. |
| 5,730,752 A | 3/1998 | Alden et al. |
| 5,733,074 A | 3/1998 | Stöck et al. |
| 5,741,226 A | 4/1998 | Strukel et al. |
| 5,766,164 A | 6/1998 | Mueller et al. |
| 5,772,659 A | 6/1998 | Becker et al. |
| 5,792,135 A | 8/1998 | Madhani et al. |
| 5,792,138 A | 8/1998 | Shipp |
| 5,792,165 A | 8/1998 | Klieman et al. |
| 5,797,959 A | 8/1998 | Castro et al. |
| 5,805,140 A | 9/1998 | Rosenberg et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,957 A | 11/1998 | Schulz et al. |
| 5,843,109 A | 12/1998 | Mehta et al. |
| 5,851,212 A | 12/1998 | Zirps et al. |
| 5,858,018 A | 1/1999 | Shipp et al. |
| 5,873,873 A | 2/1999 | Smith et al. |
| 5,873,882 A | 2/1999 | Straub et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,627 A | 5/1999 | Spaulding |
| 5,906,628 A | 5/1999 | Miyawaki et al. |
| 5,911,699 A | 6/1999 | Anis et al. |
| 5,916,229 A | 6/1999 | Evans |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |

(56) References Cited

U.S. PATENT DOCUMENTS

| | | |
|---|---|---|
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,024,741 A | 2/2000 | Williamson, IV et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,048,224 A | 4/2000 | Kay |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,096,033 A | 8/2000 | Tu et al. |
| 6,099,542 A | 8/2000 | Cohn et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,147,560 A | 11/2000 | Erhage et al. |
| 6,152,902 A | 11/2000 | Christian et al. |
| 6,154,198 A | 11/2000 | Rosenberg |
| 6,159,160 A | 12/2000 | Hsei et al. |
| 6,159,175 A | 12/2000 | Strukel et al. |
| 6,162,194 A | 12/2000 | Shipp |
| 6,165,150 A | 12/2000 | Banko |
| 6,174,310 B1 | 1/2001 | Kirwan, Jr. |
| 6,179,853 B1 | 1/2001 | Sachse et al. |
| 6,183,426 B1 | 2/2001 | Akisada et al. |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,299,591 B1 | 10/2001 | Banko |
| 6,306,131 B1 | 10/2001 | Hareyama |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,538 B1 | 8/2002 | Blewett et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,500,312 B2 | 12/2002 | Wedekamp |
| 6,506,208 B2 | 1/2003 | Hunt et al. |
| 6,511,478 B1 | 1/2003 | Burnside et al. |
| 6,511,493 B1 | 1/2003 | Moutafis et al. |
| 6,514,267 B2 | 2/2003 | Jewett |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |

(56) References Cited

U.S. PATENT DOCUMENTS

| | | |
|---|---|---|
| 6,544,260 B1 | 4/2003 | Markel et al. |
| 6,558,376 B2 | 5/2003 | Bishop |
| 6,561,983 B2 | 5/2003 | Cronin et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| D477,408 S | 7/2003 | Bromley |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,607,540 B1 | 8/2003 | Shipp |
| 6,610,059 B1 | 8/2003 | West, Jr. |
| 6,616,450 B2 | 9/2003 | Mossle et al. |
| 6,619,529 B2 | 9/2003 | Green et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,644,532 B2 | 11/2003 | Green et al. |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,899 B2 | 1/2004 | Wiener et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,716,215 B1 | 4/2004 | David et al. |
| 6,719,692 B2 | 4/2004 | Kleffner et al. |
| 6,719,776 B2 | 4/2004 | Baxter |
| 6,723,091 B2 | 4/2004 | Goble et al. |
| D490,059 S | 5/2004 | Conway et al. |
| 6,731,047 B2 | 5/2004 | Kauf et al. |
| 6,733,506 B1 | 5/2004 | McDevitt et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,770,072 B1 | 8/2004 | Truckai et al. |
| 6,773,409 B2 | 8/2004 | Truckai et al. |
| 6,773,443 B2 | 8/2004 | Truwit et al. |
| 6,773,444 B2 | 8/2004 | Messerly |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,790,173 B2 | 9/2004 | Saadat et al. |
| 6,790,216 B1 | 9/2004 | Ishikawa |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,827,712 B2 | 12/2004 | Tovey et al. |
| 6,828,712 B2 | 12/2004 | Battaglin et al. |
| 6,835,082 B2 | 12/2004 | Gonnering |
| 6,849,073 B2 | 2/2005 | Hoey et al. |
| 6,860,878 B2 | 3/2005 | Brock |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,899,685 B2 | 5/2005 | Kermode et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,929,602 B2 | 8/2005 | Hirakui et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,994,708 B2 | 2/2006 | Manzo |
| 7,001,335 B2 | 2/2006 | Adachi et al. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,066,893 B2 | 6/2006 | Hibner et al. |
| 7,066,895 B2 | 6/2006 | Podany |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,618 B2 | 8/2006 | Couture |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |

(56) References Cited

U.S. PATENT DOCUMENTS

| | | |
|---|---|---|
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,204,820 B2 | 4/2007 | Akahoshi |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,235,071 B2 | 6/2007 | Gonnering |
| 7,258,688 B1 | 8/2007 | Shah et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupré |
| 7,300,431 B2 | 11/2007 | Dubrovsky |
| 7,300,435 B2 | 11/2007 | Wham et al. |
| 7,300,446 B2 | 11/2007 | Beaupre |
| 7,303,531 B2 | 12/2007 | Lee et al. |
| 7,303,557 B2 | 12/2007 | Wham et al. |
| 7,306,597 B2 | 12/2007 | Manzo |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,364,577 B2 | 4/2008 | Wham et al. |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,494,468 B2 | 2/2009 | Rabiner et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,544,200 B2 | 6/2009 | Houser |
| 7,549,564 B2 | 6/2009 | Boudreaux |
| 7,559,450 B2 | 7/2009 | Wales et al. |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,095 B2 | 9/2009 | Shipp et al. |
| 7,585,181 B2 | 9/2009 | Olsen |
| 7,588,176 B2 | 9/2009 | Timm et al. |
| 7,601,119 B2 | 10/2009 | Shahinian |
| 7,607,557 B2 | 10/2009 | Shelton, IV et al. |
| 7,621,930 B2 | 11/2009 | Houser |
| 7,641,653 B2 | 1/2010 | Dalla Betta et al. |
| 7,645,278 B2 | 1/2010 | Ichihashi et al. |
| 7,654,431 B2 | 2/2010 | Hueil et al. |
| 7,659,833 B2 | 2/2010 | Warner et al. |
| 7,665,647 B2 | 2/2010 | Shelton, IV et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,846 B2 | 4/2010 | Ryan |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| 7,721,935 B2 | 5/2010 | Racenet et al. |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,751,115 B2 | 7/2010 | Song |
| D621,503 S | 8/2010 | Otten et al. |
| 7,766,210 B2 | 8/2010 | Shelton, IV et al. |
| 7,766,693 B2 | 8/2010 | Sartor et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,784,662 B2 | 8/2010 | Wales et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,806,891 B2 | 10/2010 | Nowlin et al. |

(56) References Cited

U.S. PATENT DOCUMENTS

| | | |
|---|---|---|
| 7,810,693 B2 | 10/2010 | Broehl et al. |
| 7,811,283 B2 | 10/2010 | Moses et al. |
| 7,819,819 B2 | 10/2010 | Quick et al. |
| 7,821,143 B2 | 10/2010 | Wiener |
| D627,066 S | 11/2010 | Romero |
| 7,824,401 B2 | 11/2010 | Manzo et al. |
| 7,832,611 B2 | 11/2010 | Boyden et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,892,606 B2 | 2/2011 | Thies et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,824 B2 | 3/2011 | Masuda et al. |
| 7,922,061 B2 | 4/2011 | Shelton, IV et al. |
| 7,922,651 B2 | 4/2011 | Yamada et al. |
| D637,288 S | 5/2011 | Houghton |
| D638,540 S | 5/2011 | Ijiri et al. |
| 7,936,203 B2 | 5/2011 | Zimlich |
| 7,951,095 B2 | 5/2011 | Makin et al. |
| 7,951,165 B2 | 5/2011 | Golden et al. |
| 7,959,050 B2 | 6/2011 | Smith et al. |
| 7,959,626 B2 | 6/2011 | Hong et al. |
| 7,972,329 B2 | 7/2011 | Refior et al. |
| 7,976,544 B2 | 7/2011 | McClurken et al. |
| 7,981,050 B2 | 7/2011 | Ritchart et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,070,711 B2 | 12/2011 | Bassinger et al. |
| 8,070,762 B2 | 12/2011 | Escudero et al. |
| 8,075,558 B2 | 12/2011 | Truckai et al. |
| 8,089,197 B2 | 1/2012 | Rinner et al. |
| 8,097,012 B2 | 1/2012 | Kagarise |
| 8,105,323 B2 | 1/2012 | Buysse et al. |
| 8,142,461 B2 | 3/2012 | Houser et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,877 B2 | 5/2012 | Klimovitch et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,502 B2 | 6/2012 | Smith et al. |
| 8,207,651 B2 | 6/2012 | Gilbert |
| 8,210,411 B2 | 7/2012 | Yates et al. |
| 8,226,675 B2 | 7/2012 | Houser et al. |
| 8,235,917 B2 | 8/2012 | Joseph et al. |
| 8,236,019 B2 | 8/2012 | Houser |
| 8,236,020 B2 | 8/2012 | Smith et al. |
| 8,241,271 B2 | 8/2012 | Millman et al. |
| 8,246,575 B2 | 8/2012 | Viola |
| 8,246,615 B2 | 8/2012 | Behnke |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,273,087 B2 | 9/2012 | Kimura et al. |
| D669,992 S | 10/2012 | Schafer et al. |
| D669,993 S | 10/2012 | Merchant et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,888 B2 | 10/2012 | Whitman |
| 8,298,223 B2 | 10/2012 | Wham et al. |
| 8,298,225 B2 | 10/2012 | Gilbert |
| 8,303,576 B2 | 11/2012 | Brock |
| 8,303,580 B2 | 11/2012 | Wham et al. |
| 8,303,583 B2 | 11/2012 | Hosier et al. |
| 8,319,400 B2 | 11/2012 | Houser et al. |
| 8,323,302 B2 | 12/2012 | Robertson et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,967 B2 | 1/2013 | Stulen |
| 8,357,103 B2 | 1/2013 | Mark et al. |
| 8,366,727 B2 | 2/2013 | Witt et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,545 B2 | 4/2013 | Smith et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,460,288 B2 | 6/2013 | Tamai et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,359 B2 | 8/2013 | Whitman et al. |
| 8,512,365 B2 | 8/2013 | Wiener et al. |
| 8,523,889 B2 | 9/2013 | Stulen et al. |
| 8,531,064 B2 | 9/2013 | Robertson et al. |
| 8,535,340 B2 | 9/2013 | Allen |
| 8,535,341 B2 | 9/2013 | Allen |
| 8,546,996 B2 | 10/2013 | Messerly et al. |
| 8,546,999 B2 | 10/2013 | Houser et al. |
| 8,568,400 B2 | 10/2013 | Gilbert |
| 8,573,461 B2 | 11/2013 | Shelton, IV et al. |
| 8,573,465 B2 | 11/2013 | Shelton, IV |
| 8,579,928 B2 | 11/2013 | Robertson et al. |
| 8,591,459 B2 | 11/2013 | Clymer et al. |
| 8,591,506 B2 | 11/2013 | Wham et al. |

(56) References Cited

U.S. PATENT DOCUMENTS

| | | |
|---|---|---|
| 8,591,536 B2 | 11/2013 | Robertson |
| D695,407 S | 12/2013 | Price et al. |
| D696,631 S | 12/2013 | Price et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,616,431 B2 | 12/2013 | Timm et al. |
| 8,623,027 B2 | 1/2014 | Price et al. |
| 8,650,728 B2 | 2/2014 | Wan et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,690,582 B2 | 4/2014 | Rohrbach et al. |
| 8,696,366 B2 | 4/2014 | Chen et al. |
| 8,704,425 B2 | 4/2014 | Giordano et al. |
| 8,709,031 B2 | 4/2014 | Stulen |
| 8,747,351 B2 | 6/2014 | Schultz |
| 8,749,116 B2 | 6/2014 | Messerly et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,764,735 B2 | 7/2014 | Coe et al. |
| 8,773,001 B2 | 7/2014 | Wiener et al. |
| 8,779,648 B2 | 7/2014 | Giordano et al. |
| 8,784,418 B2 | 7/2014 | Romero |
| 8,808,319 B2 | 8/2014 | Houser et al. |
| 8,827,992 B2 | 9/2014 | Koss et al. |
| 8,845,537 B2 | 9/2014 | Tanaka et al. |
| 8,882,791 B2 | 11/2014 | Stulen |
| 8,888,776 B2 | 11/2014 | Dietz et al. |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,911,460 B2 | 12/2014 | Neurohr et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,547 B2 | 2/2015 | Dietz et al. |
| 8,968,283 B2 | 3/2015 | Kharin |
| 8,968,355 B2 | 3/2015 | Malkowski et al. |
| 8,974,477 B2 | 3/2015 | Yamada |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,903 B2 | 3/2015 | Weir et al. |
| 9,017,326 B2 | 4/2015 | DiNardo et al. |
| 9,039,695 B2 | 5/2015 | Giordano et al. |
| 9,044,261 B2 | 6/2015 | Houser |
| 9,050,093 B2 | 6/2015 | Aldridge et al. |
| 9,050,124 B2 | 6/2015 | Houser |
| 9,060,775 B2 | 6/2015 | Wiener et al. |
| 9,060,776 B2 | 6/2015 | Yates et al. |
| 9,066,747 B2 | 6/2015 | Robertson |
| 9,072,539 B2 | 7/2015 | Messerly et al. |
| 9,095,367 B2 | 8/2015 | Olson et al. |
| 9,107,689 B2 | 8/2015 | Robertson et al. |
| 9,113,940 B2 | 8/2015 | Twomey |
| 9,168,054 B2 | 10/2015 | Turner et al. |
| 9,198,714 B2 | 12/2015 | Worrell et al. |
| 9,220,527 B2 | 12/2015 | Houser et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,921 B2 * | 1/2016 | Messerly ........ A61B 17/320068 |
| 9,241,728 B2 | 1/2016 | Price et al. |
| 9,241,731 B2 | 1/2016 | Boudreaux et al. |
| 9,259,234 B2 | 2/2016 | Robertson et al. |
| 9,283,045 B2 | 3/2016 | Rhee et al. |
| 9,326,788 B2 | 5/2016 | Batross et al. |
| 9,339,289 B2 | 5/2016 | Robertson |
| 9,351,754 B2 | 5/2016 | Vakharia et al. |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0114851 A1 | 6/2003 | Truckai et al. |
| 2003/0144680 A1 | 7/2003 | Kellogg et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0216766 A1 * | 11/2003 | Wiener ........ A61B 17/320068 606/169 |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0132383 A1 | 7/2004 | Langford et al. |
| 2004/0147934 A1 | 7/2004 | Kiester |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0199193 A1 | 10/2004 | Hayashi et al. |
| 2004/0204728 A1 | 10/2004 | Haefner |
| 2004/0243147 A1 | 12/2004 | Lipow |
| 2004/0260300 A1 | 12/2004 | Gorensek et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0099824 A1 | 5/2005 | Dowling et al. |
| 2005/0103819 A1 | 5/2005 | Racenet et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0209620 A1 | 9/2005 | Du et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0084963 A1 | 4/2006 | Messerly |

(56) References Cited

U.S. PATENT DOCUMENTS

| | | |
|---|---|---|
| 2006/0095046 A1 | 5/2006 | Trieu et al. |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0235306 A1 | 10/2006 | Cotter et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0271030 A1 | 11/2006 | Francis et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0074584 A1 | 4/2007 | Talarico et al. |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0185380 A1 | 8/2007 | Kucklick |
| 2007/0191712 A1 | 8/2007 | Messerly et al. |
| 2007/0219481 A1 | 9/2007 | Babaev |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2007/0288055 A1 | 12/2007 | Lee |
| 2008/0009848 A1 | 1/2008 | Paraschiv et al. |
| 2008/0013809 A1 | 1/2008 | Zhu et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114364 A1 | 5/2008 | Goldin et al. |
| 2008/0125768 A1 | 5/2008 | Tahara et al. |
| 2008/0140158 A1 | 6/2008 | Hamel et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287948 A1 | 11/2008 | Newton et al. |
| 2009/0023985 A1 | 1/2009 | Ewers |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0088785 A1 | 4/2009 | Masuda |
| 2009/0112229 A1 | 4/2009 | Omori et al. |
| 2009/0118751 A1 | 5/2009 | Wiener et al. |
| 2009/0118802 A1 | 5/2009 | Mioduski et al. |
| 2009/0138006 A1 | 5/2009 | Bales et al. |
| 2009/0143799 A1 | 6/2009 | Smith et al. |
| 2009/0143800 A1 | 6/2009 | Deville et al. |
| 2009/0143806 A1 | 6/2009 | Witt et al. |
| 2009/0149801 A1 | 6/2009 | Crandall et al. |
| 2009/0163807 A1 | 6/2009 | Sliwa |
| 2009/0207923 A1 | 8/2009 | Dress |
| 2009/0216157 A1 | 8/2009 | Yamada |
| 2009/0223033 A1 | 9/2009 | Houser |
| 2009/0254077 A1 | 10/2009 | Craig |
| 2009/0254080 A1 | 10/2009 | Honda |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270899 A1 | 10/2009 | Carusillo et al. |
| 2009/0275940 A1 | 11/2009 | Malackowski et al. |
| 2009/0318945 A1 | 12/2009 | Yoshimine et al. |
| 2009/0327715 A1 | 12/2009 | Smith et al. |
| 2010/0004508 A1 | 1/2010 | Naito et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0036370 A1 | 2/2010 | Mirel et al. |
| 2010/0042077 A1 | 2/2010 | Okada |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupré |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0222714 A1 | 9/2010 | Muir et al. |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nield |
| 2010/0331742 A1 | 12/2010 | Masuda |
| 2011/0004233 A1 | 1/2011 | Muir et al. |
| 2011/0009850 A1 | 1/2011 | Main et al. |
| 2011/0077648 A1 | 3/2011 | Lee et al. |
| 2011/0082486 A1* | 4/2011 | Messerly ....... A61B 17/320092 606/169 |
| 2011/0087218 A1 | 4/2011 | Boudreaux et al. |
| 2011/0112526 A1 | 5/2011 | Fritz et al. |
| 2011/0125151 A1 | 5/2011 | Strauss et al. |
| 2011/0125174 A1 | 5/2011 | Babaev |
| 2011/0144806 A1 | 6/2011 | Sandhu et al. |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0290853 A1 | 12/2011 | Shelton, IV et al. |
| 2011/0290856 A1 | 12/2011 | Shelton, IV et al. |
| 2012/0004655 A1 | 1/2012 | Kim et al. |
| 2012/0022525 A1 | 1/2012 | Dietz et al. |
| 2012/0022530 A1 | 1/2012 | Woodruff et al. |
| 2012/0022583 A1 | 1/2012 | Sugalski et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |

(56) References Cited

U.S. PATENT DOCUMENTS

| | | |
|---|---|---|
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0101495 A1 | 4/2012 | Young et al. |
| 2012/0101501 A1 | 4/2012 | Nishimura et al. |
| 2012/0109159 A1 | 5/2012 | Jordan et al. |
| 2012/0116379 A1 | 5/2012 | Yates et al. |
| 2012/0116391 A1 | 5/2012 | Houser et al. |
| 2012/0116394 A1 | 5/2012 | Timm et al. |
| 2012/0116395 A1 | 5/2012 | Madan et al. |
| 2012/0130256 A1 | 5/2012 | Buysse et al. |
| 2012/0130365 A1 | 5/2012 | McLawhorn |
| 2012/0136354 A1 | 5/2012 | Rupp |
| 2012/0138660 A1 | 6/2012 | Shelton, IV |
| 2012/0143211 A1 | 6/2012 | Kishi |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203143 A1 | 8/2012 | Sanai et al. |
| 2012/0203247 A1 | 8/2012 | Shelton, IV et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0215220 A1 | 8/2012 | Manzo et al. |
| 2012/0245582 A1 | 9/2012 | Kimball et al. |
| 2012/0253370 A1 | 10/2012 | Ross et al. |
| 2012/0269676 A1 | 10/2012 | Houser et al. |
| 2012/0330307 A1 | 12/2012 | Ladtkow et al. |
| 2013/0012957 A1 | 1/2013 | Shelton, IV et al. |
| 2013/0030433 A1 | 1/2013 | Heard |
| 2013/0035680 A1 | 2/2013 | Ben-Haim et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0165929 A1 | 6/2013 | Muir et al. |
| 2013/0217967 A1 | 8/2013 | Mohr et al. |
| 2013/0226207 A1 | 8/2013 | Stulen et al. |
| 2013/0226208 A1 | 8/2013 | Wiener et al. |
| 2013/0245659 A1 | 9/2013 | Robertson et al. |
| 2013/0253498 A1 | 9/2013 | Germain et al. |
| 2013/0267975 A1 | 10/2013 | Timm et al. |
| 2013/0274734 A1 | 10/2013 | Maass et al. |
| 2013/0282038 A1 | 10/2013 | Dannaher et al. |
| 2013/0282039 A1 | 10/2013 | Wiener et al. |
| 2013/0296908 A1 | 11/2013 | Schulte et al. |
| 2013/0338661 A1 | 12/2013 | Behnke, II |
| 2013/0345689 A1 | 12/2013 | Ruddenklau et al. |
| 2014/0005640 A1 | 1/2014 | Shelton, IV et al. |
| 2014/0005653 A1 | 1/2014 | Shelton, IV et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005676 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0012299 A1 | 1/2014 | Stoddard et al. |
| 2014/0066962 A1 | 3/2014 | Robertson et al. |
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0135804 A1 | 5/2014 | Weisenburgh, II et al. |
| 2014/0155921 A1 | 6/2014 | Price et al. |
| 2014/0180280 A1 | 6/2014 | Sigmon, Jr. |
| 2014/0243864 A1 | 8/2014 | Voegele et al. |
| 2014/0276970 A1 | 9/2014 | Messerly et al. |
| 2015/0045819 A1 | 2/2015 | Houser et al. |
| 2015/0066067 A1 | 3/2015 | Stulen |
| 2015/0073460 A1 | 3/2015 | Stulen |
| 2015/0112335 A1 | 4/2015 | Boudreaux et al. |
| 2015/0119914 A1 | 4/2015 | Neurohr et al. |
| 2015/0119915 A1 | 4/2015 | Neurohr et al. |
| 2015/0119916 A1 | 4/2015 | Dietz et al. |
| 2015/0123348 A1 | 5/2015 | Robertson et al. |
| 2015/0157355 A1 | 6/2015 | Price et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |
| 2015/0196318 A1 | 7/2015 | Messerly et al. |
| 2015/0250495 A1 | 9/2015 | Robertson et al. |
| 2015/0257780 A1 | 9/2015 | Houser |
| 2015/0257781 A1 | 9/2015 | Houser et al. |
| 2015/0265308 A1 | 9/2015 | Houser et al. |
| 2015/0327883 A1 | 11/2015 | Messerly et al. |
| 2015/0328484 A1 | 11/2015 | Messerly et al. |
| 2015/0340586 A1 | 11/2015 | Wiener et al. |
| 2015/0351789 A1 | 12/2015 | Robertson et al. |
| 2016/0030076 A1 | 2/2016 | Faller et al. |
| 2016/0089209 A1 | 3/2016 | Parihar et al. |
| 2016/0089533 A1 | 3/2016 | Turner et al. |
| 2016/0095617 A1 | 4/2016 | Price et al. |
| 2016/0106509 A1 | 4/2016 | Worrell et al. |

FOREIGN PATENT DOCUMENTS

| | | |
|---|---|---|
| CN | 1233944 A | 11/1999 |
| CN | 1253485 A | 5/2000 |
| CN | 1634601 A | 7/2005 |
| CN | 1640365 A | 7/2005 |
| CN | 1694649 A | 11/2005 |
| CN | 1922563 A | 2/2007 |
| CN | 1951333 A | 4/2007 |
| CN | 101040799 A | 9/2007 |
| CN | 101467917 A | 1/2009 |
| DE | 3904558 A1 | 8/1990 |
| DE | 9210327 U1 | 11/1992 |
| DE | 4323585 A1 | 1/1995 |
| DE | 19608716 C1 | 4/1997 |
| DE | 20021619 U1 | 3/2001 |
| DE | 10042606 A1 | 8/2001 |
| EP | 0136855 B1 | 9/1984 |
| EP | 0171967 A2 | 2/1986 |
| EP | 1839599 A1 | 10/1987 |
| EP | 0336742 A2 | 4/1989 |
| EP | 0342448 A1 | 11/1989 |
| EP | 0424685 B1 | 5/1991 |
| EP | 0443256 A1 | 8/1991 |
| EP | 0456470 A1 | 11/1991 |
| EP | 0598976 A2 | 1/1994 |
| EP | 0677275 A2 | 3/1995 |
| EP | 0482195 B1 | 1/1996 |
| EP | 0695535 A1 | 2/1996 |
| EP | 0741996 A2 | 11/1996 |
| EP | 0612570 B1 | 6/1997 |
| EP | 1108394 A2 | 6/2001 |
| EP | 1138264 A1 | 10/2001 |

(56) References Cited

FOREIGN PATENT DOCUMENTS

| | | |
|---|---|---|
| EP | 0908148 B1 | 1/2002 |
| EP | 1229515 A2 | 8/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1433425 B1 | 6/2006 |
| EP | 1256323 B1 | 9/2006 |
| EP | 1698289 A2 | 9/2006 |
| EP | 1704824 A1 | 9/2006 |
| EP | 1749479 A1 | 2/2007 |
| EP | 1815950 A1 | 8/2007 |
| EP | 1844720 A1 | 10/2007 |
| EP | 1862133 A1 | 12/2007 |
| EP | 1875875 A1 | 1/2008 |
| EP | 1199045 B1 | 6/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1997438 A2 | 12/2008 |
| EP | 1477104 B1 | 1/2009 |
| EP | 2014218 A2 | 1/2009 |
| EP | 2042112 A2 | 4/2009 |
| EP | 1832259 B1 | 6/2009 |
| EP | 2074959 A1 | 7/2009 |
| EP | 2106758 A1 | 10/2009 |
| EP | 2111813 A1 | 10/2009 |
| EP | 2200145 A1 | 6/2010 |
| EP | 1214913 B1 | 7/2010 |
| EP | 2238938 A1 | 10/2010 |
| EP | 2298154 A2 | 3/2011 |
| EP | 1510178 B1 | 6/2011 |
| EP | 1946708 B1 | 6/2011 |
| EP | 2305144 A1 | 6/2011 |
| EP | 2335630 A1 | 6/2011 |
| EP | 1502551 B1 | 7/2011 |
| EP | 2361562 A1 | 8/2011 |
| EP | 2365608 A2 | 9/2011 |
| EP | 2420197 A2 | 2/2012 |
| EP | 2422721 A2 | 2/2012 |
| EP | 1927321 B1 | 4/2012 |
| EP | 2510891 A1 | 10/2012 |
| EP | 2316359 B1 | 3/2013 |
| EP | 1586275 B1 | 5/2013 |
| EP | 1616529 B1 | 9/2013 |
| EP | 2583633 B1 | 10/2014 |
| EP | 2113210 B1 | 3/2016 |
| GB | 1482943 A | 8/1977 |
| GB | 2032221 A | 4/1980 |
| GB | 2317566 A | 4/1998 |
| GB | 2379878 B | 11/2004 |
| GB | 2447767 B | 8/2011 |
| JP | S 50-100891 A | 8/1975 |
| JP | S 59-68513 U | 5/1984 |
| JP | S 59141938 A | 8/1984 |
| JP | 62-221343 A | 9/1987 |
| JP | S 62-227343 A | 10/1987 |
| JP | 62-292153 A | 12/1987 |
| JP | S 62-292154 A | 12/1987 |
| JP | 63-109386 A | 5/1988 |
| JP | 63-315049 A | 12/1988 |
| JP | H 01-151452 A | 6/1989 |
| JP | H 01-198540 A | 8/1989 |
| JP | 02-71510 U | 5/1990 |
| JP | 2-286149 A | 11/1990 |
| JP | H 02-292193 A | 12/1990 |
| JP | H 03-37061 A | 2/1991 |
| JP | 04-25707 U | 2/1992 |
| JP | H 04-64351 A | 2/1992 |
| JP | 4-30508 U | 3/1992 |
| JP | H 04-150847 A | 5/1992 |
| JP | H 04-152942 A | 5/1992 |
| JP | 05-095955 A | 4/1993 |
| JP | H 05-115490 A | 5/1993 |
| JP | H 06-070938 A | 3/1994 |
| JP | 6-104503 A | 4/1994 |
| JP | 6-507081 A | 8/1994 |
| JP | H 06-217988 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 08-299351 A | 11/1996 |
| JP | H 08-336545 A | 12/1996 |
| JP | H 09-503146 A | 3/1997 |
| JP | H 09-135553 A | 5/1997 |
| JP | H 09-140722 A | 6/1997 |
| JP | H 10-005237 A | 1/1998 |
| JP | 10-295700 A | 11/1998 |
| JP | H 11-501543 A | 2/1999 |
| JP | H 11-128238 A | 5/1999 |
| JP | H 11-192235 A | 7/1999 |
| JP | 11-253451 A | 9/1999 |
| JP | H 11-318918 A | 11/1999 |
| JP | 2000-041991 A | 2/2000 |
| JP | 2000-070279 A | 3/2000 |
| JP | 2000-210299 A | 8/2000 |
| JP | 2000-287987 A | 10/2000 |
| JP | 2001-029353 A | 2/2001 |
| JP | 2001-502216 A | 2/2001 |
| JP | 2001-309925 A | 11/2001 |
| JP | 2002-186901 A | 7/2002 |
| JP | 2002-204808 A | 7/2002 |
| JP | 2002-263579 A | 9/2002 |
| JP | 2002-301086 A | 10/2002 |
| JP | 2002-330977 A | 11/2002 |
| JP | 2002-542690 A | 12/2002 |
| JP | 2003-000612 A | 1/2003 |
| JP | 2003-010201 | 1/2003 |
| JP | 2003-510158 A | 3/2003 |
| JP | 2003-116870 A | 4/2003 |
| JP | 2003-126104 A | 5/2003 |
| JP | 2003-126110 A | 5/2003 |
| JP | 2003-310627 A | 5/2003 |
| JP | 2003-530921 A | 10/2003 |
| JP | 2003-339730 A | 12/2003 |
| JP | 2004-129871 A | 4/2004 |
| JP | 2004-147701 A | 5/2004 |
| JP | 2005027026 A | 1/2005 |
| JP | 2005-040222 A | 2/2005 |
| JP | 2005-066316 A | 3/2005 |
| JP | 2005-074088 A | 3/2005 |
| JP | 2005-534451 A | 11/2005 |
| JP | 2006-6410 A | 1/2006 |
| JP | 2006-512149 A | 4/2006 |
| JP | 2006-116194 A | 5/2006 |
| JP | 2006-158525 A | 6/2006 |
| JP | 2006-218296 A | 8/2006 |
| JP | 2006217716 A | 8/2006 |
| JP | 2006-288431 A | 10/2006 |
| JP | 2007-050181 A | 3/2007 |
| JP | 2007-229454 A | 9/2007 |
| JP | 2007-527747 A | 10/2007 |
| JP | 2008-508065 A | 3/2008 |
| JP | 2008-119250 A | 5/2008 |
| JP | 2008-521503 A | 6/2008 |
| JP | D1339835 S | 8/2008 |
| JP | 2008-212679 A | 9/2008 |
| JP | 2008-536562 A | 9/2008 |
| JP | 2008-284374 A | 11/2008 |
| JP | 2009-511206 A | 3/2009 |
| JP | 2009-517181 A | 4/2009 |
| JP | 4262923 B2 | 5/2009 |
| JP | 2009-523567 A | 6/2009 |
| JP | 2009-236177 A | 10/2009 |

(56) References Cited

FOREIGN PATENT DOCUMENTS

| | | |
|---|---|---|
| JP | 2009-254819 A | 11/2009 |
| JP | 2010-000336 A | 1/2010 |
| JP | 2010-514923 A | 5/2010 |
| JP | 2010-534522 A | 11/2010 |
| JP | 2010-540186 A | 12/2010 |
| JP | 2011-505198 A | 2/2011 |
| JP | 2012-235658 A | 11/2012 |
| JP | 5208761 B2 | 6/2013 |
| JP | 5714508 B2 | 5/2015 |
| RU | 2154437 C1 | 8/2000 |
| RU | 22035 U1 | 3/2002 |
| WO | WO 92/22259 A2 | 12/1992 |
| WO | WO 93/08757 A1 | 5/1993 |
| WO | WO 93/14708 A1 | 8/1993 |
| WO | WO 93/16646 A1 | 9/1993 |
| WO | WO 93/20877 A1 | 10/1993 |
| WO | WO 94/21183 A1 | 9/1994 |
| WO | WO 94/24949 A1 | 11/1994 |
| WO | WO 95/09572 A1 | 4/1995 |
| WO | WO 95/34259 A1 | 12/1995 |
| WO | WO 96/30885 A1 | 10/1996 |
| WO | WO 96/39086 A1 | 12/1996 |
| WO | WO 98/16156 A1 | 4/1998 |
| WO | WO 98/26739 A1 | 6/1998 |
| WO | WO 98/35621 A1 | 8/1998 |
| WO | WO 98/37815 A1 | 9/1998 |
| WO | WO 98/47436 A1 | 10/1998 |
| WO | WO 99/20213 A1 | 4/1999 |
| WO | WO 99/52489 A1 | 10/1999 |
| WO | WO 00/64358 A2 | 11/2000 |
| WO | WO 00/74585 A2 | 12/2000 |
| WO | WO 01/24713 A1 | 4/2001 |
| WO | WO 01/54590 A1 | 8/2001 |
| WO | WO 01/67970 A1 | 9/2001 |
| WO | WO 01/95810 A2 | 12/2001 |
| WO | WO 02/24080 A2 | 3/2002 |
| WO | WO 02/38057 A1 | 5/2002 |
| WO | WO 02/062241 A1 | 8/2002 |
| WO | WO 03/082133 A1 | 10/2003 |
| WO | WO 2004/012615 A1 | 2/2004 |
| WO | WO 2004/026104 A2 | 4/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/060141 A2 | 7/2004 |
| WO | WO 2004/098426 A1 | 11/2004 |
| WO | WO 2004/112618 A2 | 12/2004 |
| WO | WO 2005/117735 A1 | 12/2005 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/101661 A2 | 9/2006 |
| WO | WO 2006/119139 A2 | 11/2006 |
| WO | WO 2006/119376 A2 | 11/2006 |
| WO | WO 2006/129465 A1 | 12/2006 |
| WO | WO 2007/008703 A2 | 1/2007 |
| WO | WO 2007/008710 A2 | 1/2007 |
| WO | WO 2007/038538 A1 | 4/2007 |
| WO | WO 2007/040818 A1 | 4/2007 |
| WO | WO 2007/047380 A2 | 4/2007 |
| WO | WO 2007/047531 A2 | 4/2007 |
| WO | WO 2007/056590 A1 | 5/2007 |
| WO | WO 2007/087272 A2 | 8/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/051764 A2 | 5/2008 |
| WO | WO 2008/089174 A2 | 7/2008 |
| WO | WO 2008/118709 A1 | 10/2008 |
| WO | WO 2008/130793 A1 | 10/2008 |
| WO | WO 2009/010565 A1 | 1/2009 |
| WO | WO 2009/018067 A1 | 2/2009 |
| WO | WO 2009/018406 A2 | 2/2009 |
| WO | WO 2009/027065 A1 | 3/2009 |
| WO | WO 2009/046234 A2 | 4/2009 |
| WO | WO 2009/073402 A2 | 6/2009 |
| WO | WO 2009/120992 A2 | 10/2009 |
| WO | WO 2010/017149 A1 | 2/2010 |
| WO | WO 2010/068783 A1 | 6/2010 |
| WO | WO 2011/008672 A2 | 1/2011 |
| WO | WO 2011/052939 A2 | 5/2011 |
| WO | WO 2011/100321 A2 | 8/2011 |
| WO | WO 2011/144911 A1 | 11/2011 |
| WO | WO 2012/061722 A2 | 5/2012 |
| WO | WO 2012/128362 A1 | 9/2012 |
| WO | WO 2012/135705 A1 | 10/2012 |
| WO | WO 2012/135721 A1 | 10/2012 |
| WO | WO 2013/018934 A1 | 2/2013 |
| WO | WO 2013/062978 A2 | 5/2013 |
| WO | WO 2014/092108 A1 | 6/2014 |

OTHER PUBLICATIONS

International Search Report for PCT/US2013/035361, dated Sep. 27, 2013 (6 pages).
International Search Report for PCT/US2013/035364, dated Sep. 27, 2013 (7 pages).
International Search Report for PCT/US2013/035367, dated Oct. 7, 2013 (4 pages).
International Search Report for PCT/US2013/035370, dated Apr. 23, 2014 (9 pages).
International Preliminary Report on Patentability for PCT/US2013/035368, dated Oct. 14, 2014 (6 pages).
International Preliminary Report on Patentability for PCT/US2013/035361, dated Oct. 14, 2014 (9 pages).
International Preliminary Report on Patentability for PCT/US2013/035364, dated Oct. 14, 2014 (9 pages).
International Preliminary Report on Patentability for PCT/US2013/035367, dated Oct. 14, 2014 (7 pages).
International Preliminary Report on Patentability for PCT/US2013/035370, dated Oct. 14, 2014 (12 pages).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., "Fundamentals of Heat and Mass Transfer", Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

(56) References Cited

OTHER PUBLICATIONS

Sullivan, "Optimal Choice for Number of Strands in a Litz-Wire Transformer Winding," IEEE Transactions on Power Electronics, vol. 14, No. 2, Mar. 1999, pp. 283-291.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
U.S. Appl. No. 13/751,680, filed Jan. 28, 2013.

\* cited by examiner

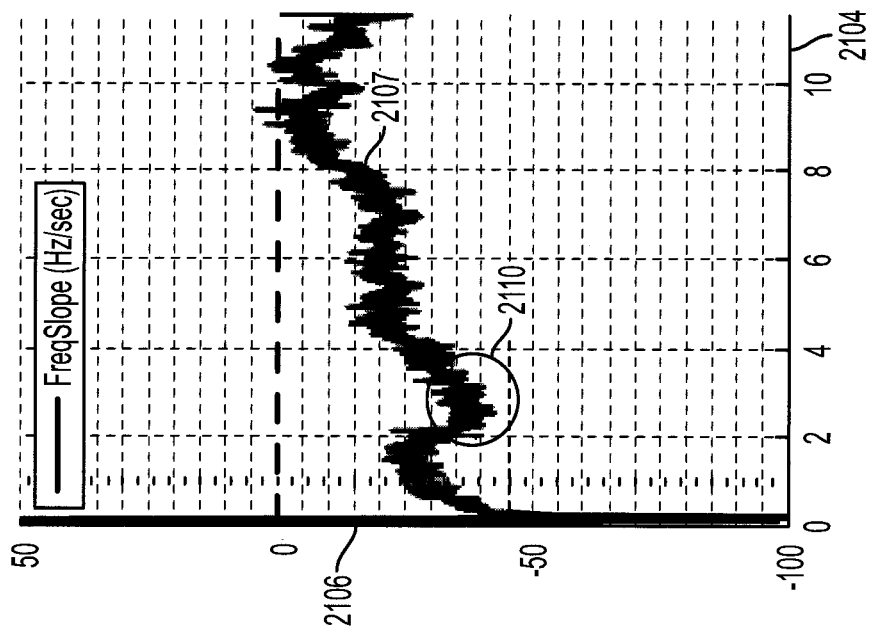
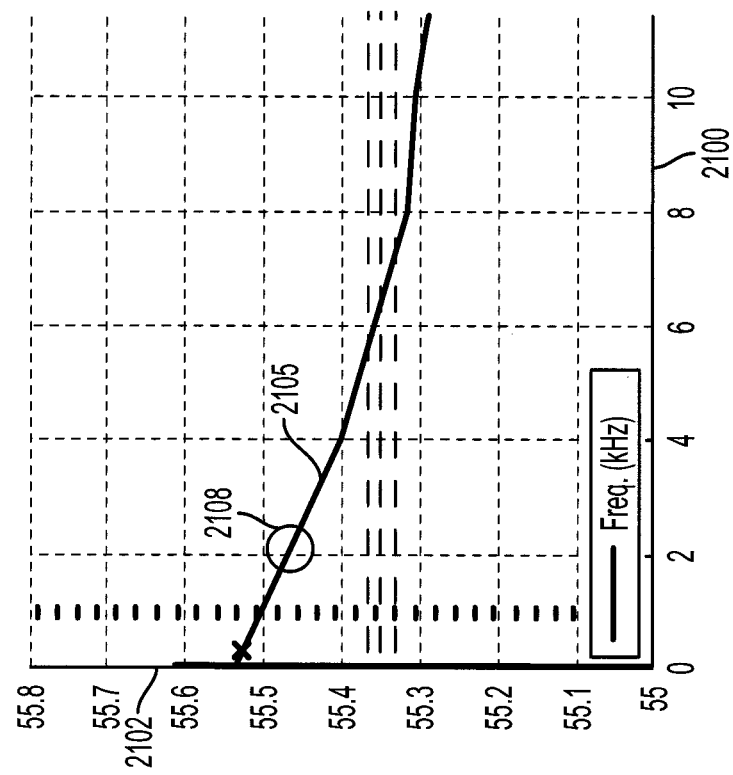
FIG. 51B
FIG. 51A

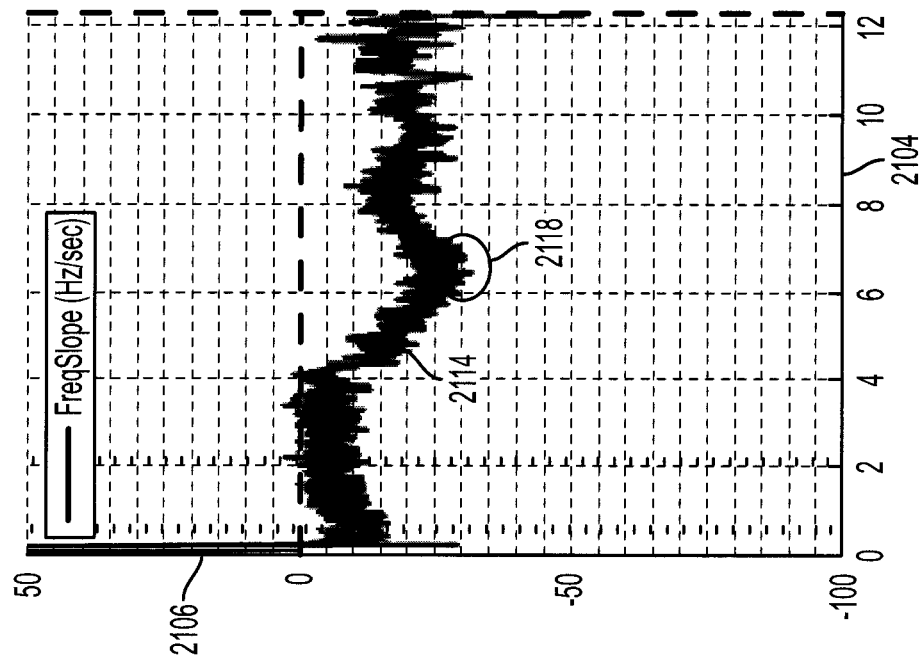
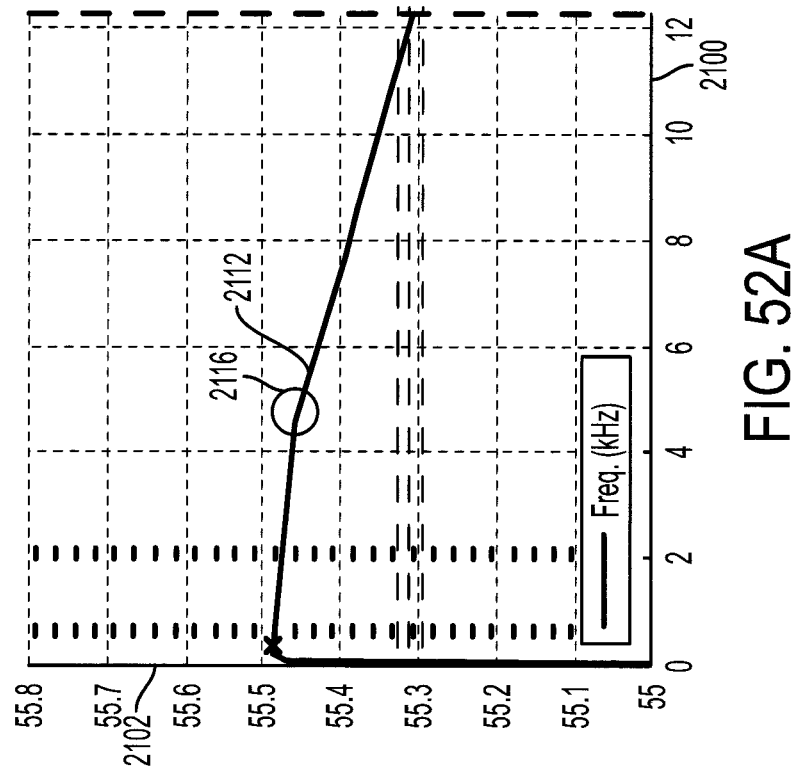
FIG. 52B
FIG. 52A

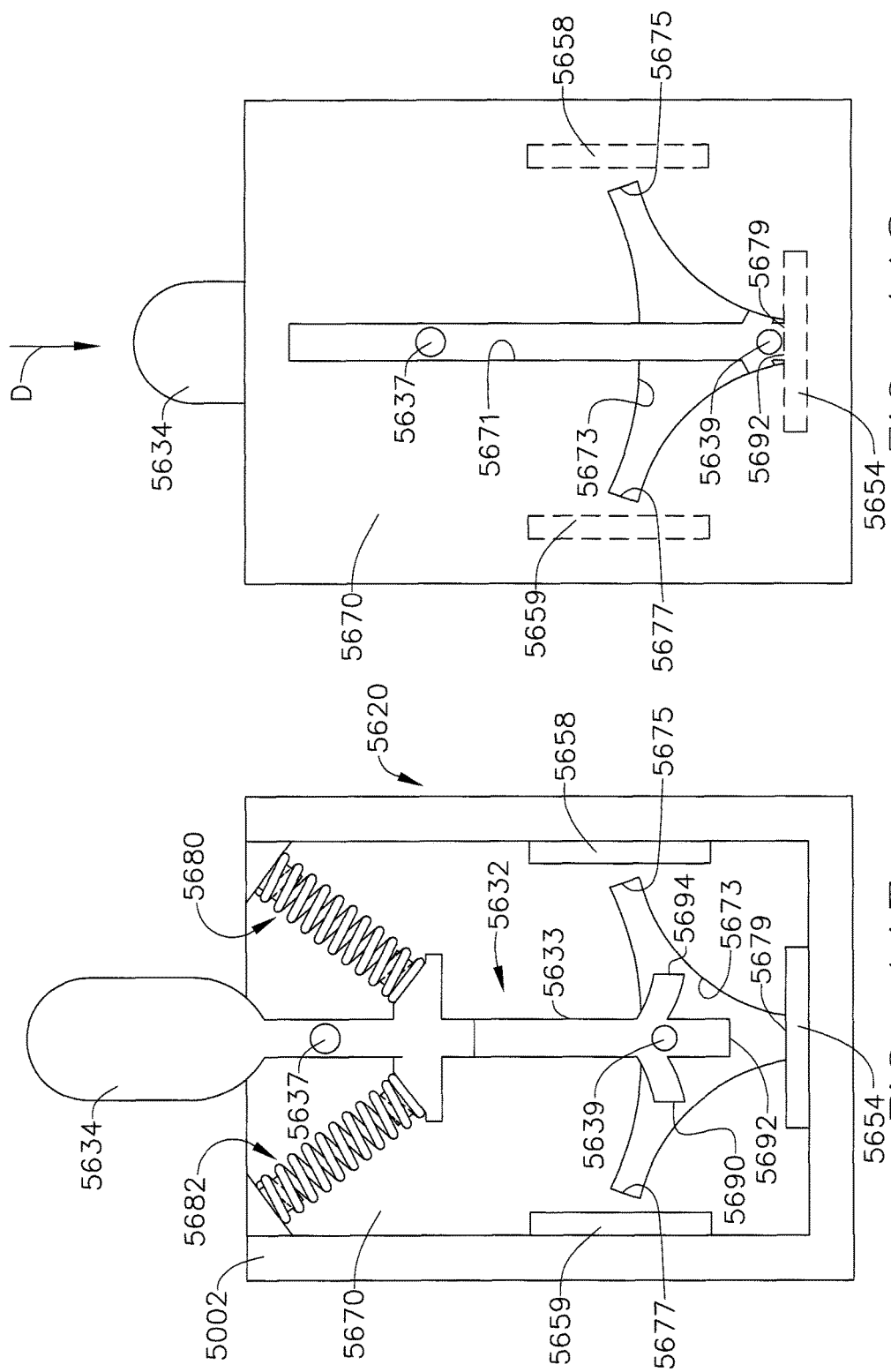

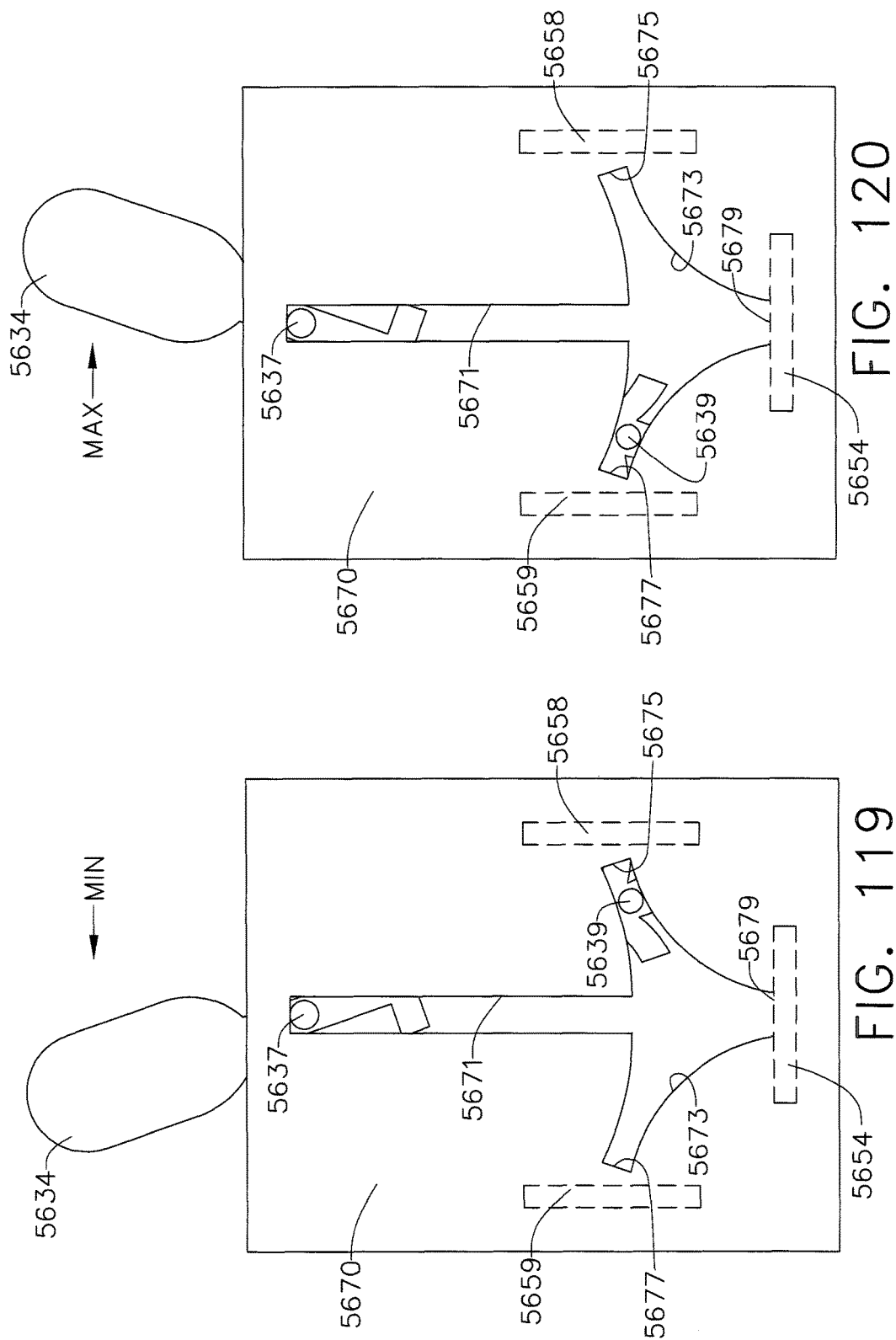

DEVICES AND TECHNIQUES FOR CUTTING AND COAGULATING TISSUE

PRIORITY CLAIM

This application is a continuation of U.S. patent application Ser. No. 13/839,014, filed on Mar. 15, 2013, now U.S. Pat. No. 9,237,921, which is incorporated herein by reference in its entirety and claims the benefit of U.S. Provisional Application Ser. No. 61/621,876, which was filed on Apr. 9, 2012 and is also incorporated herein by reference in its entirety.

TECHNICAL FIELD

The present disclosure generally relates to ultrasonic surgical systems and, more particularly, to ultrasonic and electrosurgical systems that allows surgeons to perform cutting and coagulation.

BACKGROUND

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically realized by an-end effector, or blade tip, at the distal end of the instrument, which transmits ultrasonic energy to tissue brought into contact with the end effector. Ultrasonic instruments of this nature can be configured for open surgical use, laparoscopic, or endoscopic surgical procedures including robotic-assisted procedures.

Some surgical instruments utilize ultrasonic energy for both precise cutting and controlled coagulation. Ultrasonic energy cuts and coagulates by using lower temperatures than those used by electrosurgery. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

A primary challenge of ultrasonic technology for medical devices, however, continues to be sealing of blood vessels. Work done by the applicant and others has shown that optimum vessel sealing occurs when the inner muscle layer of a vessel is separated and moved away from the adventitia layer prior to the application of standard ultrasonic energy. Current efforts to achieve this separation have involved increasing the clamp force applied to the vessel.

Furthermore, the user does not always have visual feedback of the tissue being cut. Accordingly, it would be desirable to provide some form of feedback to indicate to the user that the cut is complete when visual feedback is unavailable. Moreover, without some form of feedback indicator to indicate that the cut is complete, the user may continue to activate the harmonic instrument even though the cut is complete, which cause possible damage to the harmonic instrument and surrounding tissue by the heat that is generated when activating a harmonic instrument with little to nothing between the jaws.

The ultrasonic transducer may be modeled as an equivalent circuit having first branch comprising a static capacitance and a second "motional" branch comprising a serially connected inductance, resistance and capacitance that defines the electromechanical properties of the resonator. Conventional ultrasonic generators may include a tuning inductor for tuning out the static capacitance at a resonant frequency so that substantially all of generator's current output flows into the motional branch. The motional branch current, along with the drive voltage, define the impedance and phase magnitude. Accordingly, using a tuning inductor, the generator's current output represents the motional branch current, and the generator is thus able to maintain its drive output at the ultrasonic transducer's resonant frequency. The tuning inductor also transforms the phase impedance plot of the ultrasonic transducer to improve the generator's frequency lock capabilities. However, the tuning inductor must be matched with the specific static capacitance of an ultrasonic transducer. A different ultrasonic transducer having a different static capacitance requires a different tuning inductor.

Electrosurgical devices for applying electrical energy to tissue in order to treat and/or destroy the tissue are also finding increasingly widespread applications in surgical procedures. An electrosurgical device typically includes a hand piece, an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator in communication with the hand piece. The electrical energy may be in the form of radio frequency ("RF") energy. RF energy is a form of electrical energy that may be in the frequency range of 300 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

It would be desirable to provide a surgical instrument that overcomes some of the deficiencies of current instruments. The surgical system described herein overcomes those deficiencies.

FIGURES

The novel features of the described forms are set forth with particularity in the appended claims. The described forms, however, both as to organization and methods of operation, may be best understood by reference to the following description, taken in conjunction with the accompanying drawings in which:

FIG. 13 is a schematic diagram of a tissue impedance module coupled to a blade and a clamp arm assembly with tissue located there between.

FIGS. 51A and 51B are graphical representations of resonant frequency and frequency slope, respectively, displayed by one form of an ultrasonic instrument during an ultrasonic bite.

FIGS. 52A and 52B are graphical representations of resonant frequency and frequency slope, respectively, displayed by one form of an ultrasonic instrument during another ultrasonic tissue bite.

FIG. 117 is a diagrammatic depiction of a switch assembly that may be employed in connection with the various ultrasonic handle assemblies according to various forms described herein.

FIG. 118 is another diagrammatic depiction of the switch assembly of FIG. 117 in an actuated position wherein a central switch has been actuated according to various forms described herein.

FIG. 119 is another diagrammatic depiction of the switch assembly of FIGS. 117 and 118 in another actuated position wherein a right switch has been actuated according to various forms described herein.

FIG. 120 is another diagrammatic depiction of the switch assembly of FIGS. 117-119 in another actuated position wherein a left switch has been actuated according to various forms described herein.

DESCRIPTION

Figure 1:
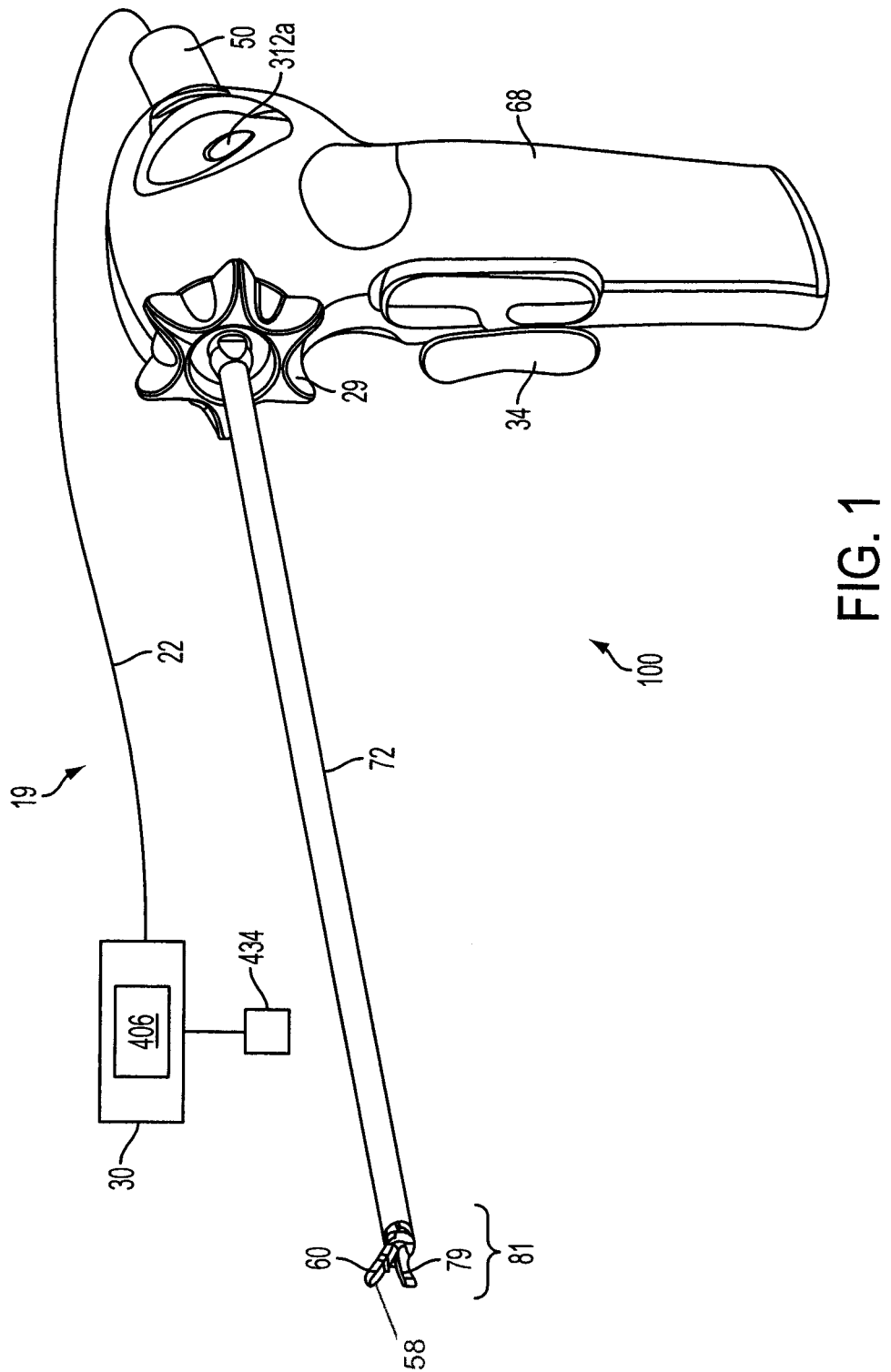
FIG. 1 is a perspective view illustrating one form of an ultrasonic surgical instrument.

Applicant of the present application also owns the following patent applications that were filed on Mar. 15, 2013 and which are each herein incorporated by reference in their respective entireties:

U.S. patent application Ser. No. 13/839,093 entitled, "SWITCH ARRANGEMENTS FOR ULTRASONIC SURGICAL INSTRUMENTS," now U.S. Patent Application Publication No. 2013/0267975;

U.S. patent application Ser. No. 13/839,242 entitled, "ROTATABLE ELECTRICAL CONNECTION FOR ULTRASONIC SURGICAL INSTRUMENTS," now U.S. Pat. No. 9,241,731;

U.S. patent application Ser. No. 13/839,351 entitled, "SERIAL COMMUNICATION PROTOCOL FOR MEDICAL DEVICE," now U.S. Pat. No. 9,226,766; and U.S. patent application Ser. No. 13/839,470 entitled, "TECHNIQUES FOR CUTTING AND COAGULATING TISSUE FOR ULTRASONIC SURGICAL INSTRUMENTS," now U.S. Patent Application Publication No. 2013/0296908.

Before explaining various forms of ultrasonic surgical instruments in detail, it should be noted that the illustrative forms are not limited in application or use to the details of construction and arrangement of parts illustrated in the accompanying drawings and description. The illustrative forms may be implemented or incorporated in other forms, variations and modifications, and may be practiced or carried out in various ways. Further, unless otherwise indicated, the terms and expressions employed herein have been chosen for the purpose of describing the illustrative forms for the convenience of the reader and are not for the purpose of limitation thereof.

Further, it is understood that any one or more of the following-described forms, expressions of forms, examples, can be combined with any one or more of the other following-described forms, expressions of forms, and examples.

Various forms are directed to improved ultrasonic surgical instruments configured for effecting tissue dissecting, cutting, and/or coagulation during surgical procedures. In one form, an ultrasonic surgical instrument apparatus is configured for use in open surgical procedures, but has applications in other types of surgery, such as laparoscopic, endoscopic, and robotic-assisted procedures. Versatile use is facilitated by selective use of ultrasonic energy.

The various forms will be described in combination with an ultrasonic instrument as described herein. Such description is provided by way of example, and not limitation, and is not intended to limit the scope and applications thereof. For example, any one of the described forms is useful in combination with a multitude of ultrasonic instruments including those described in, for example, U.S. Pat. Nos. 5,938,633; 5,935,144; 5,944,737; 5,322,055; 5,630,420; and 5,449,370.

As will become apparent from the following description, it is contemplated that forms of the surgical instrument described herein may be used in association with an oscillator unit of a surgical system, whereby ultrasonic energy from the oscillator unit provides the desired ultrasonic actuation for the present surgical instrument. It is also contemplated that forms of the surgical instrument described herein may be used in association with a signal generator unit of a surgical system, whereby electrical energy in the form of radio frequencies (RF), for example, is used to provide feedback to the user regarding the surgical instrument. The ultrasonic oscillator and/or the signal generator unit may be non-detachably integrated with the surgical instrument or may be provided as separate components, which can be electrically attachable to the surgical instrument.

One form of the present surgical apparatus is particularly configured for disposable use by virtue of its straightforward construction. However, it is also contemplated that other forms of the present surgical instrument can be configured for non-disposable or multiple uses. Detachable connection of the present surgical instrument with an associated oscillator and signal generator unit is presently disclosed for single-patient use for illustrative purposes only. However, non-detachable integrated connection of the present surgical instrument with an associated oscillator and/or signal generator unit is also contemplated. Accordingly, various forms of the presently described surgical instruments may be configured for single use and/or multiple use with either detachable and/or non-detachable integral oscillator and/or signal generator unit, without limitation, and all combinations of such configurations are contemplated to be within the scope of the present disclosure.

Figure 2:
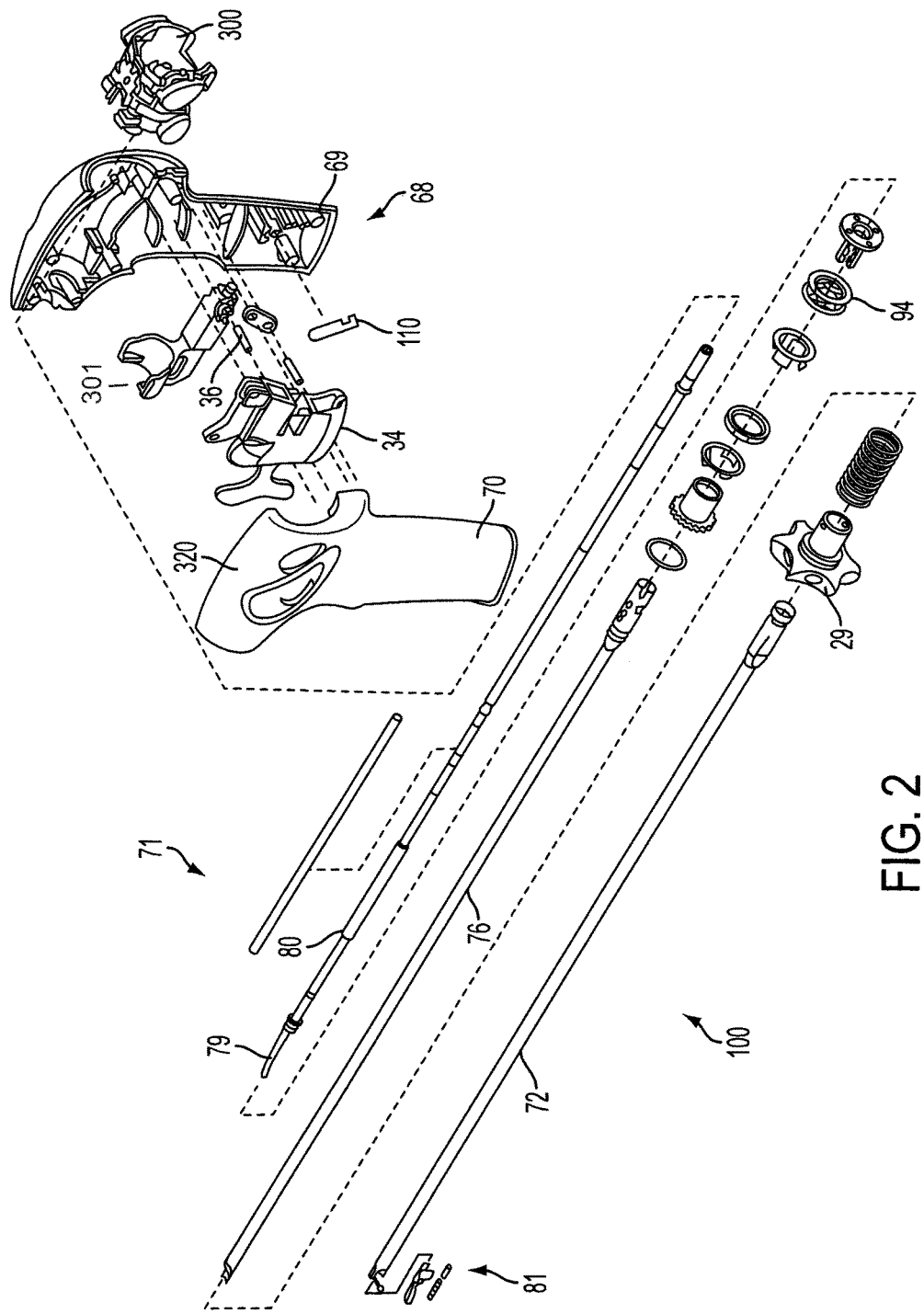
FIG. 2 is an exploded perspective assembly view of one form of an ultrasonic surgical instrument.
Figure 3:
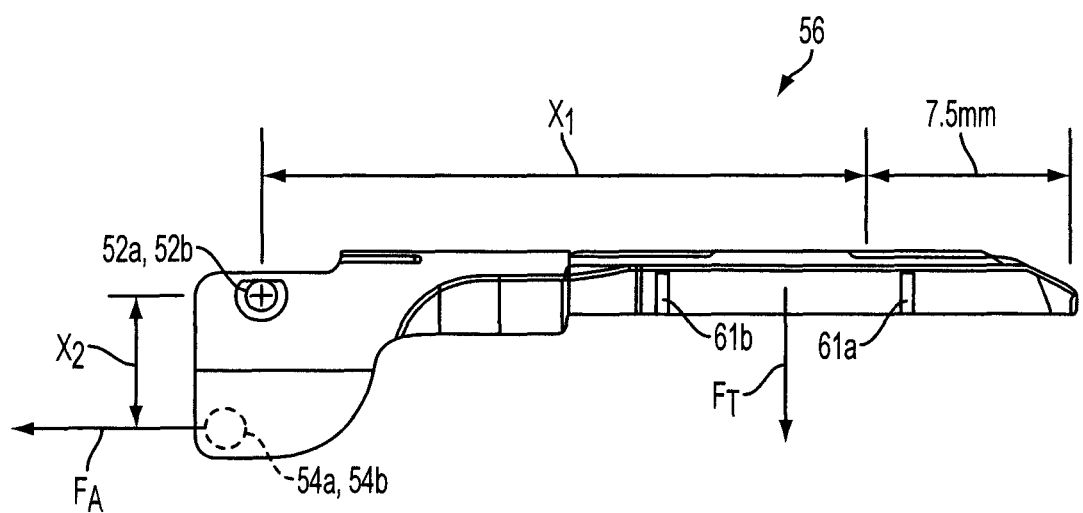
FIG. 3 is a schematic of one form of a clamp arm illustrating force calculations.

With reference to FIGS. 1-3, one form of a surgical system 19 including an ultrasonic surgical instrument 100 is illustrated. The surgical system 19 includes an ultrasonic generator 30 connected to an ultrasonic transducer 50 via a suitable transmission medium such as a cable 22, and an ultrasonic surgical instrument 100. Although in the presently disclosed form, the generator 30 is shown separate from the surgical instrument 100, in one form, the generator 30 may be formed integrally with the surgical instrument 100 to form a unitary surgical system 19. The generator 30 comprises an input device 406 located on a front panel of the generator 30 console. The input device 406 may comprise any suitable device that generates signals suitable for programming the operation of the generator 30 as subsequently described with reference to FIG. 9. Still with reference to FIGS. 1-3, the cable 22 may comprise multiple electrical conductors for the application of electrical energy to positive (+) and negative (−) electrodes of the ultrasonic transducer 50. It will be noted that, in some applications, the ultrasonic transducer 50 may be referred to as a "hand piece" or "handle assembly" because the surgical instrument 100 of the surgical system 19 may be configured such that a surgeon may grasp and manipulate the ultrasonic transducer 50 during various procedures and operations. A suitable generator 30 is the GEN 300 available from Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Hand piece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

In accordance with the described forms, the ultrasonic generator 30 produces an electrical signal or drive signal of a particular voltage, current, and frequency, e.g., 55,500 cycles per second (Hz). The generator is 30 connected by the cable 22 to the handle assembly 68, which contains piezo-ceramic elements forming the ultrasonic transducer 50. In response to a switch 312a on the handle assembly 68 or a foot switch 434 connected to the generator 30 by another cable the generator signal is applied to the transducer 50, which causes a longitudinal vibration of its elements. The transducer 50 is secured to the handle assembly 68 via a connector 300. When installed, the transducer 50 is acoustically coupled to the surgical blade 79 via a structure or waveguide 80 (FIG. 2). The structure 80 and blade 79 are consequently vibrated at ultrasonic frequencies when the drive signal is applied to the transducer 50. The structure 80 is designed to resonate at the selected frequency, thus amplifying the motion initiated by the transducer 50. In one form, the generator 30 is configured to produce a particular voltage, current, and/or frequency output signal that can be stepped with high resolution, accuracy, and repeatability.

Figure 4:
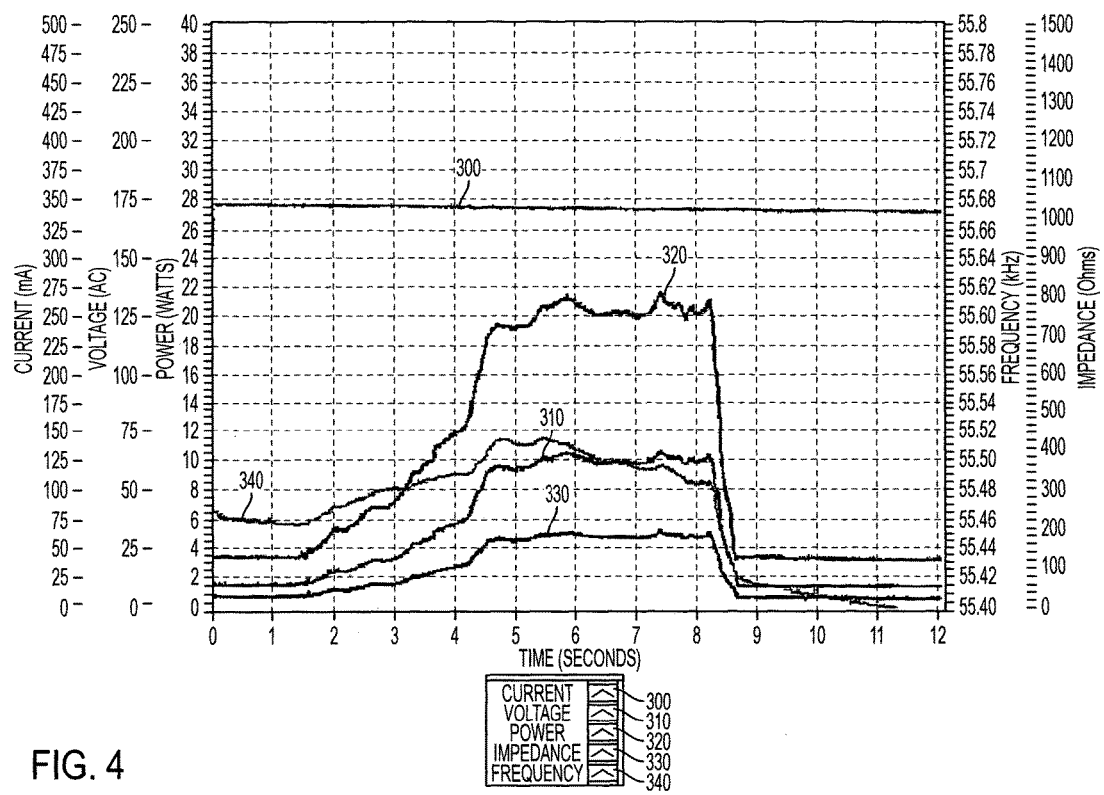
FIG. 4 is a graphical representation of current, voltage, power, impedance, and frequency waveforms of a conventional oscillator at high power and lightly loaded.

Referring to FIG. 4, in current systems a conventional oscillator is activated at time 0 resulting in current 300 rising to a desired set point of approximately 340 mA. At approximately 2 seconds a light load is applied resulting in corresponding increases to voltage 310, power 320, impedance 330, and changes in resonant frequency 340.

Figure 5:
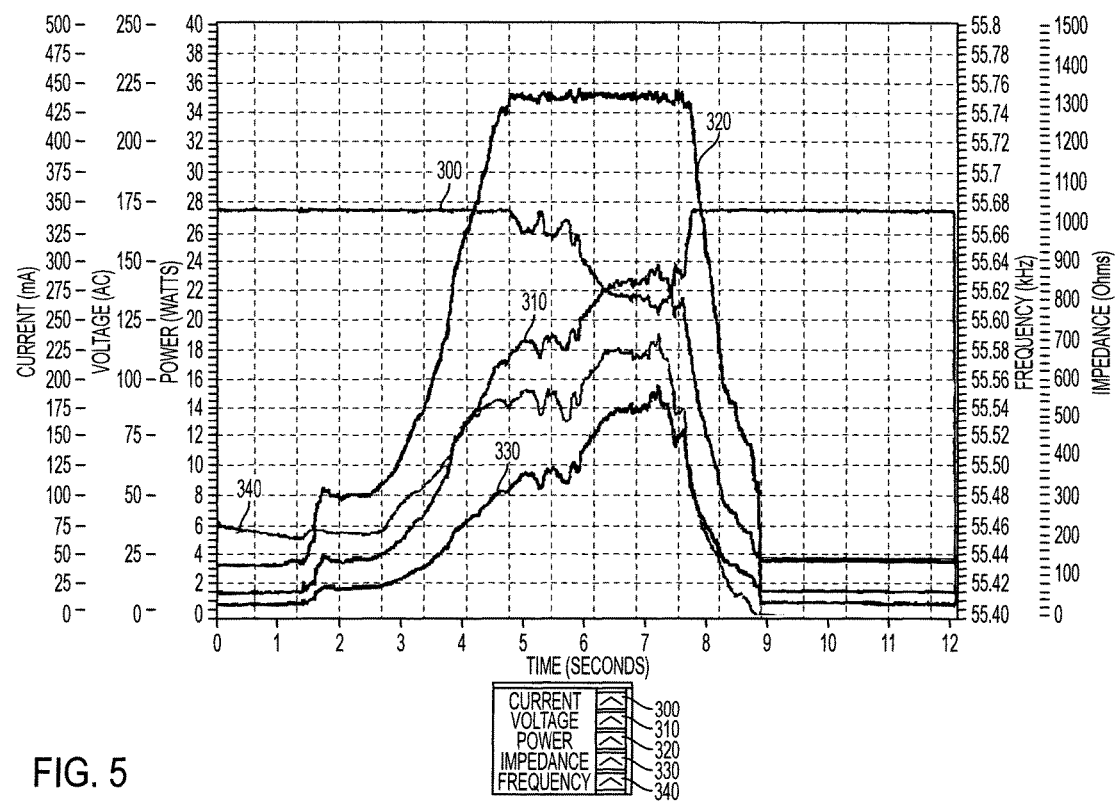
FIG. 5 is a graphical representation of current, voltage, power, impedance, and frequency waveforms of a conventional oscillator at high power and heavily loaded.

Referring to FIG. 5, in current systems a conventional oscillator is activated at time 0 resulting in the current 300 rising to a desired set point of approximately 340 mA. At approximately 2 seconds an increasing load is applied resulting in corresponding increases to the voltage 310, power 320, impedance 330, and changes in resonant frequency 340. At approximately 7 seconds, the load has increased to the point that the oscillator enters into a flat power mode where further increases in load maintain the power at 35 W as long as the oscillator stays within voltage limits of the power supply. The current 300 and therefore, displacement, varies during flat power mode. At approximately 11.5 seconds, the load is reduced to the point where the current 300 returns to the desired set point of approximately 340 mA. The voltage 310, power 320, impedance 330, and resonant frequency 340 vary with the load.

With reference now back to FIGS. 1-3, the handle assembly 68 may be a multi-piece assembly adapted to isolate the operator from the vibrations of the acoustic assembly contained within the ultrasonic transducer 50. The handle assembly 68 can be shaped to be held by a user in a conventional manner, but it is contemplated that the present ultrasonic surgical instrument 100 principally be grasped and manipulated by a trigger-like arrangement provided by a handle assembly of the instrument, as will be described. While a multi-piece handle assembly 68 is illustrated, the handle assembly 68 may comprise a single or unitary component. The proximal end of the ultrasonic surgical instrument 100 receives and is fitted to the distal end of the ultrasonic transducer 50 by insertion of the transducer 50 into the handle assembly 68. In one form, the ultrasonic surgical instrument 100 may be attached to and removed from the ultrasonic transducer 50 as a unit. In other forms, the ultrasonic surgical instrument 100 and the ultrasonic transducer 50 may be formed as an integral unit. The ultrasonic surgical instrument 100 may include a handle assembly 68, comprising a mating housing portion 69, a housing portion 70, and a transmission assembly 71. When the present instrument is configured for endoscopic use, the construction can be dimensioned such that the transmission assembly 71 has an outside diameter of approximately 5.5 mm. The elongated transmission assembly 71 of the ultrasonic surgical instrument 100 extends orthogonally from the instrument handle assembly 68. The transmission assembly 71 can be selectively rotated with respect to the handle assembly 68 by a rotation knob 29 as further described below. The handle assembly 68 may be constructed from a durable plastic, such as polycarbonate or a liquid crystal polymer. It is also contemplated that the handle assembly 68 may alternatively be made from a variety of materials including other plastics, ceramics, or metals.

The transmission assembly 71 may include an outer tubular member or an outer sheath 72, an inner tubular actuating member 76, a waveguide 80, and an end effector 81 comprising, for example, the blade 79, a clamp arm 56, and one or more clamp pads 58. The transducer 50 and transmission assembly 71 (including or excluding the end effector 81) may be referred to as an ultrasonic drive system. As subsequently described, the outer sheath 72, the actuating member 76, and the waveguide 80 or transmission rod may be joined together for rotation as a unit (together with the ultrasonic transducer 50) relative to the handle assembly 68. The waveguide 80, which is adapted to transmit ultrasonic energy from the ultrasonic transducer 50 to the blade 79 may be flexible, semi-flexible, or rigid. The waveguide 80 also may be configured to amplify the mechanical vibrations transmitted through the waveguide 80 to the blade 79 as is well known in the art. The waveguide 80 may further have features to control the gain of the longitudinal vibration along the waveguide 80 and features to tune the waveguide 80 to the resonant frequency of the system. In particular, the waveguide 80 may have any suitable cross-sectional dimension. For example, the waveguide 80 may have a substantially uniform cross-section or the waveguide 80 may be tapered at various sections or may be tapered along its entire length. In one expression of the current form, the waveguide diameter is about 0.113 inches nominal to minimize the amount of deflection at the blade 79 so that gapping in the proximal portion of the end effector 81 is minimized.

The blade 79 may be integral with the waveguide 80 and formed as a single unit. In an alternate expression of the current form, the blade 79 may be connected by a threaded connection, a welded joint, or other coupling mechanisms. The distal end of the blade 79 is disposed near an anti-node in order to tune the acoustic assembly to a preferred resonant frequency $f_o$ when the acoustic assembly is not loaded by tissue. When the ultrasonic transducer 50 is energized, the distal end of the blade 79 is configured to move longitudinally in the range of, for example, approximately 10 to 500 microns peak-to-peak, and preferably in the range of about 20 to about 200 microns at a predetermined vibration frequency $f_o$ of, for example, 55,500 Hz.

With particular reference to FIGS. 1-3, therein is illustrated one form of the clamp member 60 for use with the present ultrasonic surgical instrument 100 and which is configured for cooperative action with the blade 79. The clamp member 60 in combination with the blade 79 is commonly referred to as the end effector 81, and the clamp member 60 is also commonly referred to as the jaw. The clamp member 60 includes a pivotally movable clamp arm 56, which is connected to the distal end of the outer sheath 72 and the actuating member 76, in combination with a tissue engaging pad or clamp pad 58. The clamp arm 56 is pivotally movable by a trigger 34 and the end effector 81 is rotatably movable by the rotation knob 29. For example, the trigger 34 may be translatable by the hand of the clinician in a proximal direction. For example, the handle 34 may pivot about the pivot pin 36. Proximal motion or pivoting of the trigger 34 may cause distal motion of a yoke 301 mechanically coupled to the tubular actuating member 76. Distal motion of the tubular actuating member may cause the clamp arm 56 to pivot to close against the blade 79. Additional details of closure mechanisms for ultrasonic surgical devices are provided herein below with respect to FIGS. 93-95 and in U.S. patent application Ser. Nos. 12/503,769, 12/503,770, and 12/503,766, each of which is incorporated herein by reference in its entirety.

In one expression of the form, the clamp pad 58 is formed from TEFLON® a trademark name of E. I. Du Pont de Nemours and Company, a low coefficient of friction polymer material, or any other suitable low-friction material. The clamp pad 58 mounts on the clamp arm 56 for cooperation with the blade 79, with pivotal movement of the clamp arm 56 positioning the clamp pad 58 in substantially parallel relationship to, and in contact with, the blade 79, thereby defining a tissue treatment region. By this construction, tissue is grasped between the clamp pad 58 and the blade 79. As illustrated, the clamp pad 58 may be provided with a non-smooth surface, such as a saw tooth-like configuration to enhance the gripping of tissue in cooperation with the blade 79. The saw tooth-like configuration, or teeth, provide traction against the movement of the blade 79. The teeth also provide counter traction to the blade 79 and clamping movement. As would be appreciated by one skilled in the art, the saw tooth-like configuration is just one example of many tissue engaging surfaces to prevent movement of the tissue relative to the movement of the blade 79. Other illustrative examples include bumps, criss-cross patterns, tread patterns, a bead, or sand blasted surface.

Due to sinusoidal motion, the greatest displacement or amplitude of motion is located at the most distal portion of the blade 79, while the proximal portion of the tissue treatment region is on the order of 50% of the distal tip amplitude. During operation, the tissue in the proximal region of the end effector 81 will desiccate and thin, and the distal portion of the end effector 81 will transect tissue in that distal region, thereby allowing the desiccated and thinned tissue within the proximal region to slide distally into the more active region of the end effector 81 to complete the tissue transection.

FIG. 3 illustrates a force diagram and the relationship between the actuation force $F_A$ (provided by the actuating member 76) and transection force $F_T$ (measured at the midpoint of the optimal tissue treatment area).

$$F_T = F_A(X_2/X_1) \tag{1}$$

Where $F_A$ equals the spring preload of a proximal spring 94 (less frictional losses), which, in one form, is about 12.5 pounds, and $F_T$ equals about 4.5 pounds.

$F_T$ is measured in the region of the clamp arm/blade interface where optimal tissue treatment occurs as defined by tissue marks 61$a$ and 61$b$. The tissue marks 61$a$, $b$ are etched or raised on the clamp arm 56 to provide a visible mark to the surgeon so the surgeon has a clear indication of the optimal tissue treatment area. The tissue marks 61$a$, $b$ are about 7 mm apart in distance, and more preferably about 5 mm apart in distance.

Figure 9:
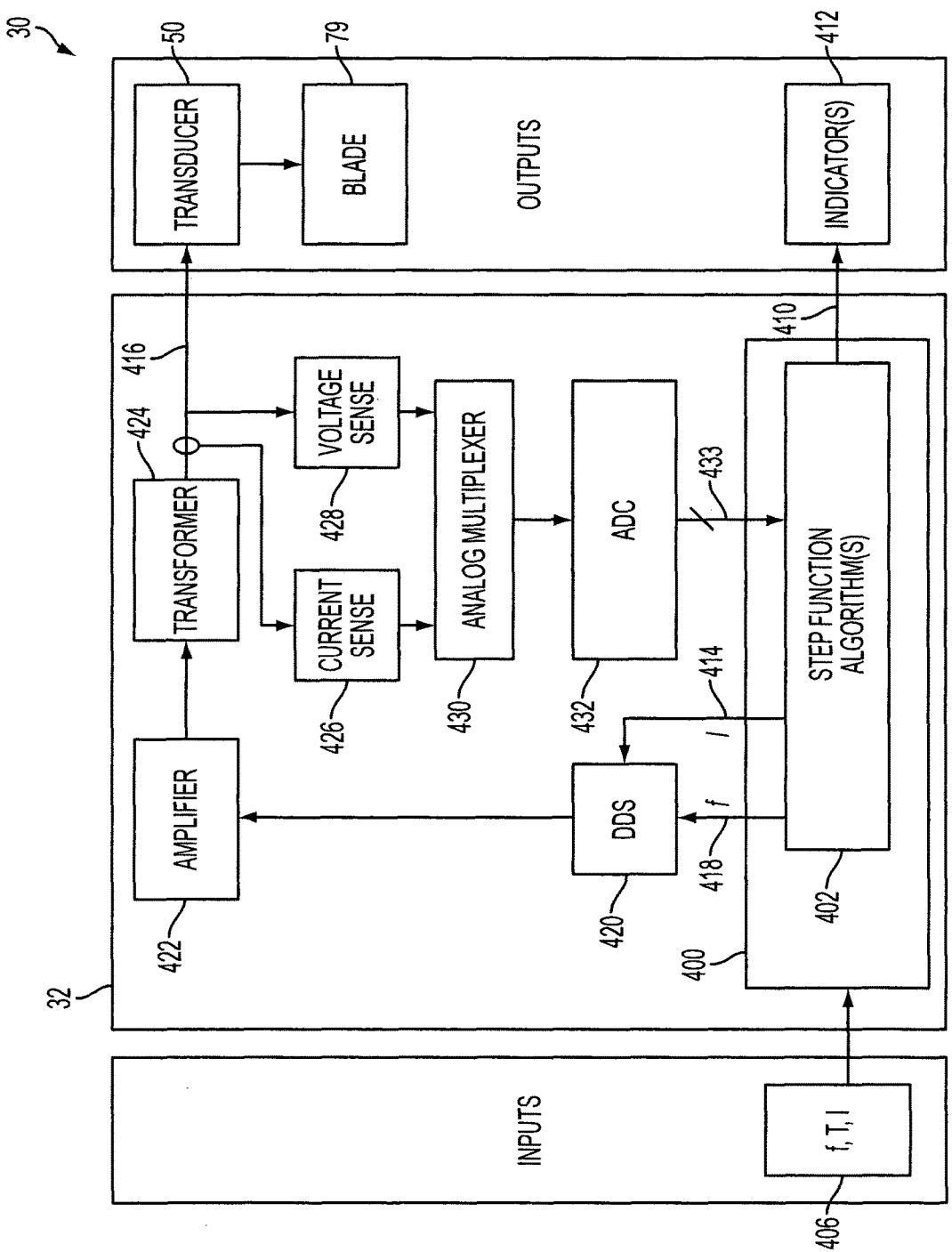
FIG. 9 illustrates one form of a drive system of a generator, which creates the ultrasonic electrical signal for driving an ultrasonic transducer.

FIG. 9 illustrates one form of a drive system 32 of the generator 30, which creates an ultrasonic electrical signal for driving an ultrasonic transducer, also referred to as a drive signal. The drive system 32 is flexible and can create an ultrasonic electrical drive signal 416 at a desired frequency and power level setting for driving the ultrasonic transducer 50. In various forms, the generator 30 may comprise several separate functional elements, such as modules and/or blocks. Although certain modules and/or blocks may be described by way of example, it can be appreciated that a greater or lesser number of modules and/or blocks may be used and still fall within the scope of the forms. Further, although various forms may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one form, the generator 30 drive system 32 may comprise one or more embedded applications implemented as firmware, software, hardware, or any combination thereof. The generator 30 drive system 32 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one form, the generator 30 drive system 32 comprises a hardware component implemented as a processor 400 for executing program instructions for monitoring various measurable characteristics of the ultrasonic surgical instrument 100 (FIG. 1) and generating a step function output signal for driving the ultrasonic transducer 50 in cutting and/or coagulation operating modes. It will be appreciated by those skilled in the art that the generator 30 and the drive system 32 may comprise additional or fewer components and only a simplified version of the generator 30 and the drive system 32 are described herein for conciseness and clarity. In various forms, as previously discussed, the hardware component may be implemented as a DSP, PLD, ASIC, circuits, and/or registers. In one form, the processor 400 may be configured to store and execute computer software program instructions to generate the step function output signals for driving various components of the ultrasonic surgical instrument 100, such as the transducer 50, the end effector 81, and/or the blade 79.

In one form, under control of one or more software program routines, the processor 400 executes the methods in accordance with the described forms to generate a step function formed by a stepwise waveform of drive signals comprising current (I), voltage (V), and/or frequency (f) for various time intervals or periods. The stepwise waveforms of the drive signals may be generated by forming a piecewise linear combination of constant functions over a plurality of time intervals created by stepping the generator 30 drive signals, e.g., output drive current (I), voltage (V), and/or frequency (f). The time intervals or periods (T) may be predetermined (e.g., fixed and/or programmed by the user) or may be variable. Variable time intervals may be defined by setting the drive signal to a first value and maintaining the drive signal at that value until a change is detected in a monitored characteristic. Examples of monitored characteristics may comprise, for example, transducer impedance, tissue impedance, tissue heating, tissue transection, tissue coagulation, and the like. The ultrasonic drive signals generated by the generator 30 include, without limitation, ultrasonic drive signals capable of exciting the ultrasonic transducer 50 in various vibratory modes such as, for example, the primary longitudinal mode and harmonics thereof as well flexural and torsional vibratory modes.

In one form, the executable modules comprise one or more step function algorithm(s) 402 stored in memory that when executed causes the processor 400 to generate a step function formed by a stepwise waveform of drive signals comprising current (I), voltage (V), and/or frequency (f) for various time intervals or periods (T). The stepwise waveforms of the drive signals may be generated by forming a piecewise linear combination of constant functions over two or more time intervals created by stepping the generator's 30 output drive current (I), voltage (V), and/or frequency (f). The drive signals may be generated either for predetermined fixed time intervals or periods (T) of time or variable time intervals or periods of time in accordance with the one or more stepped output algorithm(s) 402. Under control of the processor 400, the generator 30 steps (e.g., increment or decrement) the current (I), voltage (V), and/or frequency (f) up or down at a particular resolution for a predetermined period (T) or until a predetermined condition is detected, such as a change in a monitored characteristic (e.g., transducer impedance, tissue impedance). The steps can change in programmed increments or decrements. If other steps are desired, the generator 30 can increase or decrease the step adaptively based on measured system characteristics.

In operation, the user can program the operation of the generator 30 using the input device 406 located on the front panel of the generator 30 console. The input device 406 may comprise any suitable device that generates signals 408 that can be applied to the processor 400 to control the operation of the generator 30. In various forms, the input device 406 includes buttons, switches, thumbwheels, keyboard, keypad, touch screen monitor, pointing device, remote connection to a general purpose or dedicated computer. In other forms, the input device 406 may comprise a suitable user interface. Accordingly, by way of the input device 406, the user can set or program the current (I), voltage (V), frequency (f), and/or period (T) for programming the step function output of the generator 30. The processor 400 then displays the selected power level by sending a signal on line 410 to an output indicator 412.

In various forms, the output indicator 412 may provide visual, audible, and/or tactile feedback to the surgeon to indicate the status of a surgical procedure, such as, for example, when tissue cutting and coagulating is complete based on a measured characteristic of the ultrasonic surgical instrument 100, e.g., transducer impedance, tissue impedance, or other measurements as subsequently described. By way of example, and not limitation, visual feedback comprises any type of visual indication device including incandescent lamps or light emitting diodes (LEDs), graphical user interface, display, analog indicator, digital indicator, bar graph display, digital alphanumeric display. By way of example, and not limitation, audible feedback comprises any type of buzzer, computer generated tone, computerized speech, voice user interface (VUI) to interact with computers through a voice/speech platform. By way of example, and not limitation, tactile feedback comprises any type of vibratory feedback provided through the instrument housing handle assembly 68.

In one form, the processor 400 may be configured or programmed to generate a digital current signal 414 and a digital frequency signal 418. These signals 414, 418 are applied to a direct digital synthesizer (DDS) circuit 420 to adjust the amplitude and the frequency (f) of the current output signal 416 to the transducer 50. The output of the DDS circuit 420 is applied to an amplifier 422 whose output is applied to a transformer 424. The output of the transformer 424 is the signal 416 applied to the ultrasonic transducer 50, which is coupled to the blade 79 by way of the waveguide 80 (FIG. 2).

In one form, the generator 30 comprises one or more measurement modules or components that may be configured to monitor measurable characteristics of the ultrasonic instrument 100 (FIG. 1). In the illustrated form, the processor 400 may be employed to monitor and calculate system characteristics. As shown, the processor 400 measures the impedance Z of the transducer 50 by monitoring the current supplied to the transducer 50 and the voltage applied to the transducer 50. In one form, a current sense circuit 426 is employed to sense the current flowing through the transducer 50 and a voltage sense circuit 428 is employed to sense the output voltage applied to the transducer 50. These signals may be applied to the analog-to-digital converter 432 (ADC) via an analog multiplexer 430 circuit or switching circuit arrangement. The analog multiplexer 430 routes the appropriate analog signal to the ADC 432 for conversion. In other forms, multiple ADCs 432 may be employed for each measured characteristic instead of the multiplexer 430 circuit. The processor 400 receives the digital output 433 of the ADC 432 and calculates the transducer impedance Z based on the measured values of current and voltage. The processor 400 adjusts the output drive signal 416 such that it can generate a desired power versus load curve. In accordance with programmed step function algorithms 402, the processor 400 can step the drive signal 416, e.g., the current or frequency, in any suitable increment or decrement in response to the transducer impedance Z.

To actually cause the surgical blade 79 to vibrate, e.g., actuate the blade 79, the user activates the foot switch 434 (FIG. 1) or the switch 312a (FIG. 1) on the handle assembly 68. This activation outputs the drive signal 416 to the transducer 50 based on programmed values of current (I), frequency (f), and corresponding time periods (T). After a predetermined fixed time period (T), or variable time period based on a measurable system characteristic such as changes in the impedance Z of the transducer 50, the processor 400 changes the output current step or frequency step in accordance with the programmed values. The output indicator 412 communicates the particular state of the process to the user.

Figure 6:
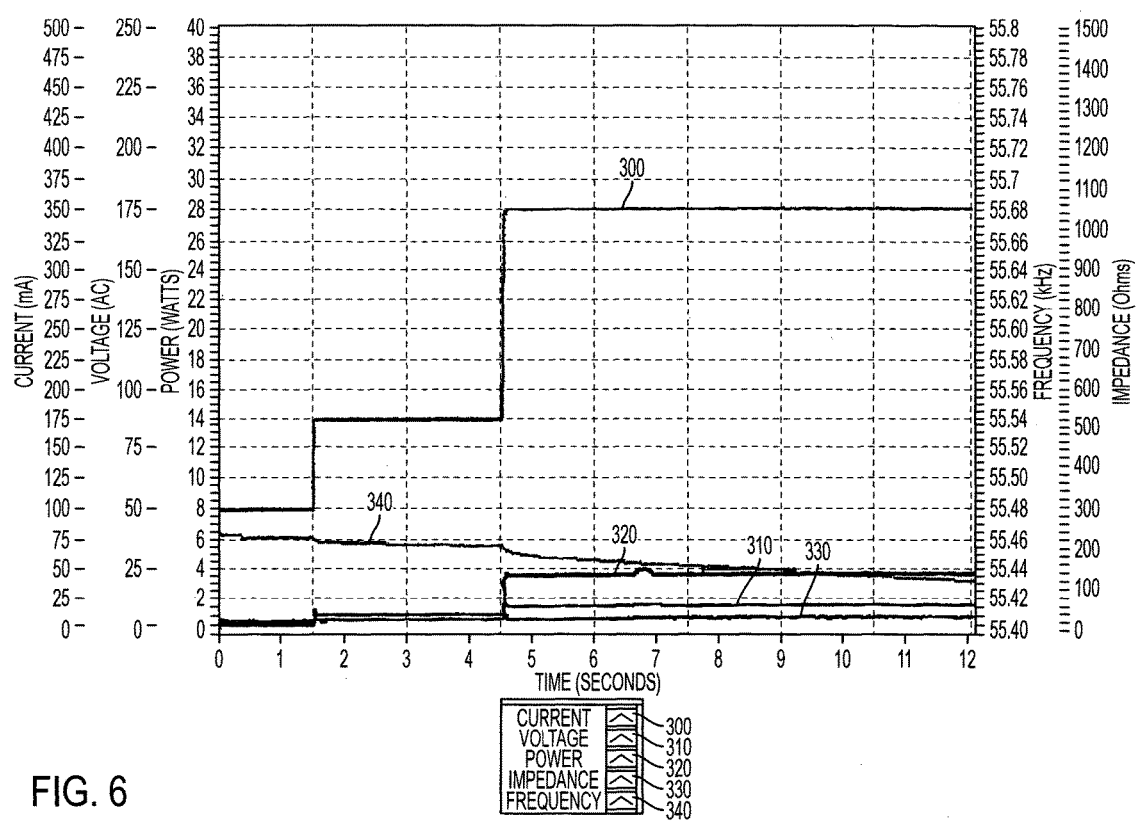
FIG. 6 is a graphical representation of a current step function waveform and voltage, power, impedance, and frequency waveforms of one form of an oscillator and unloaded.

The programmed operation of the generator 30 can be further illustrated with reference to FIGS. 6, 7, and 8, where graphical representations of current 300, voltage 310, power 320, impedance 330, and frequency 340 are shown for the generator 30 in an unloaded state, a lightly loaded state, and a heavily loaded state, respectively. FIG. 6 is a graphical representation of current 300, voltage 310, power 320, impedance 330, and frequency 340 waveforms of one form of the generator 30 in an unloaded state. In the illustrated form, the current 300 output of the generator 30 is stepped. As shown in FIG. 6, the generator 30 is initially activated at about time 0 resulting in the current 300 rising to a first set point $I_1$ of about 100 mA. The current 300 is maintained at the first set point $I_1$, for a first period $T_1$. At the end of the first period $T_1$, e.g., about 1 second in the illustrated form, the current 300 set point $I_1$ is changed, e.g., stepped, by the generator 30 in accordance with the software, e.g., the step function algorithm(s) 402, to a second set point $I_2$ of about 175 mA for a second period $T_2$, e.g., about 2 seconds in the illustrated form. At the end of the second period $T_2$, e.g., at about 3 seconds in the illustrated form, the generator 30 software changes the current 300 to a third set point $I_3$ of about 350 mA. The voltage 310, current 300, power 320, and frequency respond only slightly because there is no load on the system.

Figure 7:
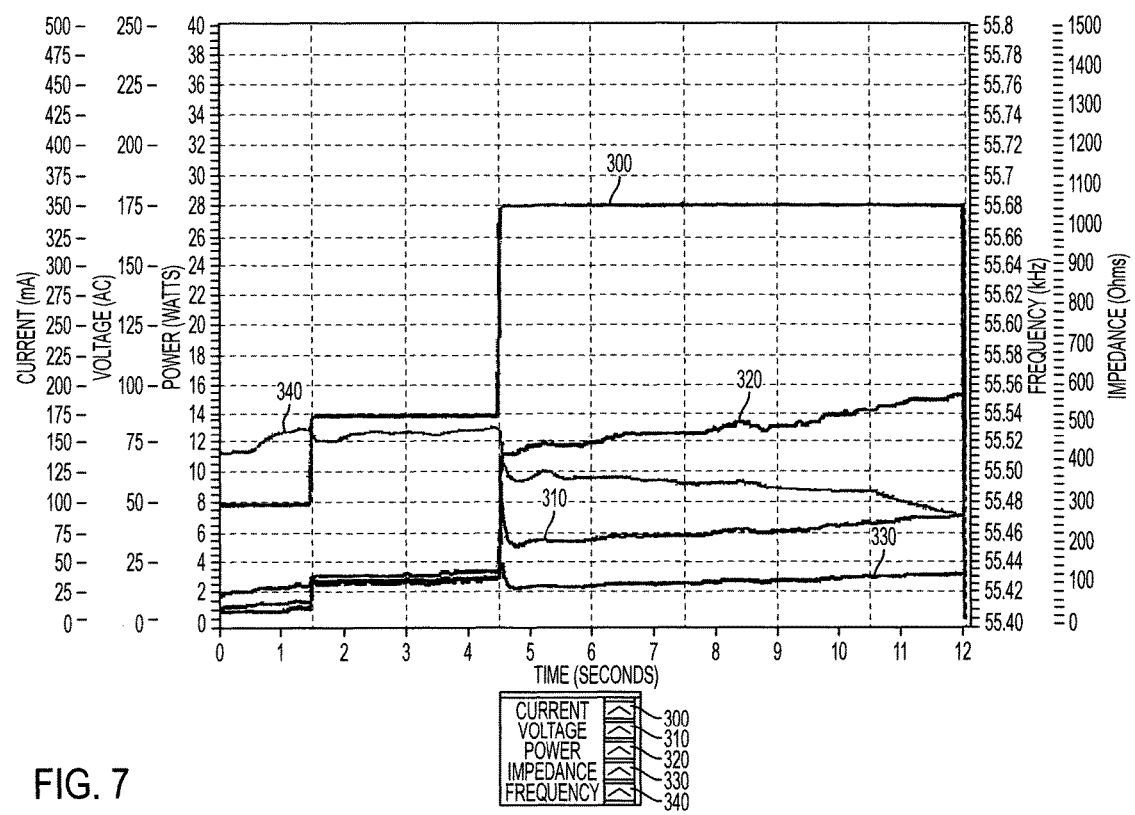
FIG. 7 is a graphical representation of a current step function waveform and voltage, power, impedance, and frequency waveforms of one form of an oscillator and lightly loaded.

FIG. 7 is a graphical representation of the current 300, voltage 310, power 320, impedance 330, and frequency 340 waveforms of one form of the generator 30 under a lightly loaded state. Referring to FIG. 7, the generator 30 is activated at about time 0 resulting in the current 300 rising to the first current 300 set point $I_1$ of about 100 mA. At about 1 second the current 300 set point is changed within the generator 30 by the software to $I_2$ of about 175 mA, and then again at about 3 seconds the generator 30 changes the current 300 set point to $I_3$ of about 350 mA. The voltage 310, current 300, power 320, and frequency 340 are shown responding to the light load similar to that shown in FIG. 4.

Figure 8:
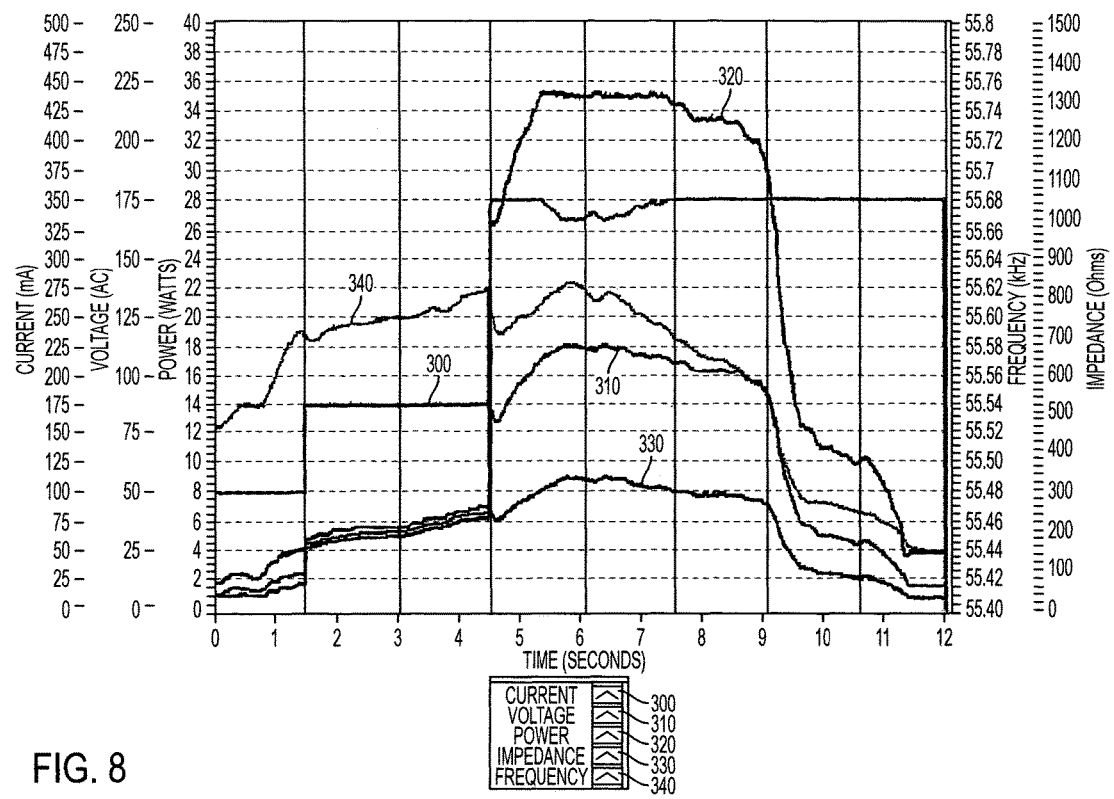
FIG. 8 is a graphical representation of a current step function waveform and voltage, power, impedance, and frequency waveforms of one form of an oscillator and heavily loaded.

FIG. 8 is a graphical representation of the current 300, voltage 310, power 320, impedance 330, and frequency 340 waveforms of one form of the generator 30 under a heavily loaded state. Referring to FIG. 8, the generator 30 is activated at about time 0 resulting in the current 300 rising to the first set point $I_1$ of about 100 mA. At about 1 second the current 300 set point is changed within the generator 30 by the software to $I_2$ of about 175 mA, and then again at about 3 seconds the generator 30 changes the current 300 set point to $I_3$ of about 350 mA. The voltage 310, current 300, power 320, and frequency 340 are shown responding to the heavy load similar to that shown in FIG. 5.

It will be appreciated by those skilled in the art that the current 300 step function set points (e.g., $I_1$, $I_2$, $I_3$) and the time intervals or periods (e.g., $T_1$, $T_2$) of duration for each of the step function set points described in FIGS. 6-8 are not limited to the values described herein and may be adjusted to any suitable value as may be desired for a given set of surgical procedures. Additional or fewer current set points and periods of duration may be selected as may be desired for a given set of design characteristics or performance constraints. As previously discussed, the periods may be predetermined by programming or may be variable based on measurable system characteristics. The forms are not limited in this context. For example, in certain forms, the amplitudes (set points) of consecutive pulses may increase, decrease or stay the same. For example, in certain forms, the amplitudes of consecutive pulses may be equal. Also, in certain forms, the time intervals or periods of the pulses may take any suitable value including, for example, fractions of a second, minutes, hours, etc. In one example form, the time interval or periods of the pulses may be 55 seconds.

Having described operational details of various forms of the surgical system 19, operations for the above surgical system 19 may be further described in terms of a process for cutting and coagulating a blood vessel employing a surgical instrument comprising the input device 406 and the transducer impedance measurement capabilities described with reference to FIG. 9. Although a particular process is described in connection with the operational details, it can be appreciated that the process merely provides an example of how the general functionality described herein can be implemented by the surgical system 19. Further, the given process does not necessarily have to be executed in the order presented herein unless otherwise indicated. As previously discussed, the input device 406 may be employed to program the stepped output (e.g., current, voltage, frequency) to the ultrasonic transducer 50/blade 79 assembly.

Accordingly, with reference now to FIGS. 1-3 and 6-9, one technique for sealing a vessel includes separating and moving the inner muscle layer of the vessel away from the adventitia layer prior to the application of standard ultrasonic energy to transect and seal the vessel. Although conventional methods have achieved this separation by increasing the force applied to the clamp member 60, disclosed is an alternative apparatus and method for cutting and coagulating tissue without relying on clamp force alone. In order to more effectively separate the tissue layers of a vessel, for example, the generator 30 may be programmed to apply a frequency step function to the ultrasonic transducer 50 to mechanically displace the blade 79 in multiple modes in accordance with the step function. In one form, the frequency step function may be programmed by way of the user interface 406, wherein the user can select a stepped-frequency program, the frequency (f) for each step, and the corresponding time period (T) of duration for each step for which the ultrasonic transducer 50 will be excited. The user may program a complete operational cycle by setting multiple frequencies for multiple periods to perform various surgical procedures.

In certain forms, the amplitudes of consecutive steps or pulses may increase, decrease or stay the same. For example, in certain forms, the amplitudes of consecutive pulses may be equal. Also, in certain forms, the time periods of the pulses may take any suitable value including, for example, fractions of a second, minutes, hours, etc. In one example form, the time period of the pulses may be 55 seconds.

In one form, a first ultrasonic frequency may be set initially to mechanically separate the muscle tissue layer of a vessel prior to applying a second ultrasonic frequency to cut and seal the vessel. By way of example, and not limitation, in accordance with one implementation of the program, initially, the generator 30 is programmed to output a first drive frequency $f_1$ for a first period $T_1$ of time (for example less than approximately 1 second), wherein the first frequency $f_1$ is significantly off resonance, for example, $f_o/2$, $2f_o$ or other structural resonant frequencies, where $f_o$ is the resonant frequency (e.g., 55.5 kHz). The first frequency $f_1$ provides a low level of mechanical vibration action to the blade 79 that, in conjunction with the clamp force, mechanically separates the muscle tissue layer (subtherapeutic) of the vessel without causing significant heating that generally occurs at resonance. After the first period $T_1$, the generator 30 is programmed to automatically switch the drive frequency to the resonant frequency $f_o$ for a second period $T_2$ to transect and seal the vessel. The duration of the second period $T_2$ may be programmed or may be determined by the length of time it actually takes to cut and seal the vessel as determined by the user or may be based on measured system characteristics such as the transducer impedance Z as described in more detail below.

In one form, the tissue/vessel transection process (e.g., separating the muscle layer of the vessel from the adventitia layer and transecting/sealing the vessel) may be automated by sensing the impedance Z characteristics of the transducer 50 to detect when the transection of the tissue/vessel occurs. The impedance Z can be correlated to the transection of the muscle layer and to the transection/sealing of the vessel to provide a trigger for the processor 400 to generate the frequency and/or current step function output. As previously discussed with reference to FIG. 9, the impedance Z of the transducer 50 may be calculated by the processor 400 based on the current flowing through transducer 50 and the voltage applied to the transducer 50 while the blade 79 is under various loads. Because the impedance Z of the transducer 50 is proportional to the load applied to the blade 79, as the load on the blade 79 increases, the impedance Z of the transducer 50 increases, and as the load on the blade 79 decreases the impedance Z of the transducer 50 decreases. Accordingly, the impedance Z of the transducer 50 can be monitored to detect the transection of the inner muscle tissue layer of the vessel from the adventitia layer and can also be monitored to detect when the vessel has been transected and sealed.

In one form, the ultrasonic surgical instrument 110 may be operated in accordance with a programmed step function algorithm responsive to the transducer impedance Z. In one form, a frequency step function output may be initiated based on a comparison of the transducer impedance Z and one or more predetermined thresholds that have been correlated with tissue loads against the blade 79. When the transducer impedance Z transitions above or below (e.g., crosses) a threshold, the processor 400 applies a digital frequency signal 418 to the DDS circuit 420 to change the frequency of the drive signal 416 by a predetermined step in accordance with the step function algorithm(s) 402 responsive to the transducer impedance Z. In operation, the blade 79 is first located at the tissue treatment site. The processor 400 applies a first digital frequency signal 418 to set a first drive frequency f1 that is off resonance (e.g., $f_o/2$, $2f_o$ or other structural resonant frequencies, where $f_o$ is the resonant frequency). The drive signal 416 is applied to the transducer 50 in response to activation of the switch 312a on the handle assembly 68 or the foot switch 434. During this period the ultrasonic transducer 50 mechanically activates the blade 79 at the first drive frequency $f_1$. A force or load may be applied to the clamp member 60 and the blade 79 to facilitate this process. During this period, the processor 400 monitors the transducer impedance Z until the load on the blade 79 changes and the transducer impedance Z crosses a predetermined threshold to indicate that the tissue layer has been transected. The processor 400 then applies a second digital frequency signal 418 to set a second drive frequency $f_2$, e.g., the resonant frequency $f_o$ or other suitable frequency for transecting, coagulating, and sealing tissue. Another portion of the tissue (e.g., the vessel) is then grasped between the clamp member 60 and the blade 79. The transducer 50 is now energized by the drive signal 416 at the second drive frequency $f_2$ by actuating either the foot switch 434 or the switch 312a on the handle assembly 68. It will be appreciated by those skilled in the art that the drive current (I) output also may be stepped as described with reference to FIGS. 6-8 based on the transducer impedance Z.

According to one step function algorithm 402, the processor 400 initially sets a first drive frequency $f_1$ that is significantly off resonance to separate the inner muscle layer of the vessel from the adventitia layer. During this period of operation the processor 400 monitors the transducer impedance Z to determine when the inner muscle layer is transected or separated from the adventitia layer. Because the transducer impedance Z is correlated to the load applied to the blade 79, for example, cutting more tissue decrease the load on the blade 79 and the transducer impedance Z. The transection of the inner muscle layer is detected when the transducer impedance Z drops below a predetermined threshold. When the change in transducer impedance Z indicates that the vessel has been separated from the inner muscle layer, the processor 400 sets the drive frequency to the resonant frequency $f_o$. The vessel is then grasped between the blade 79 and the clamp member 60 and the transducer 50 is activated by actuating either the foot switch or the switch on the handle assembly 68 to transect and seal the vessel. In one form, the impedance Z change may range between about 1.5 to about 4 times a base impedance measurements from an initial point of contact with the tissue to a point just before the muscle layer is transected and sealed.

Figure 10:
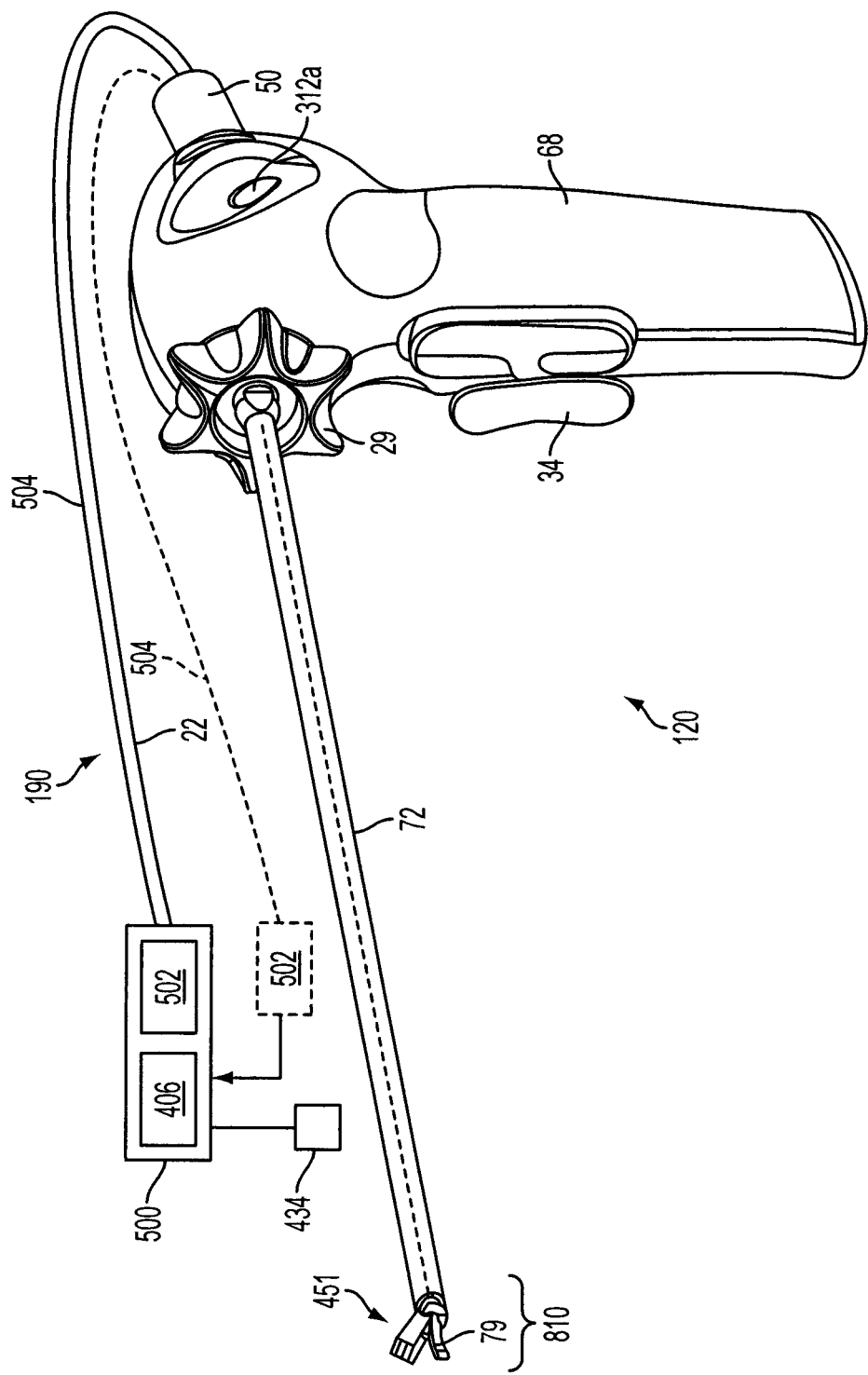
FIG. 10 illustrates one form of a surgical system comprising an ultrasonic surgical instrument and a generator comprising a tissue impedance module.

FIG. 10 illustrates one form of a surgical system 190 comprising an ultrasonic surgical instrument 120 and a generator 500 comprising a tissue impedance module 502. Although in the presently disclosed form, the generator 500 is shown separate from the surgical instrument 120, in one form, the generator 500 may be formed integrally with the surgical instrument 120 to form a unitary surgical system 190. In one form, the generator 500 may be configured to monitor the electrical impedance of the tissue $Z_t$ and to control the characteristics of time and power level based on the tissue impedance $Z_t$. In one form, the tissue impedance $Z_t$ may be determined by applying a subtherapeutic radio frequency (RF) signal to the tissue and measuring the current through the tissue by way of a return electrode on the clamp member 60. In the form illustrated in FIG. 10, an end effector 810 portion of the surgical system 190 comprises a clamp arm assembly 451 connected to the distal end of the outer sheath 72. The blade 79 forms a first (e.g., energizing) electrode and the clamp arm assembly 451 comprises an electrically conductive portion that forms a second (e.g., return) electrode. The tissue impedance module 502 is coupled to the blade 79 and the clamp arm assembly 451 through a suitable transmission medium such as a cable 504. The cable 504 comprises multiple electrical conductors for applying a voltage to the tissue and providing a return path for current flowing through the tissue back to the impedance module 502. In various forms, the tissue impedance module 502 may be formed integrally with the generator 500 or may be provided as a separate circuit coupled to the generator 500 (shown in phantom to illustrate this option). The generator 500 is substantially similar to the generator 30 with the added feature of the tissue impedance module 502.

Figure 11:
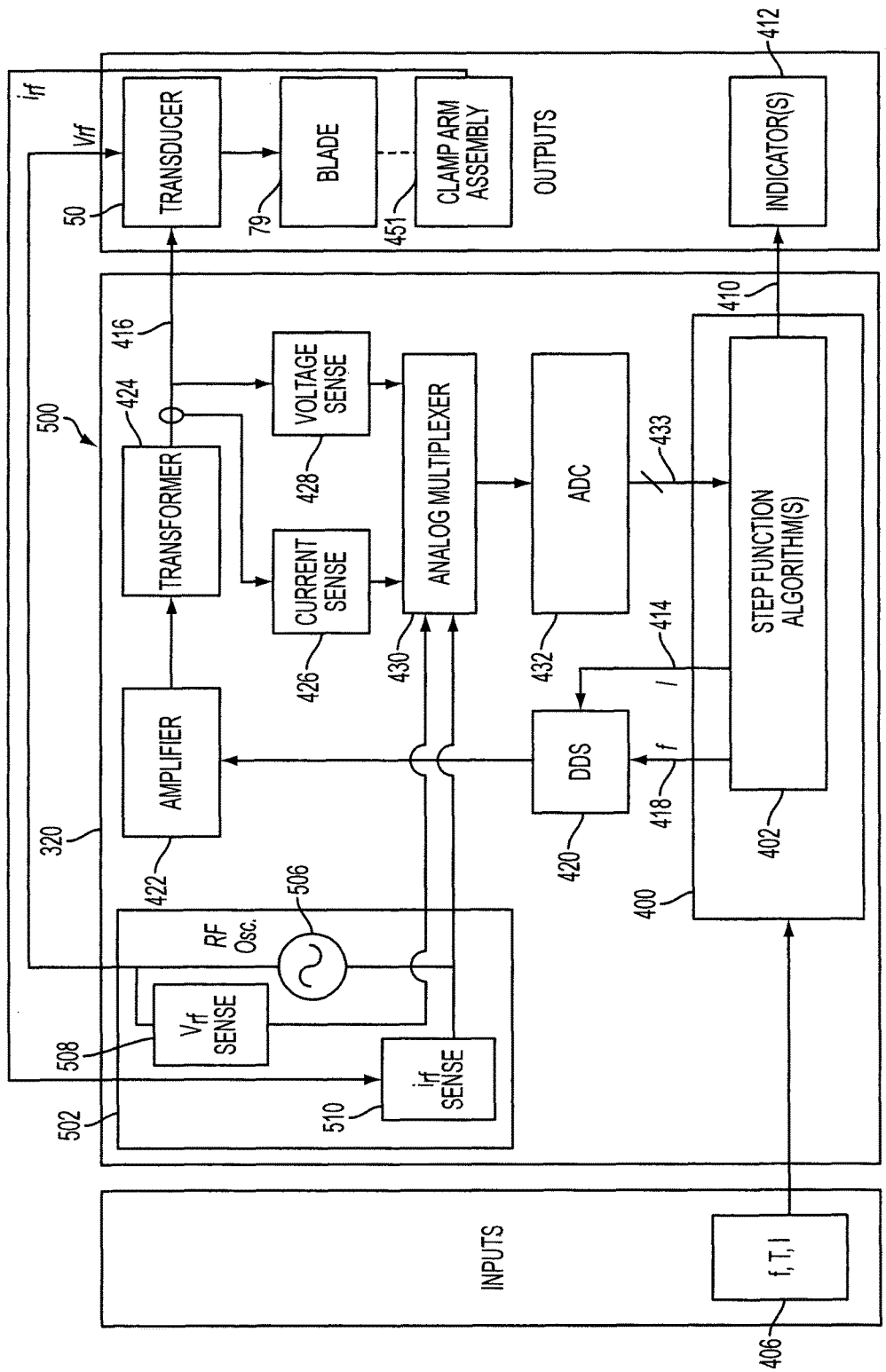
FIG. 11 illustrates one form of a drive system of a generator comprising a tissue impedance module.

FIG. 11 illustrates one form of a drive system 321 of the generator 500 comprising the tissue impedance module 502. The drive system 321 generates the ultrasonic electrical drive signal 416 to drive the ultrasonic transducer 50. In one form, the tissue impedance module 502 may be configured to measure the impedance $Z_t$ of tissue grasped between the blade 79 and the clamp arm assembly 451. The tissue impedance module 502 comprises an RF oscillator 506, a voltage sensing circuit 508, and a current sensing circuit 510. The voltage and current sensing circuits 508, 510 respond to the RF voltage $v_{rf}$ applied to the blade 79 electrode and the RF current $i_{rf}$ flowing through the blade 79 electrode, the tissue, and the conductive portion of the clamp arm assembly 451. The sensed voltage $v_{rf}$ and current $i_{rf}$ are converted to digital form by the ADC 432 via the analog multiplexer 430. The processor 400 receives the digitized output 433 of the ADC 432 and determines the tissue impedance $Z_t$ by calculating the ratio of the RF voltage $v_{rf}$ to current $i_{rf}$ measured by the voltage sense circuit 508 and the current sense circuit 510. In one form, the transection of the inner muscle layer and the tissue may be detected by sensing the tissue impedance $Z_t$. Accordingly, detection of the tissue impedance $Z_t$ may be integrated with an automated process for separating the inner muscle layer from the outer adventitia layer prior to transecting the tissue without causing a significant amount of heating, which normally occurs at resonance.

Figure 12:
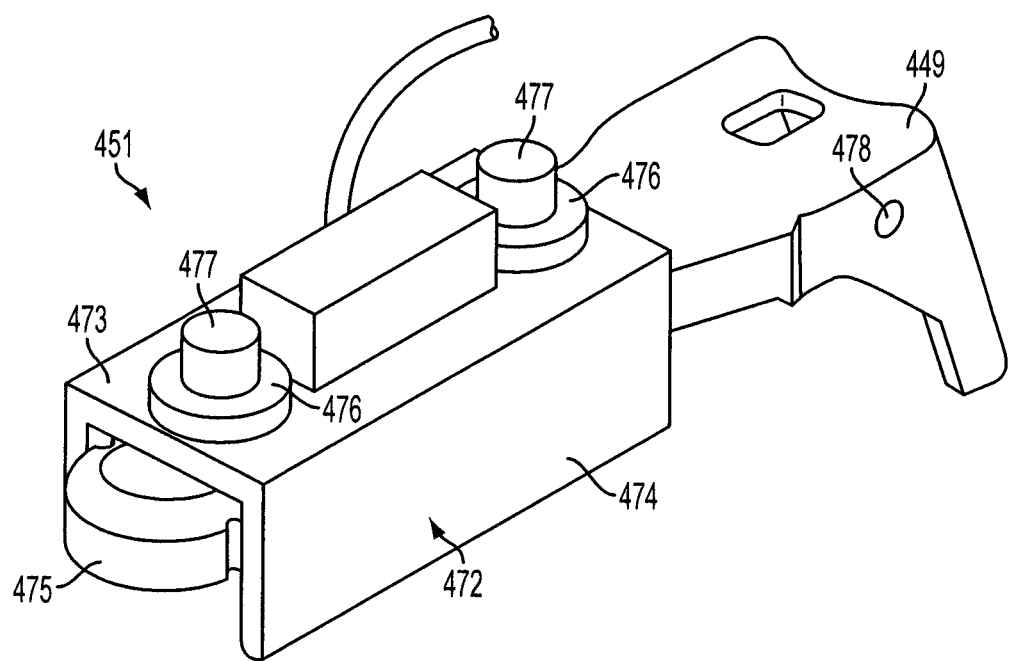
FIG. 12 illustrates one form of a clamp arm assembly that may be employed with a surgical system.

FIG. 12 illustrates one form of the clamp arm assembly 451 that may be employed with the surgical system 190 (FIG. 10). In the illustrated form, the clamp arm assembly 451 comprises a conductive jacket 472 mounted to a base 449. The conductive jacket 472 is the electrically conductive portion of the clamp arm assembly 451 that forms the second, e.g., return, electrode. In one implementation, the clamp arm 56 (FIG. 3) may form the base 449 on which the conductive jacket 472 is mounted. In various forms, the conductive jacket 472 may comprise a center portion 473 and at least one downwardly-extending sidewall 474 which can extend below the bottom surface 475 of the base 449. In the illustrated form, the conductive jacket 472 has two sidewalls 474 extending downwardly on opposite sides of the base 449. In other forms, the center portion 473 may comprise at least one aperture 476 which can be configured to receive a projection 477 extending from the base 449. In such forms, the projections 477 can be press-fit within the apertures 476 in order to secure the conductive jacket 472 to the base 449. In other forms, the projections 477 can be deformed after they are inserted into the apertures 476. In various forms, fasteners can be used to secure the conductive jacket 472 to the base 449.

In various forms, the clamp arm assembly 451 may comprise a non-electrically conductive or insulative material, such as plastic and/or rubber, for example, positioned intermediate the conductive jacket 472 and the base 449. The electrically insulative material can prevent current from flowing, or shorting, between the conductive jacket 472 and the base 449. In various forms, the base 449 may comprise at least one aperture 478, which can be configured to receive a pivot pin (not illustrated). The pivot pin can be configured to pivotably mount the base 449 to the sheath 72 (FIG. 10), for example, such that the clamp arm assembly 451 can be rotated between open and closed positions relative to the sheath 72. In the illustrated form, the base 449 includes two apertures 478 positioned on opposite sides of the base 449. In one form, a pivot pin may be formed of or may comprise a non-electrically conductive or insulative material, such as plastic and/or rubber, for example, which can be configured to prevent current from flowing into the sheath 72 even if the base 449 is in electrical contact with the conductive jacket 472, for example. Additional clamp arm assemblies comprising various forms of electrodes may be employed. Examples of such clamp arm assemblies are described in commonly-owned and U.S. patent application Ser. Nos. 12/503,769, 12/503,770, and 12/503,766, each of which is incorporated herein by reference in its entirety.

Figure 13:
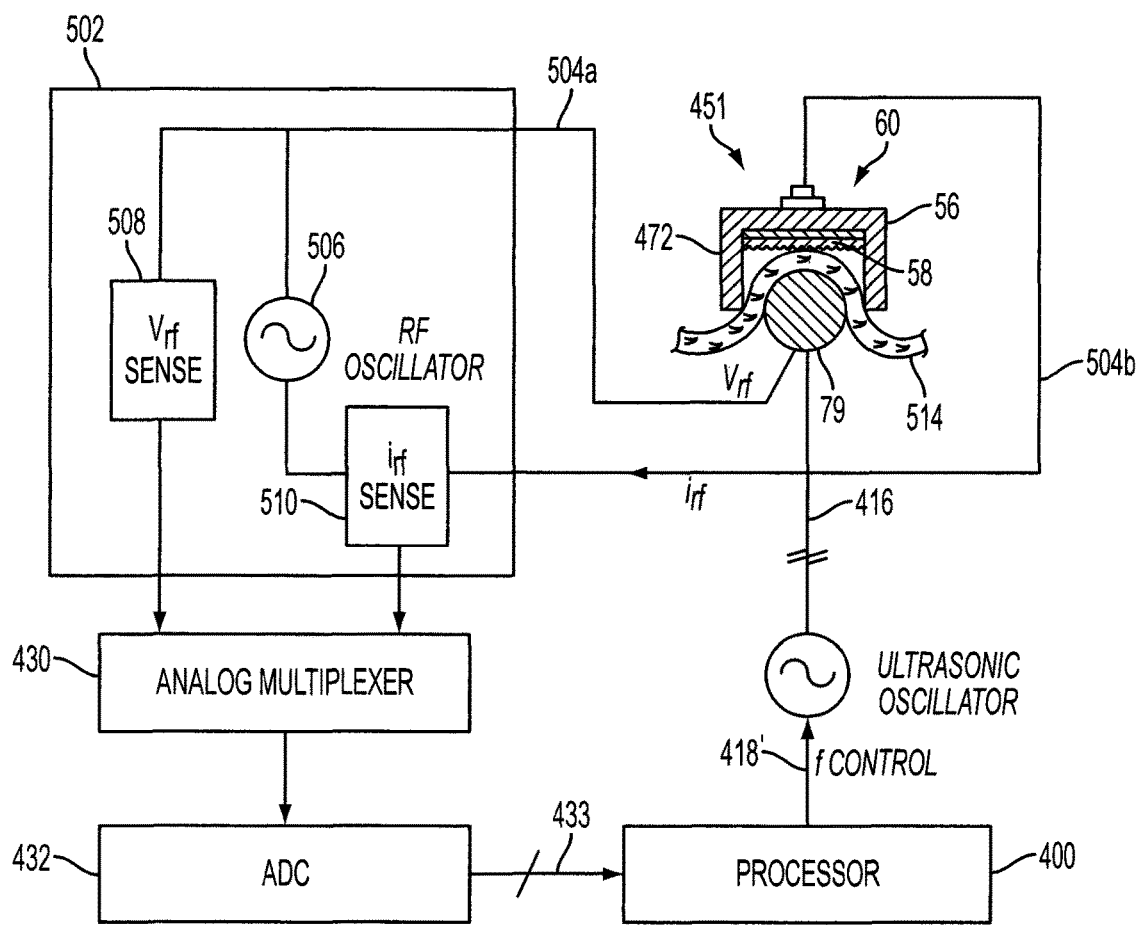

FIG. 13 is a schematic diagram of the tissue impedance module 502 coupled to the blade 79 and the clamp arm assembly 415 with tissue 514 located there between. With reference now to FIGS. 10-13, the generator 500 comprises the tissue impedance module 502 configured for monitoring the impedance of the tissue 514 ($Z_t$) located between the blade 79 and the clamp arm assembly 451 during the tissue transection process. The tissue impedance module 502 is coupled to the ultrasonic surgical instrument 120 by way of the cable 504. The cable 504 includes a first "energizing" conductor 504a connected to the blade 79 (e.g., positive [+] electrode) and a second "return" conductor 504b connected to the conductive jacket 472 (e.g., negative [−] electrode) of the clamp arm assembly 451. In one form, RF voltage $v_{rf}$ is applied to the blade 79 to cause RF current $i_{rf}$ to flow through the tissue 514. The second conductor 504b provides the return path for the current $i_{rf}$ back to the tissue impedance module 502. The distal end of the return conductor 504b is connected to the conductive jacket 472 such that the current $i_{rf}$ can flow from the blade 79, through the tissue 514 positioned intermediate the conductive jacket 472 and the blade 79, and the conductive jacket 472 to the return conductor 504b. The impedance module 502 connects in circuit, by way of the first and second conductors 504a, b. In one form, the RF energy may be applied to the blade 79 through the ultrasonic transducer 50 and the waveguide 80 (FIG. 2). It is worthwhile noting that the RF energy applied to the tissue 514 for purposes of measuring the tissue impedance $Z_t$ is a low level subtherapeutic signal that does not contribute in a significant manner, or at all, to the treatment of the tissue 514.

Having described operational details of various forms of the surgical system 190, operations for the above surgical system 190 may be further described with reference to FIGS. 10-13 in terms of a process for cutting and coagulating a blood vessel employing a surgical instrument comprising the input device 406 and the tissue impedance module 502. Although a particular process is described in connection with the operational details, it can be appreciated that the process merely provides an example of how the general functionality described herein can be implemented by the surgical system 190. Further, the given process does not necessarily have to be executed in the order presented herein unless otherwise indicated. As previously discussed, the input device 406 may be employed to program the step function output (e.g., current, voltage, frequency) to the ultrasonic transducer 50/blade 79 assembly.

In one form, a first conductor or wire may be connected to the outer sheath 72 of the instrument 120 and a second conductor or wire may be connected to the blade 79/transducer 50. By nature of the design, the blade 79 and the transducer 50 are electrically isolated from the outer sheath 72 as well as other elements of the actuation mechanism for the instrument 120 including the base 449 and the inner sheath 76. The outer sheath 79 and other elements of the actuation mechanism including the base 449 and the inner sheath 76 are all electrically continuous with one another— that is, they are all metallic and touch one another. Accordingly, by connecting a first conductor to the outer sheath 72 and connecting a second conductor to the blade 79 or the transducer 50 such that the tissue resides between these two conductive pathways, the system can monitor the electrical impedance of the tissue as long as the tissue contacts both the blade 79 and the base 449. To facilitate this contact, the base 449 itself may include outwardly and possibly downwardly protruding features to assure tissue contact while, effectively integrating conductive jacket 472 into base 449.

In one form, the ultrasonic surgical instrument 120 may be operated in accordance with a programmed step function algorithm 402 responsive to the tissue impedance $Z_t$. In one form, a frequency step function output may be initiated based on a comparison of the tissue impedance $Z_t$ and predetermined thresholds that have been correlated with various tissue states (e.g., desiccation, transection, sealing). When the tissue impedance $Z_t$ transitions above or below (e.g., crosses) a threshold, the processor 400 applies a digital frequency signal 418 to the DDS circuit 420 to change the frequency of an ultrasonic oscillator by a predetermined step in accordance with the step function algorithm 402 responsive to the tissue impedance $Z_t$.

In operation, the blade 79 is located at the tissue treatment site. The tissue 514 is grasped between the blade 79 and the clamp arm assembly 451 such that the blade 79 and the conductive jacket 472 make electrical contact with the tissue 514. The processor 400 applies a first digital frequency signal 418 to set a first drive frequency $f_1$ that is off resonance (e.g., $f_o/2$, $2f_o$ or other structural resonant frequencies, where $f_o$ is the resonant frequency). The blade 79 is electrically energized by the low level subtherapeutic RF voltage $v_{rf}$ supplied by the tissue impedance module 502. The drive signal 416 is applied to the transducer 50/blade 79 in response to actuation of the switch 312a on the handle assembly 68 or the foot switch 434 until the tissue impedance $Z_t$ changes by a predetermined amount. A force or load is then applied to the clamp arm assembly 451 and the blade 79. During this period the ultrasonic transducer 50 mechanically activates the blade 79 at the first drive frequency $f_1$ and as a result, the tissue 514 begins to desiccate from the ultrasonic action applied between the blade 79 and the one or more clamp pads 58 of the clamp arm assembly 451 causing the tissue impedance $Z_t$ to increase. Eventually, as the tissue is transected by the ultrasonic action and applied clamp force, the tissue impedance $Z_t$ becomes very high or infinite as the tissue fully transects such that no conductive path exists between the blade 79 and the conductive jacket 472. It will be appreciated by those skilled in the art that the drive current (I) output also may be stepped as described with reference to FIGS. 6-8 based on the tissue impedance $Z_t$.

In one form, the tissue impedance $Z_t$ may be monitored by the impedance module 502 in accordance with the following process. A measurable RF current i1 is conveyed through the first energizing conductor 504a to the blade 79, through the tissue 514, and back to the impedance module 502 through the conductive jacket 472 and the second conductor 504b. As the tissue 514 is desiccated and cut by the ultrasonic action of the blade 79 acting against the one or more clamp pads 58, the impedance of the tissue 514 increases and thus the current i1 in the return path, i.e., the second conductor 504b, decreases. The impedance module 502 measures the tissue impedance $Z_t$ and conveys a representative signal to the ADC 432 whose digital output 433 is provided to the processor 400. The processor 400 calculates the tissue impedance $Z_t$ based on these measured values of $v_{rf}$ and $i_{rf}$.

The processor 400 steps the frequency by any suitable increment or decrement in response to changes in tissue impedance $Z_t$. The processor 400 controls the drive signals 416 and can make any necessary adjustments in amplitude and frequency in response to the tissue impedance $Z_t$. In one form, the processor 400 can cut off the drive signal 416 when the tissue impedance $Z_t$ reaches a predetermined threshold value.

Accordingly, by way of example, and not limitation, in one form, the ultrasonic surgical instrument 120 may be operated in accordance with a programmed stepped output algorithm to separate the inner muscle layer of a vessel from the adventitia layer prior to transecting and sealing the vessel. As previously discussed, according to one step function algorithm, the processor 400 initially sets a first drive frequency f1 that is significantly off resonance. The transducer 50 is activated to separate the inner muscle layer of the vessel from the adventitia layer and the tissue impedance module 502 applies a subtherapeutic RF voltage $v_{rf}$ signal to the blade 79. During this period $T_1$ of operation the processor 400 monitors the tissue impedance $Z_t$ to determine when the inner muscle layer is transected or separated from the adventitia layer. The tissue impedance $Z_t$ is correlated to the load applied to the blade 79, for example, when the tissue becomes desiccated or when the tissue is transected the tissue impedance $Z_t$ becomes extremely high or infinite. The change in tissue impedance $Z_t$ indicates that the vessel has been separated or transected from the inner muscle layer and the generator 500 is deactivated for a second period of time $T_2$. The processor 400 then sets the drive frequency to the resonant frequency $f_o$. The vessel is then grasped between the blade 79 and the clamp arm assembly 451 and the transducer 50 is reactivated to transect and seal the vessel. Continuous monitoring of the tissue impedance $Z_t$ provides an indication of when the vessel is transected and sealed. Also, the tissue impedance $Z_t$ may be monitored to provide an indication of the completeness of the tissue cutting and/or coagulating process or to stop the activation of the ultrasonic generator 500 when the tissue impedance $Z_t$ reaches a predetermined threshold value. The threshold for the tissue impedance $Z_t$ may be selected, for example, to indicate that the vessel has been transected. In one form, the tissue impedance $Z_t$ may range between about 10 Ohms to about 1000 Ohms from an initial point to a point just before the muscle layer is transected and sealed.

The applicants have discovered that experiments that run varying current set points (both increasing and decreasing) and dwell times indicate that the described forms can be used to separate the inner muscle layer from the outer adventitia layer prior to completing the transection resulting in improved hemostasis and potentially lower total energy (heat) at the transection site. Furthermore, although the surgical instruments 100, 120 have been described in regards to threshold impedance detection schemes to determine when the muscle layer is separated from the adventitia, other forms that do not employ any detection scheme are within the scope of the present disclosure. For example, forms of the surgical instruments 100, 120 may be employed in simplified surgical systems wherein non-resonant power is applied to separate the layers for a predetermined time of approximately 1 second or less, prior to applying a resonant power to cut the tissue. The forms are not limited in this context.

Having described operational details of various forms of the surgical systems 19 (FIG. 1) and 190 (FIG. 10), operations for the above surgical systems 19, 190 may be further described generally in terms of a process for cutting and coagulating tissue employing a surgical instrument comprising the input device 406 and the tissue impedance module 502. Although a particular process is described in connection with the operational details, it can be appreciated that the process merely provides an example of how the general functionality described herein can be implemented by the surgical systems 19, 190. Further, the given process does not necessarily have to be executed in the order presented herein unless otherwise indicated. As previously discussed, the input device 406 may be employed to program the stepped output (e.g., current, frequency) to the ultrasonic transducer 50/blade 79 assembly.

Figure 14:
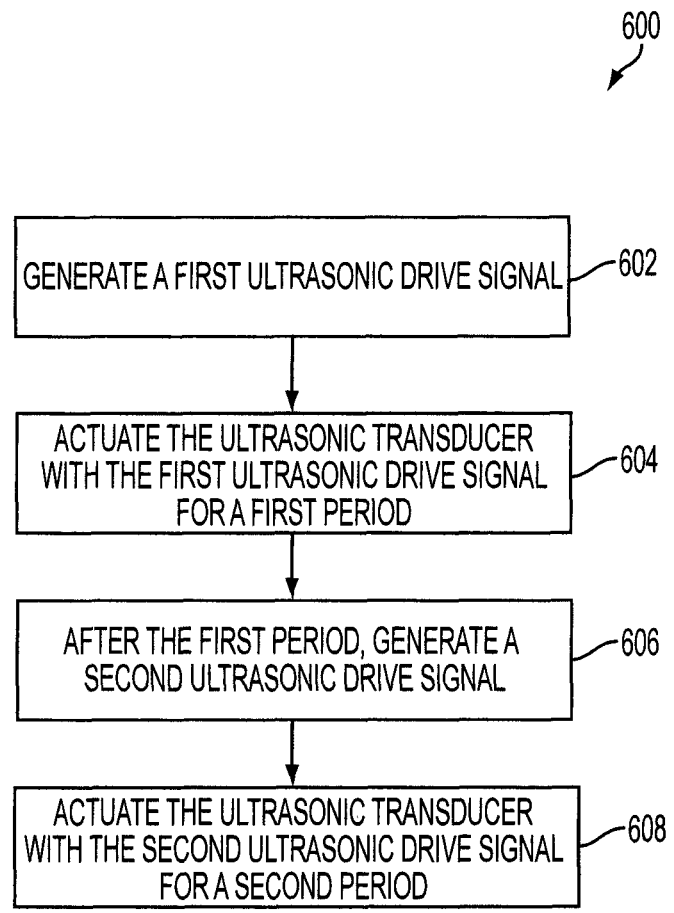
FIG. 14 illustrates one form of a method for driving an end effector coupled to an ultrasonic drive system of a surgical instrument.

FIG. 14 illustrates one form of a method 600 for driving an end effector coupled to an ultrasonic drive system of a surgical instrument. The method 600, and any of the other methods, algorithms, etc., described herein, may be initiated in any suitable manner. For example, the method 600 and any of the other methods, algorithms, etc. described herein may be initiated in response to user input provided via any one or combination of buttons, switches, and/or foot pedals including, for example, those described herein. With reference to FIGS. 1-3, and 6-14, by way of example, and not limitation, the ultrasonic surgical instruments 100, 120 may be operated in accordance with the method 600 to separate the inner muscle layer of a vessel from the adventitia layer prior to transecting and sealing the vessel. Accordingly, in various forms, an end effector (e.g., end effector 81, 810) of a surgical instrument (e.g., surgical instrument 100, 120) may be driven in accordance with the method 600. A generator (e.g., generator 30, 500) is coupled to an ultrasonic drive system. The ultrasonic drive system comprises an ultrasonic transducer (e.g., ultrasonic transducer 50) coupled to a waveguide (e.g., waveguide 80). The end effector 81 is coupled to the waveguide 80. The ultrasonic drive system and end effector 81 are configured to resonate at a resonant frequency (e.g., 55.5 kHz). In one form, at 602, the generator 30 generates a first ultrasonic drive signal. At 604, the ultrasonic transducer 50 is actuated with the first ultrasonic drive signal for a first period in response to activating a switch (e.g., switch 34) on a handle assembly (e.g., handle assembly 68) or a foot switch (e.g., foot switch 434) connected to the generator 30. After the first period, at 606, the generator 30 generates a second ultrasonic drive signal. At 608, the ultrasonic transducer 50 is actuated with the second ultrasonic drive signal for a second period in response to activating the switch 34 on the handle assembly 68 or the foot switch 434 connected to the generator 30. The first drive signal is different from the second drive signal over the respective first and second periods. The first and second drive signals define a step function waveform over the first and second periods.

In one form, the generator 30 generates a third ultrasonic drive signal. The ultrasonic transducer 50 is actuated with the third ultrasonic drive signal for a third period. The third drive signal is different from the first second drive signals over the first, second, and third periods. The first, second, and third drive signals define a step function waveform over the first, second, and third periods. In one form, generating the first, second, and third ultrasonic drive signals comprises generating a corresponding first, second, and third drive current and actuating the ultrasonic transducer 50 with the first drive current for the first period, actuating the ultrasonic transducer 50 with the second drive current for the second period, and actuating the ultrasonic transducer 50 with the third drive current for the third period.

In certain forms, the first, second and third drive currents may increase, decrease or stay the same relative to one another. For example, in certain forms, some or all of the first, second and third drive currents are equal. Also, in certain forms, the first, second and third periods may take any suitable value including, for example, fractions of a second, minutes, hours, etc. In one example form, some or all of the first, second and third periods may be 55 seconds.

In one form, the generator 30 generates the first ultrasonic drive signal at a first frequency, which is different from the resonant frequency. The ultrasonic transducer 50 is then actuated with the first ultrasonic drive signal at the first frequency for the first period. Actuation at the first frequency provides a first level of mechanical vibration to the end effector 81 suitable for separating a first tissue from a second tissue, for example, to separate the inner muscle layer of a vessel from the adventitia layer. The generator 30 generates the second ultrasonic drive signal at the resonant frequency, e.g., 55.5 kHz, and the actuates the ultrasonic transducer 50 with the second ultrasonic drive signal at the resonant frequency for the second period subsequent to the first period. Actuation at the second, resonant frequency provides a second level of mechanical vibration to the end effector 81 suitable for transecting and sealing the first tissue, such as the vessel, once it separated from the inner muscle layer. In one form, the second ultrasonic drive signal at the resonant frequency is generated automatically by the generator 30 after the first period. In one form, the first frequency is substantially different from the resonant frequency and the first period is less than about one second. For example, in one form, the first frequency is defined by the following equation: $f1=2*fo$, wherein $f1$ is the first frequency and $fo$ is the resonant frequency. In another form, the first frequency is defined by the following equation: $f1=fo/2$, wherein $f1$ is the first frequency and $fo$ is the resonant frequency. The first, second, and third ultrasonic drive signals are also envisioned to excite be vibratory modes of the ultrasonic transducer 50 in longitudinal, flexural, and torsional modes and harmonics thereof.

In one form, the generator 30 monitors a measurable characteristic of the ultrasonic drive system and generates any one of the first and second drive signals based on the measured characteristic. For example, the generator 30 monitors the impedance Z of the ultrasonic transducer 50. The generator 30 comprises electronic circuitry suitable for measuring the impedance of the transducer 50. For example, a current sense circuit (e.g., current sense circuit 426) senses the current flowing through the transducer 50 and a voltage sense circuit (e.g., voltage sense circuit 428) senses the output voltage applied to the transducer 50. A multiplexer (e.g., multiplexer 430) routes the appropriate analog signal to an analog-to-digital converter (e.g., ADC 432), whose digital output is provided to a processor (e.g., processor 400). The processor 400 calculates the transducer impedance Z based on the measured values of current and voltage.

In one form, the generator 500 comprises an impedance module (e.g., tissue impedance module 502) to measure the impedance of a tissue portion contacting an end effector (e.g., end effector 810). The impedance module 502 includes an RF oscillator (e.g., RF oscillator 506) to generate a subtherapeutic RF signal. The subtherapeutic RF signal is applied to a blade (e.g., blade 79) portion of the end effector 810, which forms an energizing electrode. The tissue portion is grasped between the end effector 810 and a return electrode of a clamp arm assembly (e.g., clamp arm assembly 451) and the impedance of the tissue (e.g., tissue 514). The tissue impedance is then measured by a voltage sense circuit (e.g., voltage sense circuit 508) and current sense circuit (e.g., current sense circuit 510) and of the impedance module 502. These signals are applied to the ADC 432 via the multiplexer 430. The digital output of the ADC 432 is provided to the processor 400, which calculates the tissue impedance Zt based on the measured values of current through the tissue and the voltage applied to the blade 79 portion of the end effector 810.

Figure 15A:
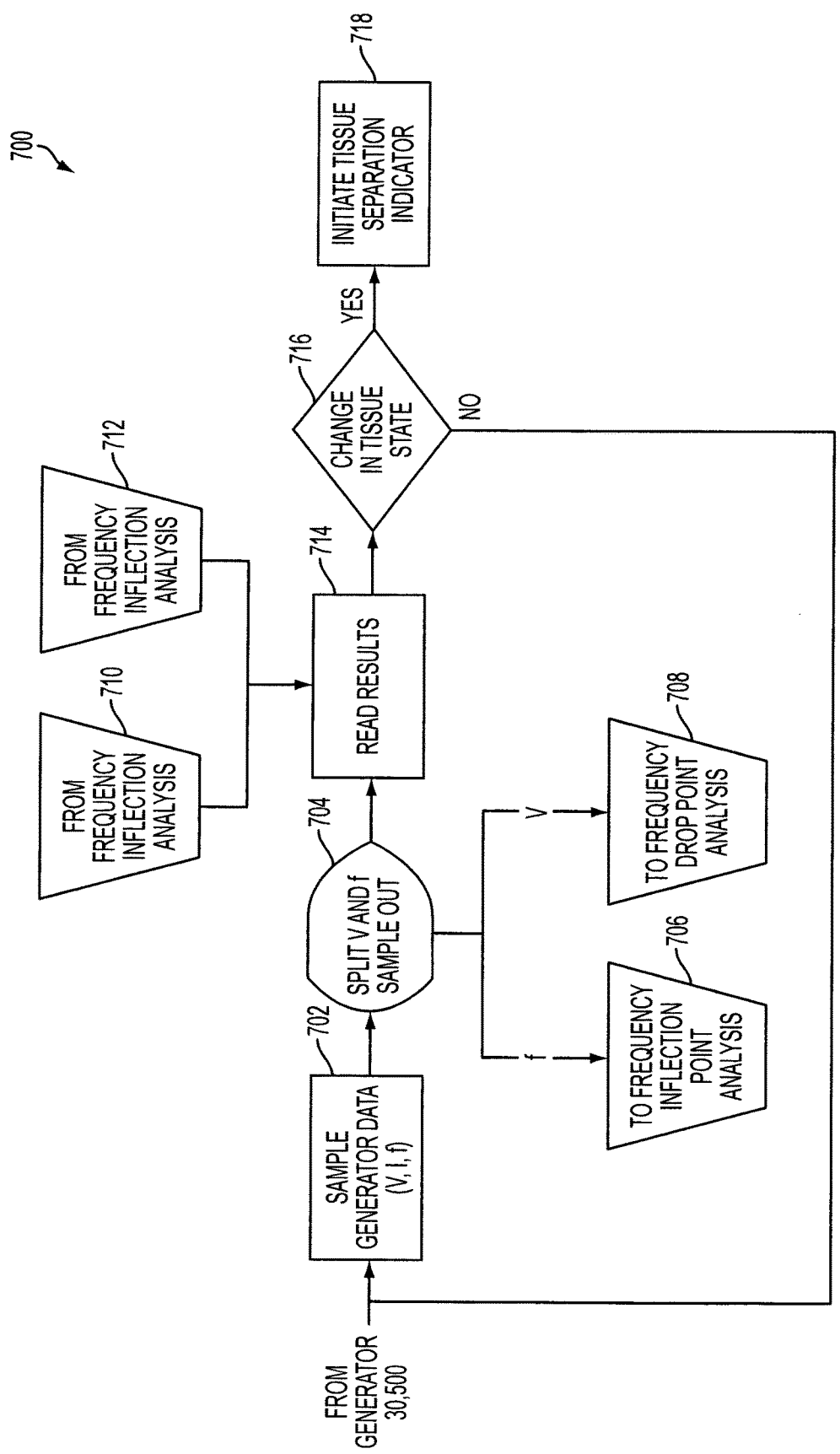
FIG. 15A illustrates a logic flow diagram of one form of determining a change in tissue state and activating an output indicator accordingly.
Figure 15B:
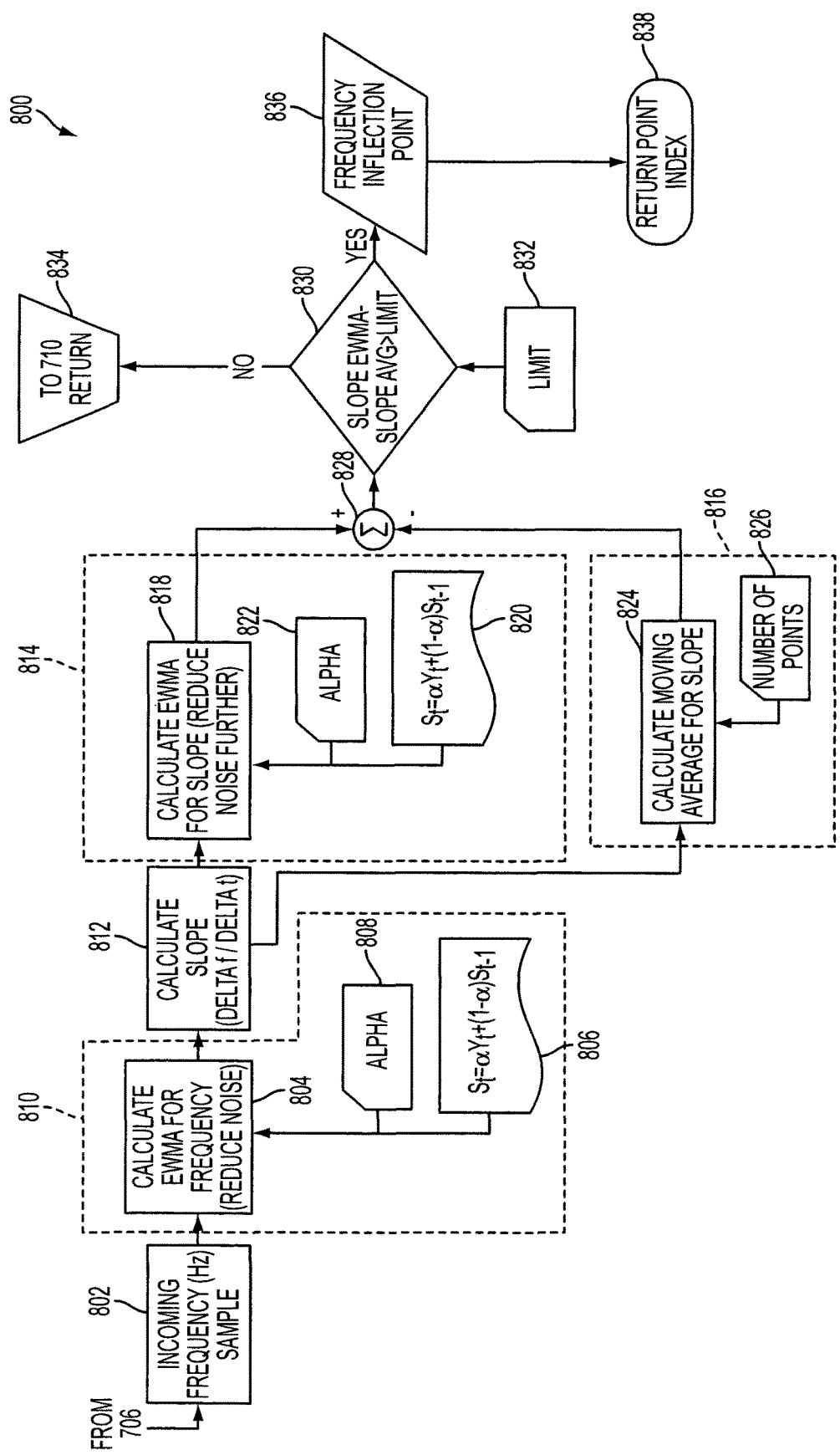
FIG. 15B is a logic flow diagram illustrating one form of the operation of the frequency inflection point analysis module.
Figure 15C:
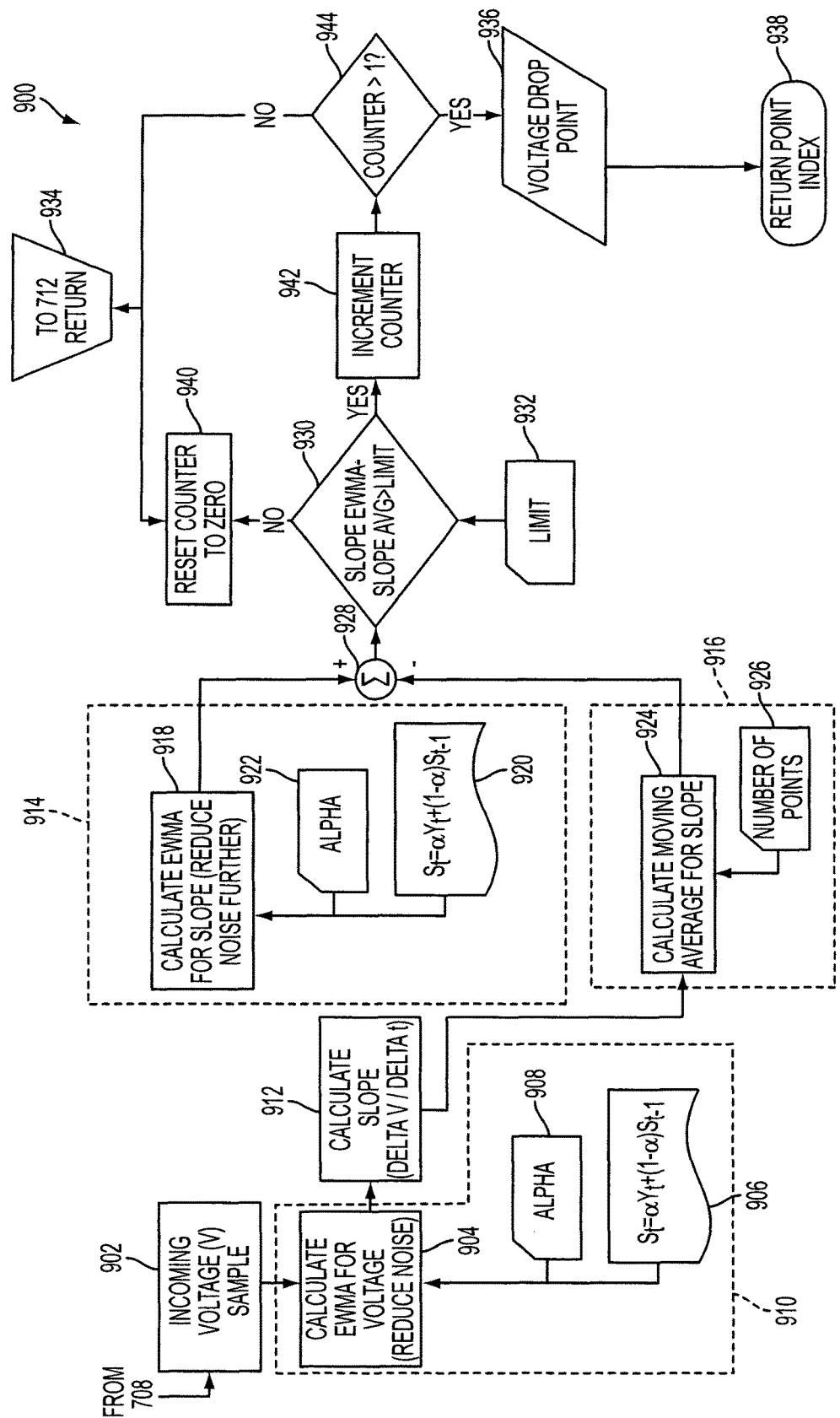
FIG. 15C is a logic flow diagram 900 illustrating one form of the operation of the voltage drop analysis module.

FIGS. 15A-C illustrate various forms of logic flow diagrams of 700, 800, 900 of operations for determining a change of state of tissue being manipulated by an ultrasonic surgical instrument and providing feedback to the user to indicate that the tissue has undergone such change of state or that there is a high likelihood that the tissue has undergone such change of state. The operations 700, 800, 900, and various permutations thereof, may be utilized in any implementation where the state of tissue is monitored. For example, one or more of the operations 700, 800, 900, etc. may be executed automatically when the surgical system is in use. Also, operations 700, 800, 900, etc. may be triggered based on clinician input, for example, via one or more buttons, switches and pedals, etc. (e.g., the buttons, switches and pedals, etc. described herein). As used herein, the tissue may undergo a change of state when the tissue is separated from other layers of tissue or bone, when the tissue is cut or transected, when the tissue is coagulated, and so forth while being manipulated with an end effector of an ultrasonic surgical instrument, such as, for example, the end effector 81, 810 of the ultrasonic surgical instrument 100, 120 shown in FIGS. 1 and 10. A change in tissue state may be determined based on the likelihood of an occurrence of a tissue separation event.

In various forms, the feedback is provided by the output indicator 412 shown in FIGS. 9 and 11. The output indicator 412 is particularly useful in applications where the tissue being manipulated by the end effector 81, 810 is out of the user's field of view and the user cannot see when a change of state occurs in the tissue. The output indicator 412 communicates to the user that a change in tissue state has occurred as determined in accordance with the operations described with respect to the logic flow diagrams 700, 800, 900. As previously discussed, the output indicator 412 may be configured to provide various types of feedback to the user including, without limitation, visual, audible, and/or tactile feedback to indicate to the user (e.g., surgeon, clinician) that the tissue has undergone a change of state or condition of the tissue. By way of example, and not limitation, as previously discussed, visual feedback comprises any type of visual indication device including incandescent lamps or LEDs, graphical user interface, display, analog indicator, digital indicator, bar graph display, digital alphanumeric display. By way of example, and not limitation, audible feedback comprises any type of buzzer, computer generated tone, computerized speech, VUI to interact with computers through a voice/speech platform. By way of example, and not limitation, tactile feedback comprises any type of vibratory feedback provided through the instrument housing handle assembly 68. The change of state of the tissue may be determined based on transducer and tissue impedance measurements as previously described, or based on voltage, current, and frequency measurements in accordance with the operations described with respect to the logic flow diagrams 700, 800, 900 described below with respect to FIGS. 15A-C.

In one form, the logic flow diagrams 700, 800, 900 may be implemented as executable modules (e.g., algorithms) comprising computer readable instructions to be executed by the processor 400 (FIGS. 9, 11, 14) portion of the generator 30, 500. In various forms, the operations described with respect to the logic flow diagrams 700, 800, 900 may be implemented as one or more software components, e.g., programs, subroutines, logic; one or more hardware components, e.g., processors, DSPs, PLDs, ASICs, circuits, registers; and/or combinations of software and hardware. In one form, the executable instructions to perform the operations described by the logic flow diagrams 700, 800, 900 may be stored in memory. When executed, the instructions cause the processor 400 to determine a change in tissue state in accordance with the operations described in the logic flow diagrams 800 and 900 and provide feedback to the user by way of the output indicator 412. In accordance with such executable instructions, the processor 400 monitors and evaluates the voltage, current, and/or frequency signal samples available from the generator 30, 500 and according to the evaluation of such signal samples determines whether a change in tissue state has occurred. As further described below, a change in tissue state may be determined based on the type of ultrasonic instrument and the power level that the instrument is energized at. In response to the feedback, the operational mode of the ultrasonic surgical instrument 100, 120 may be controlled by the user or may be automatically or semi-automatically controlled.

FIG. 15A illustrates a logic flow diagram 700 of one form of determining a change in tissue state and activating the output indicator 412 accordingly. With reference now to the logic flow diagram 700 shown in FIG. 15A and the drive system 32 of the generator 30 shown in FIG. 9, at 702, the processor 400 portion of the drive system 32 samples the voltage (v), current (i), and frequency (f) signals of the generator 30. In the illustrated form, at 704, the frequency and voltage signal samples are analyzed separately to determine the corresponding frequency inflection and/or voltage drop points. In other forms, the current signal samples may be separately analyzed in addition to the voltage and frequency signal samples or in place of the voltage signal samples. At 706, the present frequency signal sample is provided to a frequency inflection point analysis module for determining a change in tissue state as illustrated in the logic flow diagram 800 in FIG. 15B. At 708, the present voltage signal sample is provided to a voltage drop point analysis module for determining a change in tissue state as illustrated in the logic flow diagram 900 in FIG. 15C.

The frequency inflection point analysis module and the voltage drop point analysis module determine when a change in tissue state has occurred based on correlated empirical data associated with a particular ultrasonic instrument type and the energy level at which the instrument is driven. At 714, the results 710 from the frequency inflection point analysis module and/or the results 712 from the voltage drop point analysis module are read by the processor 400. The processor 400 determines 716 whether the frequency inflection point result 710 and/or the voltage drop point result 712 indicates a change in tissue state. If the results 710, 714 do not indicate a change in tissue state, the processor 400 continues along the "No" branch to 702 and reads an additional voltage and frequency signal sample from the generator 30. In forms that utilize the generator current in the analysis, the processor 400 would now also read an additional current signal sample from the generator 30. If the results 710, 714 indicate a sufficient change in tissue state, the processor 400 continues along the "Yes" branch to 718 and activates the output indicator 412.

As previously discussed, the output indicator 412 may provide visual, audible, and/or tactile feedback to alert the user of the ultrasonic surgical instrument 100, 120 that a change in tissue state has occurred. In various forms, in response to the feedback from the output indicator 412, the operational mode of the generator 30, 500 and/or the ultrasonic instrument 100, 120 may be controlled manually, automatically, or semi-automatically. The operational modes include, without limitation, disconnecting or shutting down the output power of the generator 30, 500, reducing the output power of the generator 30, 500, cycling the output power of the generator 30, 500, pulsing the output power of the generator 30, 500, and/or outputting a high-power momentary surge from the generator 30, 500. The operational modes of the ultrasonic instrument in response to the change in tissue state can be selected, for example, to minimize heating effects of the end effector 81, 810, e.g., of the clamp pad 58 (FIGS. 1-3), to prevent or minimize possible damage to the surgical instrument 100, 120 and/or surrounding tissue. This is advantageous because heat is generated rapidly when the transducer 50 is activated with nothing between the jaws of the end effector 81, 810 as is the case when a change in tissue state occurs such as when tissue has substantially separated from the end effector.

FIG. 15B is a logic flow diagram 800 illustrating one form of the operation of the frequency inflection point analysis module. At 802, a frequency sample is received by the processor 400 from 706 of the logic flow diagram 700. At 804, the processor 400 calculates an exponentially weighted moving average (EWMA) for the frequency inflection analysis. The EWMA is calculated to filter out noise from the generator from the frequency samples. The EWMA is calculated in accordance with a frequency moving average equation 806 and an alpha value ($\alpha$) 808:

$$S_{tf} = \alpha Y_{tf} + (1-\alpha) S_{tf}-1 \quad (2)$$

Where:
$S_{tf}$=the current moving average of the sampled frequency signal;
$S_{tf-t}$=the previous moving average of the sampled frequency signal;
$\alpha$=the smoothing factor; and
$Y_{tf}$=current data point of the sampled frequency signal.

The $\alpha$ value 808 may vary from about 0 to about 1 in accordance with a desired filtering or smoothing factor, wherein small $\alpha$ values 808 approaching about 0 provide a large amount of filtering or smoothing and large $\alpha$ values 808 approaching about 1 provide a small amount of filtering or smoothing. The $\alpha$ value 808 may be selected based on the ultrasonic instrument type and power level. In one form, blocks 804, 806, and 808 may be implemented as a variable digital low pass filter 810 with the $\alpha$ value 808 determining the cutoff point of the filter 810. Once the frequency samples are filtered, the slope of the frequency samples is calculated at 812 as:

$$\text{Frequency Slope} = \text{delta} f / \text{delta} t \quad (3)$$

The calculated Frequency Slope data points are provided to a "slow response" moving average filter 814 to calculate the EWMA moving average for the Frequency Slope to further reduce system noise. In one form, the "slow response" moving average filter 814 may be implemented by calculating the EWMA for the Frequency Slope at 818 in accordance with the frequency slope moving average equation 820 and alpha value ($\alpha'$) 822:

$$S'_{tf} = \alpha' Y'_{tf} + (1-\alpha') S'_{tf-1} \quad (4)$$

Where:
$S'_{tf}$=the current moving average of the frequency slope of the sampled frequency signal;
$S'_{tf-1}$=the previous moving average of the frequency slope of the sampled frequency signal;
$\alpha'$=the smoothing factor; and
$Y'_{tf}$=current slope data point of the sampled frequency signal.

The $\alpha'$ value 822 varies from about 0 to about 1, as previously discussed with respect to digital filter block 810 in accordance with a desired filtering or smoothing factor, wherein small $\alpha'$ value 822 approaching 0 provide a large amount of filtering or smoothing and large $\alpha'$ value 822 approaching 1 provide a small amount of filtering or smoothing. The $\alpha'$ value 822 may be selected based on the ultrasonic instrument type and power level.

The calculated Frequency Slope data points are provided to a "fast response" filter 816 to calculate the moving average for the Frequency Slope. At 824, the "fast response" filter 816 calculates the moving average for the Frequency Slope based on a number of data points 826.

In the illustrated form, the output of the "slow response" moving average filter 814 "Slope EWMA" is applied to a (+) input of an adder 828 and the output of the "fast response" filter 816 "Slope Avg" is applied to (−) input of the adder 828. The adder 828 computes the difference between the outputs of the "slow response" moving average filter 814 and the "fast response" filter 816. The difference between these outputs is compared at 830 to a predetermined limit 832. The limit 832 is determined based on the type of ultrasonic instrument and the power level at which the particular type of ultrasonic instrument is energized at. The limit 832 value may be predetermined and stored in memory in the form of a look-up table or the like. If the difference between the "Slope EWMA" and the "Slope Avg" is not greater than the limit 832, the processor 400 continues along the "No" branch and returns a value 834 to the results 710 block that indicates that no inflection point was found in the sampled frequency signal and, therefore, no change in tissue state was detected. However, if the difference between the "Slope EWMA" and the "Slope Avg" is greater than the limit 832, the processor 400 continues along the "Yes" branch and determines that a frequency inflection point 836 was found and returns point index 838 to the results 710 block indicating that an inflection point was found in the sampled frequency data and, therefore, a change in tissue state was detected. As previously discussed with reference to FIG. 15A, if a frequency inflection point 836 is found, then, at 718 (FIG. 15A) the processor 400 activates the change in tissue state indicator 718.

FIG. 15C is a logic flow diagram 900 illustrating one form of the operation of the voltage drop analysis module. At 902, a voltage sample is received by the processor 400 from 708 of the logic flow diagram 700. At 904, the processor 400 calculates an exponentially weighted moving average (EWMA) for the voltage drop point analysis. The EWMA is calculated to filter out noise from the generator from the voltage samples. The EWMA is calculated in accordance with a voltage moving average equation 906 and an alpha value ($\alpha$) 908:

$$S_{tv} = \alpha Y_{tv} + (1-\alpha) S_{tv-1} \quad (5)$$

Where:
$S_{tv}$=the current moving average of the sampled voltage signal;
$S_{tv-1}$=the previous moving average of the sampled voltage signal;
$\alpha$=the smoothing factor; and
$Y_{tv}$=current data point of the sampled voltage signal.

As previously discussed, the α value 908 may vary from 0 to 1 in accordance with a desired filtering or smoothing factor and may be selected based on the ultrasonic instrument type and power level. In one form, blocks 904, 906, and 908 may be implemented as a variable digital low pass filter 910 with the α value 908 determining the cutoff point of the filter 910. Once the voltage samples are filtered, the slope of the voltage samples is calculated at 912 as:

$$\text{Voltage Slope} = \text{delta}v/\text{delta}t \quad (6)$$

The calculated Voltage Slope data points are provided to a "slow response" moving average filter 914 to calculate the EWMA moving average for the Voltage Slope to further reduce system noise. In one form, the "slow response" moving average filter 914 may be implemented by calculating the EWMA for the Voltage Slope at 918 in accordance with the voltage slope moving average equation 920 and alpha value (α') 822:

$$S'_{t_v} = \alpha' Y'_{t_v} + (1-\alpha')S'_{t_v-1} \quad (7)$$

Where:
$S'_{t_v}$ = the current moving average of the voltage slope of the sampled voltage signal;
$S'_{t_v-1}$ = the previous moving average of the voltage slope of the sampled voltage signal;
α' = the smoothing factor; and
$Y'_{t_v}$ = current slope data point of the sampled voltage signal.

The α' value 922 varies from about 0 to about 1, as previously discussed with respect to digital filter block 910 in accordance with a desired filtering or smoothing factor, wherein small α' value 922 approaching about 0 provide a large amount of filtering or smoothing and large α' value 922 approaching about 1 provide a small amount of filtering or smoothing. The α' value 922 may be selected based on the ultrasonic instrument type and power level.

The calculated Voltage Slope data points are provided to a "fast response" filter 916 to calculate the moving average for the Voltage Slope. At 924, the "fast response" filter 916 calculates the moving average for the Voltage Slope based on a number of data points 926.

In the illustrated form, the output of the "slow response" moving average filter 914 "Slope EWMA" is applied to a (+) input of an adder 928 and the output of the "fast response" filter 916 "Slope Avg" is applied to (−) input of the adder 928. The adder 928 computes the difference between the outputs of the "slow response" moving average filter 914 and the "fast response" filter 916. The difference between these outputs is compared at 930 to a predetermined limit 932. The limit 932 is determined based on the type of ultrasonic instrument and the power level at which the particular type of ultrasonic instrument is energized at. The limit 932 value may be predetermined and stored in memory in the form of a look-up table or the like. If the difference between the "Slope EWMA" and the "Slope Avg" is not greater than the limit 932, the processor 400 continues along the "No" branch and resets a counter to zero at 940, then returns a value 934 to the results 710 block that indicates that no voltage drop point was found in the sampled voltage signals and, therefore, no change in tissue state was detected. However, if the difference between the "Slope EWMA" and the "Slope Avg" is greater than the limit 932, the processor 400 continues along the "Yes" branch and increments a counter at 942. At 944, the processor 400 decides whether the counter is greater than 1, or some other predetermined threshold value for example. In other words, the processor 400 takes at least two data points in regards to the voltage drop point. If the counter is not greater than the threshold (e.g., 1 in the illustrated form) the processor 400 continues along the "No" branch and returns a value 934 to the results 710 block that indicates that no voltage drop point was found in the sampled voltage signals and, therefore, no change in tissue state was detected. If the counter is greater than the threshold (e.g., 1 in the illustrated form) the processor 400 continues along the "Yes" branch and determines that a voltage drop point 936 was found and returns a point index 938 to the results 712 block indicating that a voltage drop point was found in the sampled voltage signals and, therefore, a change in tissue state was detected. As previously discussed with reference to FIG. 15A, if a voltage point 836 is found, then, at 718 (FIG. 15A) the processor 400 activates the change in tissue state indicator 718.

Figure 16:
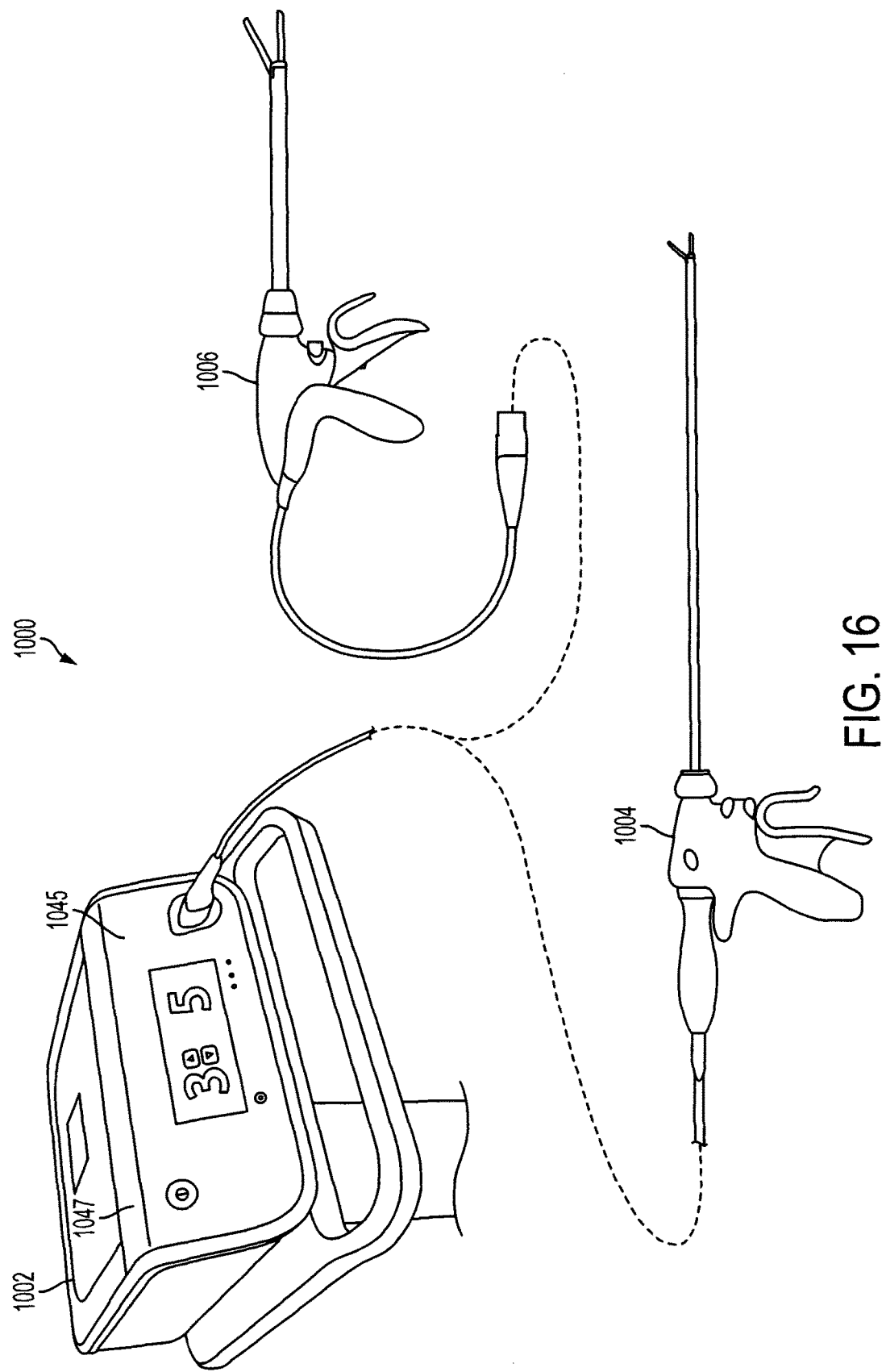
FIG. 16 illustrates one form of a surgical system comprising a generator and various surgical instruments usable therewith.
Figure 16A:
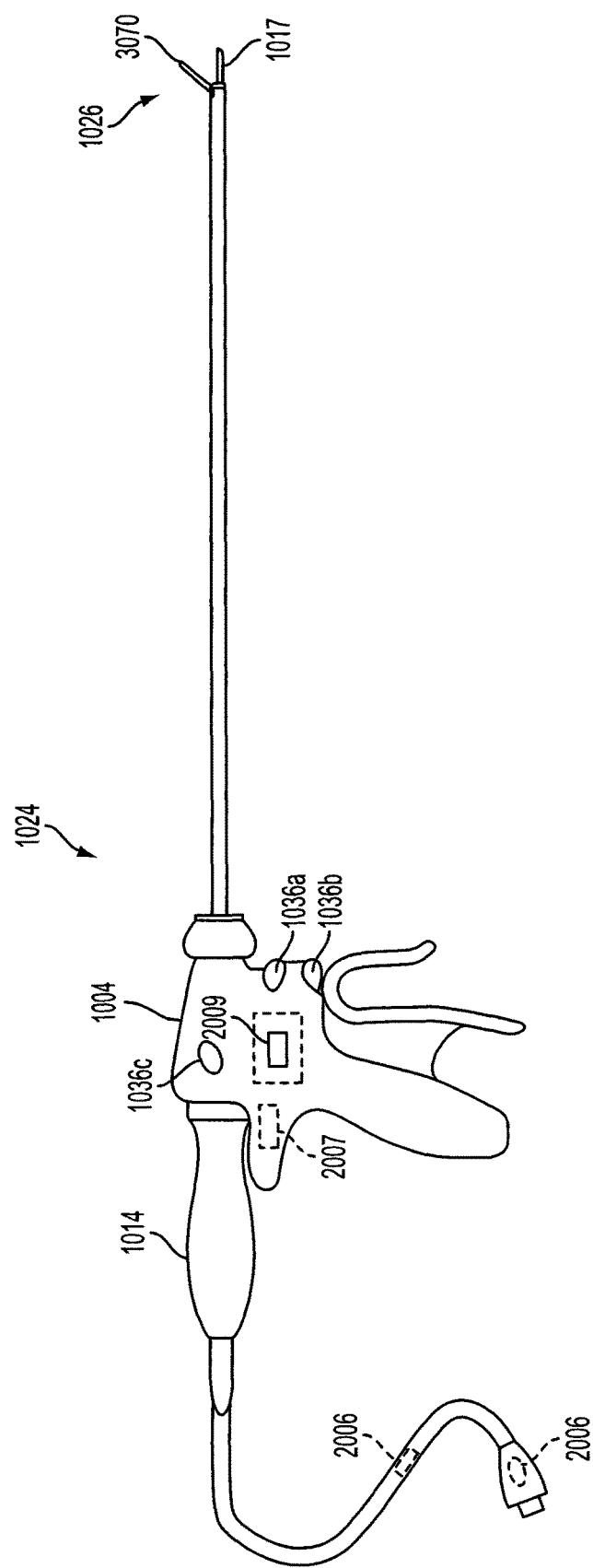
FIG. 16A is a diagram of the ultrasonic surgical instrument of FIG. 16.

FIG. 16 illustrates one form of a surgical system 1000 comprising a generator 1002 and various surgical instruments 1004, 1006 usable therewith. FIG. 16A is a diagram of the ultrasonic surgical instrument 1004 of FIG. 16. The generator 1002 is configurable for use with surgical devices. According to various forms, the generator 1002 may be configurable for use with different surgical devices of different types including, for example, the ultrasonic device 1004 and electrosurgical or RF surgical devices, such as, the RF device 1006. Although in the form of FIG. 16, the generator 1002 is shown separate from the surgical devices 1004, 1006, in one form, the generator 1002 may be formed integrally with either of the surgical devices 1004, 1006 to form a unitary surgical system. The generator 1002 comprises an input device 1045 located on a front panel of the generator 1002 console. The input device 1045 may comprise any suitable device that generates signals suitable for programming the operation of the generator 1002.

Figure 17:
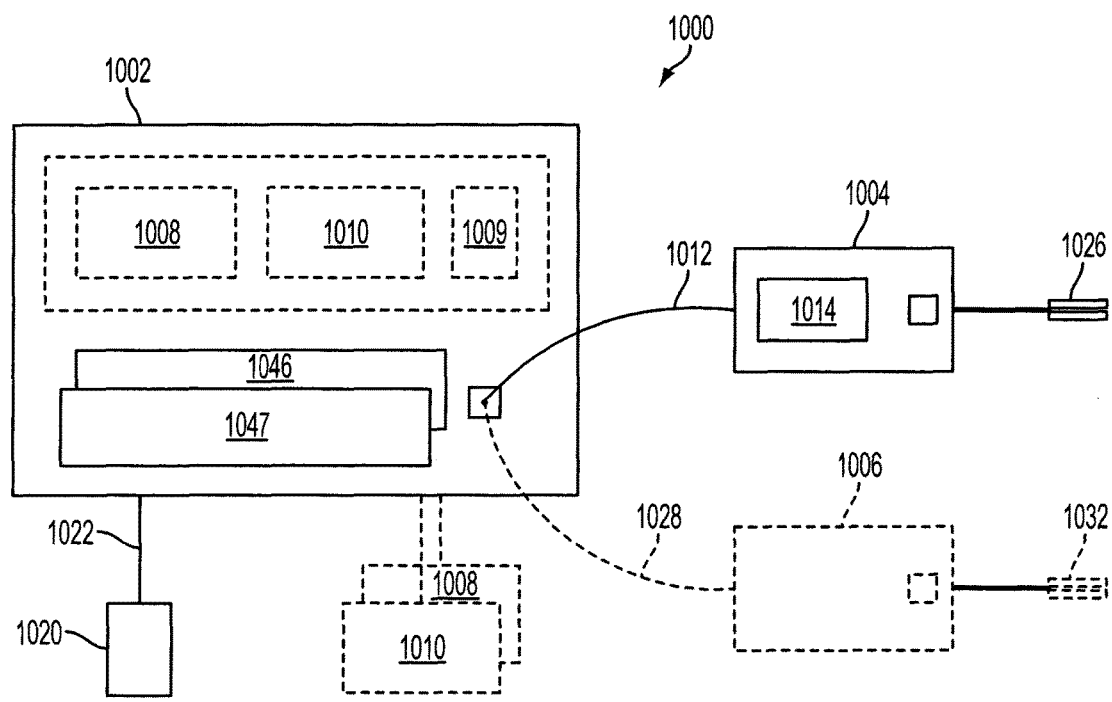
FIG. 17 is a diagram of the surgical system of FIG. 16.

FIG. 17 is a diagram of the surgical system 1000 of FIG. 16. In various forms, the generator 1002 may comprise several separate functional elements, such as modules and/or blocks. Different functional elements or modules may be configured for driving the different kinds of surgical devices 1004, 1006. For example, an ultrasonic generator module 1008 may drive ultrasonic devices such as the ultrasonic device 1004. An electrosurgery/RF generator module 1010 may drive the electrosurgical device 1006. For example, the respective modules 1008, 1010 may generate respective drive signals for driving the surgical devices 1004, 1006. In various forms, the ultrasonic generator module 1008 and/or the electrosurgery/RF generator module 1010 each may be formed integrally with the generator 1002. Alternatively, one or more of the modules 1008, 1010 may be provided as a separate circuit module electrically coupled to the generator 1002. (The modules 1008 and 1010 are shown in phantom to illustrate this option.) Also, in some forms, the electrosurgery/RF generator module 1010 may be formed integrally with the ultrasonic generator module 1008, or vice versa. Also, in some forms, the generator 1002 may be omitted entirely and the modules 1008, 1010 may be executed by processors or other hardware within the respective instruments 1004, 1006.

In accordance with the described forms, the ultrasonic generator module 1008 may produce a drive signal or signals of particular voltages, currents, and frequencies, e.g., 55,500 cycles per second (Hz). The drive signal or signals may be provided to the ultrasonic device 1004, and specifically to the transducer 1014, which may operate, for example, as described above. The transducer 1014 and a waveguide extending through the shaft 1015 (waveguide not shown in FIG. 16A) may collectively form an ultrasonic drive system driving an ultrasonic blade 1017 of an end effector 1026. In one form, the generator 1002 may be configured to produce a drive signal of a particular voltage, current, and/or frequency output signal that can be stepped or otherwise modified with high resolution, accuracy, and repeatability.

The generator 1002 may be activated to provide the drive signal to the transducer 1014 in any suitable manner. For example, the generator 1002 may comprise a foot switch 1020 coupled to the generator 1002 via a footswitch cable 1022. A clinician may activate the transducer 1014 by depressing the foot switch 1020. In addition, or instead of the foot switch 1020 some forms of the ultrasonic device 1004 may utilize one or more switches positioned on the hand piece that, when activated, may cause the generator 1002 to activate the transducer 1014. In one form, for example, the one or more switches may comprise a pair of toggle buttons 1036a, 1036b (FIG. 16A), for example, to determine an operating mode of the device 1004. When the toggle button 1036a is depressed, for example, the ultrasonic generator 1002 may provide a maximum drive signal to the transducer 1014, causing it to produce maximum ultrasonic energy output. Depressing toggle button 1036b may cause the ultrasonic generator 1002 to provide a user-selectable drive signal to the transducer 1014, causing it to produce less than the maximum ultrasonic energy output. The device 1004 additionally or alternatively may comprise a second switch (not shown) to, for example, indicate a position of a jaw closure trigger for operating jaws of the end effector 1026. Also, in some forms, the ultrasonic generator 1002 may be activated based on the position of the jaw closure trigger, (e.g., as the clinician depresses the jaw closure trigger to close the jaws, ultrasonic energy may be applied).

Additionally or alternatively, the one or more switches may comprises a toggle button 1036c that, when depressed, causes the generator 1002 to provide a pulsed output. The pulses may be provided at any suitable frequency and grouping, for example. In certain forms, the power level of the pulses may be the power levels associated with toggle buttons 1036a, 1036b (maximum, less than maximum), for example.

It will be appreciated that a device 1004 may comprise any combination of the toggle buttons 1036a, 1036b, 1036c. For example, the device 1004 could be configured to have only two toggle buttons: a toggle button 1036a for producing maximum ultrasonic energy output and a toggle button 1036c for producing a pulsed output at either the maximum or less than maximum power level. In this way, the drive signal output configuration of the generator 1002 could be 5 continuous signals and 5 or 4 or 3 or 2 or 1 pulsed signals. In certain forms, the specific drive signal configuration may be controlled based upon, for example, EEPROM settings in the generator 1002 and/or user power level selection(s).

In certain forms, a two-position switch may be provided as an alternative to a toggle button 1036c. For example, a device 1004 may include a toggle button 1036a for producing a continuous output at a maximum power level and a two-position toggle button 1036b. In a first detented position, toggle button 1036b may produce a continuous output at a less than maximum power level, and in a second detented position the toggle button 1036b may produce a pulsed output (e.g., at either a maximum or less than maximum power level, depending upon the EEPROM settings).

In accordance with the described forms, the electrosurgery/RF generator module 1010 may generate a drive signal or signals with output power sufficient to perform bipolar electrosurgery using radio frequency (RF) energy. In bipolar electrosurgery applications, the drive signal may be provided, for example, to electrodes of the electrosurgical device 1006, for example. Accordingly, the generator 1002 may be configured for therapeutic purposes by applying electrical energy to the tissue sufficient for treating the tissue (e.g., coagulation, cauterization, tissue welding).

The generator 1002 may comprise an input device 1045 (FIG. 16) located, for example, on a front panel of the generator 1002 console. The input device 1045 may comprise any suitable device that generates signals suitable for programming the operation of the generator 1002. In operation, the user can program or otherwise control operation of the generator 1002 using the input device 1045. The input device 1045 may comprise any suitable device that generates signals that can be used by the generator (e.g., by one or more processors contained in the generator) to control the operation of the generator 1002 (e.g., operation of the ultrasonic generator module 1008 and/or electrosurgery/RF generator module 1010). In various forms, the input device 1045 includes one or more of buttons, switches, thumbwheels, keyboard, keypad, touch screen monitor, pointing device, remote connection to a general purpose or dedicated computer. In other forms, the input device 1045 may comprise a suitable user interface, such as one or more user interface screens displayed on a touch screen monitor, for example. Accordingly, by way of the input device 1045, the user can set or program various operating parameters of the generator, such as, for example, current (I), voltage (V), frequency (f), and/or period (T) of a drive signal or signals generated by the ultrasonic generator module 1008 and/or electrosurgery/RF generator module 1010.

The generator 1002 may also comprise an output device 1047 (FIG. 16), such as an output indicator, located, for example, on a front panel of the generator 1002 console. The output device 1047 includes one or more devices for providing a sensory feedback to a user. Such devices may comprise, for example, visual feedback devices (e.g., a visual feedback device may comprise incandescent lamps, light emitting diodes (LEDs), graphical user interface, display, analog indicator, digital indicator, bar graph display, digital alphanumeric display, LCD display screen, LED indicators), audio feedback devices (e.g., an audio feedback device may comprise speaker, buzzer, audible, computer generated tone, computerized speech, voice user interface (VUI) to interact with computers through a voice/speech platform), or tactile feedback devices (e.g., a tactile feedback device comprises any type of vibratory feedback, haptic actuator).

Although certain modules and/or blocks of the generator 1002 may be described by way of example, it can be appreciated that a greater or lesser number of modules and/or blocks may be used and still fall within the scope of the forms. Further, although various forms may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components. Also, in some forms, the various modules described herein may be implemented utilizing similar hardware positioned within the instruments 100, 120, 1004, 1006 (i.e., the generator 30, 50, 1002 may be omitted).

In one form, the ultrasonic generator drive module 1008 and electrosurgery/RF drive module 1010 may comprise one or more embedded applications implemented as firmware, software, hardware, or any combination thereof. The modules 1008, 1010 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one form, the modules 1008, 1010 comprise a hardware component implemented as a processor for executing program instructions for monitoring various measurable characteristics of the devices 1004, 1006 and generating a corresponding output control signals for operating the devices 1004, 1006. In forms in which the generator 1002 is used in conjunction with the device 1004, the output control signal may drive the ultrasonic transducer 1014 in cutting and/or coagulation operating modes. Electrical characteristics of the device 1004 and/or tissue may be measured and used to control operational aspects of the generator 1002 and/or provided as feedback to the user. In forms in which the generator 1002 is used in conjunction with the device 1006, the output control signal may supply electrical energy (e.g., RF energy) to the end effector 1032 in cutting, coagulation and/or desiccation modes. Electrical characteristics of the device 1006 and/or tissue may be measured and used to control operational aspects of the generator 1002 and/or provide feedback to the user. In various forms, as previously discussed, the hardware component may be implemented as a DSP, PLD, ASIC, circuits, and/or registers. In one form, the processor may be configured to store and execute computer software program instructions to generate the step function output signals for driving various components of the devices 1004, 1006, such as the ultrasonic transducer 1014 and the end effectors 1026, 1032.

Figure 18:
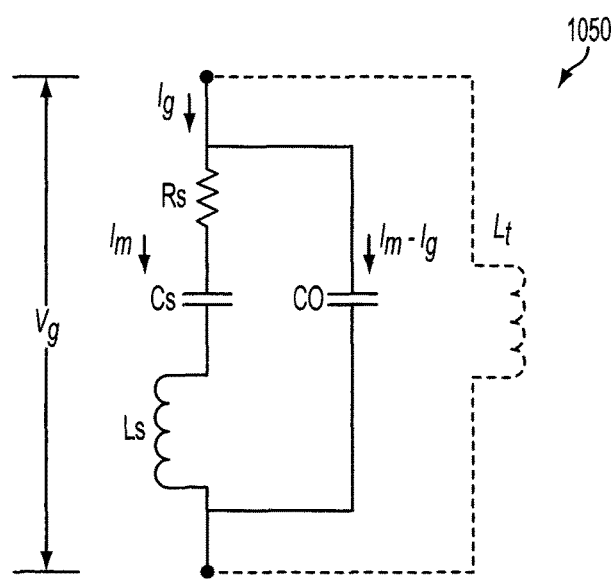
FIG. 18 is a model illustrating motional branch current in one form.

FIG. 18 illustrates an equivalent circuit 1050 of an ultrasonic transducer, such as the ultrasonic transducer 1014, according to one form. The circuit 1050 comprises a first "motional" branch having a serially connected inductance $L_s$, resistance $R_s$ and capacitance $C_s$ that define the electromechanical properties of the resonator, and a second capacitive branch having a static capacitance $C_o$. Drive current $I_g$ may be received from a generator at a drive voltage $V_g$, with motional current $I_m$ flowing through the first branch and current $I_g$-$I_m$ flowing through the capacitive branch. Control of the electromechanical properties of the ultrasonic transducer may be achieved by suitably controlling $I_g$ and $V_g$. As explained above, conventional generator architectures may include a tuning inductor $L_t$ (shown in phantom in FIG. 18) for tuning out in a parallel resonance circuit the static capacitance Co at a resonant frequency so that substantially all of generator's current output $I_g$ flows through the motional branch. In this way, control of the motional branch current $I_m$ is achieved by controlling the generator current output $I_g$. The tuning inductor $L_t$ is specific to the static capacitance $C_o$ of an ultrasonic transducer, however, and a different ultrasonic transducer having a different static capacitance requires a different tuning inductor $L_t$. Moreover, because the tuning inductor $L_t$ is matched to the nominal value of the static capacitance Co at a single resonant frequency, accurate control of the motional branch current $I_m$ is assured only at that frequency, and as frequency shifts down with transducer temperature, accurate control of the motional branch current is compromised.

Forms of the generator 1002 do not rely on a tuning inductor $L_t$ to monitor the motional branch current $I_m$. Instead, the generator 1002 may use the measured value of the static capacitance $C_o$ in between applications of power for a specific ultrasonic surgical device 1004 (along with drive signal voltage and current feedback data) to determine values of the motional branch current $I_m$ on a dynamic and ongoing basis (e.g., in real-time). Such forms of the generator 1002 are therefore able to provide virtual tuning to simulate a system that is tuned or resonant with any value of static capacitance $C_o$ at any frequency, and not just at single resonant frequency dictated by a nominal value of the static capacitance $C_o$.

Figure 19:
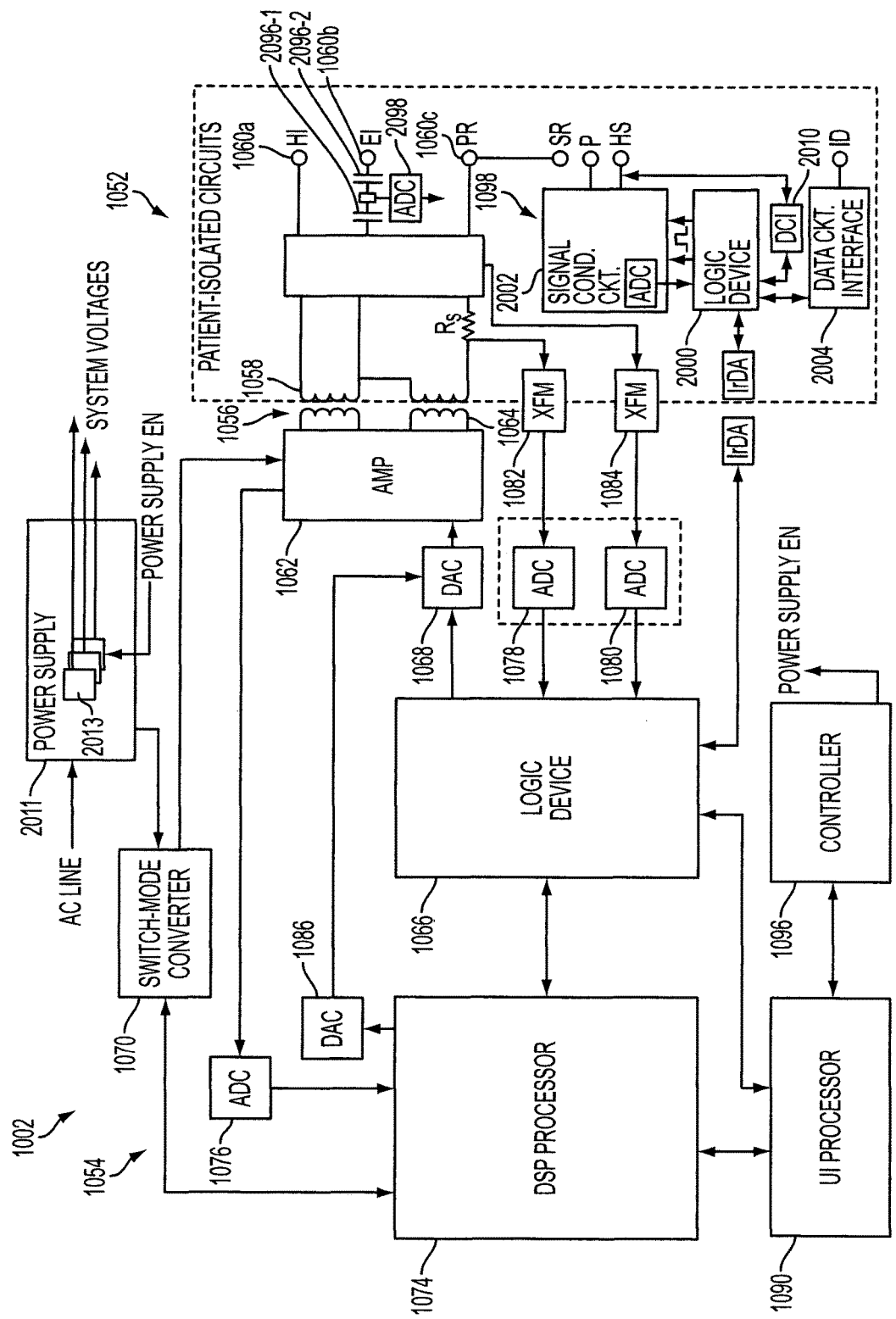
FIG. 19 is a structural view of a generator architecture in one form.

FIG. 19 is a simplified block diagram of one form of the generator 1002 for proving inductorless tuning as described above, among other benefits. Additional details of the generator 1002 are described in commonly assigned and contemporaneously filed U.S. patent application Ser. No. 12/896,360, entitled "Surgical Generator For Ultrasonic And Electrosurgical Devices," now U.S. Pat. No. 9,060,775, the disclosure of which is incorporated herein by reference in its entirety. With reference to FIG. 19, the generator 1002 may comprise a patient isolated stage 1052 in communication with a non-isolated stage 1054 via a power transformer 1056. A secondary winding 1058 of the power transformer 1056 is contained in the isolated stage 1052 and may comprise a tapped configuration (e.g., a center-tapped or a non-center-tapped configuration) to define drive signal outputs 1060a, 1060b, 1060c for outputting drive signals to different surgical devices, such as, for example, an ultrasonic surgical device 1004 and an electrosurgical device 1006. In particular, drive signal outputs 1060a, 1060c may output an ultrasonic drive signal (e.g., a 420V RMS drive signal) to an ultrasonic surgical device 1004, and drive signal outputs 1060b, 1060c may output an electrosurgical drive signal (e.g., a 100V RMS drive signal) to an electrosurgical device 1006, with output 1060b corresponding to the center tap of the power transformer 1056.

In certain forms, the ultrasonic and electrosurgical drive signals may be provided simultaneously to distinct surgical instruments and/or to a single surgical instrument having the capability to deliver both ultrasonic and electrosurgical energy to tissue. An example of a blade 79 and clamp arm assembly 415 of one example form of such a surgical instrument is provided above in conjunction with FIG. 13. It will be appreciated that the electrosurgical signal, provided either to a dedicated electrosurgical instrument and/or to a combined ultrasonic/electrosurgical instrument may be either a therapeutic or sub-therapeutic level signal.

The non-isolated stage 1054 may comprise a power amplifier 1062 having an output connected to a primary winding 1064 of the power transformer 1056. In certain forms the power amplifier 1062 may be comprise a push-pull amplifier. For example, the non-isolated stage 1054 may further comprise a logic device 1066 for supplying a digital output to a digital-to-analog converter (DAC) 1068, which in turn supplies a corresponding analog signal to an input of the power amplifier 1062. In certain forms the logic device 1066 may comprise a programmable gate array (PGA), a field-programmable gate array (FPGA), programmable logic device (PLD), among other logic circuits, for example. The logic device 1066, by virtue of controlling the input of the power amplifier 1062 via the DAC 1068, may therefore control any of a number of parameters (e.g., frequency, waveform shape, waveform amplitude) of drive signals appearing at the drive signal outputs 1060a, 1060b, 1060c. In certain forms and as discussed below, the logic device 1066, in conjunction with a processor (e.g., a digital signal processor discussed below), may implement a number of digital signal processing (DSP)-based and/or other control algorithms to control parameters of the drive signals output by the generator 1002.

Power may be supplied to a power rail of the power amplifier 1062 by a switch-mode regulator 1070. In certain forms the switch-mode regulator 1070 may comprise an adjustable buck regulator, for example. The non-isolated stage 1054 may further comprise a first processor 1074, which in one form may comprise a DSP processor such as an Analog Devices ADSP-21469 SHARC DSP, available from Analog Devices, Norwood, Mass., for example, although in various forms any suitable processor may be employed. In certain forms the processor 1074 may control operation of the switch-mode power converter 1070 responsive to voltage feedback data received from the power amplifier 1062 by the DSP processor 1074 via an analog-to-digital converter (ADC) 1076. In one form, for example, the DSP processor 1074 may receive as input, via the ADC 1076, the waveform envelope of a signal (e.g., an RF signal) being amplified by the power amplifier 1062. The DSP processor 1074 may then control the switch-mode regulator 1070 (e.g., via a pulse-width modulated (PWM) output) such that the rail voltage supplied to the power amplifier 1062 tracks the waveform envelope of the amplified signal. By dynamically modulating the rail voltage of the power amplifier 1062 based on the waveform envelope, the efficiency of the power amplifier 1062 may be significantly improved relative to a fixed rail voltage amplifier schemes.

In certain forms, the logic device 1066, in conjunction with the DSP processor 1074, may implement a direct digital synthesizer (DDS) control scheme to control the waveform shape, frequency and/or amplitude of drive signals output by the generator 1002. In one form, for example, the logic device 1066 may implement a DDS control algorithm by recalling waveform samples stored in a dynamically-updated look-up table (LUT), such as a RAM LUT, which may be embedded in an FPGA. This control algorithm is particularly useful for ultrasonic applications in which an ultrasonic transducer, such as the ultrasonic transducer 1014, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 1002 is impacted by various sources of distortion present in the output drive circuit (e.g., the power transformer 1056, the power amplifier 1062), voltage and current feedback data based on the drive signal may be input into an algorithm, such as an error control algorithm implemented by the DSP processor 1074, which compensates for distortion by suitably pre-distorting or modifying the waveform samples stored in the LUT on a dynamic, ongoing basis (e.g., in real-time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 1054 may further comprise an ADC 1078 and an ADC 1080 coupled to the output of the power transformer 1056 via respective isolation transformers 1082, 1084 for respectively sampling the voltage and current of drive signals output by the generator 1002. In certain forms, the ADCs 1078, 1080 may be configured to sample at high speeds (e.g., 80 MSPS) to enable oversampling of the drive signals. In one form, for example, the sampling speed of the ADCs 1078, 1080 may enable approximately 200× (depending on frequency) oversampling of the drive signals. In certain forms, the sampling operations of the ADC 1078, 1080 may be performed by a singe ADC receiving input voltage and current signals via a two-way multiplexer. The use of high-speed sampling in forms of the generator 1002 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADCs 1078, 1080 may be received and processed (e.g., FIFO buffering, multiplexing) by the logic device 1066 and stored in data memory for subsequent retrieval by, for example, the DSP processor 1074. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 1066 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 1074, for example, with the frequency control signal being supplied as input to a DDS control algorithm implemented by the logic device 1066.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a PID control algorithm, in the processor 1074. Variables controlled by the control algorithm to suitably control the current amplitude of the drive signal may include, for example, the scaling of the LUT waveform samples stored in the logic device 1066 and/or the full-scale output voltage of the DAC 1068 (which supplies the input to the power amplifier 1062) via a DAC 1086.

The non-isolated stage 1054 may further comprise a second processor 1090 for providing, among other things user interface (UI) functionality. In one form, the UI processor 1090 may comprise an Atmel AT91SAM9263 processor having an ARM 926EJ-S core, available from Atmel Corporation, San Jose, Calif., for example. Examples of UI functionality supported by the UI processor 1090 may include audible and visual user feedback, communication with peripheral devices (e.g., via a Universal Serial Bus (USB) interface), communication with the footswitch 1020, communication with an input device 1009 (e.g., a touch screen display) and communication with an output device 1047 (e.g., a speaker). The UI processor 1090 may communicate with the processor 1074 and the logic device 1066 (e.g., via serial peripheral interface (SPI) buses). Although the UI processor 1090 may primarily support UI functionality, it may also coordinate with the DSP processor 1074 to implement hazard mitigation in certain forms. For example, the UI processor 1090 may be programmed to monitor various aspects of user input and/or other inputs (e.g., touch screen inputs, footswitch 1020 inputs (FIG. 17), temperature sensor inputs) and may disable the drive output of the generator 1002 when an erroneous condition is detected.

In certain forms, both the DSP processor 1074 and the UI processor 1090, for example, may determine and monitor the operating state of the generator 1002. For the DSP processor 1074, the operating state of the generator 1002 may dictate, for example, which control and/or diagnostic processes are implemented by the DSP processor 1074. For the UI processor 1090, the operating state of the generator 1002 may dictate, for example, which elements of a user interface (e.g., display screens, sounds) are presented to a user. The respective DSP and UI processors 1074, 1090 may independently maintain the current operating state of the generator 1002 and recognize and evaluate possible transitions out of the current operating state. The DSP processor 1074 may function as the master in this relationship and determine when transitions between operating states are to occur. The UI processor 1090 may be aware of valid transitions between operating states and may confirm if a particular transition is appropriate. For example, when the DSP processor 1074 instructs the UI processor 1090 to transition to a specific state, the UI processor 1090 may verify that requested transition is valid. In the event that a requested transition between states is determined to be invalid by the UI processor 1090, the UI processor 1090 may cause the generator 1002 to enter a failure mode.

The non-isolated stage 1054 may further comprise a controller 1096 for monitoring input devices 1045 (e.g., a capacitive touch sensor used for turning the generator 1002 on and off, a capacitive touch screen). In certain forms, the controller 1096 may comprise at least one processor and/or other controller device in communication with the UI processor 1090. In one form, for example, the controller 1096 may comprise a processor (e.g., a Mega168 8-bit controller available from Atmel) configured to monitor user input provided via one or more capacitive touch sensors. In one form, the controller 1096 may comprise a touch screen controller (e.g., a QT5480 touch screen controller available from Atmel) to control and manage the acquisition of touch data from a capacitive touch screen.

In certain forms, when the generator 1002 is in a "power off" state, the controller 1096 may continue to receive operating power (e.g., via a line from a power supply of the generator 1002, such as the power supply 2011 discussed below). In this way, the controller 196 may continue to monitor an input device 1045 (e.g., a capacitive touch sensor located on a front panel of the generator 1002) for turning the generator 1002 on and off. When the generator 1002 is in the power off state, the controller 1096 may wake the power supply (e.g., enable operation of one or more DC/DC voltage converters 2013 of the power supply 2011) if activation of the "on/off" input device 1045 by a user is detected. The controller 1096 may therefore initiate a sequence for transitioning the generator 1002 to a "power on" state. Conversely, the controller 1096 may initiate a sequence for transitioning the generator 1002 to the power off state if activation of the "on/off" input device 1045 is detected when the generator 1002 is in the power on state. In certain forms, for example, the controller 1096 may report activation of the "on/off" input device 1045 to the processor 1090, which in turn implements the necessary process sequence for transitioning the generator 1002 to the power off state. In such forms, the controller 196 may have no independent ability for causing the removal of power from the generator 1002 after its power on state has been established.

In certain forms, the controller 1096 may cause the generator 1002 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 1052 may comprise an instrument interface circuit 1098 to, for example, provide a communication interface between a control circuit of a surgical device (e.g., a control circuit comprising hand piece switches) and components of the non-isolated stage 1054, such as, for example, the programmable logic device 1066, the DSP processor 1074 and/or the UI processor 190. The instrument interface circuit 1098 may exchange information with components of the non-isolated stage 1054 via a communication link that maintains a suitable degree of electrical isolation between the stages 1052, 1054, such as, for example, an infrared (IR)-based communication link. Power may be supplied to the instrument interface circuit 1098 using, for example, a low-dropout voltage regulator powered by an isolation transformer driven from the non-isolated stage 1054.

In one form, the instrument interface circuit 198 may comprise a logic device 2000 (e.g., logic circuit, programmable logic circuit, PGA, FPGA, PLD) in communication with a signal conditioning circuit 2002. The signal conditioning circuit 2002 may be configured to receive a periodic signal from the logic circuit 2000 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical device control circuit (e.g., by using a conductive pair in a cable that connects the generator 102 to the surgical device) and monitored to determine a state or configuration of the control circuit. The control circuit may comprise a number of switches, resistors and/or diodes to modify one or more characteristics (e.g., amplitude, rectification) of the interrogation signal such that a state or configuration of the control circuit is uniquely discernable based on the one or more characteristics. In one form, for example, the signal conditioning circuit 2002 may comprises an ADC for generating samples of a voltage signal appearing across inputs of the control circuit resulting from passage of interrogation signal therethrough. The logic device 2000 (or a component of the non-isolated stage 1054) may then determine the state or configuration of the control circuit based on the ADC samples.

In one form, the instrument interface circuit 1098 may comprise a first data circuit interface 2004 to enable information exchange between the logic circuit 2000 (or other element of the instrument interface circuit 1098) and a first data circuit disposed in or otherwise associated with a surgical device. In certain forms, for example, a first data circuit 2006 (FIG. 16A) may be disposed in a cable integrally attached to a surgical device hand piece, or in an adaptor for interfacing a specific surgical device type or model with the generator 1002. The data circuit 2006 may be implemented in any suitable manner and may communicate with the generator according to any suitable protocol including, for example, as described herein with respect to the circuit 6006. In certain forms, the first data circuit may comprise a non-volatile storage device, such as an electrically erasable programmable read-only memory (EEPROM) device. In certain forms and referring again to FIG. 19, the first data circuit interface 2004 may be implemented separately from the logic device 2000 and comprise suitable circuitry (e.g., discrete logic devices, a processor) to enable communication between the programmable logic device 2000 and the first data circuit. In other forms, the first data circuit interface 2004 may be integral with the logic device 2000.

In certain forms, the first data circuit 2006 may store information pertaining to the particular surgical device with which it is associated. Such information may include, for example, a model number, a serial number, a number of operations in which the surgical device has been used, and/or any other type of information. This information may be read by the instrument interface circuit 1098 (e.g., by the logic device 2000), transferred to a component of the non-isolated stage 1054 (e.g., to logic device 1066, DSP processor 1074 and/or UI processor 1090) for presentation to a user via an output device 1047 and/or for controlling a function or operation of the generator 1002. Additionally, any type of information may be communicated to first data circuit 2006 for storage therein via the first data circuit interface 2004 (e.g., using the logic device 2000). Such information may comprise, for example, an updated number of operations in which the surgical device has been used and/or dates and/or times of its usage.

As discussed previously, a surgical instrument may be detachable from a hand piece (e.g., instrument 1024 may be detachable from hand piece 1014) to promote instrument interchangeability and/or disposability. In such cases, conventional generators may be limited in their ability to recognize particular instrument configurations being used and to optimize control and diagnostic processes accordingly. The addition of readable data circuits to surgical device instruments to address this issue is problematic from a compatibility standpoint, however. For example, designing a surgical device to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical devices with current generator platforms.

Additionally, forms of the generator 1002 may enable communication with instrument-based data circuits. For example, the generator 1002 may be configured to communicate with a second data circuit 2007 contained in an instrument (e.g., instrument 1024) of a surgical device (FIG. 16A). In some forms, the second data circuit 2007 may be implemented in a many similar to that of the data circuit 6006 described herein. The instrument interface circuit 1098 may comprise a second data circuit interface 2010 to enable this communication. In one form, the second data circuit interface 2010 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information. In some forms, the second data circuit 2007 may store information about the electrical and/or ultrasonic properties of an associated transducer 1014, end effector 1026, or ultrasonic drive system. For example, the first data circuit 2006 may indicate a burn-in frequency slope, as described herein. Additionally or alternatively, any type of information may be communicated to second data circuit for storage therein via the second data circuit interface 2010 (e.g., using the logic device 2000). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 1002 and provide an indication to a user (e.g., an LED indication or other visible indication) based on the received data.

In certain forms, the second data circuit and the second data circuit interface 2010 may be configured such that communication between the logic device 2000 and the second data circuit can be effected without the need to provide additional conductors for this purpose (e.g., dedicated conductors of a cable connecting a hand piece to the generator 1002). In one form, for example, information may be communicated to and from the second data circuit using a 1-wire bus communication scheme implemented on existing cabling, such as one of the conductors used transmit interrogation signals from the signal conditioning circuit 2002 to a control circuit in a hand piece. In this way, design changes or modifications to the surgical device that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical device instrument.

In certain forms, the isolated stage 1052 may comprise at least one blocking capacitor 2096-1 connected to the drive signal output 1060*b* to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 2096-2 may be provided in series with the blocking capacitor 2096-1, with current leakage from a point between the blocking capacitors 2096-1, 2096-2 being monitored by, for example, an ADC 2098 for sampling a voltage induced by leakage current. The samples may be received by the logic circuit 2000, for example. Based changes in the leakage current (as indicated by the voltage samples in the form of FIG. 19), the generator 1002 may determine when at least one of the blocking capacitors 2096-1, 2096-2 has failed. Accordingly, the form of FIG. 19 provides a benefit over single-capacitor designs having a single point of failure.

In certain forms, the non-isolated stage 1054 may comprise a power supply 2011 for outputting DC power at a suitable voltage and current. The power supply may comprise, for example, a 400 W power supply for outputting a 48 VDC system voltage. The power supply 2011 may further comprise one or more DC/DC voltage converters 2013 for receiving the output of the power supply to generate DC outputs at the voltages and currents required by the various components of the generator 1002. As discussed above in connection with the controller 1096, one or more of the DC/DC voltage converters 2013 may receive an input from the controller 1096 when activation of the "on/off" input device 1045 by a user is detected by the controller 1096 to enable operation of, or wake, the DC/DC voltage converters 2013.

Having described operational details of various forms of the surgical systems 19 (FIG. 1), 190 (FIG. 10), 1000 (FIG. 16) operations for the above surgical systems 19, 190, 1000 may be further described generally in terms of a process for cutting and coagulating tissue employing a surgical instrument comprising an input device 406, 1045 and the generator 1002. Although a particular process is described in connection with the operational details, it can be appreciated that the process merely provides an example of how the general functionality described herein can be implemented by any one of the surgical systems 19, 190, 1000. Further, the given process does not necessarily have to be executed in the order presented herein unless otherwise indicated. As previously discussed, any one the input devices 406, 1045 may be employed to program the output (e.g., impedance, current, voltage, frequency) of the surgical devices 100 (FIG. 1), 120 (FIG. 10), 1002 (FIG. 16), 1006 (FIG. 16).

Figure 20:
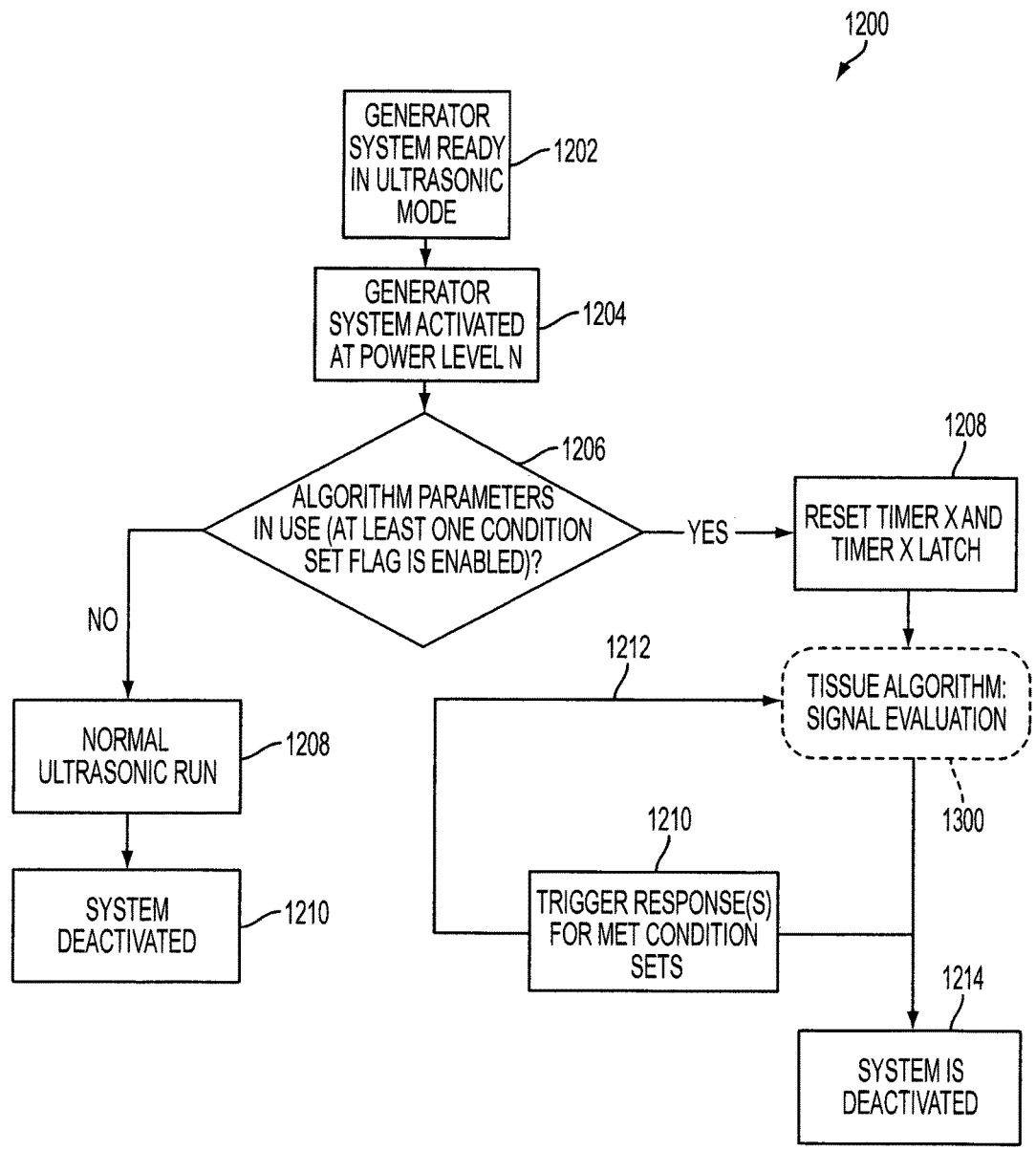
FIG. 20 is a logic flow diagram of a tissue algorithm that may be implemented in one form of a generator.
Figure 21:
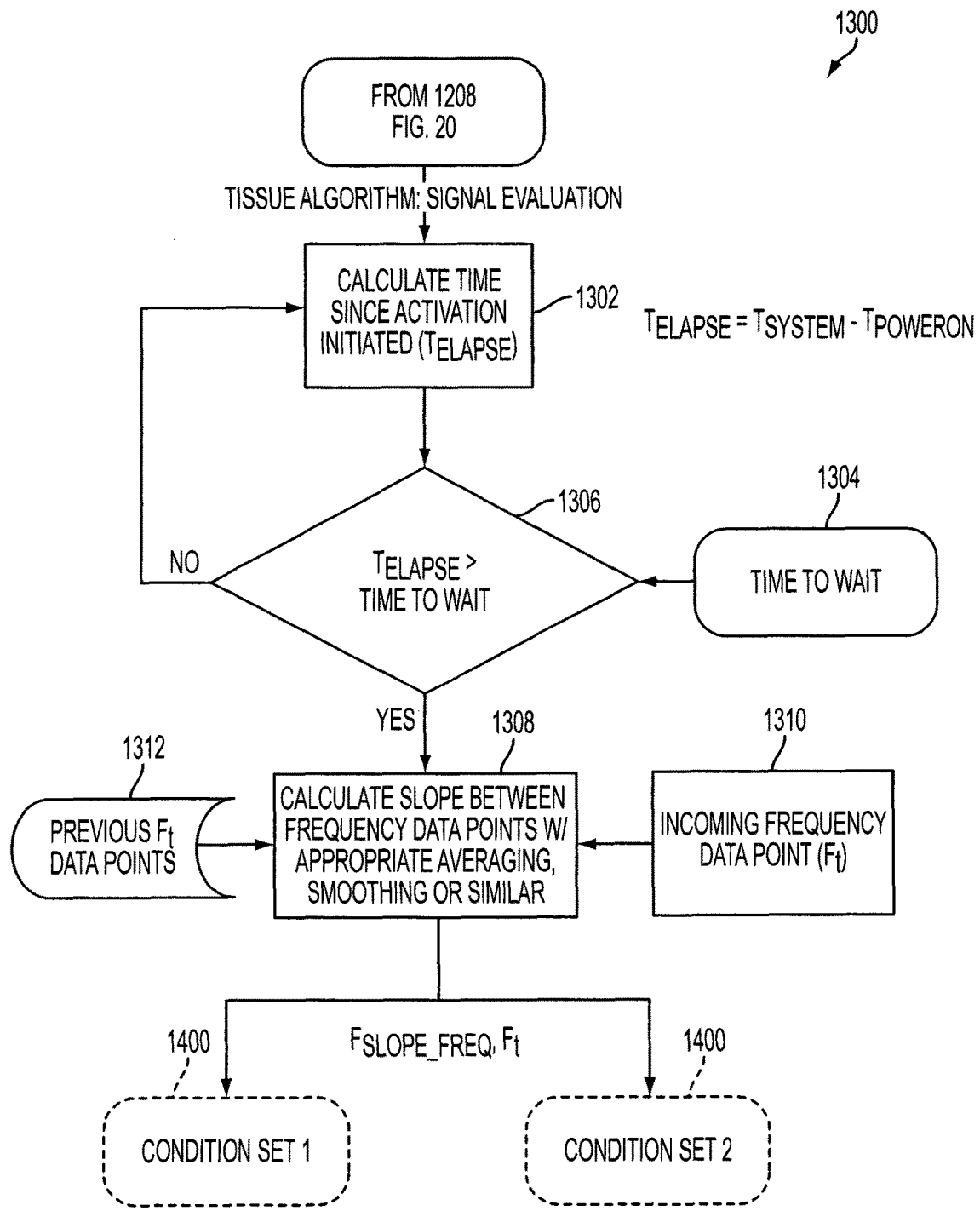
FIG. 21 is a logic flow diagram of a signal evaluation tissue algorithm portion of the tissue algorithm shown in FIG. 20 that may be implemented in one form of a generator.
Figure 22:
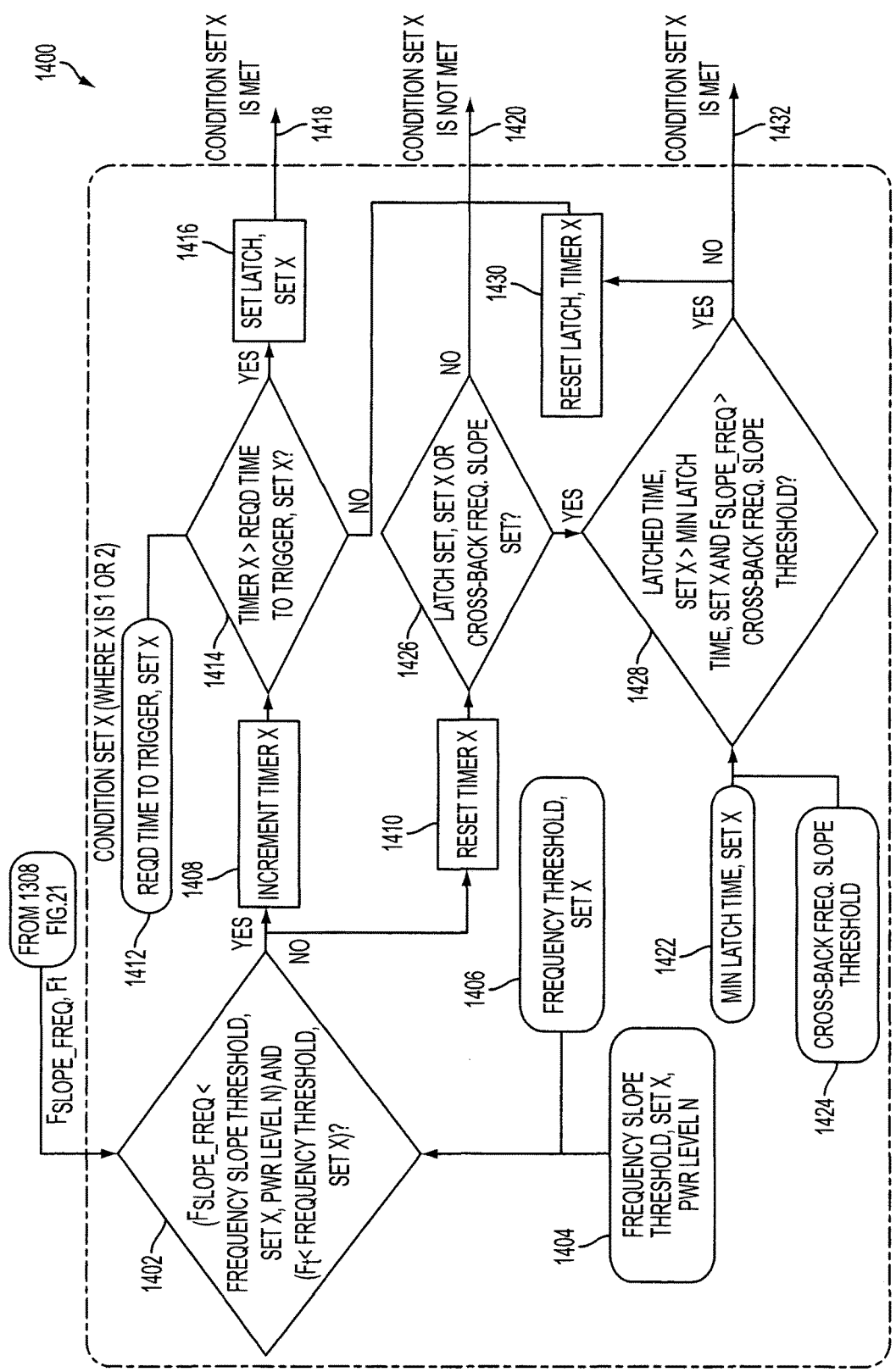
FIG. 22 is a logic flow diagram for evaluating condition sets for the signal evaluation tissue algorithm shown in FIG. 21 that may be implemented in one form of a generator.

FIGS. 20-22 illustrate various forms of logic flow diagrams of 1200, 1300, 1400 related to a tissue algorithm for detecting when rapid heating of the ultrasonic end effector 1026 blade occurs and provide the opportunity for generating visual, audible and/or tactile feedback and/or changing an operational mode of the instrument and/or generator. For example, feedback may be provided via the output indicator 412 (FIGS. 9, 11) and/or the output device 1047 (FIG. 16) (e.g., annunciation, modulation of power output and/or display of content). According to the present disclosure, when multiple reference numbers are used to described an element such as "ultrasonic surgical instrument 100, 120, 1004," it should be understood to reference any one of the elements, such as, for example, "ultrasonic surgical instrument 100," or "ultrasonic surgical instrument 120," or "ultrasonic surgical instrument 1004." It will be appreciated however, that any of the algorithms described herein are suitable for execution with any of the instruments 100, 120, 1004 described herein.

In various forms, feedback may be provided by the output indicator 412 shown in FIGS. 9 and 11 or the output device 1047 in FIG. 16. These feedback devices (e.g., output indicator 412, output device 1047) are particularly useful in applications where the tissue being manipulated by the end effector 81 (FIG. 1), 810 (FIG. 10), 1026 (FIG. 16) is out of the user's field of view and the user cannot see when a change of state occurs in the tissue. The feedback device communicates to the user that a change in tissue state has occurred as determined in accordance with the operations described with respect to the logic flow diagrams 700, 800, 900, 1200, 1300, 1400 as they relate to corresponding tissue algorithms. The feedback devices may be configured to provide various types of feedback according to the current state or condition of the tissue. A change of state of the tissue may be determined based on transducer and/or tissue measurements based on voltage, current, and frequency measurements in accordance with the operations described, for example, with respect to the logic flow diagrams 700, 800, 900 described above in connection with FIGS. 15A-C and the logic flow diagrams 1200, 1300, 1400 described below in connection with FIGS. 20-22, as well as the various other logic flow diagrams described herein In one form, the logic flow diagrams 1200, 1300, 1400 may be implemented as executable modules (e.g., algorithms) comprising computer readable instructions to be executed by the processor 400 (FIGS. 9, 11, 14) portion of the generator 30, 500 or the generator 1002 (FIGS. 16, 17, 19). In various forms, the operations described with respect to the logic flow diagrams 1200, 1300, 1400 may be implemented as one or more than one software component, e.g., program, subroutine, logic; one or more than one hardware components, e.g., processor, DSP, PLD, PGA, FPGA, ASIC, circuit, logic circuit, register; and/or combinations of software and hardware. In one form, the executable instructions to perform the operations described by the logic flow diagrams 1200, 1300, 1400 may be stored in memory. When executed, the instructions cause the processor 400, the DSP processor 1074 (FIG. 19) or logic device 1066 (FIG. 19) to determine a change in tissue state in accordance with the operations described in the logic flow diagrams 1200, 1300, and 1400 and provide feedback to the user by way of the output indicator 412 (FIGS. 9, 11) or output indicator 1047 (FIGS. 16, 17). In accordance with such executable instructions, the processor 400, DSP processor 1074, and/or logic device 1066 monitors and evaluates the voltage, current, and/or frequency signal samples available from the generator 30, 500, 1002 and according to the evaluation of such signal samples determines whether a change in tissue state has occurred. As further described below, a change in tissue state may be determined based on the type of ultrasonic instrument and the power level that the instrument is energized at. In response to the feedback, the operational mode of any one of the ultrasonic surgical instruments 100, 120, 1004 may be controlled by the user or may be automatically or semi-automatically controlled.

A brief summary of a tissue algorithm represented by way of the logic flow diagrams 1200, 1300, 1400 will now be described in connection with any one of the ultrasonic surgical instruments 100, 120, 1004 driven by a corresponding generator 30 (FIG. 1), 500 (FIG. 10), 1002 (FIG. 17). In one aspect, the tissue algorithm detects when the temperature of the blade portion (and therefore resonance) of the ultrasonic end effector 81 (FIG. 1), 810 (FIG. 10), 1026 (FIG. 17) is changing rapidly (of most interest is an increasing change). For a clamping or shears type instrument, this change may correspond to a common clinical scenario, among others, when minimal-to-no tissue, tissue debris or fluid is adjacent the blade and the blade is activated against the clamp arm, clamp pad or other suitable tissue biasing member. For non-clamping applications where an instrument with or without a clamp arm and associated mechanisms is used to effect tissue, this change corresponds to conditions where rapid heating occurs such as when the blade is activated against bone or other hard materials or when excessive force is used to couple the blade to tissue targets. These are illustrative cases; one can imagine other clinical scenarios where rapid blade heating may occur and such a tissue algorithm as described here is of benefit.

The tissue algorithm represented by the logic flow diagrams 1200, 1300, 1400 and any of the algorithms described herein may be employed in conjunction with any of the generators 30, 500, 1002 described herein, and other suitable generators such as the GEN 04, GEN 11 generators available from Ethicon Endo-Surgery, Inc. of Cincinnati, Ohio, and related devices, systems, that may leverage the algorithm or technology disclosed herein. Accordingly, in the description of the tissue algorithm in conjunction with the flow diagrams 1200, 1300, 1400 reference is made to the generators 30, 500, 1002 described in connection with corresponding FIGS. 1-9, 10-13, and 16-19.

Accordingly, with reference now to FIGS. 1-14, the frequency of the blade/hand piece resonant system of any one of the ultrasonic surgical instruments 100, 120, 1004 is dependent on temperature. When, for example, an ultrasonic shear type end effector cuts through a clamped piece of tissue, the blade heats and thins the tissue until ultimately it cuts through the tissue. At this point, the blade resides against the tissue pad and, if clamp pressure remains between the two, the blade and pad interface will draw power via the mechanical or vibratory motion of the blade relative to the pad. The power "deposited" at the interface will be largely conducted into the blade tip as the pad material is quite insulative. It is this thermal energy that alters the stiffness of the blade tip and the system resonance will change accordingly due to these localized (to the tip) conditions. The generator 30, 500, 1002 tracks this resonance. The shears example illustrates one scenario for which the algorithm is of use. Additional scenarios are back-cutting with a shears device with the clamp arm closed, blade cutting against tough or hard tissue, or any scenario in which knowing the thermal condition of the blade end-effector is desired. A tissue algorithm that applies logic to this tracking of resonance and, therefore, blade tip thermal condition is now described in connection with logic flow diagrams 1200, 1300, 1400 in FIGS. 20-22.

In addition, the description of the tissue algorithm described in connection with logic flow diagrams 1200, 1300, 1400 will be accompanied with illustrative examples via data obtained using any one of the ultrasonic surgical instruments 100, 120, 1004 comprising a corresponding generator 30, 500, 1002 described herein.

Figure 62:
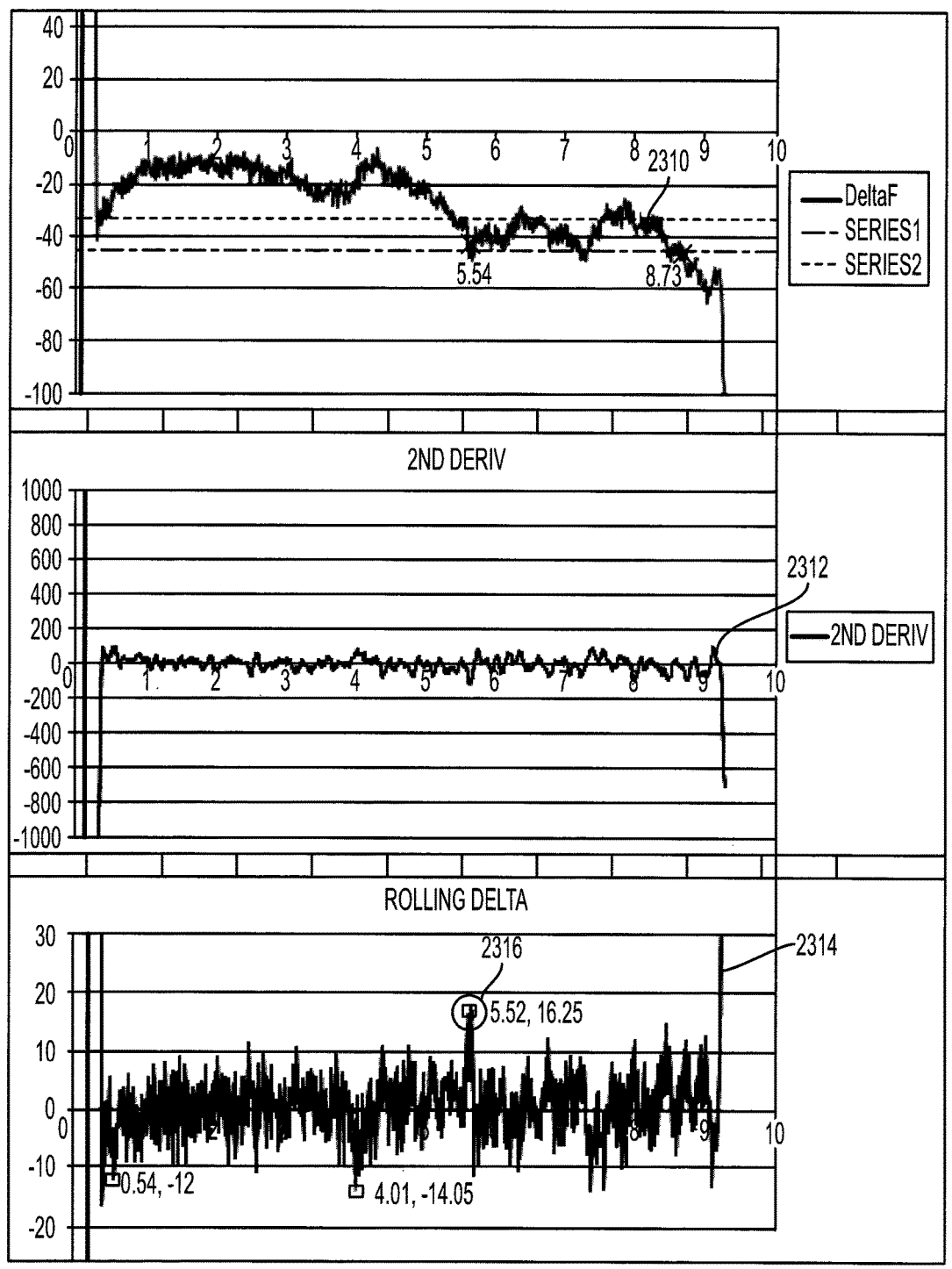
FIG. 62 is a graphical representation of a frequency slope, a second time derivative of frequency, and a rolling delta demonstrating a load event.
Figure 63:
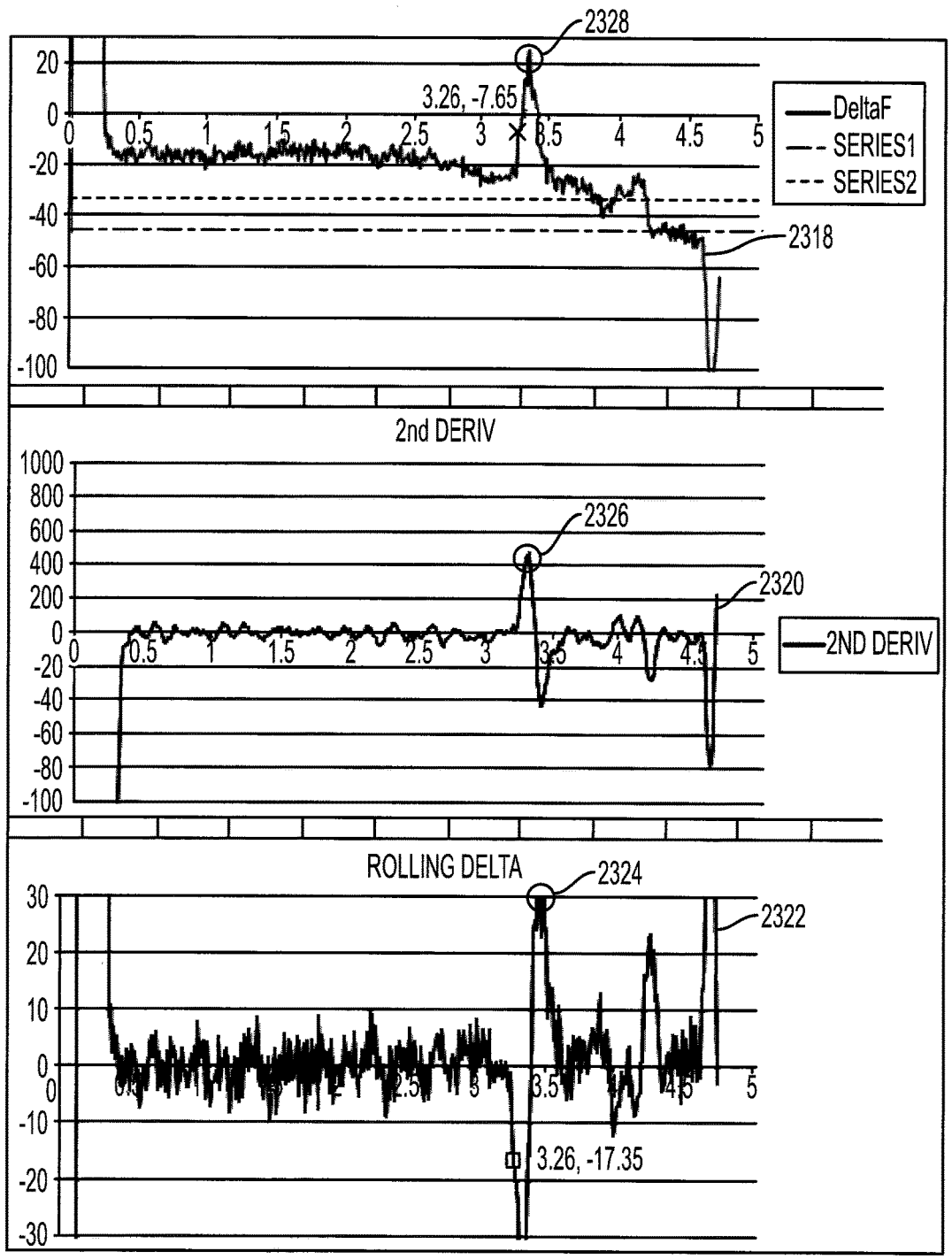
FIG. 63 is graphical representation of another form of a frequency slope, a second time derivative of frequency and a rolling delta demonstrating another load event.
Figure 64:
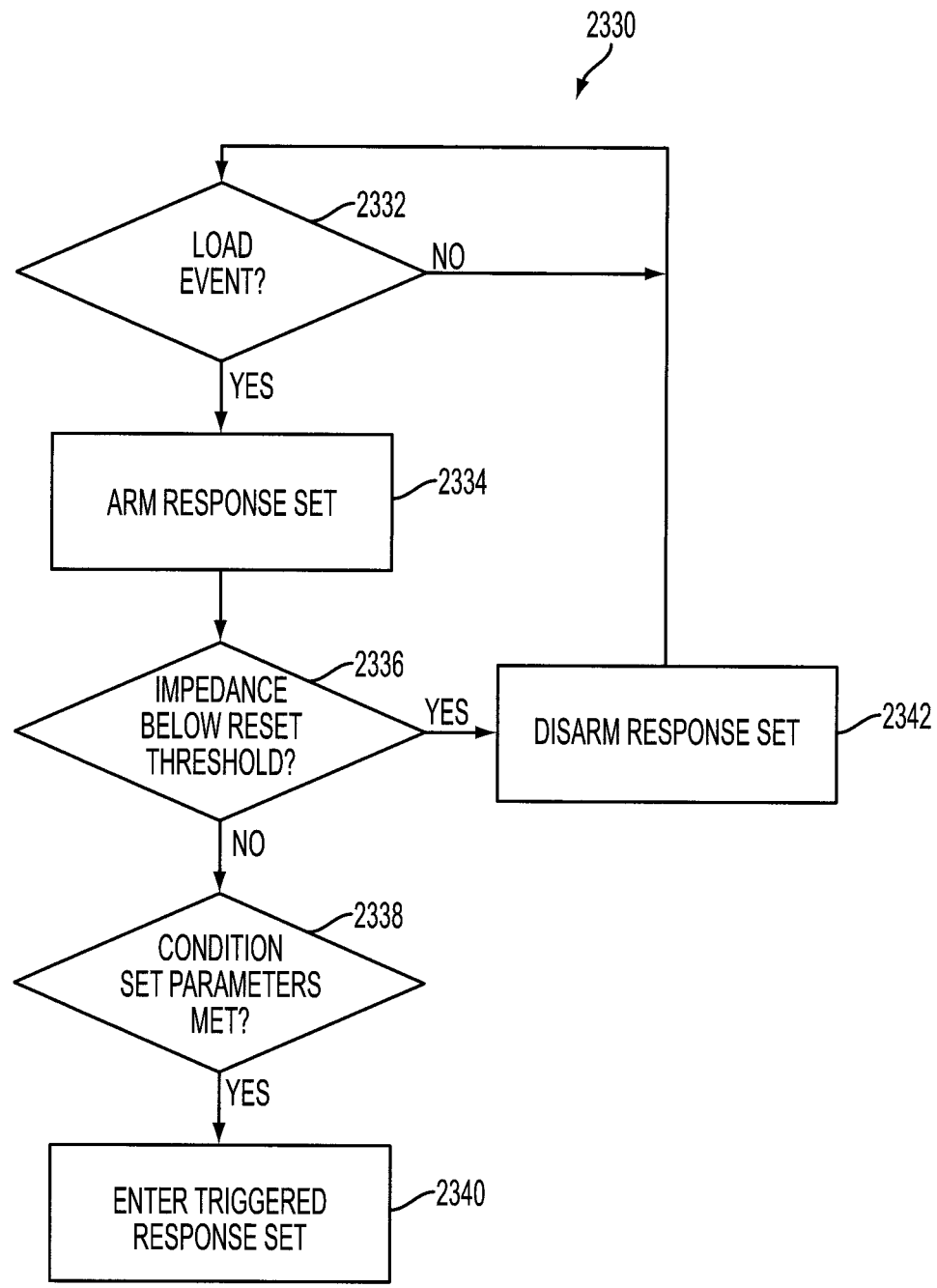
FIG. 64 is a logic flow diagram for implementing one form of an algorithm applying a Condition Set including a load event trigger that may be implemented in one form of a generator.

The tissue algorithm described in connection with logic flow diagrams 1200, 1300, 1400 relies on the monitoring of electrical drive signals, especially those correlating to the resonant frequency of the drive signal. The algorithm monitors the resonant frequency and its change with time (i.e., the first derivative of frequency with respect to time). Throughout this disclosure, this change in frequency with time is referred to as frequency slope. Frequency slope is calculated locally (from a time perspective) by calculating the change in frequency of adjacent (or relatively near) data points and dividing by the corresponding change in time. Because of signal transients, averaging or any of a multitude of applicable filtering or smoothing techniques (such that trends are more easily discernable and prevents turning on/off condition sets rapidly) may be employed. The data plots shown in FIGS. 62, 63, 64 illustrate the calculation of frequency slope and the use of averaging techniques (e.g., exponentially weighted moving average or EWMA) to obtain frequency slope values useful for control/monitoring. Other descriptions of frequency slope include, without limitation, "first derivative of frequency" and "frequency change with respect to time."

FIG. 20 is a logic flow diagram 1200 of a tissue algorithm that may be implemented in one form of a generator 30, 500, 1002 and/or an onboard generator or control circuit of an instrument. At a general level, the tissue algorithm described in connection with logic flow diagram 1200 assesses the electrical signals in real time against a set of logic conditions that correlate to events of interest (e.g., blade of ultrasonic instrument is rapidly heating). Accordingly, the generator 30, 500, 1002 determines when a set of logic conditions occur and triggers a corresponding set of responses. The terms "Condition Set" and "Response set" are defined as follows:

(1) Condition Set—a set of logic conditions that electrical signals are monitored against in real time.

(2) Response Set—one or more responses of the generator 30, 500, 1002 system to a Condition Set having been met.

At 1202, the generator 30, 500, 1002 is placed in an ultrasonic drive mode in a ready state.

At 1204, the generator 30, 500, 1002 is activated at a predetermined power level N. When the user activates the surgical system 19, 190, 1000, the corresponding generator 30, 500, 1002 responds by seeking the surgical system 19, 190, 1000 resonance and then ramping the output to the end effectors 81, 810, 1026 to the targeted levels for the commanded power level.

At 1206, the tissue algorithm determines whether parameters associated with the tissue algorithm are in use by determining when at least one Condition Sets/Response Sets flag is enabled. When no such flags are enabled, the algorithm proceeds along "NO" path where at 1208 the surgical system 19, 190, 1000 is operated in normal ultrasonic mode and at 1210, the corresponding generator 30, 500, 1002 is deactivated when the tissue procedure is completed.

When at least one flag for setting Condition Sets/Response Sets is enabled, the algorithm proceeds along "YES" path and the generator 30, 500, 1002 utilizes the tissue algorithm 1300 signal evaluation after resetting a Timer X and Timer X latch. The tissue algorithm 1300, described in more detail below, may return an indication of whether a given Condition Set is currently met or "true." In one form, the at least one flag for setting Condition Sets/Response Sets may be stored in an EEPROM image of an instrument 100, 120, 1004 attached to the respective generator 30, 500, 1002. The EEPROM flags for setting the Condition Sets/Response Sets to an enabled state are contained in TABLE 1.

TABLE 1

| Enable/Disable Flag Functions for Tissue Algorithm | | Value to Enable Function | Value for "Normal" Drive |
|---|---|---|---|
| Name | Description | | |
| Condition Set 1 Pulsing flag | If Condition Set 1 is met and this function is enabled, the generator pulses power per the pulsing parameters as a part of Response Set 1 | 1 | 0 |
| Condition Set 1 LCD display flag | If Condition Set 1 is met and this function is enabled, the generator LCD displays an assigned graphics screen as part of Response Set 1 | 1 | 0 |
| Condition Set 1 Audio flag | If Condition Set 1 is met and this function is enabled, the generator plays an assigned audio file as part of Response Set 1 | 1 | 0 |

TABLE 1-continued

| Enable/Disable Flag Functions for Tissue Algorithm | | Value to Enable Function | Value for "Normal" Drive |
|---|---|---|---|
| Name | Description | | |
| Condition Set 2 Pulsing flag | If Condition Set 2 is met and this function is enabled, the generator pulses power per the pulsing parameters as a part of Response Set 2 | 1 | 0 |
| Condition Set 2 LCD display flag | If Condition Set 2 is met and this function is enabled, the generator LCD displays an assigned graphics screen as part of Response Set 2 | 1 | 0 |
| Condition Set 2 Audio flag | If Condition Set 2 is met and this function is enabled, the generator plays an assigned audio file as part of Response Set 2 | 1 | 0 |

In one form, the tissue algorithm 1300 signal evaluation portion of the logic flow diagram 1200 utilizes two Condition Sets and each of these two Conditions Sets has a Response Set, which are described in more detail in connection with logic flow diagrams 1300, 1400. The tissue algorithm 1300 logic may be illustrated as follows: when Condition Set 1 is met, Response Set 1 is triggered. Having two condition sets enables a hierarchical response (differentiated responses based upon condition level) and also provides the ability to manage a complicated series of events.

At 1210, responses for Condition Sets that are met are triggered. Loop 1212 is repeated until the Condition Sets are met and the generator 30, 500, 1002 is deactivated at 1214.

The pulsing response is more detailed and requires further explanation than the relatively simple audio and LCD display responses. When a pulsing response is triggered, the generator 30, 500, 1002 drives a pulsed output as defined by the by the following four parameters:

(1) First Pulse Amplitude (EEPROM parameter, one value for each power level)—the drive amplitude for the first pulse;

(2) First Pulse Time (EEPROM parameter)—the time over which the first pulse amplitude is driven;

(3) Second Pulse Amplitude (EEPROM parameter, one value for each power level)—the drive amplitude for the second pulse; and (4) Second Pulse Time (EEPROM parameter)—the time over which the second pulse amplitude is driven.

In certain forms, the First Pulse Amplitude and Second Pulse Amplitude may increase, decrease or stay the same relative to one another. For example, in certain forms, the First Pulse Amplitude and Second Pulse Amplitude may be equal. Also, in certain forms, the First Pulse Time Period and Second Pulse Time Period may take any suitable values including, for example, fractions of a second, minutes, hours, etc. In one example form, the First Pulse Time Period and the Second Pulse Time Period may be 55 seconds.

When driving a pulsed output, the generator 30, 500, 1002 drives the first pulse, then the second pulse and then repeats. The pulse amplitude may be expressed in units of: percentage of the commanded power level's output current. The commanded power level may be set by the activation switch (MIN or MAX) and the generator setting when MIN is activated.

FIG. 21 is a logic flow diagram 1300 of a signal evaluation tissue algorithm portion of the tissue algorithm shown in FIG. 20 that may be implemented in one form of a generator. The tissue algorithm 1300 may determine whether one or more Condition Sets are met (and, therefore, whether corresponding Response Sets should be triggered at 1210). The tissue algorithm signal evaluation flow shown in FIG. 21 shows the application of a "time to wait" parameter 1304 and the calculation of a frequency slope (also referred to as local frequency slope because it is a running calculation).

At 1302, the algorithm calculates the time since activation was initiated at 1204 (FIG. 20). This time is expressed as $T_{Elapse}$, which is $T_{System}$-$T_{PowerOn}$. As previously discussed, when the user activates the surgical system 19, 190, 1000, the corresponding generator 30, 500, 1002 responds by seeking the resonance of the ultrasonic system 100, 120, 1004 and then ramping the output to the corresponding end effectors 81, 810, 1026 to the targeted levels for the commanded power level.

During this time, the associated signal transients can make the application of algorithm logic difficult. The algorithm, therefore, utilizes the "time to wait" parameter 1304 that is stored in the EEPROM image located in a hand piece portion of the ultrasonic surgical instrument 100, 120, 1004. The "time to wait" parameter 1304 (EEPROM parameter) is defined as the time at the beginning of an activation during which the generator 30, 500, 1002 does not apply the tissue algorithm to lessen the influence of resonance seek and drive ramp signal transients on algorithm logic. A typical "time to wait" parameter 1304 value is about 0.050 to 0.600 seconds (50 to 600 msec).

At 1306, $T_{Elapse}$ is compared to the "time to wait" parameter 1304 value. When $T_{Elapse}$ is less than or equal to the "time to wait" parameter 1304 value, the algorithm proceeds along "NO" path to calculate at 1302 a new $T_{Elapse}$. When $T_{Elapse}$ is greater than the "time to wait" parameter 1304 value, the algorithm proceeds along "YES" path to evaluate the signal.

At 1308, the algorithm performs the Signal Evaluation/Monitoring function. As previously stated, one aspect of the function algorithm is to monitor frequency slope. In a physical sense, frequency slope correlates to heat flux into or out of the resonant system comprising the blade and the hand piece acoustical subassembly, such as the ultrasonic systems 100, 120, 1004 disclosed herein. The changes in frequency and frequency slope during activation on tissue are dominated by the changing conditions occurring at the end-effector (tissue drying out, separating and blade contacting the clamp arm pad). When the blade is being heated (i.e., heat flux into the blade), the frequency slope is negative. When the blade is being cooled (i.e., heat flux out of the blade), the frequency slope is positive. Accordingly, the algorithm calculates the slope between frequency data points, i.e., incoming frequency data points 1310 ($F_t$) and previous $F_t$ data points 1312. The calculated frequency slope also may be referred to as a local frequency slope because it is a running calculation. The local frequency slope may be referred to as $F_{slope\_Freq}$, $F_t$, which is the frequency slope ($F_{slope\_Freq}$) at the resonance frequency ($F_t$). The local frequency slope may be routed to a Condition Set 1, Condition Set 2 1400, for example, for evaluation in accordance with the flow diagram 1400 shown in FIG. 22. Although two Condition Sets are shown, it will be appreciated that additional Condition Sets may be added in some example forms.

FIG. 22 is a logic flow diagram 1400 for evaluating condition sets for the signal evaluation tissue algorithm shown in FIG. 21 that may be implemented in one form of a generator, such as 30, 50, 1002. The logic flow diagram 1400 evaluates Condition Set X, where X is either 1 or 2, for example.

In accordance with the tissue algorithm, at 1402, the local frequency slope calculated at 1308 (FIG. 21) is compared against a frequency slope threshold parameter 1404 value for Condition Set X at Power Level N. The frequency slope threshold parameters 1404 may be stored in an EEPROM located in the attached instrument 100, 120, 1004, where one EEPROM parameter value is stored for each power level. When the local frequency slope calculated at 1308 drops below the frequency slope threshold parameter 1404 value, a first Response Set may be triggered at 1210 (FIG. 20). When the blade is being heated at a relatively rapid rate, the frequency slope will become more negative and the tissue algorithm identifies this condition by way of the frequency slope dropping below the frequency slope threshold parameter 1404 value. Again, the frequency slope indicates the rate of thermal change or heat flux into or out of the blade.

In accordance with the tissue algorithm, also at 1402, the resonant frequency is compared against a frequency threshold parameter 1406 value for Condition set X. The frequency threshold parameter 1406 value may be stored in an EEPROM located in the attached instrument 100, 120, 1004. When the resonant frequency drops below the threshold frequency parameter 1406 value, a second Response Set may be triggered at 1210 (FIG. 20). As a blade is continually heated, the frequency will continue to drop. A frequency threshold parameter 1406 value is intended to improve algorithm robustness by providing additional information about the thermal condition of the blade (in addition to the more dynamic indicator, the frequency slope). Frequency drop from some known condition such as room temperature gives a good indication of the thermal state of the resonant system relative to these known thermal conditions.

In some forms, frequency slope and resonant frequency may be utilized in a common Condition Set. For example, a Condition Set may not be met unless the frequency slope and resonant frequency both meet given thresholds. For example, at 1402, when the frequency slope ($F_{slope\_Freq}$) is less than the frequency slope threshold parameter 1404 value and the resonant frequency ($F_t$) is less than the frequency threshold parameter 1406 value, the algorithm proceeds along "YES" path to 1408 to increment a Timer X (where X corresponds to the particular Condition Set being evaluated by the tissue algorithm).

In comparing the electrical signals, e.g., the frequency slope ($F_{Slope\_Freq}$) and the resonant frequency ($F_t$), against respective thresholds parameters 1404, 1406, borderline conditions where the signal bounces back-and-forth across the threshold can be taken into consideration as follows. In one aspect, the tissue algorithm employs a "required time before trigger" parameter 1412 value (which also may be stored in the instrument EEPROM) for the particular Condition Set X to account for this consideration. The "required time before trigger" parameter 1412 value is defined as the time required before trigger (EEPROM parameter)—required time for frequency slope and/or frequency to be less than their respective thresholds for a Response Set to be triggered. This is intended to prevent rapid "back and forth" triggering of a response. It may be useful, however, to track non-rapid "back and forth" triggering, which may Occur.

Thus, at 1414 the algorithm determines whether the Timer X value is greater than the "required time before trigger" parameter 1412 value for Condition Set X. When the Timer X value is greater than the "required time before trigger" parameter 1412 value, the algorithm proceeds along "YES" path to set a latch for Condition Set X at 1416. Output 1418 indicates that the Condition Set X is met. When the Timer X value is less than or equal to the "required time before trigger" parameter 1412 value, the algorithm proceeds along "NO" path to indicate at output 1420 that the Condition Set X is not met.

At 1402, when either the frequency slope ($F_{Slope\_Freq}$) is greater than or equal to the frequency slope threshold parameter 1404 value or the resonant frequency ($F_t$) is greater than then or equal to the frequency threshold parameter 1406 value, the algorithm proceeds along "NO" path to reset the Timer X at 1410 (where X corresponds to the particular Condition Set being evaluated by the tissue algorithm).

For additional robustness, two latching parameters are employed by the algorithm. Without the use of latching, the algorithm is configured to end a response set when either (a) the system is deactivated or (b) when the signal or signals are no longer below their respective thresholds. Two latching parameters can be utilized. They are a "minimum latch time" parameter 1422 and a "cross-back frequency slope threshold" parameter 1424. These latch parameters 1422, 1424 are important for robustness around: (a) clamp arm pad surfaces that become more lubricious with elevated temperature and (b) pulsing output where signal transients at the pulse transitions are expected.

The minimum latch time parameter 1422 (EEPROM parameter) can be defined as the minimum amount of time for response(s) to a Condition Set X to be triggered. Considerations for minimum latch time include: (a) the length of time required to play a triggered audible response (e.g., in one form, a "pre-alert" WAV audio file may be about 0.5 seconds long), (b) the typical (about 0.5 to 1.0 sec) or extreme (about 1.5 to 2.0 sec) user response times for an event, or (c) the typical tissue re-grasp time for a multi-cut (known as "marching") application (about 1.1-2.0 seconds with a mean of about 1.6 seconds).

The cross-back frequency slope threshold parameter 1424 (EEPROM parameter) can be defined as the frequency slope threshold above which a triggered response stops (i.e., is no longer triggered). This provides for a higher "cross-back-over" frequency slope threshold that is tasked with distinguishing between activating against the pad and jaw opened (versus distinguishing between activating on tissue and activating on the pad).

In accordance with the tissue algorithm portion represented by logic flow diagram 1400, after the Timer X is reset at 1410, at 1426, the tissue algorithm determines whether either the latch for Condition Set X or the Cross-back Frequency Slope Latch is set. When both latches are not set, the algorithm proceeds along "NO" to indicate at output 1420 that the Condition Set X is not met. When either one of the latches is set, the algorithm proceeds along "YES" path to 1428.

At 1428, the algorithm determines whether the Latched Time for Condition Set X is greater than the minimum latch time parameter 1422 value for Condition Set X and whether the frequency slope ($F_{slope\_Freq}$) is greater than the cross-back frequency slope threshold parameter 1424 value the algorithm proceeds along "YES" path to reset the Latch for Timer X at 1430 and to indicate at output 1420 that the Condition Set X is not met. When the Latched Time for Condition Set X is less than or equal to the minimum latch time parameter 1422 value for Condition Set X and the frequency slope ($F_{slope\_Freq}$) is less than or equal to the cross-back frequency slope threshold parameter 1424 value the algorithm proceeds along "NO" path to indicate at output 1432 that the Condition Set X is met.

As shown in FIGS. 21 and 22, there are two identical Condition Sets 1 and 2 from a flow perspective. These Conditions Sets 1 and 2 have replicate sets of parameters as contained in TABLE 2. Algorithm parameters that are shared by the Condition Sets 1 and 2 are contained in TABLE 3.

TABLE 2 contains a summary of the replicated algorithm EEPROM parameters for each of the Condition Sets and the number parameters per Condition Set.

TABLE 2

Algorithm EEPROM Parameter Summary, Replicated Parameters for Each of the Condition Sets

| Replicated Parameters for Each of the Condition Sets | # of Parameters per Condition Set |
| --- | --- |
| Required time before triggered | 1 |
| Minimum latch time | 1 |
| Frequency Slope Thresholds (one for each power level) | 5 |
| Frequency Threshold | 1 |

TABLE 3 contains a summary of the shared algorithm EEPROM parameters for each of the Condition Sets (not replicated) and the number parameters.

TABLE 3

Algorithm EEPROM Parameter Summary, Common Parameters to all Condition Sets

| Parameters Shared by Condition Sets (not replicated) | # of Parameters |
| --- | --- |
| Time to wait | 1 |
| Cross-back Frequency Slope Threshold | 1 |
| First Pulse Amplitudes (one for each power level) | 5 |
| First Pulse Time | 1 |
| Second Pulse Amplitudes (one for each power level) | 5 |
| Second Pulse Time | 1 |

Figure 27:
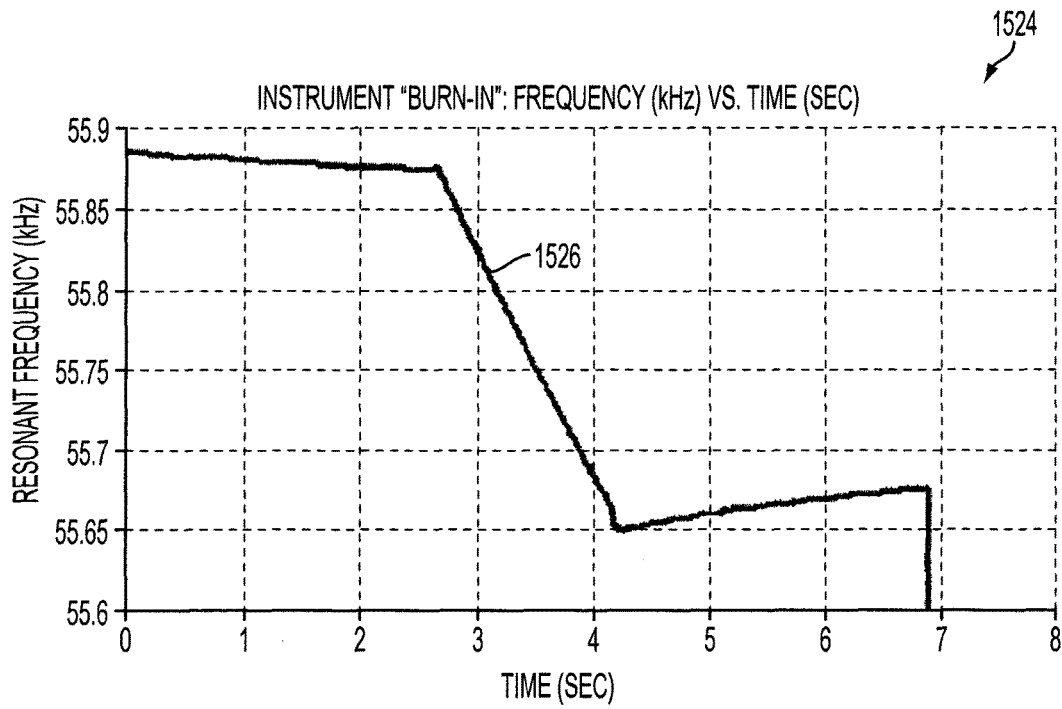
FIG. 27 is a graphical representation of frequency versus time waveform of one form of a generator during a burn-in test as it relates to the graphical representation shown in FIG. 26.
Figure 28:
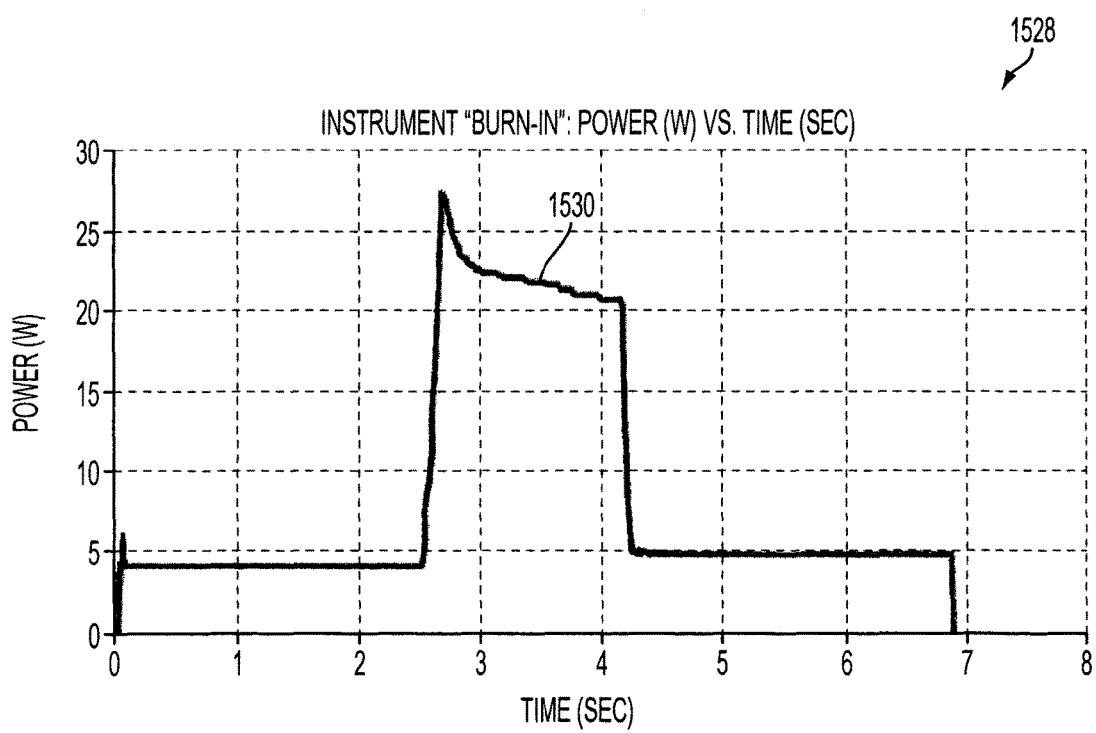
FIG. 28 is a graphical representation of power consumption versus time waveform of one form of a generator during a burn-in test as it relates to the graphical representation shown in FIG. 26.
Figure 29:
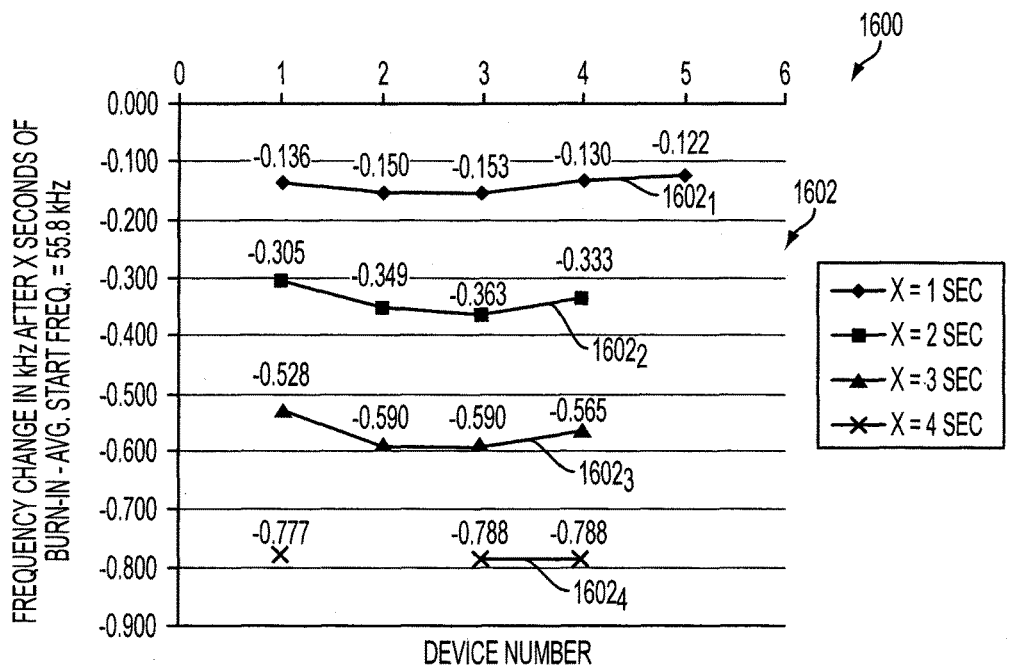
FIG. 29 is a graphical representation of frequency change over time waveform of several generator/instrument combinations during burn-in tests.
Figure 30:
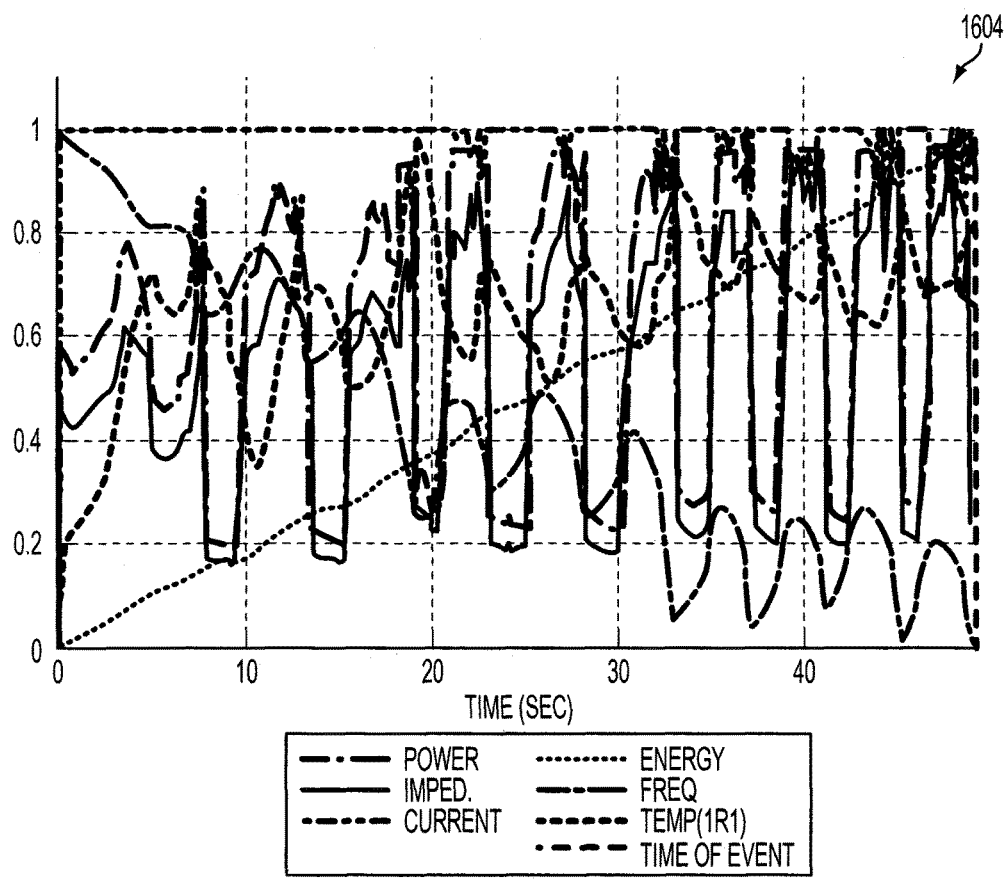
FIG. 30 is a graphical representation of normalized combined impedance, current, frequency, power, energy, and temperature waveforms of one form of a generator coupled to an ultrasonic instrument to make 10 successive cuts on excised porcine jejunum tissue as quickly as possible while keeping the generator running throughout.
Figure 32:
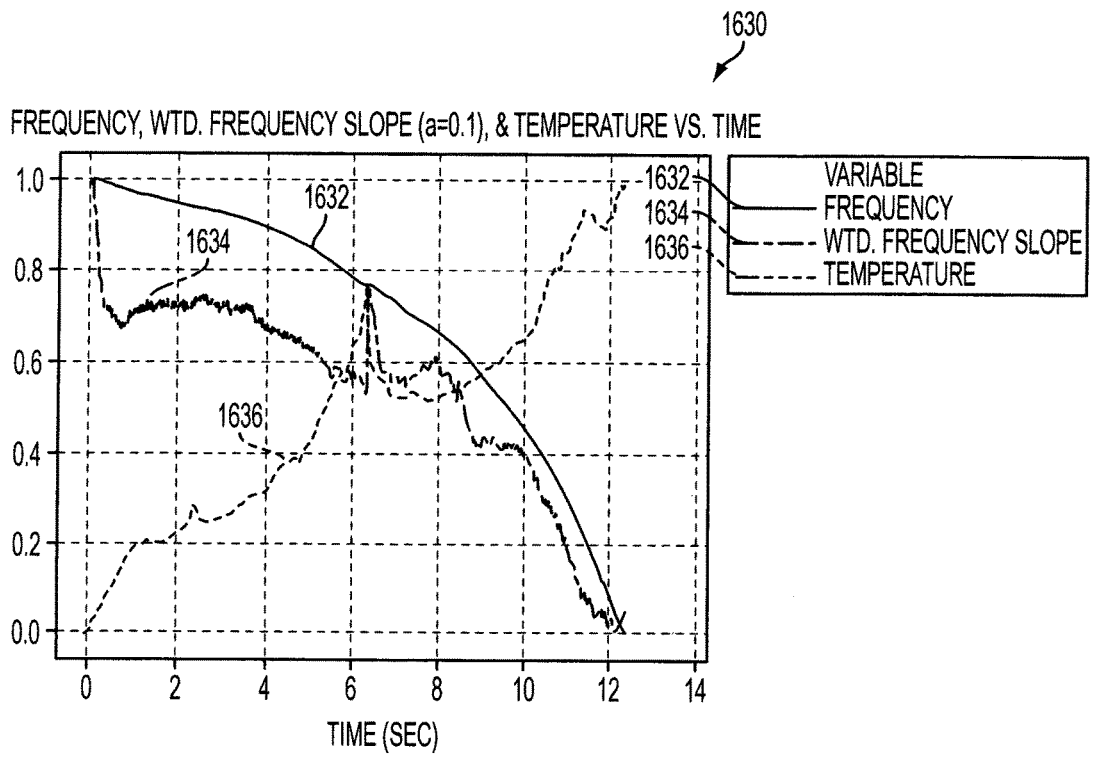
FIG. 32 is a combined graphical representation of frequency, weighted frequency slope waveform calculated via exponentially weighted moving average with an alpha value of 0.1, and temperature versus time waveform of one form of a generator.
Figure 33:
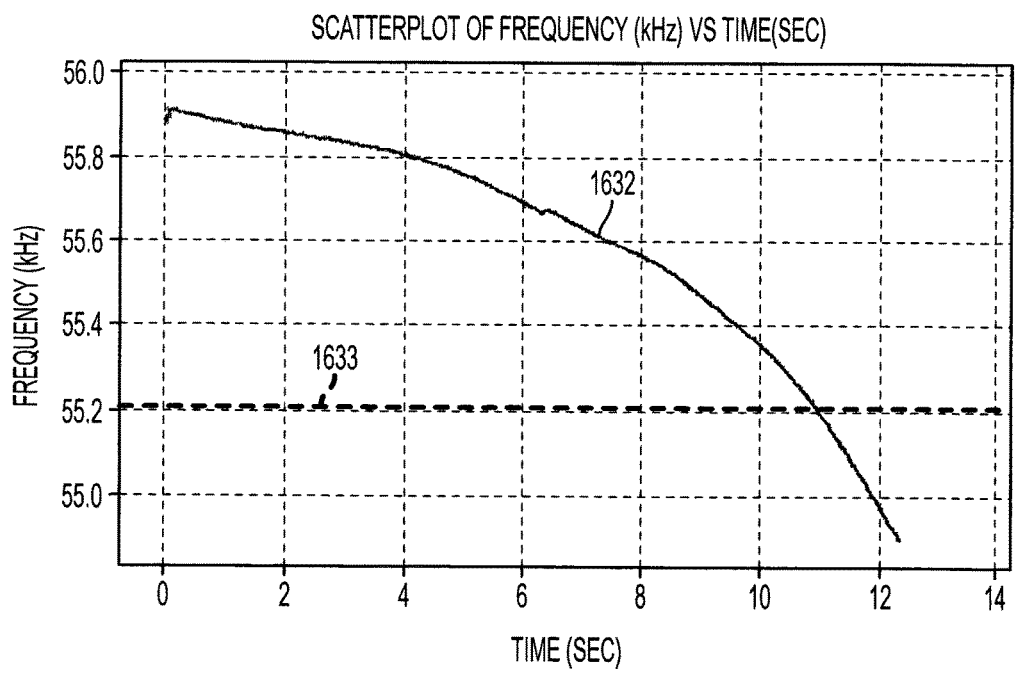
FIG. 33 is a graphical representation of a frequency versus time waveform shown in FIG. 32.
Figure 34:
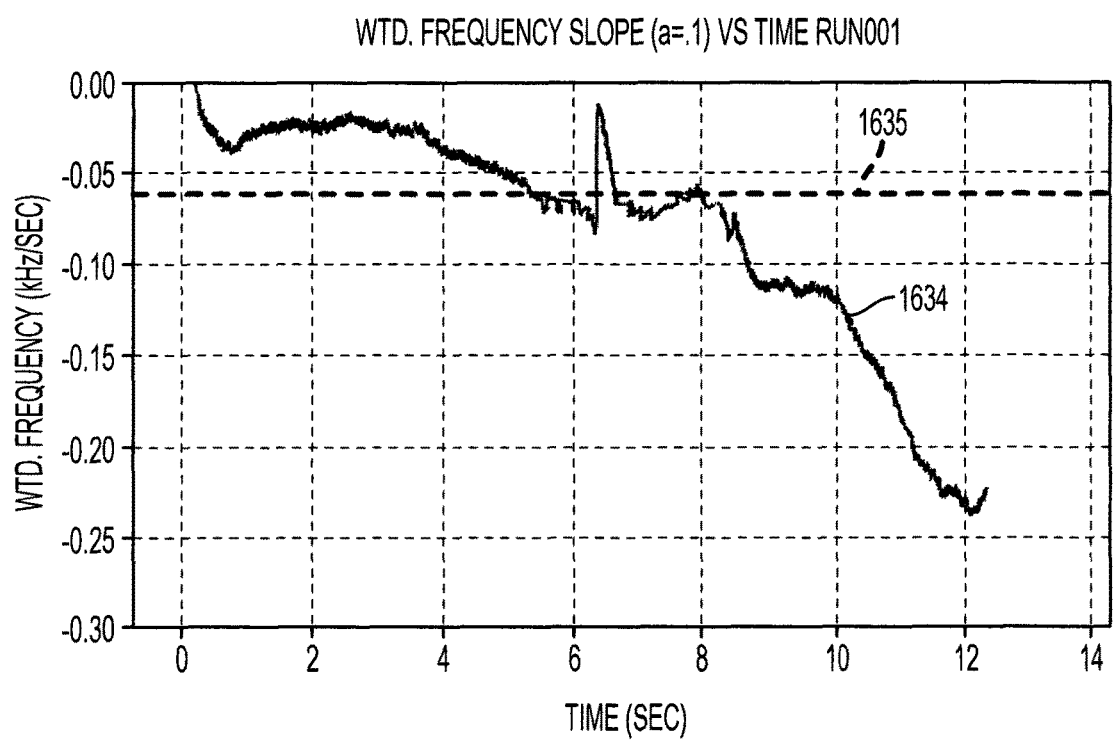
FIG. 34 is a graphical representation of the weighted frequency slope versus time waveform shown in FIG. 32.

For clarity of disclosure, the tissue algorithm described in connection with the logic flow diagrams 1200, 1300, 1400 shown in respective FIGS. 20-22 will now be described in terms of four examples. The basic application of the tissue algorithm includes the monitoring of frequency slope, resonant frequency, or both against their respective thresholds. Accordingly, a first example includes the monitoring of frequency slope against its respective threshold and is illustrated in FIGS. 23-28. A second example includes the monitoring of resonant frequency against its respective threshold and is illustrated in FIGS. 29-31. A third example includes the monitoring both the frequency slope and the resonant frequency, against their respective threshold and is illustrated in FIGS. 32-34. Finally, a fourth example also includes the monitoring both of the frequency slope and the resonant frequency, against their respective threshold.

Example 1

Monitoring Frequency Slope Against Respective Threshold

A first example case includes the monitoring of frequency slope against a respective threshold is illustrated with reference to FIGS. 23-28. The first example, and most simple, is the example of triggering a Response Set based only on the frequency slope. TABLE 4 contains representative parameters for this objective for surgical instruments such as any one of the surgical instruments 19, 190, 1000 disclosed herein comprising a corresponding ultrasonic instrument such as ultrasonic instruments 100, 120, 1004 disclosed herein.

TABLE 4

Representative Parameters for Triggering an Audio Indication by Frequency Slope Threshold Only (one Condition Set utilized)

| Parameter | Value* |
| --- | --- |
| Condition Set 1 Pulsing flag | 0 |
| Condition Set 1 LCD display flag | 0 |
| Condition Set 1 Audio flag | 1 |
| Required time before triggered, Condition Set 1 | 50 msec |
| Minimum latch time, Condition Set 1 | 0 msec* |
| Frequency Slope Thresholds (one for each power level), Condition Set 1 | level 5: −0.060 kHz/sec<br>level 4: −0.053 kHz/sec<br>level 3: −0.045 kHz/sec<br>level 2: −0.038 kHz/sec<br>level 1: −0.030 kHz/sec |
| Frequency Threshold, Condition Set 1 | 56,000 Hz* |
| Time to wait | 100 msec |
| Cross-back Frequency Slope Threshold | −0.020 kHz/sec |
| First Pulse Amplitudes (one for each power level) | N/A |
| First Pulse Time | N/A |
| Second Pulse Amplitudes (one for each power level) | N/A |
| Second Pulse Time | N/A |

*These parameter values are set to an appropriate extreme such that they do not effectively take part in the logic flow (e.g., set to always be "true").

Figure 23A:
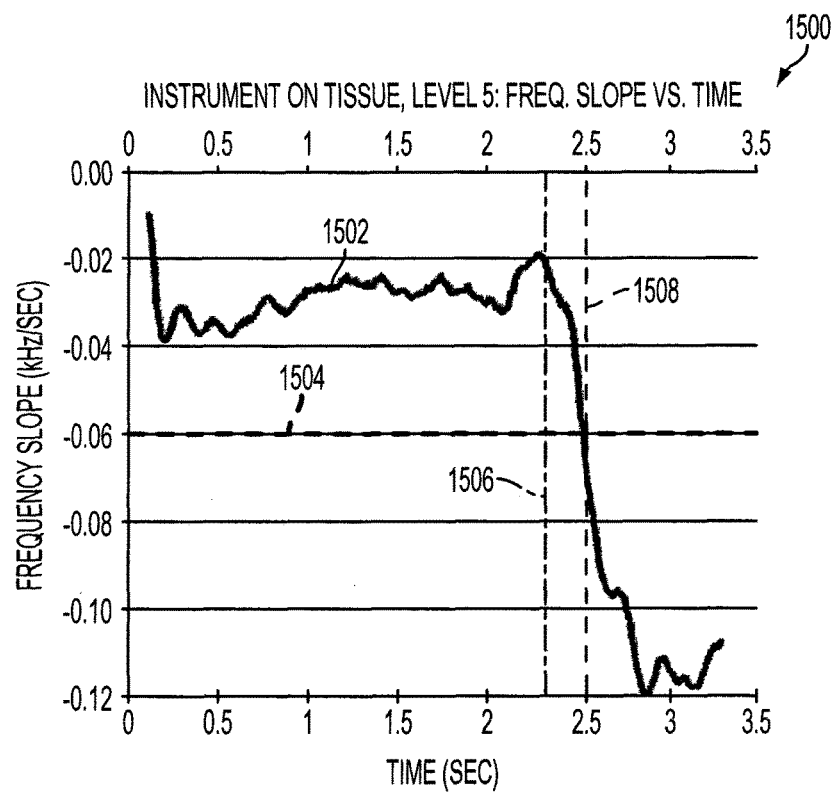
FIG. 23A is a graphical representation of frequency slope (first time derivative of frequency) versus time waveform of one form of a generator during a typical tissue cut.
Figure 23B:
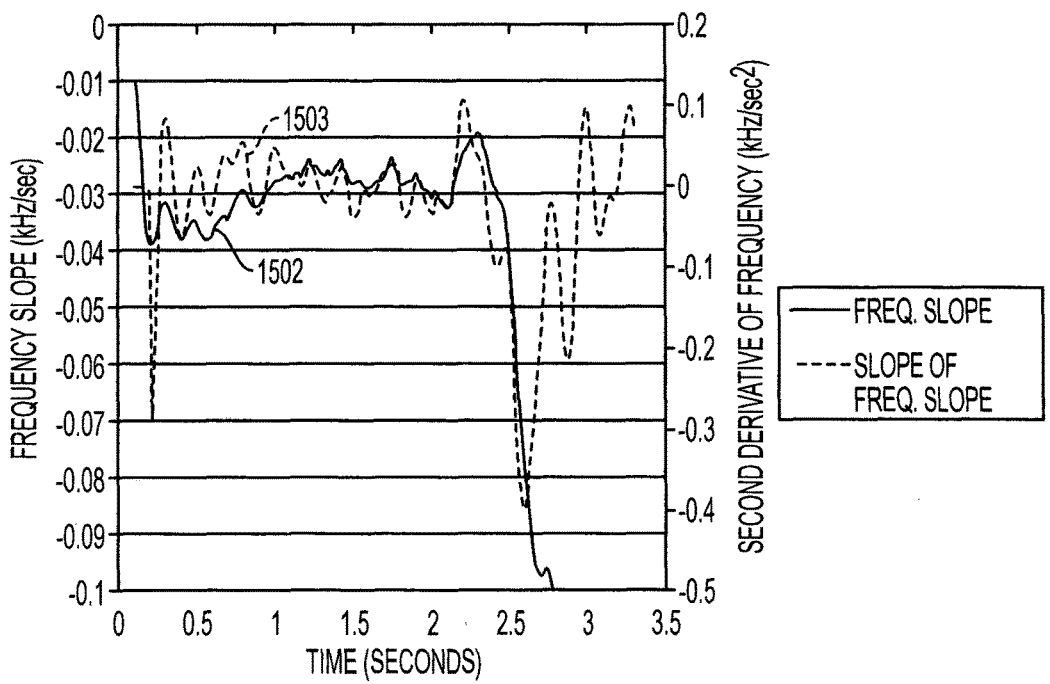
FIG. 23B is a graphical representation of slope of frequency slope (second time derivative of frequency) versus time waveform shown in dashed line superimposed over the waveform shown in FIG. 23A of one form of a generator during a typical tissue cut.
Figure 24:
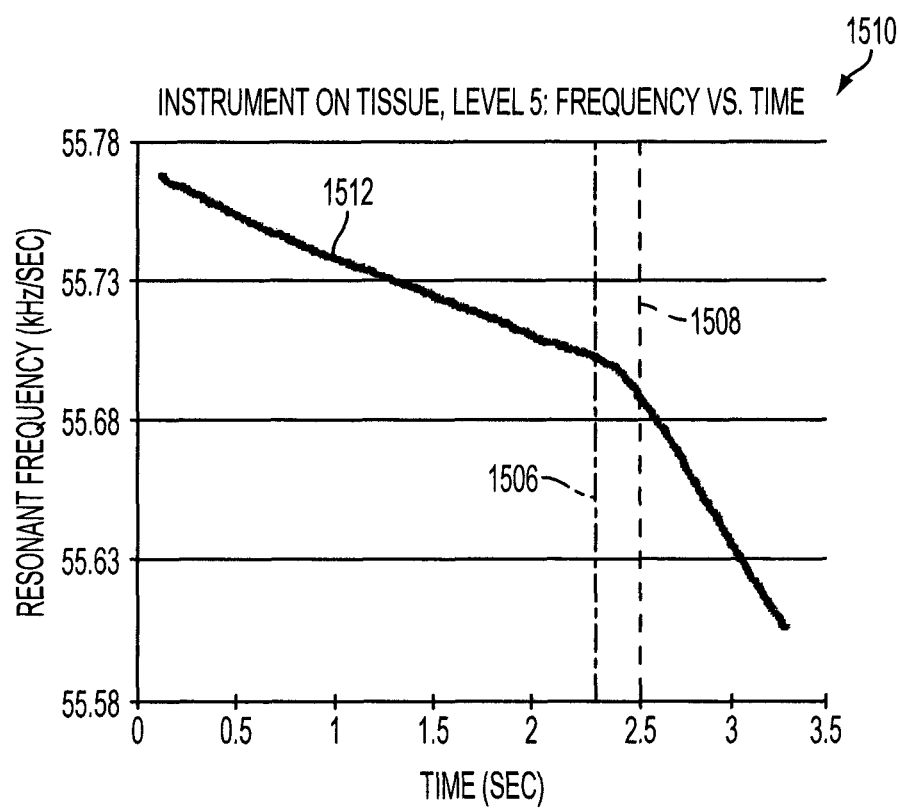
FIG. 24 is a graphical representation of frequency versus time waveform of one form of a generator during a typical tissue cut as it relates to the graphical representation shown in FIG. 23A.
Figure 25:
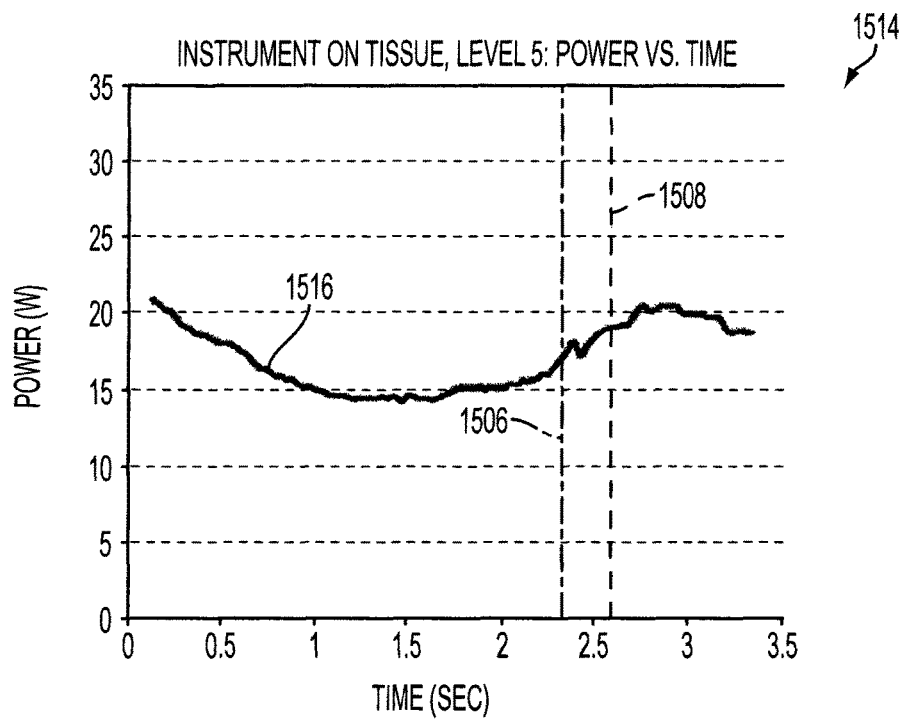
FIG. 25 is a graphical representation of drive power versus time waveform of one form of a generator during a typical tissue cut as it relates to the graphical representation shown in FIG. 23A.

FIGS. 23-25 show signal data produced by a generator with the representative/illustrative parameters contained in TABLE 4. The generator may be similar to any one of the generators 30, 500, 1002 disclosed herein, which forms a portion of the respective surgical systems 19, 190, 1000 operating in ultrasonic mode (e.g., ultrasonic system 19, 190, 1000) applied on tissue in accordance with the present disclosure.

Figure 26:
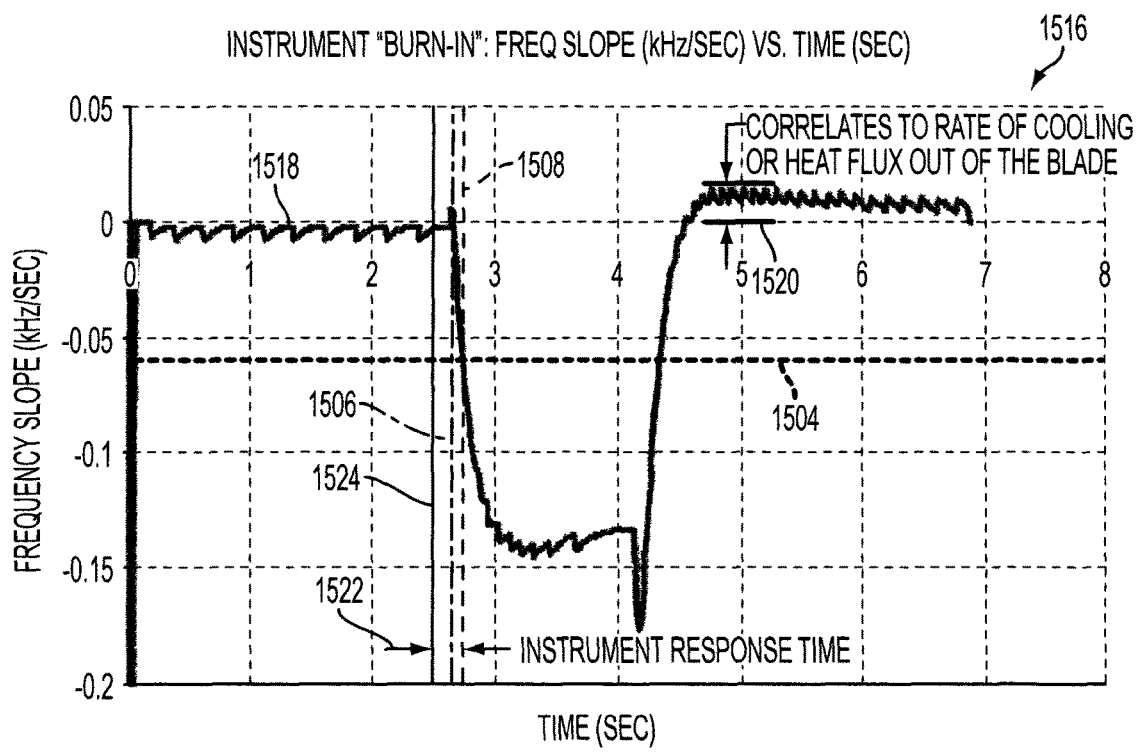
FIG. 26 is a graphical representation of frequency slope versus time waveform of one form of a generator during a burn-in test.

The use of only the frequency slope to trigger a Response Set may be further demonstrated in the "burn-in" scenario or test. FIGS. 26-28 show signal data produced by a generator with the representative/illustrative parameters contained in TABLE 4 during a "burn-in" scenario or test. A "burn-in" simulates the use case where a user activates a shears type ultrasonic surgical instrument without intervening tissue (e.g., back-cutting with jaws closed). This test also may be useful for quantifying device characteristics, such as, for example, "response time."

The response time of an ultrasonic instrument may be defined as the time required for an ultrasonic system (instrument, hand piece, and generator with tissue algorithm) to respond to the clamp arm pad coming into contact with the blade. The ultrasonic system is usually initially activated "in-air" (i.e., unloaded), the clamp arm is closed against the blade and held for a period of time and then the clamp arm is opened and the ultrasonic system is deactivated. The response time is the time between the point at which the quiescent power (power in-air) begins to change due to the clamp arm pad initiating contact with the blade and the point at which the Response Set is triggered. This is also a test that enables quantification of the rate of cooling—the higher the rate of cooling (assuming similar convective boundary conditions) the more thermal energy or residual heat there is in the blade. The rate of cooling is proportional to the frequency slope (to reinforce: a positive frequency slope value correlates to the instantaneous heat flux out of the blade). As will be detailed later, the rate of cooling also may be monitored and used for control purposes so that, for example, if the rate of cooling as defined by a positive frequency slope is greater than a threshold value, one knows that the blade is "carrying" a large amount of thermal energy and is dissipating it rapidly.

FIG. 23A is a graphical representation 1500 of frequency slope versus time of a waveform 1502 of one form of a generator during a typical tissue cut. Frequency slope (kHz/sec) is shown along the vertical axis and time (Sec) is shown along the horizontal axis for a typical tissue cut using any one of the ultrasonic systems comprising corresponding ultrasonic surgical instruments set on power level 5. The frequency slope threshold 1504 used for this application was −0.06 kHz/sec and is shown by the horizontal dashed line. The vertical dash-dot line 1506 shows the time (2.32 seconds) that the tissue began to separate, and the vertical dashed line 1508 shows the time (2.55 seconds) at which the ultrasonic system triggered a Response Set (in this case, per TABLE 4, an audible sound only).

FIG. 23B is a graphical representation of a second time derivative of frequency (slope of frequency slope) versus time waveform 1503 (shown in dashed line) superimposed over the waveform 1502 shown in FIG. 23 of one form of a generator during a typical tissue cut.

FIG. 24 is a graphical representation 1510 of frequency versus time waveform 1512 of one form of a generator during a typical tissue cut as it relates to the graphical representation 1500 shown in FIG. 23A. Resonant frequency (kHz) is shown along the vertical axis and time (Sec) is shown along the horizontal axis for the typical tissue cut using any one of the ultrasonic systems set on power level 5. The vertical dash-dot line 1506 shows the time (2.32 seconds) that the tissue began to separate, and the vertical dashed line 1508 shows the time (2.55 seconds) at which the ultrasonic system triggered a Response Set (in this case, an audible sound only).

FIG. 25 is a graphical representation 1514 of power consumption versus time waveform 1514 of one form of a generator during a typical tissue cut as it relates to the graphical representation 1500 shown in FIG. 23A. Power (W) is shown along the vertical axis and time (Sec) is shown along the horizontal axis for the typical tissue cut using any one of the ultrasonic systems set on power level 5. The vertical dash-dot line 1506 shows the time (2.32 seconds) that the tissue began to separate, and the vertical dashed line 1508 shows the time (2.55 seconds) at which the ultrasonic system triggered a Response Set (in this case, an audible sound only).

FIG. 26 is a graphical representation 1516 of frequency slope versus time waveform 1518 of one form of a generator during a burn-in test. The parameters for this test are consistent with those contained in TABLE 4. Frequency slope (kHz/sec) is shown along the vertical axis and time (Sec) is shown along the horizontal axis for a typical tissue cut using any one of the ultrasonic systems set on power level 5. The frequency slope threshold 1504 used for this application was −0.06 kHz/sec as is shown by the horizontal dashed line. The vertical dotted line 1524 shows the point in time (2.49 seconds) that the quiescent power begins to change due to clamping, the vertical dash-dot line 1506 shows the time (2.66 seconds) at which power has completed ramp-up, and the vertical dashed line 1508 shows the time (2.72 seconds) that the ultrasonic system triggered a Response Set (in this case, an audible sound only). As shown in the graphical representation 1516, the frequency slope at 1520 correlates to the rate of cooling or heat flux out of the blade. Also, the response time 1522 of the ultrasonic system is measured as the time lapse between the point in time (2.49 seconds) that the quiescent power begins to change due to clamping and the time (2.72 seconds) that the ultrasonic system triggered a Response Set.

FIG. 27 is a graphical representation 1524 of a frequency versus time waveform 1526 of one form of a generator during a burn-in test as it relates to the graphical representation 1516 shown in FIG. 26. Resonant frequency (kHz) is shown along the vertical axis and time (Sec) is shown along the horizontal axis for the typical tissue cut using any one of the ultrasonic systems set on power level 5.

FIG. 28 is a graphical representation 1528 of a power consumption versus time waveform 1530 of one form of a generator during a burn-in test as it relates to the graphical representation 1516 shown in FIG. 26. Power (W) is shown along the vertical axis and time (Sec) is shown along the horizontal axis for the typical tissue cut using any one of the ultrasonic systems set on power level 5.

Example 2

Triggering a Response Set Based Only on the Frequency Threshold

A second example case includes triggering a Response Set based only on the frequency threshold with reference to FIGS. 29-35. TABLE 5 contains representative parameters for this objective in connection with surgical instruments such as any one of the surgical instruments 19, 190, 1000 disclosed herein comprising corresponding ultrasonic instruments such as the ultrasonic instrument 100, 120, 1004 disclosed herein. It will be appreciated that triggering via frequency threshold may be of limited utility as it is less indicative of dynamic end-effector conditions and is presented herein for completeness of disclosure. The inclusion of frequency slope in the tissue algorithm discussed in connection with logic flow diagrams 1200, 1300, 1400 is intended for use in combination logic (combined with use of the frequency slope threshold) which is covered in the next section of this specification.

TABLE 5

Representative Parameters for Triggering an Audio Indication by Frequency Threshold Only (one Condition Set utilized)

| Parameter | Value* |
|---|---|
| Condition Set 1 Pulsing flag | 0 |
| Condition Set 1 LCD display flag | 0 |
| Condition Set 1 Audio flag | 1 |
| Required time before triggered, Condition Set 1 | 50 msec |
| Minimum latch time, Condition Set 1 | 0 msec* |
| Frequency Slope Thresholds (one for each power level), Condition Set 1 | level 5: 1.00 kHz/sec* level 4: 1.00 kHz/sec* level 3: 1.00 kHz/sec* level 2: 1.00 kHz/sec* level 1: 1.00 kHz/sec* |
| Frequency Threshold, Condition Set 1 | 55,100 Hz* |
| Time to wait | 100 msec |
| Cross-back Frequency Slope Threshold | −1.00 kHz/sec |
| First Pulse Amplitudes (one for each power level) | N/A |

TABLE 5-continued

Representative Parameters for Triggering an Audio Indication
by Frequency Threshold Only (one Condition Set utilized)

| Parameter | Value* |
| --- | --- |
| First Pulse Time | N/A |
| Second Pulse Amplitudes (one for each power level) | N/A |
| Second Pulse Time | N/A |

*These parameter values are set to an appropriate extreme such that they do not effectively take part in logic flow (e.g., set to always be "true")

FIGS. 29-34 show waveforms produced by a generator with the representative/illustrative parameters contained in TABLE 5. The generator may be similar to any one of the generators 30, 500, 1002 disclosed herein, which forms a portion of the respective surgical systems 19, 190, 1000 operating in ultrasonic mode (e.g., ultrasonic system 19, 190, 1000) applied on tissue in accordance with the present disclosure.

The selection of 55,100 Hz as the frequency threshold in TABLE 5 was based on test data for two abuse cases: (1) where an ultrasonic instrument is activated against the tissue pad for a prolonged period of time; and (2) where an ultrasonic instrument is used to make 10 successive cuts on excised porcine jejunum tissue as quickly as possible while keeping the generator running throughout. Each of these two abuse cases will be discussed in more detail with reference to respective FIG. 29 and FIGS. 30-31A-C.

FIG. 29 is a graphical representation 1600 of frequency change 1602 over time of waveforms of several generators during a burn-in test. Frequency change (kHz) after X seconds of burn-in is shown along the vertical axis and ultrasonic surgical instrument device number is shown along the horizontal axis. FIG. 29 shows frequency change data after prolonged burn-ins of an ultrasonic surgical instrument where the ultrasonic surgical instrument is activated against the tissue pad for a prolonged period of time (a prolonged burn-in). The selection of 55,100 Hz limits this condition to no more than a 4 second time span or a frequency drop of about a 700 Hz from a nominal room temperature resonant frequency of 55,800 Hz. Frequency change data 16021, 16022, 16023, 16024 was pulled from the generator 30, 500, 1002 data at corresponding 1, 2, 3, and 4 seconds into the burn-in. The nominal start frequency for the five ultrasonic surgical instruments was 55.8 kHz (blades started at room temperature). The second and fifth devices did not run long enough to generate a full set of data for all times.

FIG. 30 is a graphical representation 1604 of normalized combined impedance, current, and frequency versus time waveforms of and power consumption, energy supplied, and temperature for one form of a generator coupled to a corresponding ultrasonic instrument used to make 10 successive cuts on tissue (e.g., on excised porcine jejunum tissue) as quickly as possible while keeping the generator running throughout. This data and the methods used to obtain it represent abusive use conditions.

Figure 31A:
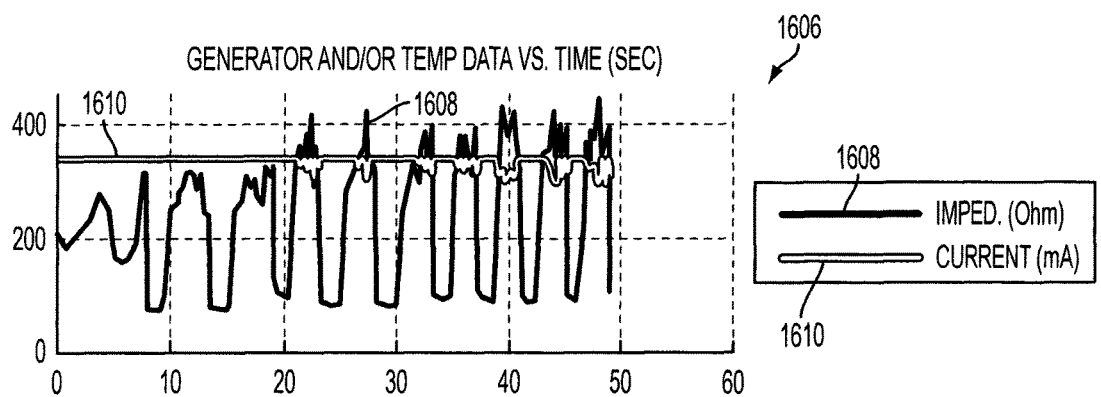
FIG. 31A is a graphical representation of impedance and current versus time waveforms of one form of a generator during successive tissue cuts over a period of time.
Figure 31B:
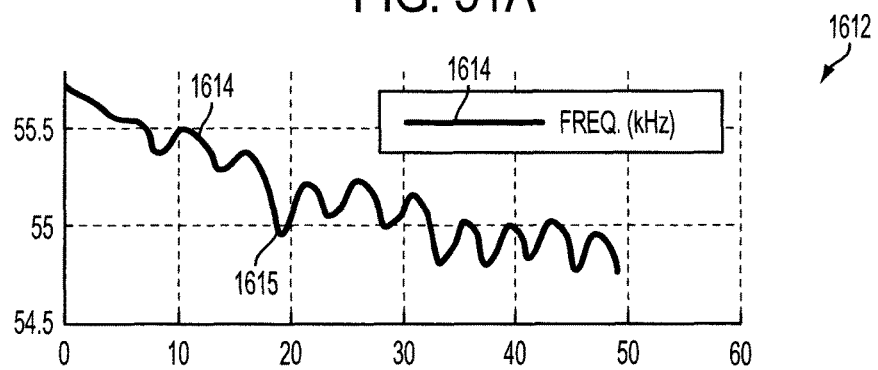
FIG. 31B is a graphical representation of frequency versus time waveform of one form of a generator during successive tissue cuts over a period of time.
Figure 31C:
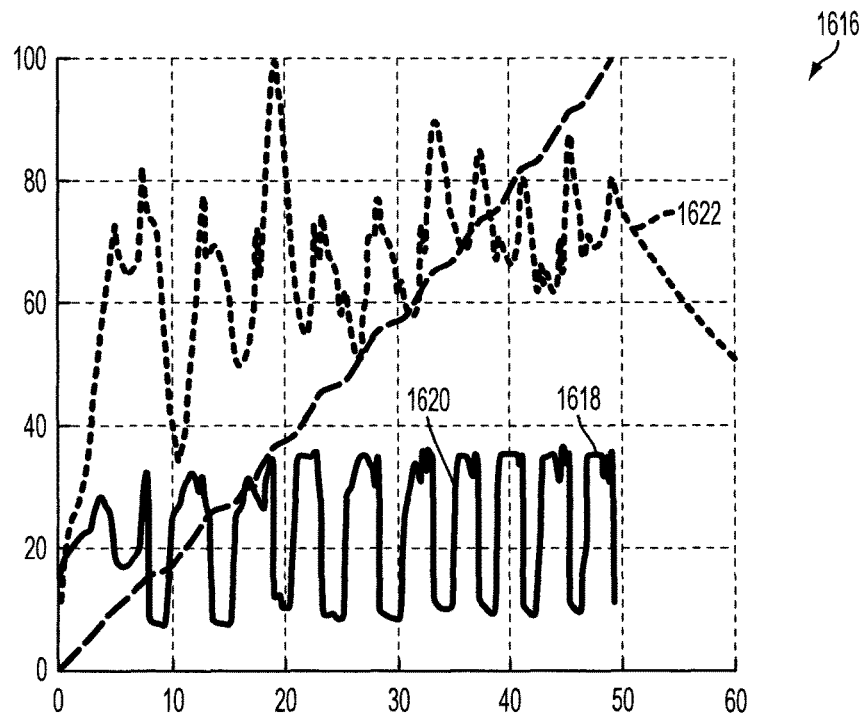
FIG. 31C is a graphical representation of power, energy, and temperature versus time waveforms of one form of a generator during successive tissue cuts over a period of time.

The representative data in FIG. 30 is shown more clearly with reference to FIGS. 31A-C. FIG. 31A is a graphical representation 1606 of impedance versus time waveform 1608 and current versus time waveform 1610 of one form of a generator during successive tissue cuts over a period of time. Impedance (Ohm) and Current (mA) are shown along the vertical axis and time (Sec) along the horizontal axis.

FIG. 31B is a graphical representation 1612 of resonant frequency waveform 1614 versus time of a signal of one form of a generator during successive tissue cuts over a period of time. Resonant frequency (kHz) is shown along the vertical axis and time (Sec) along the horizontal axis.

FIG. 31C is a graphical representation 1616 of a power waveform 1618, energy waveform 1620, and temperature waveform 1622 versus time of one form of a generator during successive tissue cuts over a period of time. Power (W), Energy (J), and Temp (C) are shown along the horizontal axis and time (Sec) along the horizontal axis.

Accordingly, with reference now to FIGS. 31A-C, as shown in the graphical representation 1612, it can be seen that after the resonant frequency curve 1614 has dropped 700 Hz (from 55.8 kHz to 55.1 kHz) at 1615 on the third cut (which is a particularly abusive cut wherein the tissue was tip loaded. After the resonance frequency waveform 1614 has dropped 700 Hz (from 55.8 kHz to 55.1 kHz) on the third cut, the ultrasonic instrument begins to saturate the generator and the current waveform 1610 dips slightly in all successive cuts. Since the drive current waveform 1610 is proportional to blade tip displacement, a dipping current waveform 1610 results in slower speed of tissue effect and therefore a lower energy deposition rate (and lower rate of heating, i.e., frequency slope is less negative). Management of this change due to dipping current waveform 1610 within an application sequence is possible using both frequency change and frequency slope change as will be described in connection with Examples 3 and 4 in subsequent sections of this specification.

FIG. 32 is a combined graphical representation 1630 of a frequency waveform 1632, weighted frequency slope waveform 1634 (calculated via exponentially weighted moving average with an alpha value of 0.1), and temperature waveform 1636 versus time generated by a generator similar to one form of the generators described herein. The ultrasonic system had a room temperature resonant frequency (longitudinal mode) slightly higher than that for which TABLE 5 was constructed. Therefore, the frequency threshold 1633 was increased accordingly from the 55,100 Hz shown in TABLE 5 to about 55,200 Hz shown in FIG. 33 as indicated by the dashed line. The activation was performed on tissue (e.g., on excised porcine jejunum tissue) with an ultrasonic system having a room temperature resonance of about 55.9 kHz set on power level 5. Tissue separation occurs at 6.25 seconds; one side of the tissue separates from the blade at about 8 seconds; and full separation occurs at about 10 seconds. FIG. 33 is a graphical representation of a frequency versus time waveform 1632 of one form of a generator 30, 500, 1002. Frequency (kHz) is shown along the vertical axis and Time (Sec) is shown along the horizontal axis. FIG. 33 shows the example of using a frequency threshold 1633 only using parameters consistent with those shown in TABLE 5, but adjusted to about 55,200 Hz as indicated by the dashed line 1633. The resonant frequency 1632 crosses the frequency threshold 1633 (dashed horizontal line—set at 700 Hz below room temperature resonance) at about 11 seconds and a Response Set may be triggered at this time.

FIG. 34 is a graphical representation 1634 of weighted frequency slope versus time waveform 1634 of one form of a generator. Weighted frequency slope (kHz/Sec) is shown along the vertical axis and Time (Sec) is shown along the horizontal axis. The frequency slope waveform 1634 is calculated via exponentially weighted moving average with an alpha value of 0.1. In FIG. 34, the frequency slope waveform 1634 crosses the frequency slope threshold 1635 (dashed horizontal line) and a Response Set may be triggered at about 5.8 seconds.

The remaining Examples 3 and 4 relate to the use of multiple Condition Sets, which require a more complex application of the tissue algorithm and includes the monitoring of frequency slope and/or frequency against their respective thresholds and may include a hierarchical approach to triggering response sets.

Example 3

Triggering a Response Set Based on Both the Frequency Slope Threshold and the Frequency Threshold A third example case includes triggering a Response Set based on both the frequency slope threshold and the frequency threshold. TABLE 6 contains representative parameters for this objective in connection with surgical instruments such as any one of the surgical instruments 19, 190, 1000 disclosed herein comprising corresponding ultrasonic instruments such as the ultrasonic instruments 100, 120, 1004 disclosed herein.

TABLE 6

Representative Parameters for Triggering Audio Indications by Frequency Slope and Frequency Thresholds (two Condition Sets utilized)

| Parameter | Value* |
|---|---|
| Condition Set 1 Pulsing flag | 0 |
| Condition Set 1 LCD display flag | 0 |
| Condition Set 1 Audio flag | 1 |
| Condition Set 2 Pulsing flag | 0 |
| Condition Set 2 LCD display flag | 0 |
| Condition Set 2 Audio flag | 1 |
| Required time before triggered, Condition Set 1 | 50 msec |
| Minimum latch time, Condition Set 1 | 0 msec* |
| Frequency Slope Thresholds (one for each power level), Condition Set 1 | level 5: −0.060 kHz/sec<br>level 4: −0.053 kHz/sec<br>level 3: −0.045 kHz/sec<br>level 2: −0.038 kHz/sec<br>level 1: −0.030 kHz/sec |
| Frequency Threshold, Condition Set 1 | 56,000 Hz* |
| Required time before triggered, Condition Set 2 | 50 msec |
| Minimum latch time, Condition Set 2 | 0 msec* |
| Frequency Slope Thresholds (one for each power level), Condition Set 2 | level 5: 1.00 kHz/sec*<br>level 4: 1.00 kHz/sec*<br>level 3: 1.00 kHz/sec*<br>level 2: 1.00 kHz/sec*<br>level 1: 1.00 kHz/sec* |
| Frequency Threshold, Condition Set 2 | 55,100 Hz |
| Time to wait | 100 msec |
| Cross-back Frequency Slope Threshold | −0.020 kHz/sec |
| First Pulse Amplitudes (one for each power level) | N/A |
| First Pulse Time | N/A |
| Second Pulse Amplitudes (one for each power level) | N/A |
| Second Pulse Time | N/A |

*These parameter values are set to an appropriate extreme such that they do not effectively take part in logic flow (e.g. set to always be "true")

In this case of Example 3, a tiered or hierarchical response is demonstrated. The combined logic of the frequency slope threshold and the frequency threshold will be illustrated using the same graphical representations shown in FIGS. 32-34. In FIG. 34, Condition Set 1 is triggered by the frequency slope waveform 1634 crossing the frequency slope threshold 1635 value at about 6 seconds. The Response Set for Condition Set 1 may include a low level audible indicator, for example. As the user continues to activate the instrument with minimal intervening tissue, Condition Set 2 is triggered as the resonant frequency drops below the frequency threshold 1633 at about 11 seconds as shown in FIG. 33. The Response Set for Condition Set 2 may be an elevated audible indicator, for example.

Example 4

Triggering a Response Set Based on Both the Frequency Slope Threshold and the Frequency Threshold A fourth example extends to the application of both frequency and frequency slope thresholds during abusive conditions of the surgical instrument. For various reasons, the frequency slope signal levels may diminish (i.e., become less negative) with extended application.

In abusive conditions, frequency, frequency slope, and current waveforms may deviate from normal operation may be generated while the ultrasonic instrument is constantly activated at a power level 5, where the jaws of the ultrasonic instrument were opened for 1 second, then closed for 1 second and repeated for 17 cycles.

When an ultrasonic instrument is activated multiple times directly against the pad, the characteristic frequency slope waveform in a first region before the generator saturates becomes less negative than in a second after the generator saturates due, in large part, to the system efficiency and resulting displacement/current drop. In the non-saturation region of the frequency slope waveform, the ultrasonic system has not yet saturated and current is maintained at or near the target current for power level 5. In the saturation region of the frequency slope waveform, the current (and therefore blade tip displacement) continually drops causing the frequency slope to increase (rate of heating drops). Note that at after several abusive cycles, e.g., the fourth abuse cycle, which is the approximate demarcation between the non-saturation and saturation regions, the resonant frequency drops consistent with FIGS. 29-31A-C. Separate Conditions Sets for each of the non-saturation and saturation regions may be applied. A first frequency slope threshold may be employed in the non-saturation region when resonant frequency conditions are above a predetermined frequency threshold and a second, less negative frequency slope threshold may be employed in the saturation region when resonant frequency conditions are below the same predetermined frequency threshold.

A weighted frequency slope (kHz/sec) versus time waveform may be of one form of a generator. When the instrument is used abusive conditions against the pad, the characteristic frequency slope waveform in the non-saturation region becomes less negative than in the saturation region due to material softening and a corresponding reduction in pad coefficient of friction. In the non-saturation region of the frequency slope waveform corresponds to when the tissue pad has not yet begun to heat significantly. In the saturation region of the frequency slope waveform, the pad begins to soften and the interface between the blade and the pad becomes more lubricious causing the frequency slope waveform to increase (rate of heating drops). Separate Conditions Sets for each of the non-saturation and saturation regions may be warranted. A first frequency slope threshold may be employed in the non-saturation region when resonant frequency conditions are above a predetermined frequency slope threshold and a second, less negative frequency slope threshold may be employed in the saturation region when the resonant frequency is below the same predetermined frequency slope threshold.

Another example case is now considered. TABLE 7 contains parameters for an ultrasonic instrument where two Condition Sets are used to account for diminishing frequency slope signal levels due to system saturation and dropping current.

TABLE 7

Representative Parameters for Triggering Audio Indications by Frequency Slope and Frequency Thresholds, accounting for diminishing frequency slope due to system saturation (two Condition Sets utilized)

| Parameter | Value* |
| --- | --- |
| Condition Set 1 Pulsing flag | 0 |
| Condition Set 1 LCD display flag | 0 |
| Condition Set 1 Audio flag | 1 |
| Condition Set 2 Pulsing flag | 0 |
| Condition Set 2 LCD display flag | 0 |
| Condition Set 2 Audio flag | 1 |
| Required time before triggered, Condition Set 1 | 50 msec |
| Minimum latch time, Condition Set 1 | 0 msec* |
| Frequency Slope Thresholds (one for each power level), Condition Set 1 | level 5: −0.060 kHz/sec<br>level 4: −0.053 kHz/sec<br>level 3: −0.045 kHz/sec<br>level 2: −0.038 kHz/sec<br>level 1: −0.030 kHz/sec |
| Frequency Threshold, Condition Set 1 | 56,000 Hz* |
| Required time before triggered, Condition Set 2 | 50 msec |
| Minimum latch time, Condition Set 2 | 0 msec* |
| Frequency Slope Thresholds (one for each power level), Condition Set 2 | level 5: −0.045 kHz/sec<br>level 4: −0.038 kHz/sec<br>level 3: −0.030 kHz/sec<br>level 2: −0.024 kHz/sec<br>level 1: −0.020 kHz/sec |
| Frequency Threshold, Condition Set 2 | 55,100 Hz |
| Time to wait | 100 msec |
| Cross-back Frequency Slope Threshold | −0.020 kHz/sec |
| First Pulse Amplitudes (one for each power level) | N/A |
| First Pulse Time | N/A |
| Second Pulse Amplitudes (one for each power level) | N/A |
| Second Pulse Time | N/A |

*These parameter values are set to an appropriate extreme such that they do not effectively take part in logic flow (e.g., set to always be "true")

The data generated for this example run were generated using an ultrasonic instrument to make ten successive cuts in jejunum tissue as quickly as possible. Using the parameter values from TABLE 7, the Frequency vs. Time plots for the example sample case are shown in FIGS. 35-36.

Figure 35:
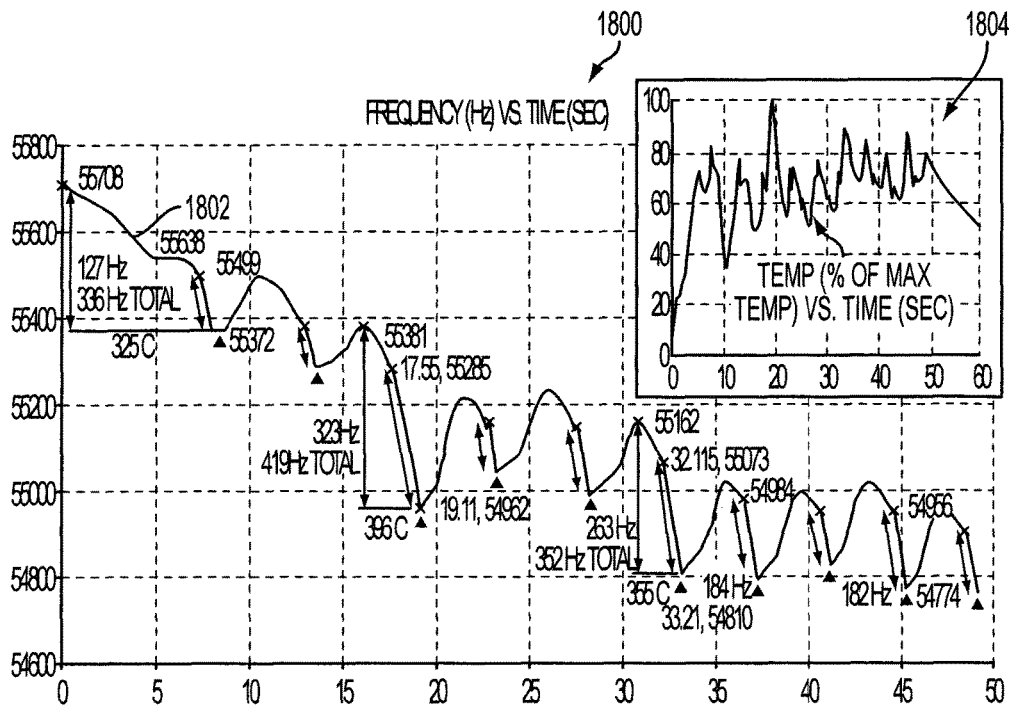
FIG. 35 is a graphical representation of a frequency versus time waveform of one form of a generator over ten cuts on jejunum tissue and a graphical representation of a temperature versus time signal.

FIG. 35 is a graphical representation 1800 of a frequency versus time waveform 1802 of one form of a generator over ten cuts on tissue (e.g., jejunum tissue) and a graphical representation 1804 of a temperature versus time waveform 1805. For the graphical representation 1800, Frequency (Hz) is shown along the vertical axis and Time (Sec) is shown along the horizontal axis. For the graphical representation 1804, Temperature (° F.) is shown along the vertical axis and Time (Sec) is shown along the horizontal axis.

Figure 36:
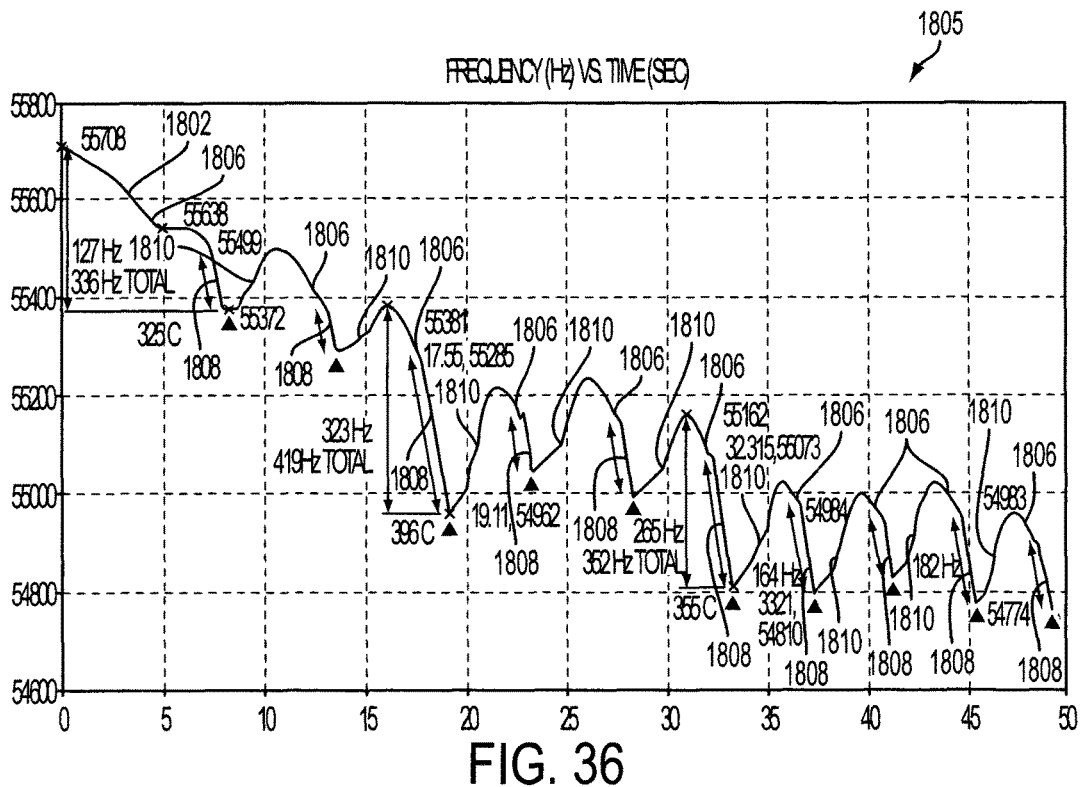
FIG. 36 is a graphical representation of the frequency versus time waveform shown in FIG. 35 of one form of a generator over ten cuts on jejunum tissue with activation of intervening tissue.

FIG. 36 is a graphical representation 1805 of the frequency versus time waveform 1802 shown in FIG. 35 of one form of a generator over ten cuts on tissue (e.g., jejunum tissue) with activation of intervening tissue at portions indicated by reference number 1806. Frequency (Hz) is shown along the vertical axis and Time (Sec) is shown along the horizontal axis.

The frequency waveform 1802 shown in FIGS. 35 and 36 is for the example case using two Condition Sets to account for diminishing frequency slope due to electrical system saturation (diminishing displacement). Note that this is the same test run as is shown in FIGS. 29-31A-C. In FIG. 36, the highlighted portions 1806 indicates activation with intervening tissue (frequency drops, shape of local frequency curve related to dryness of tissue—shallow start slope, steepens as tissue dries), the highlighted portions 1808 indicate activation with minimal or no intervening tissue (local frequency slope very steep, curve shape is more linear, steepens gradually), the section of the curve with no highlighted portions 1810 indicates time within which the device is being repositioned for the next cut, blade cools in air and cools rapidly when placed on tissue (frequency rises).

Figure 37:
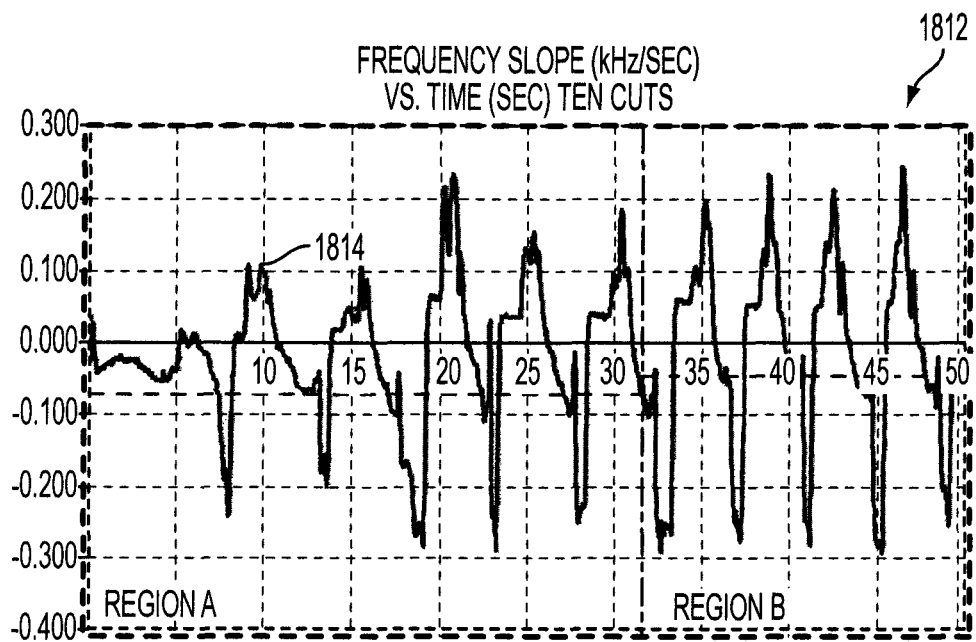
FIG. 37 is a graphical representation of a frequency slope versus time waveform of one form of a generator over ten cuts on jejunum tissue.

FIG. 37 is a graphical representation 1812 of a frequency slope versus time waveform 1814 of one form of a generator over ten cuts on jejunum tissue. Frequency slope (kHZ/Sec) is shown along the vertical axis and Time (Sec) is shown along the horizontal axis. Region B of the frequency slope waveform 1814 shows the area of the ten cut run where Condition Set 2 is triggered prior to Condition Set 1 for the first time during the ten cut run (frequency is below 55.1 kHz and frequency slope is less than −0.045 kHz/sec). The condition illustrated in Region B, where Condition Set 2 is triggered prior to Condition Set 1, is desired because the ultrasonic system is consistently saturating by this point in the run (voltage is saturating and current is diminished resulting in diminished displacement and, therefore, diminished rate of heating requiring a greater frequency slope threshold).

Figure 38:
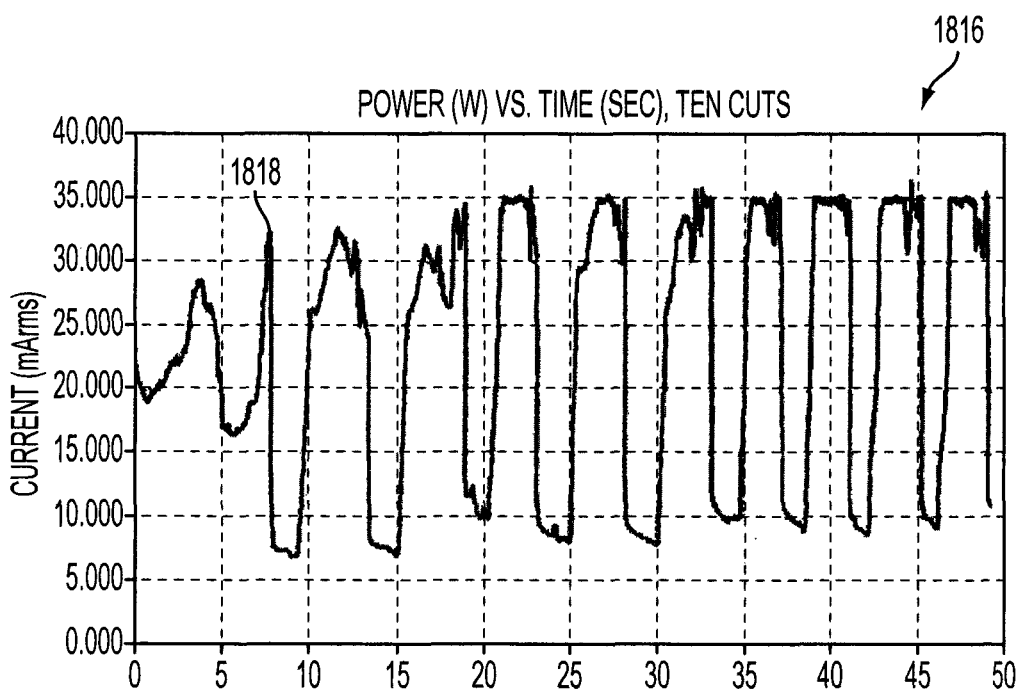
FIG. 38 is a graphical representation of a power versus time waveform representative of power consumed by a one form of a generator over ten cuts on jejunum tissue.

FIG. 38 is a graphical representation 1816 of a power versus time waveform 1818 representative of power consumed by a one form of a generator over ten cuts on tissue (e.g. jejunum tissue). Power (W) is shown along the vertical axis and Time (Sec) is shown along the horizontal axis.

Figure 39:
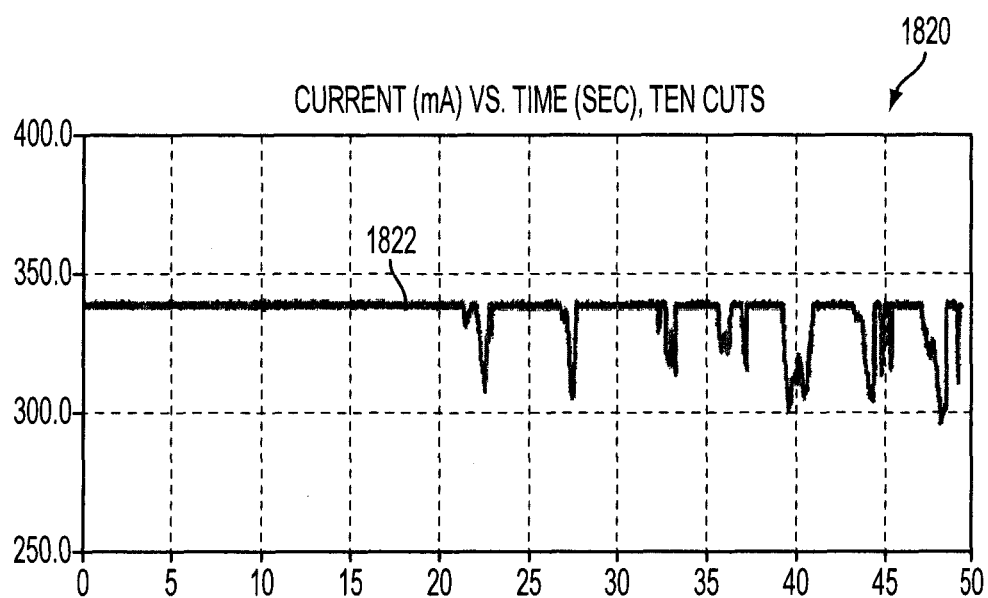
FIG. 39 is a graphical representation of a current versus time waveform of one form of a generator over ten cuts on jejunum tissue.

FIG. 39 is a graphical representation 1820 of a current versus time waveform 1822 of one form of a generator over ten cuts on jejunum tissue. Current (mA) is shown along the vertical axis and Time (Sec) is shown along the horizontal axis.

Figure 48:
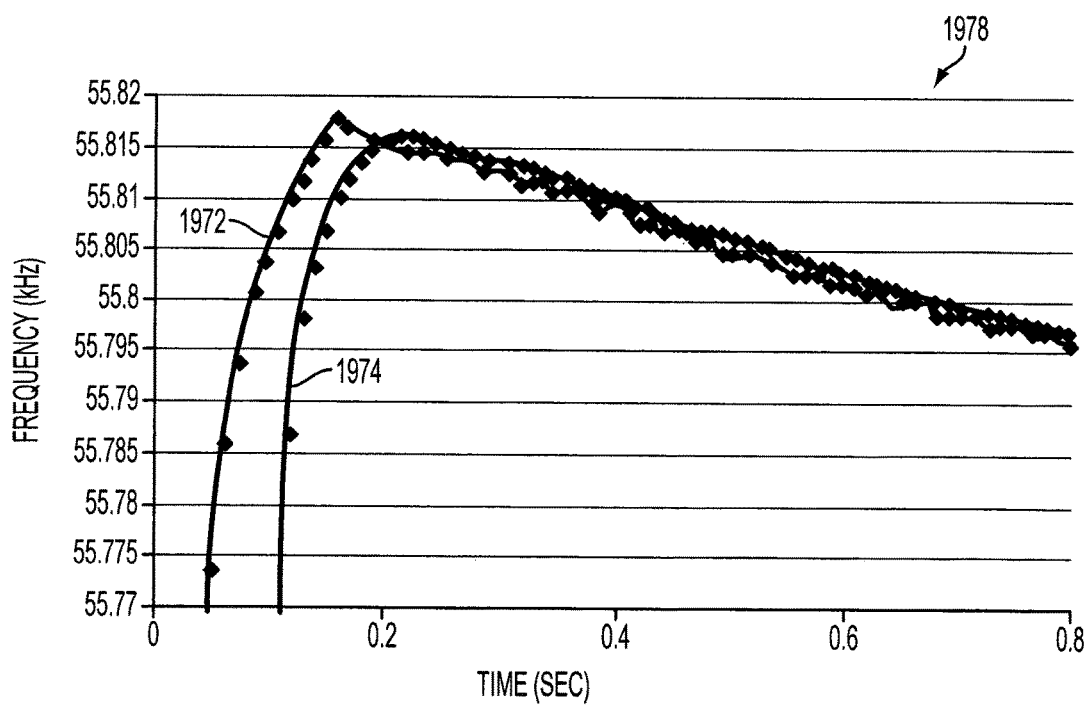
FIG. 48 is a zoomed in view of the resonant frequency and averaged resonant frequency versus time waveforms shown in FIG. 47.
Figure 49:
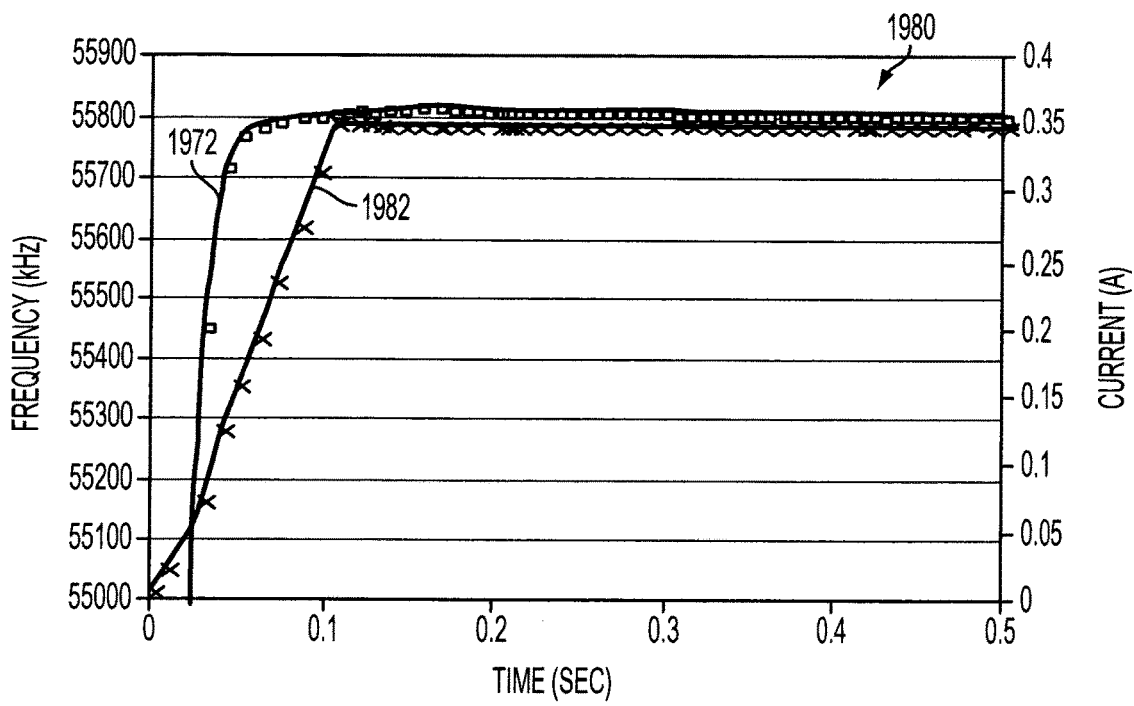
FIG. 49 is a zoomed in view of the resonant frequency and current versus time waveforms of one form of a generator.

Having described the basic application of the tissue algorithm discussed in connection with the logic flow diagrams 1200, 1300, 1400 shown in FIGS. 20-22 in terms of monitoring the frequency slope, resonant frequency, or both against their respective thresholds, the discussion now turns to a description of the latching logic and corresponding use as it relates to the tissue algorithm. The motivations for adding the latching logic to the tissue algorithm are: (a) to prevent a Condition Set from resetting (Condition Set changes from true to false) due to a blade/pad interface becoming more lubricious during a blade on pad abuse condition; and (b) to prevent a Condition Set from resetting (Condition Set changes from true to false) due to pulsed activation where periods of rapid heating are interweaved with periods of less rapid heating (sections of heat flux into the blade and sections of heat flux out of the blade are interweaved). The first and second of these motivations are shown in FIGS. 48 and 49 illustrate, respectively. As defined earlier in this disclosure, the two latch parameters addressing these motivations are "cross-back frequency slope threshold" as shown in FIG. 40 and "minimum latch time." For completeness of disclosure, FIG. 43 shows calculated frequency slope curves for the pulsed run shown in FIGS. 41 and 42A-C.

Figure 40:
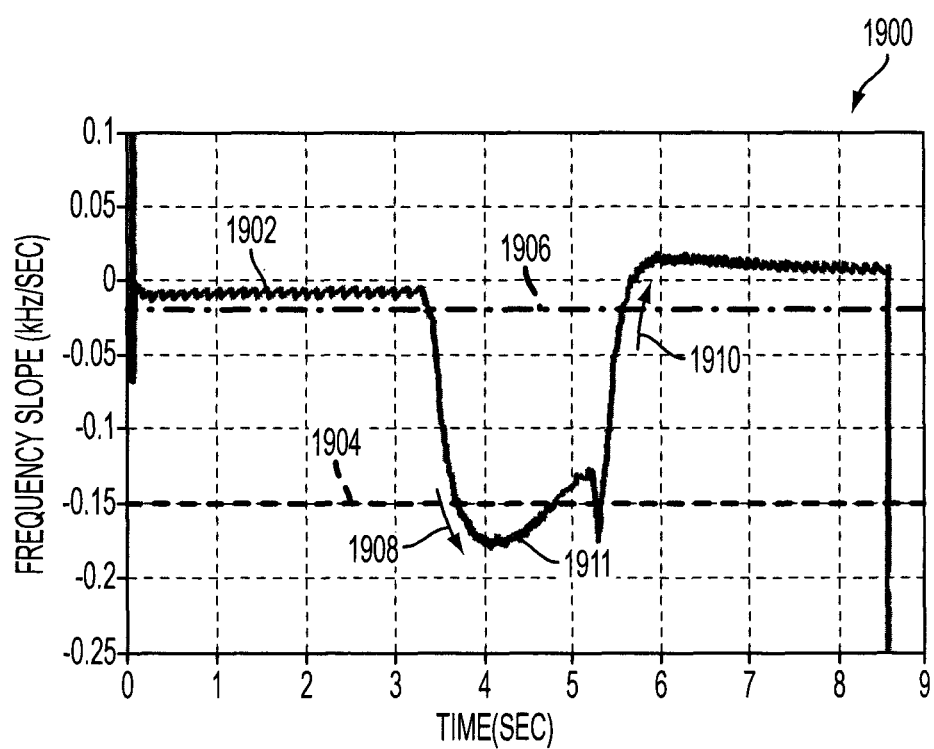
FIG. 40 is a graphical representation of a "cross-back frequency slope threshold" parameter in connection with a frequency slope vs. time waveform of one form of a generator.

FIG. 40 is a graphical representation 1900 of a "cross-back frequency slope threshold" parameter in connection with frequency slope versus time waveform 1902. As shown in FIG. 40, the "frequency slope threshold" 1904 is shown by the horizontal dashed line at −0.15 kHz/sec. The "cross-back frequency slope threshold" 1906 is shown by the horizontal dash-dot line at −0.02 kHz/sec. In this instance, the Condition Set is met and a Response Set is triggered when the local calculated frequency slope crosses the "frequency slope threshold" as shown by arrow 1908 pointing down. The Condition Set is not met (Response Set is no longer triggered) when the local calculated frequency slope crosses over the "cross-back frequency slope threshold" as shown by arrow 1910 pointing up. Note that without using the "cross-back over frequency slope threshold" in this case, the Response Set would not have been triggered when the local frequency slope crossed back over the horizontal dashed line 1904 at about 4.7 seconds shown at cross over point 1911.

Figure 41:
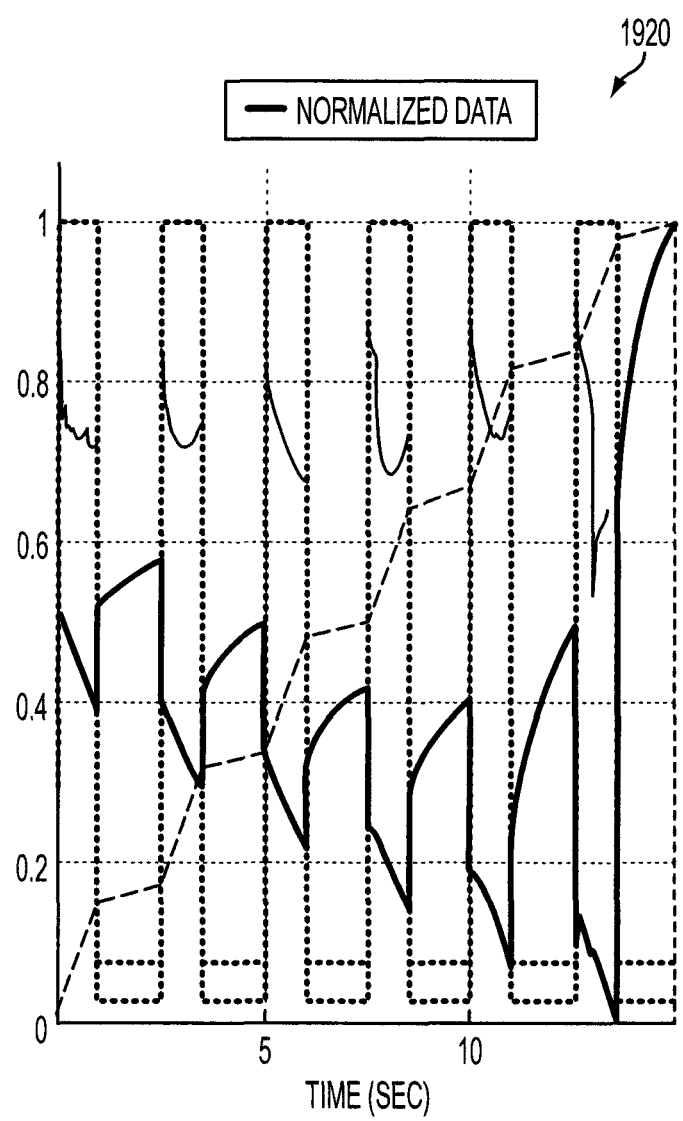
FIG. 41 is a combined graphical representation of a pulsed application of one form of an ultrasonic instrument on an excised carotid artery showing normalized power, current, energy, and frequency waveforms versus time.

FIG. 41 is a combined graphical representation 1920 of a pulsed application of one form of an ultrasonic instrument on an excised carotid artery showing normalized power, current, energy, and frequency data plotted versus time.

Figure 42A:
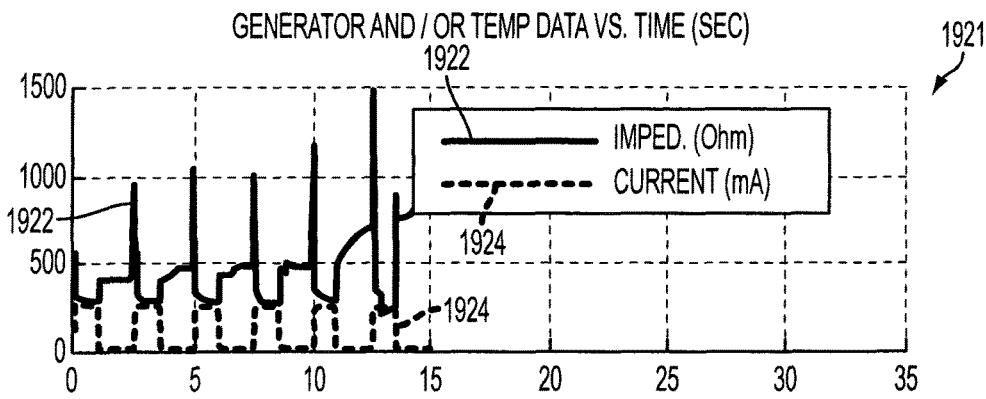
FIG. 42A is a graphical representation of impedance and current versus time waveforms of one form of a generator during successive tissue cuts over a period of time.
Figure 43:
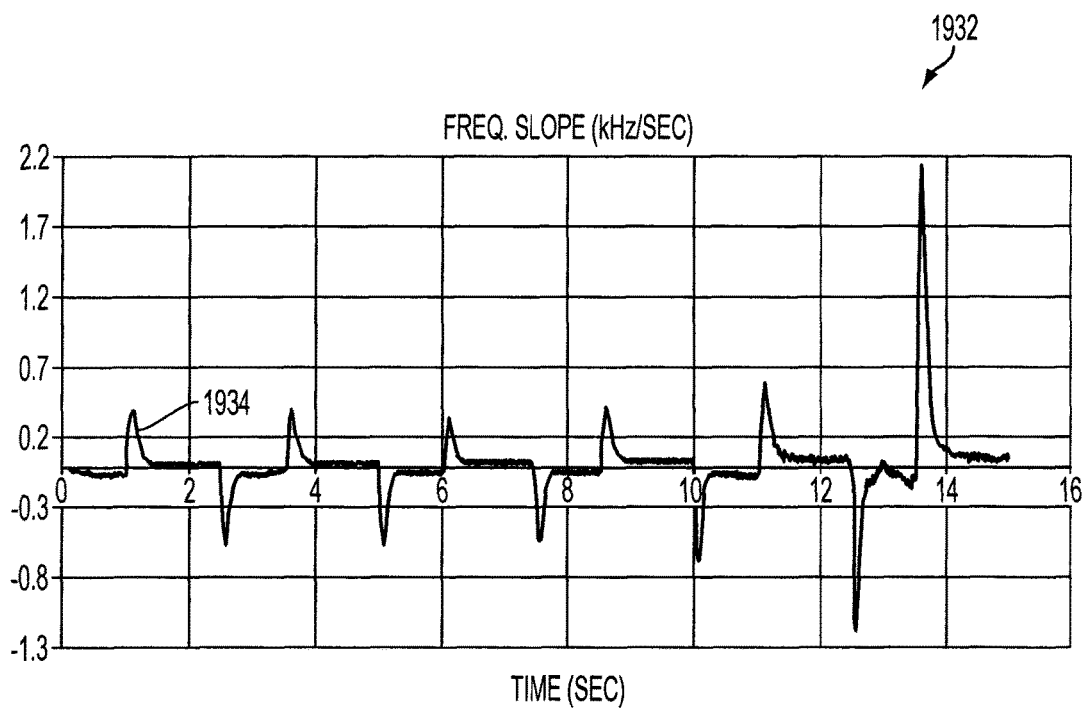
FIG. 43 is a graphical representation of a calculated frequency slope waveform for the pulsed application shown in FIG. 41 and FIGS. 50A-C plotted on a gross scale.

FIG. 42A is a graphical representation 1921 of an impedance versus time waveform 1922 and a current versus time waveform 1924 of one form of a generator during successive tissue cuts over a period of time. The impedance (Ohms) and current (mA) is shown along the vertical axis and Time (Sec) is shown along the horizontal axis.

Figure 42B:
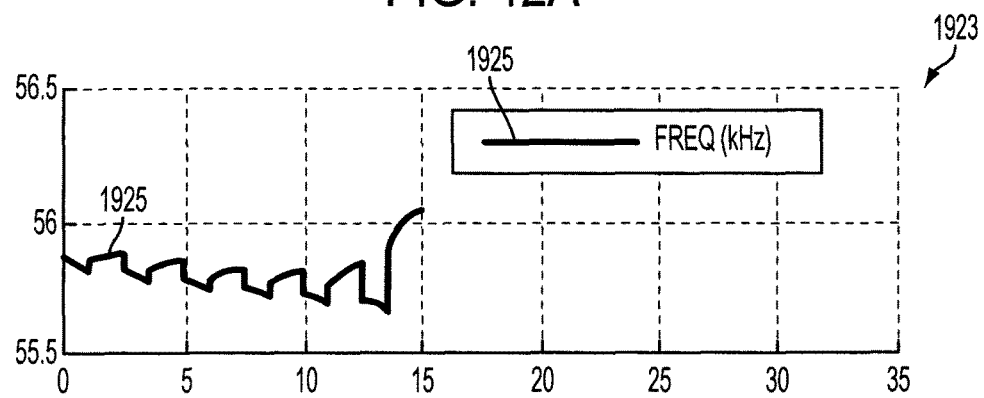
FIG. 42B is a graphical representation of a frequency versus time waveform of one form of a generator during successive tissue cuts over a period of time.

FIG. 42B is a graphical representation 1923 of a frequency versus time waveform 1925 of one form of a generator during successive tissue cuts over a period of time. Frequency (kHz) is shown along the vertical axis and Time (Sec) is shown along the horizontal axis.

Figure 42C:
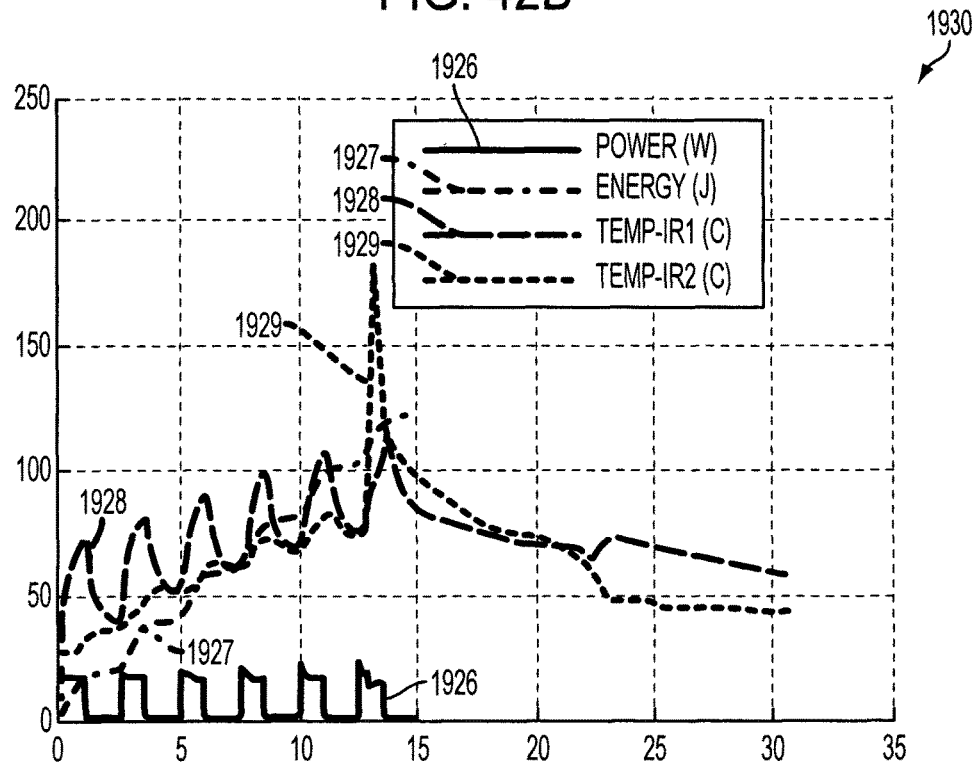
FIG. 42C is a graphical representation of power, energy, and temperature versus time waveforms of one form of a generator during successive tissue cuts over a period of time.

FIG. 42C is a graphical representation 1930 of power waveform 1926, energy waveform 1927, a first temperature waveform 1928 and a second temperature waveform 1929 plotted versus time as of one form of a generator during successive tissue cuts over a period of time. Power (W), Energy (J), and Temperature (° C.) are shown along the vertical axis and Time (Sec) is shown along the horizontal axis.

FIGS. 42A-C show a pulsed application of an ultrasonic instrument on an excised carotid artery where the First Pulse Time is 1 second, the First Pulse Amplitude is 100% of power level 3 output current. The Second Pulse Time is 1.5 seconds and the Second Pulse Amplitude is less than 10% of power level 3 output current. Of note, the resonant frequency waveform 1925 exhibits sections of both heating (heat flux into the blade) and cooling (heat flux out of the blade). The "minimum latch time" parameter, defined herein as the minimum amount of time for response(s) to a Condition Set X to be triggered, is intended to maintain triggering of a Response Set during pulsed application (one example of a latch time may be about 1 second). Of additional note, as shown in FIG. 42A, the load or impedance waveform 1922 does not drop below 200 Ohms throughout the run sequence. This may be favorable considering that the impedance waveform 1922 for a marching application consistently drops below about 150 Ohms while operating in air between cuts implying that an impedance limit may be used for resetting Condition Sets. In one aspect this impedance limit may be used for implementation of the "low drive in air" concept as disclosed in U.S. Pat. No. 5,026,387 to Thomas.

Figure 44:
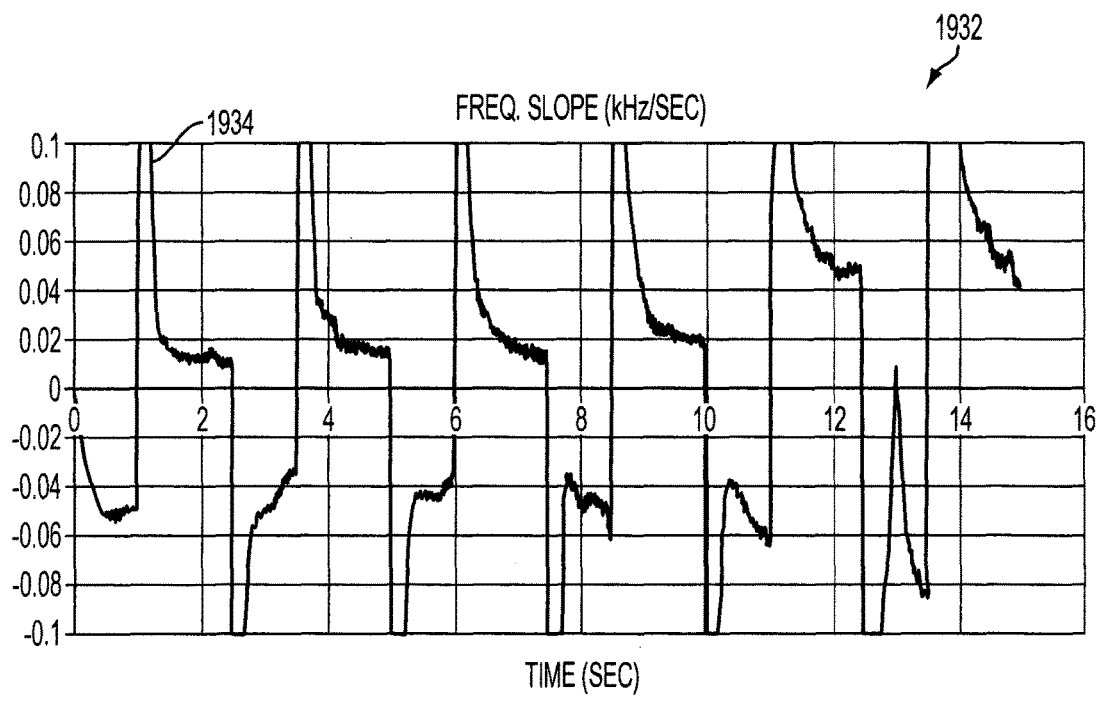
FIG. 44 is a zoomed in view of the graphical representation of the calculated frequency slope waveform for the pulsed application shown in FIG. 43.

FIG. 43 is a graphical representation 1932 of a calculated frequency slope waveform 1934 for the pulsed application shown in FIG. 41 and FIGS. 42A-C plotted on a gross scale. FIG. 44 is a zoomed in view of the graphical representation of the calculated frequency slope waveform 1934 for the pulsed application shown in FIG. 43. Both FIGS. 43 and 44 show the calculated frequency slope waveform 1934 for the pulsed application shown in FIG. 41 and FIGS. 42A-C. Frequency slope (kHz/Sec) is shown along the vertical axis and Time (Sec) is shown along the horizontal axis. Two scales are shown, where FIG. 43 shows a gross scale for frequency slope and FIG. 44 shows a "zoomed in" view. For frequency slope, the same trends seen under continuous drive are shown in pulsed drive including values that correlate well to heat flux into (negative frequency slope) and out of the blade (positive frequency slope). The transient nature of the frequency curve and frequency slope curve due to pulsing, combined with the moving average calculation of frequency slope make use of the frequency slope curve during pulsing difficult. Of note, the tissue separated at 13 seconds. As can be seen in FIG. 43 and especially FIG. 44, the rate of cooling can be used to trigger a response correlating rapid cooling in the dwell portions of pulsed outputs to the completion of a tissue transection using logic (not shown by logic flows in FIGS. 20-22) where frequency slope waveform 1934 exceeds a threshold value, in this case of about 0.04 kHz/sec when sampled at the ends (i.e., the settled regions) of the dwell periods. As can be seen in FIG. 42A, the impedance waveform 1922 can be used to trigger a response correlating high impedance (high resistance to mechanical motion or vibration) to the completion of a tissue transection using logic (again, not shown by logic flows in FIGS. 20-22) where transducer impedance waveform 1922 exceeds a threshold value, in this case of about 700 Ohms when sampled at the beginnings (i.e., the settled regions) of the dwell periods.

Figure 45:
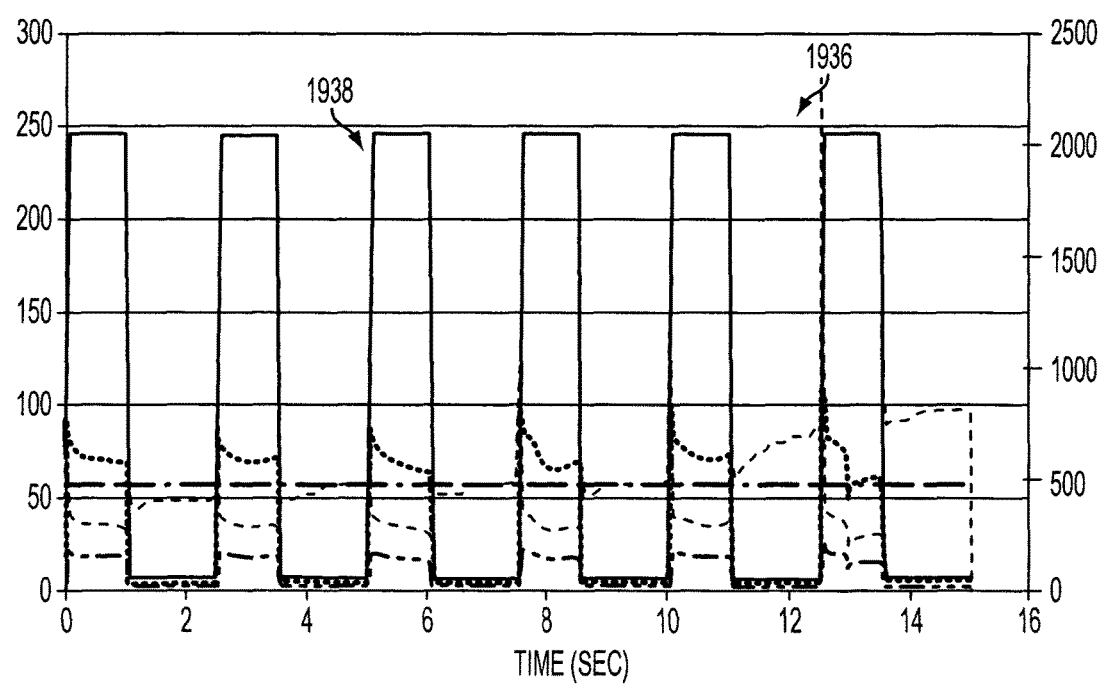
FIG. 45 is a graphical representation of other data waveforms of interest such as impedance, power, energy, temperature.

FIG. 45 is a graphical representation 1936 of other data waveforms 1938 of interest such as impedance, power, energy, temperature. In FIG. 45, the vertical scale to the right applies to the impedance curve only.

The present disclosure now turns to considerations for power level and clamp pressure profile in an ultrasonic instrument. The rate of heating of a blade to pad interface is proportional to blade displacement, interface coefficient of friction and load (clamp pressure or normal force). Testing was performed to assess the tissue algorithm at a range of displacements (power levels) and device specific combinations of clamp pressure and coefficient of friction (defined largely by pad materials and blade coatings).

Figure 46:
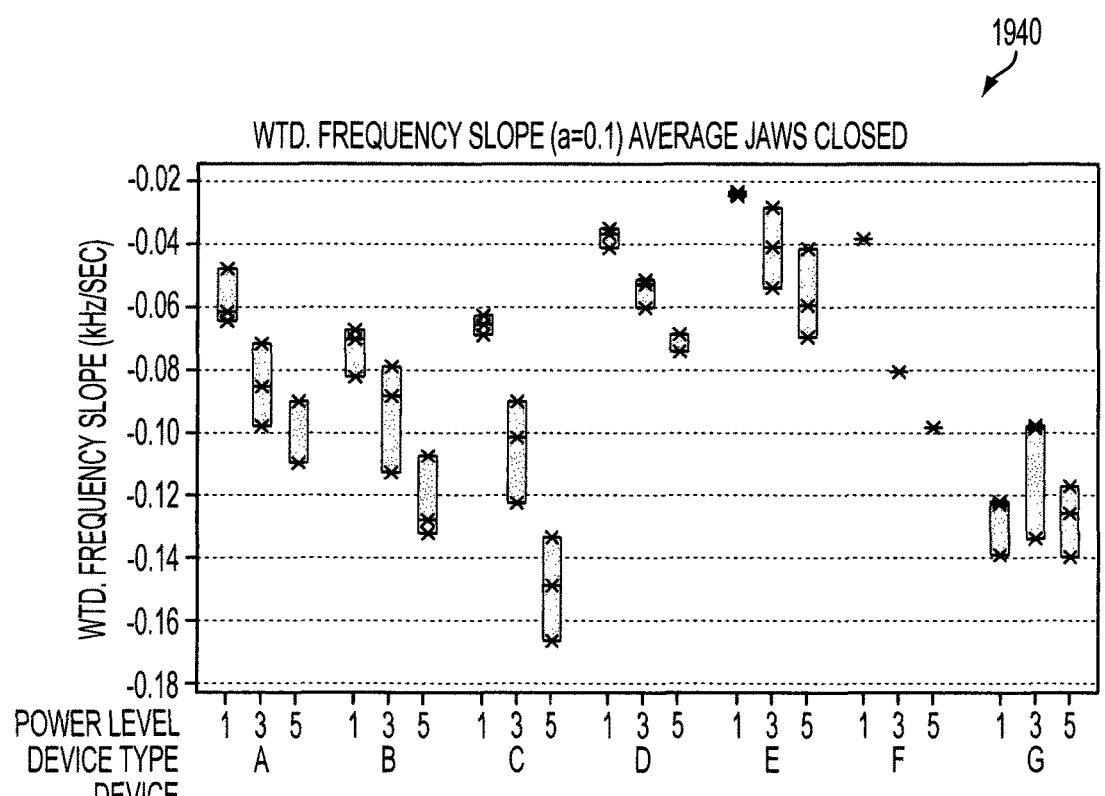
FIG. 46 is a graphical representation of a summary of weighted frequency slope versus power level for various ultrasonic instrument types.

FIG. 46 is a graphical representation 1940 of a summary of weighted frequency slope versus power level for various ultrasonic instrument types. Weighted frequency slope (kHz/Sec) is shown along the vertical axis and power level, device type, and device are shown along the horizontal axis. The instruments used to generate the data summarized in the graphical representation 1940 are generally commercially available with some exceptions. One test procedure included clamping the device, activating the device for three seconds, and calculating the average frequency slope over the full three seconds. Other metrics, however, may be employed. For most devices, the data summarized in FIG. 46 would be approximately indicative of the minimum frequency slope value. FIG. 46 shows the frequency slope summary data for burn-in testing on shears type ultrasonic instruments where the instruments were clamped, then activated for 3 seconds, then unclamped—the average frequency slope over the full three seconds of activation was calculated and plotted as shown.

Based on predetermined tests and test data from FIG. 46, the following frequency slope thresholds are suggested for the main power levels of use with some ultrasonic instruments:

(1) level 5 frequency slope threshold: −0.060 kHz/sec;
(2) level 3 frequency slope threshold: −0.045 kHz/sec;

(3) level 5 frequency slope threshold: −0.070 kHz/sec; and (4) level 3 frequency slope threshold: −0.050 kHz/sec.

System stiffness includes both blade stiffness (cantilevered beam) and pad stiffness/pad thermal stability. The more differentiated the unloaded (no tissue) system stiffness is from the loaded (clamped on tissue) system stiffness, the more robust the tissue algorithm performance. Other constraints, of course, may limit system stiffness on the high end.

Further exploration of displacement effects were analyzed based on a larger set of data. For the ultrasonic system, power levels are essentially differentiated by output current target values and, current, which is proportional to vibratory amplitude or displacement. Analysis of this data also may include digital smoothing of the frequency data to obtain usable frequency slope curves.

Figure 47:
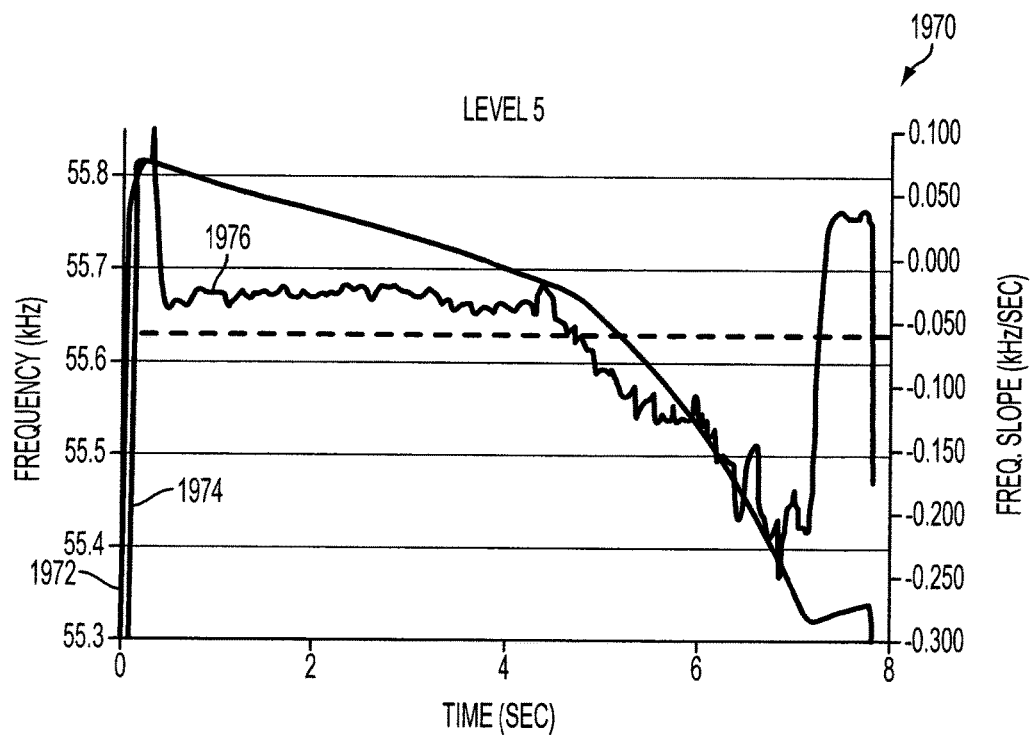
FIG. 47 is a graphical representation of resonant frequency, averaged resonant frequency, and frequency slope versus time waveforms of one form of a generator.

FIGS. 47-49 show frequency and current versus time waveforms obtained using one form of a generator and an ultrasonic instrument to excise a porcine carotid artery at power level 5.

FIG. 47 is a graphical representation 1970 of resonant frequency versus time waveform 1972, an averaged resonant frequency versus time waveform 1974, and a frequency slope versus time waveform 1976 of one form of a generator. Frequency (kHz) and Frequency Slope (kHz/Sec) are shown along the vertical axes and Time (Sec) is shown along the horizontal axis. The frequency slope waveform 1976 is based on the averaged frequency data and was obtained by post processing the frequency waveform 1972 data. The raw frequency data is plotted as well as smoothed (via simple moving average) frequency data and frequency slope (calculated from the smoothed data because the raw frequency data contains stair-stepping due to rounding of the streamed data). The average resonant frequency waveform 1974 is obtained via a 70 msec moving average (kHz) of the resonant frequency data.

FIG. 48 is a zoomed in view 1978 of the resonant frequency versus time waveform 1972 and the averaged resonant frequency versus time waveform 1974 of one form of a generator. Frequency (kHz) is shown along the vertical axis and Time (Sec) is shown along the horizontal axis.

FIG. 49 is a zoomed in view 1980 of the resonant frequency waveform 1972 and a current versus time waveform 1982 of one form of a generator. Frequency in (Hz) and Current (A) is shown along the vertical axes.

In FIGS. 48 and 49, the respective zoomed in views 1978, 1980 are shown to see the effect of smoothing frequency data and to see rise information at the start of the application, which may be helpful for assessment of parameters such as Time to Wait.

Other aspects of the tissue algorithm described herein may be applied to situations when little to no intervening tissue remains (between the ultrasonic blade and the clamp arm) and waste energy is being dumped into the end effector. Accordingly, in one form, the tissue algorithm may be modified to provide feedback to the user relative to this situation. Specifically, the tissue algorithm leverages the fact that the resonance of an ultrasonic blade changes relative to temperature (decreases with increasing temperature and increases with decreasing temperature).

In one aspect the tissue algorithm disclosed herein may be employed to monitor the frequency slope of a waveform where the algorithm monitors the change in resonant frequency slope to indicate the changing condition of the tissue. In the case shown in FIG. 50, for example, the inflection of the frequency response curve correlates to the point at which the tissue begins to separate (i.e., there is a tissue tag and the user continues to activate the instrument), which can be verified by experimentation. The change in frequency slope can be used to provide visual, audible and/or tactile feedback (e.g., distinct beeping sound, flashing light, tactile vibration, among others previously discussed) to the user (that waste energy is being dumped into the end effector) or the generator output could be controlled or stopped.

In another aspect, the tissue algorithm disclosed herein may be employed to monitor the frequency threshold of a waveform, where the algorithm monitors the change in frequency as the waveform crosses some threshold or difference from some known state (e.g., room temperature). Similar to monitoring the frequency slope, as the change in frequency drops below some threshold value or difference, an indication can be given to the user that the device end effector is heating at an accelerated rate. Again, FIG. 50 provides a graphical illustrative view of a frequency threshold.

In yet another aspect, the tissue algorithm disclosed herein may be employed to monitor the frequency slope change and the frequency threshold in combination. The combination of a significant change in frequency slope and a drop in frequency below some threshold can be used to provide an indication of high temperature.

Figure 50:
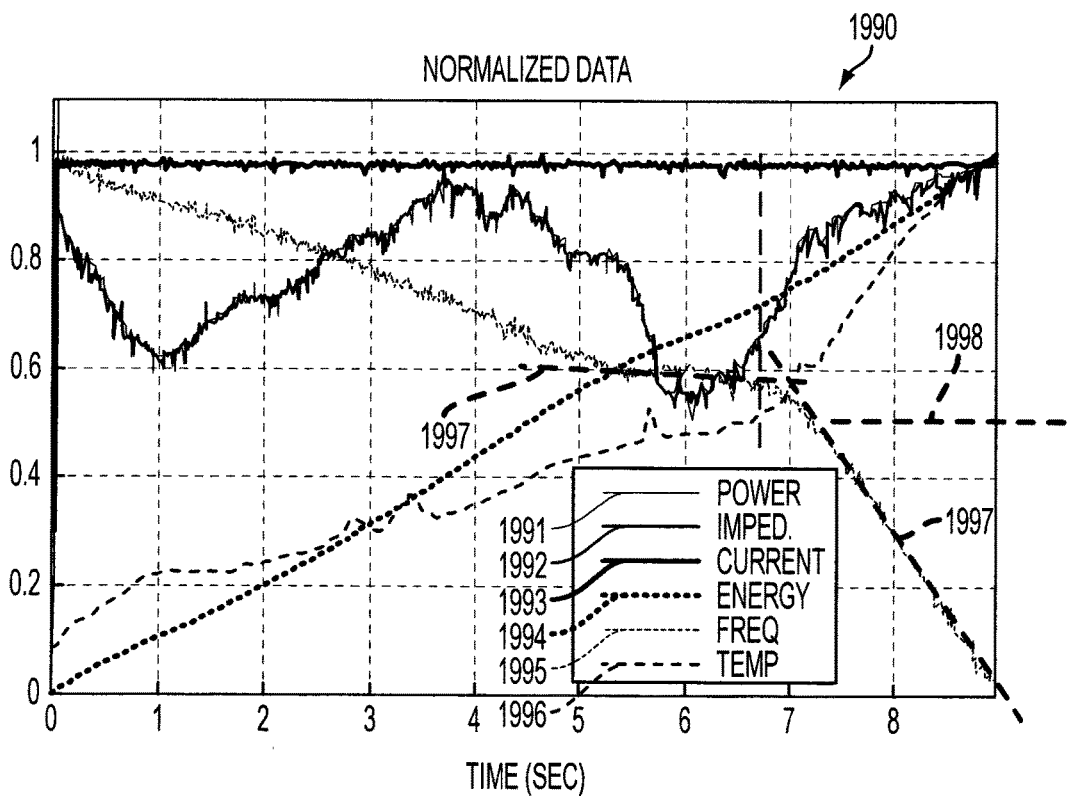
FIG. 50 is a graphical representation of normalized combined power, impedance, current, energy, frequency, and temperature waveforms of one form of a generator coupled to an ultrasonic instrument.

Turning now to FIG. 50, is a graphical representation 1990 of normalized combined power 1991, impedance 1992, current 1993, energy 1994, frequency 1995, and temperature 1996 waveforms of one form of a generator coupled to an ultrasonic instrument. As shown, the tissue begins to separate at 6.672 seconds. From this point until the tissue fully separates, about 55-60% of the total frequency drop is obtained, the temperature increases by a factor of about 1.92 (from 219° C. to 418° C.) and about 28% of the total energy applied is delivered. The local slopes of the frequency vs. time waveforms are shown by a first set of dashed lines 1997, which represents a rapid change in the resonant frequency slope. Monitoring this slope 1997 affords the opportunity to indicate a dramatic change which typically occurs when there is limited to no intervening tissue and the vast majority of power is being applied to the blade/tissue pad interface. Likewise, the frequency change from its resonance in a known state (e.g., room temperature) can be used to indicate high temperatures—a frequency change threshold is shown with a second dashed line 1998. Also, a combination of these two, frequency slope change and frequency change threshold, can be monitored for purposes of indication. Note that the frequency changes in this case from an initial value of 55,712 Hz to an end value of 55,168 Hz with the threshold shown at about 55,400 Hz.

In some example forms, surgical and/or instrument-related conditions may reduce the ability of the Condition Sets described above to accurately reflect the state of the instrument. In some situations, the blade may heat more slowly than normal, causing the resonant frequency to be higher and the frequency slope to be more gradual that expected. One example of such a situation may occur when tissue is adhered to a non-clamping surface of the blade. In this and other situations, a more gradual rate of heating is seen, even upon completion of a tissue bite when minimal or no tissue is present between the blade and clamp arm pad. This may, in turn, delay the meeting of various Condition Sets based on comparing local frequency slope to a frequency slope threshold parameter and/or comparing local resonant frequency to a frequency threshold parameter. As a result, Response Sets implementing audible tones, pulsed modes, current deactivation, etc., may be unnecessarily delayed.

FIGS. 51A and 51B are graphical representations of resonant frequency and frequency slope, respectively, displayed by one form of an ultrasonic instrument during an ultrasonic tissue bite. The bite illustrated in FIGS. 51A and 51B resulted in gradual heating of the blade of an ultrasonic instrument. FIG. 51A is a chart showing time on a horizontal axis 2100 and blade resonant frequency on a vertical axis 2104. A plot 2105 illustrates the resonant frequency of the blade over time. FIG. 51B is a chart showing time on a horizontal axis 2104 and frequency slope on a vertical axis 2106. Plot 2107 illustrates frequency slope over time. In the example cut shown in FIGS. 51A and 51B, tissue separation occurred at between 2 and 3 seconds. The tissue separation caused a small change in resonant frequency, indicated at 2108, and a shallow minimum in frequency slope, indicated at 2100. The signal features 2108, 2110, however, may not be sufficient to timely trigger a Condition Set requiring frequency slope to drop below a frequency slope threshold parameter and/or requiring resonant frequency to drop below a frequency threshold parameter.

FIGS. 52A and 52B are graphical representations of resonant frequency and frequency slope, respectively, displayed by one form of an ultrasonic instrument during another ultrasonic tissue bite. Again, the illustrated tissue bite resulted in gradual heating of the blade of an ultrasonic instrument. Plot 2112 illustrates resonant frequency versus time for the tissue bite of FIGS. 52A-52B while plot 2114 illustrates frequency slope versus time for the tissue bite of FIGS. 52A-52B. In the illustrated tissue bite, tissue began to separate from the blade at between five and seven seconds, and a tissue tag fully separated from the blade at about nine seconds. As can be seen, the tissue separation caused a small change in resonant frequency, beginning at 2116, and a small minimum in the frequency slope, as indicated by 2118. Again, however, due to slow heating of the blade, the signal features 2116, 2118 may not be sufficient to trigger a desired Condition Set.

In certain forms, generators, such as 30, 500, 1002, and/or ultrasonic surgical instruments, such as 100, 120, 1004, may be implemented with one or more Condition Sets that consider a dynamic frequency cut-off. These, and other condition sets described herein, may be actuated by the clinician upon receipt of an input signal from a switch, button or pedal or, in some forms, run on background while other algorithms are executed (e.g., instrument control algorithms). For example, a baseline resonant frequency may be captured when ultrasonic impedance exceeds a threshold impedance. For example, exceeding the threshold impedance may indicate that the clamp arm is closed (e.g., a tissue bite is about to begin). One or more Condition Sets may comprise a baseline frequency cut-off condition that is met when the resonant frequency of the blade differs from the baseline frequency by more than a baseline deviation threshold parameter. In certain forms, the baseline frequency cut-off condition is met even when other conditions based on resonant frequency or frequency slope are not met. When utilized in a logical "Or" arrangement with other conditions, baseline frequency cut-off conditions may allow certain Condition/Response Set pairs to be triggered in situations, such as those described above, where blade heating is more gradual than normal.

Figure 53:
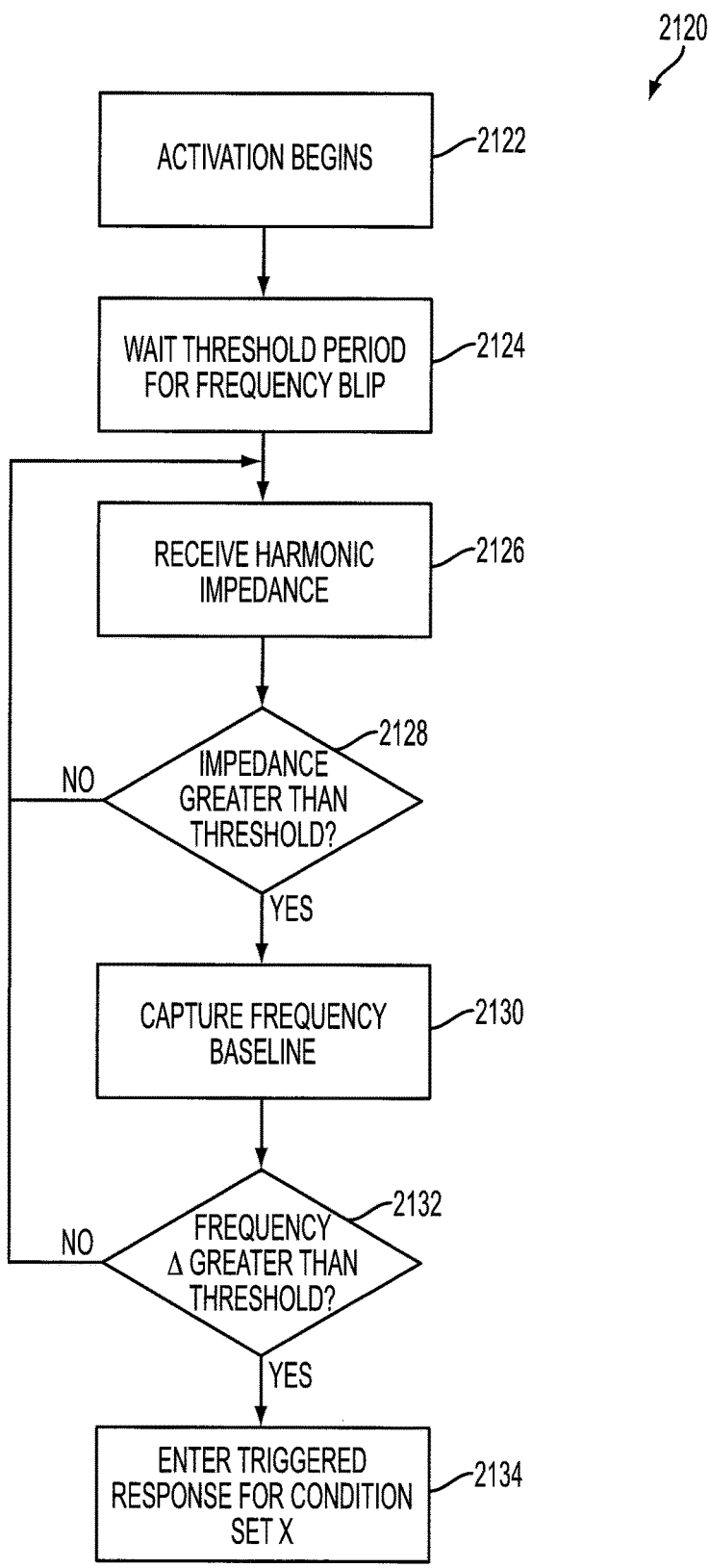
FIG. 53 is a logic flow diagram of one form of a tissue algorithm implementing a baseline frequency cut-off condition that may be implemented in one form of a generator to consider a baseline resonant frequency of an ultrasonic blade.
Figure 54A:
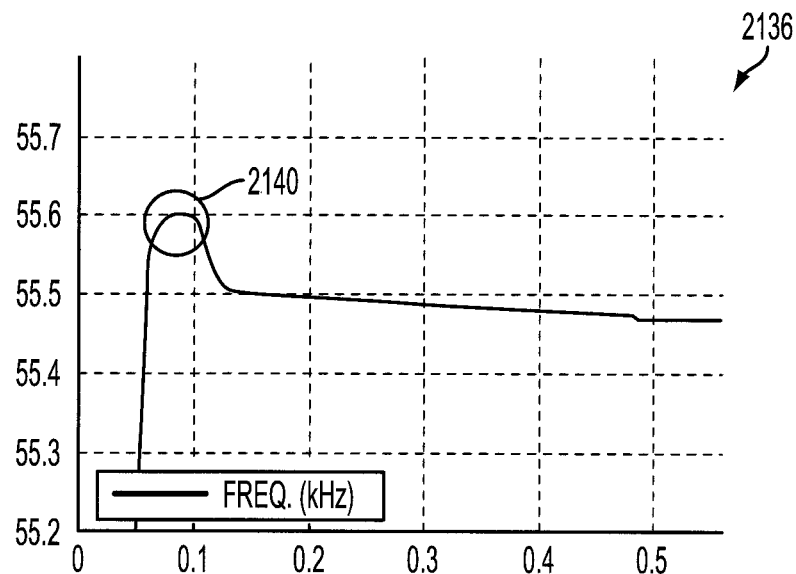
FIGS. 54A and 54B are graphical representations of blade frequency demonstrated in different example ultrasonic activations.
Figure 54B:
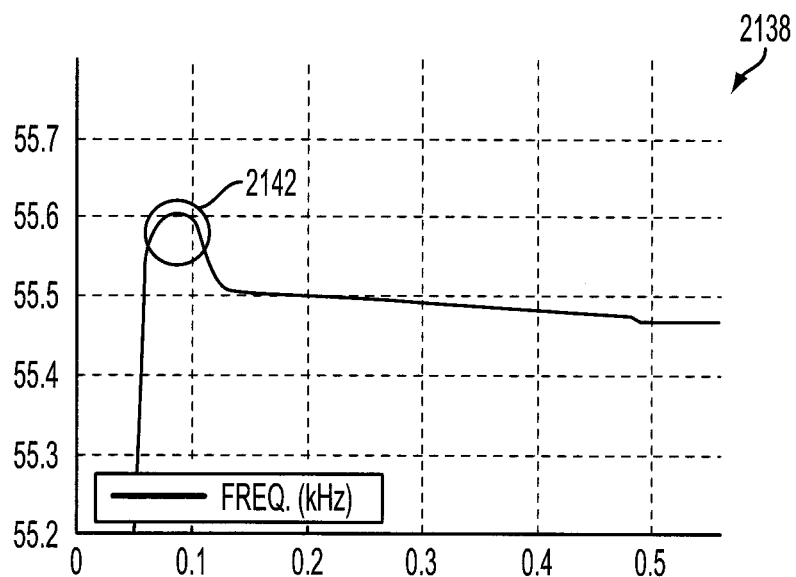

FIG. 53 is a logic flow diagram of one form of a tissue algorithm 2120 implementing a baseline frequency cut-off condition that may be implemented in one form of a generator to consider a baseline resonant frequency of an ultrasonic blade. At 2122, activation of the blade begins. For example, the generator may be activated at a particular power level, indicated as "N." Optionally, at 2124, the generator may wait a threshold time period. The threshold time period may be sufficient to allow any frequency or other transients occurring upon activation to dissipate. For example, FIGS. 54A and 54B are graphical representations of blade frequency demonstrated in different example ultrasonic activations. Plot 2136 shows frequency versus time for a first example activation, and demonstrates a transient frequency feature or blip at 2140. Plot 2138 shows frequency versus time for a second example activation, and demonstrates a transient feature or blip 2142.

Referring back to 2124, the algorithm 2120 may utilize any suitable threshold time period that extends beyond the dissipation of all or most signal transients or blips. For example, in some forms, the threshold time period may be between 0.1 and 1.0 seconds. In some example forms, the threshold time period may be between 0.2 and 0.5 seconds. In one example form, the threshold time period may be about 0.2 seconds. At, 2126 the generator may receive an indication of the ultrasonic impedance. In various example forms, the ultrasonic impedance represents an electrical impedance of the transducer blade system, and/or an impedance of the "motional branch," as described herein above. At 2128, the generator may determine whether the ultrasonic impedance is greater than a threshold impedance. For example, this may the closing of the clamp arm either against the blade or against tissue. In some forms, the generator at 2128 may not conclude that the ultrasonic impedance is greater than the threshold unless it is greater than the threshold for a set amount of time (a "time above impedance" period). The time above impedance period may be any suitable value and may be between 10 and 100 msec including, for example, 30 msec.

If the ultrasonic impedance is not above the threshold impedance at 2128 (or is not above the threshold impedance for the "time above impedance" period), the generator may return to 2126 and 2128, continuing to monitor the ultrasonic impedance until it does exceed the threshold impedance. If the ultrasonic impedance is above the threshold impedance at 2128, the generator may capture a local resonant frequency of the blade as a baseline frequency at 2130. As the activation continues, the generator may, at 2132, determine whether a frequency delta, or difference between the baseline frequency and the local resonant frequency of the blade exceeds a baseline deviation threshold parameter. If the frequency delta exceeds the baseline deviation threshold parameter, then the baseline cut-off condition may be met. If the meeting of the baseline cut-off condition causes a complete Condition Set to be met, than a corresponding Response Set may be triggered at 2134. In some forms, the baseline cut-off condition is not met until or unless the frequency delta is above the baseline deviation threshold parameter value for a time above frequency delta period.

Figure 55:
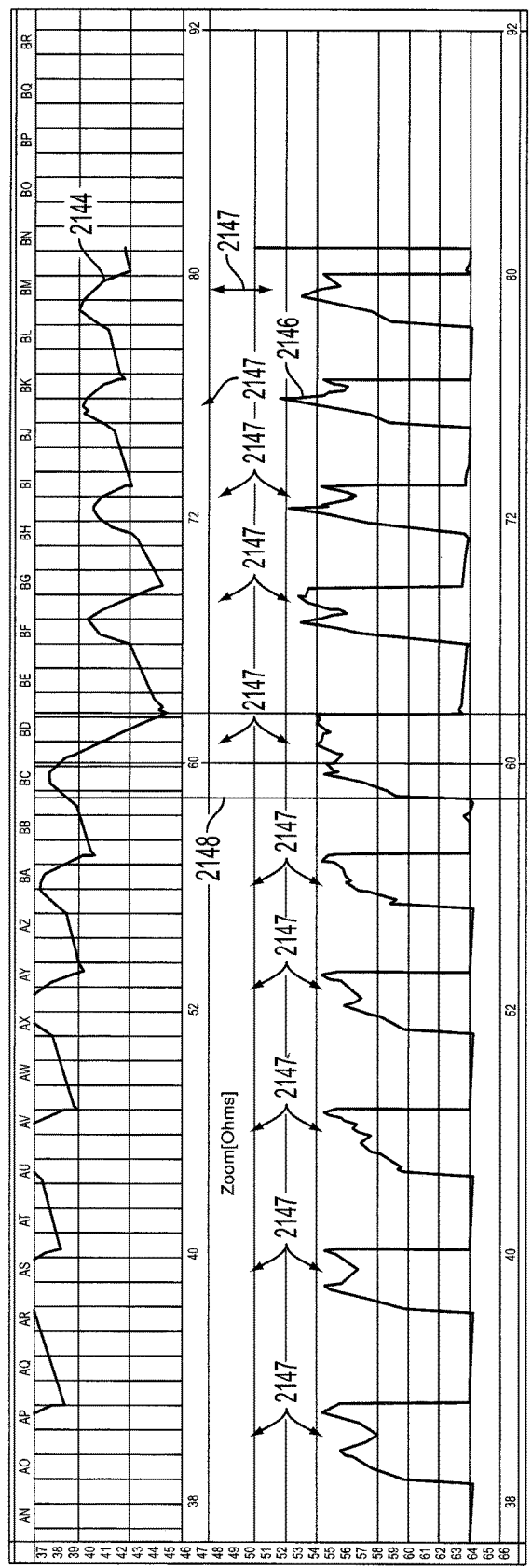
FIG. 55 is a graphical representation of resonant frequency and ultrasonic impedance over time for one form including multiple cuts with an ultrasonic blade.

In some example forms, utilizing a baseline frequency and frequency delta, as described with respect to the algorithm 2120, also addresses issues arising in surgical situations where the resonant frequency of the ultrasonic blade floats between activations or cuts. This may occur, for example, when an ultrasonic blade is used for multiple cuts without being deactivated. FIG. 55 is a graphical representation of resonant frequency 2144 and ultrasonic impedance 2150 over time for one form including multiple cuts with an ultrasonic blade. Each feature 2147 represents a distinct tissue bite, cut or other tissue treatment utilizing the ultrasonic blade. It can be seen from FIG. 55 that, at the outset of each cut, the resonant frequency spikes (e.g., as the clamp arm closes on tissue). For example as the clamp arm closes on tissue, the blade may be brought into contact with relatively cool tissue. This may cool the blade, causing the temporary positive slope of the resonant frequency, as shown. As ultrasonic energy is applied to the blade, it begins to heat, causing the illustrated decline in resonant frequency for each cut. Referring now to FIG. 55 in conjunction with the algorithm 2120, the ultrasonic impedance may exceed the harmonic threshold impedance at the outset of each cut 2147, causing the generator to capture a baseline frequency at that time. For example, line 2148 indicates an example point in time where the ultrasonic impedance exceeded the threshold impedance and a baseline frequency was taken.

Figure 56:
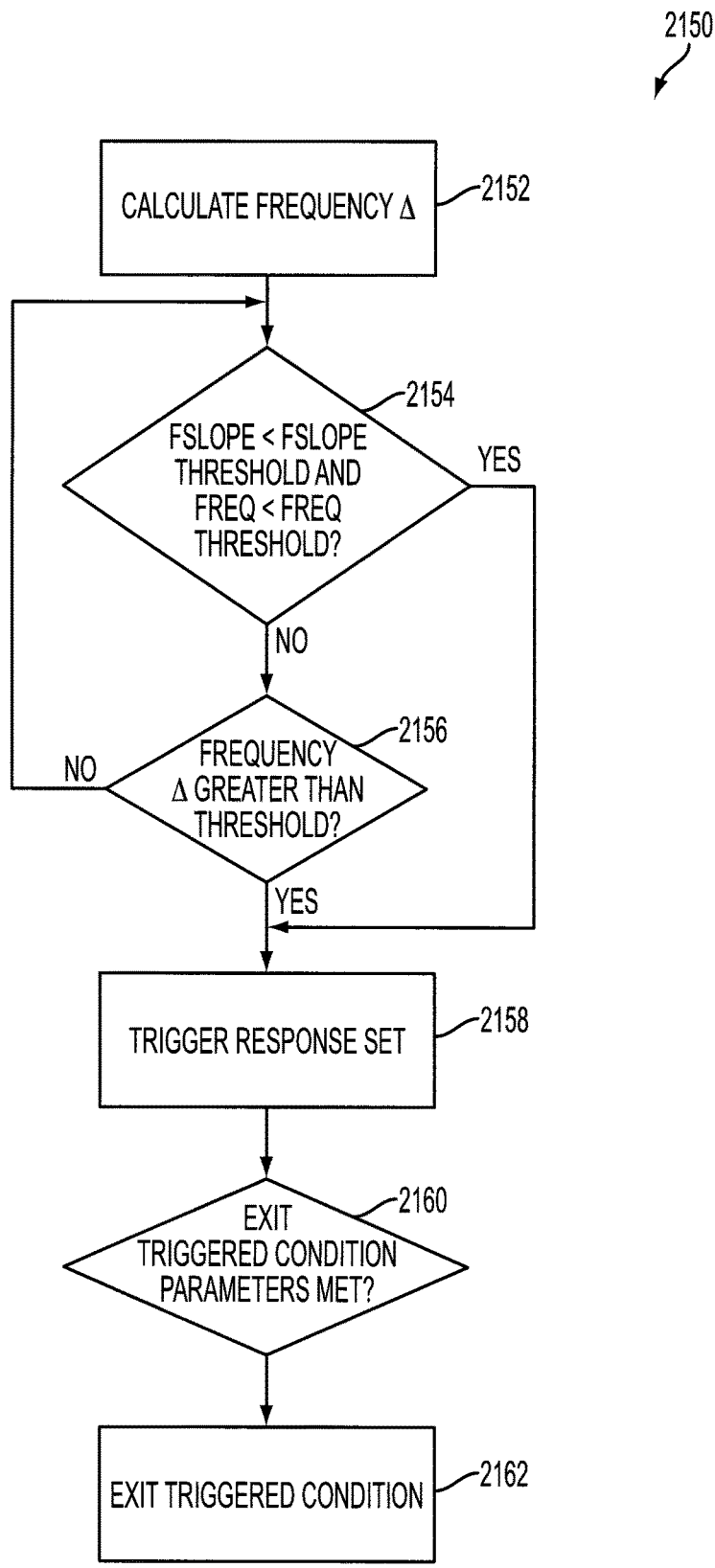
FIG. 56 is a logic flow diagram of a tissue algorithm that may be implemented in one form of a generator and/or instrument to implement a baseline frequency cut-off condition in conjunction with other conditions.

In certain forms, a baseline frequency cut-off condition may be utilized in a common Condition Set with one or more other conditions. FIG. 56 is a logic flow diagram of a tissue algorithm 2150 that may be implemented in one form of a generator and/or instrument to implement a baseline frequency cut-off condition in conjunction with other conditions. At 2152, the generator may calculate a frequency delta. The frequency delta may be calculated as described above, for example, with respect to the algorithm 2120. For example, the generator may capture a baseline frequency upon ultrasonic impedance exceeding the impedance threshold, and find the frequency delta as a difference between the local resonant frequency and the baseline frequency. At 2154, the generator may apply one or more other conditions. Such conditions may be similar to those described above with respect to FIGS. 20-22. For example, the other conditions may include whether the local frequency slope is less than a frequency slope threshold parameter 1404, whether the local resonant frequency is less than a frequency threshold parameter, etc. The other conditions may be applied in any logical manner. For example, the other conditions may be considered met of one of the other conditions is met (e.g., a logical OR), may be considered met only if all of the other conditions are met (e.g., a logical AND), etc.

If the other conditions are met at 2154, the Condition Set may be considered met, and the generator may trigger the appropriate Response Set at 2158. If the other conditions are not met at 2154, the generator may determine if the frequency delta is greater than the baseline deviation threshold parameter at 2156. If not, then the other conditions may be applied again at 2154. If yes, then the Condition Set may be considered met even though the other conditions are not met. Once a Response Set is triggered at 2128, the Response Set may continue to be executed until parameters for exiting the Response Set are determined to be met at 2160 and the triggered condition is exited at 2162. Such parameters may include, for example, the expiration of a Condition Set minimum latch time parameter, frequency slope exceeding a cross-back frequency slope threshold, etc.

Figure 57:
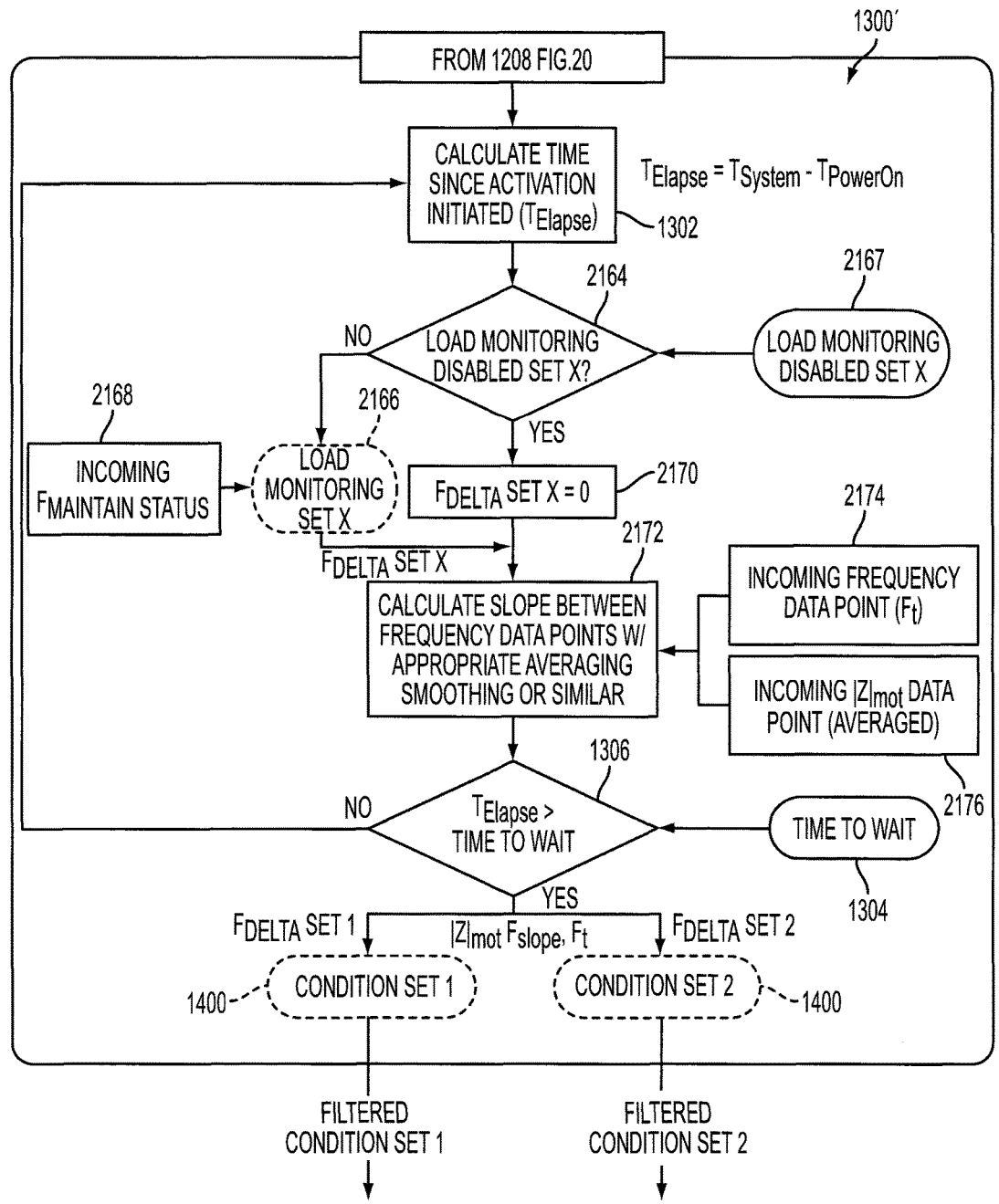
FIG. 57 is a logic flow diagram of one form of a signal evaluation tissue algorithm portion of the tissue algorithm shown in FIG. 20 considering a baseline frequency cut-off condition.

In various example forms, a baseline frequency cut-off condition may be utilized in the context of the logic flow diagrams 1200, 1300, 1400 of FIGS. 20-22 described above. For example, FIG. 57 is a logic flow diagram of one form of a signal evaluation tissue algorithm portion 1300' of the tissue algorithm 1200 shown in FIG. 20 considering a baseline frequency cut-off condition. The algorithm 1300' may be executed in a manner similar to that of the algorithm 1300 described herein above. At 2164, however, the generator may determine whether a load monitoring flag is set for a given Condition Set X. In some example forms, the load monitoring flag 2167 may indicate whether a frequency cut-off condition is to be considered.

If the load monitoring flag 2167 is not set, the frequency delta may be set to zero (e.g., a frequency delta of zero may never exceed the baseline derivation threshold, allowing the algorithm 1300' to operate in a manner similar to that of the algorithm 1300). If the load monitoring flag 2167 is set, the generator may execute a load monitoring algorithm 2166, which may receive as input a maintain status flag 2168. The maintain status flag may indicate to the generator whether to wait a threshold time period before considering ultrasonic impedance so as to avoid transient features or blips as illustrated with respect to FIGS. 54A, 54B.

The load monitoring algorithm 2166 may return the frequency delta. Additional details of how the load monitoring algorithm returns the frequency delta are provided herein below with respect to FIG. 58. Referring again to FIG. 57, at 2172, the generator may calculate a slope between two or more resonant frequency data points and may utilize appropriate averaging and/or smoothing, as described herein above. Input at 2172 may include an incoming resonant frequency data point 2174 ($F_t$) and an incoming ultrasonic impedance data point 2176 ($|Z|_{mot}$), which may be instantaneous and/or averaged over several data points. The time to wait timer may be applied at 1306 as described above. If the time to wait has elapsed, the generator may execute one or more condition set algorithms 1400/1400', as described herein. Each condition set algorithm 1400/1400' may receive as arguments the ultrasonic impedance, the frequency slope, the resonant frequency, and the frequency delta.

Figure 58:
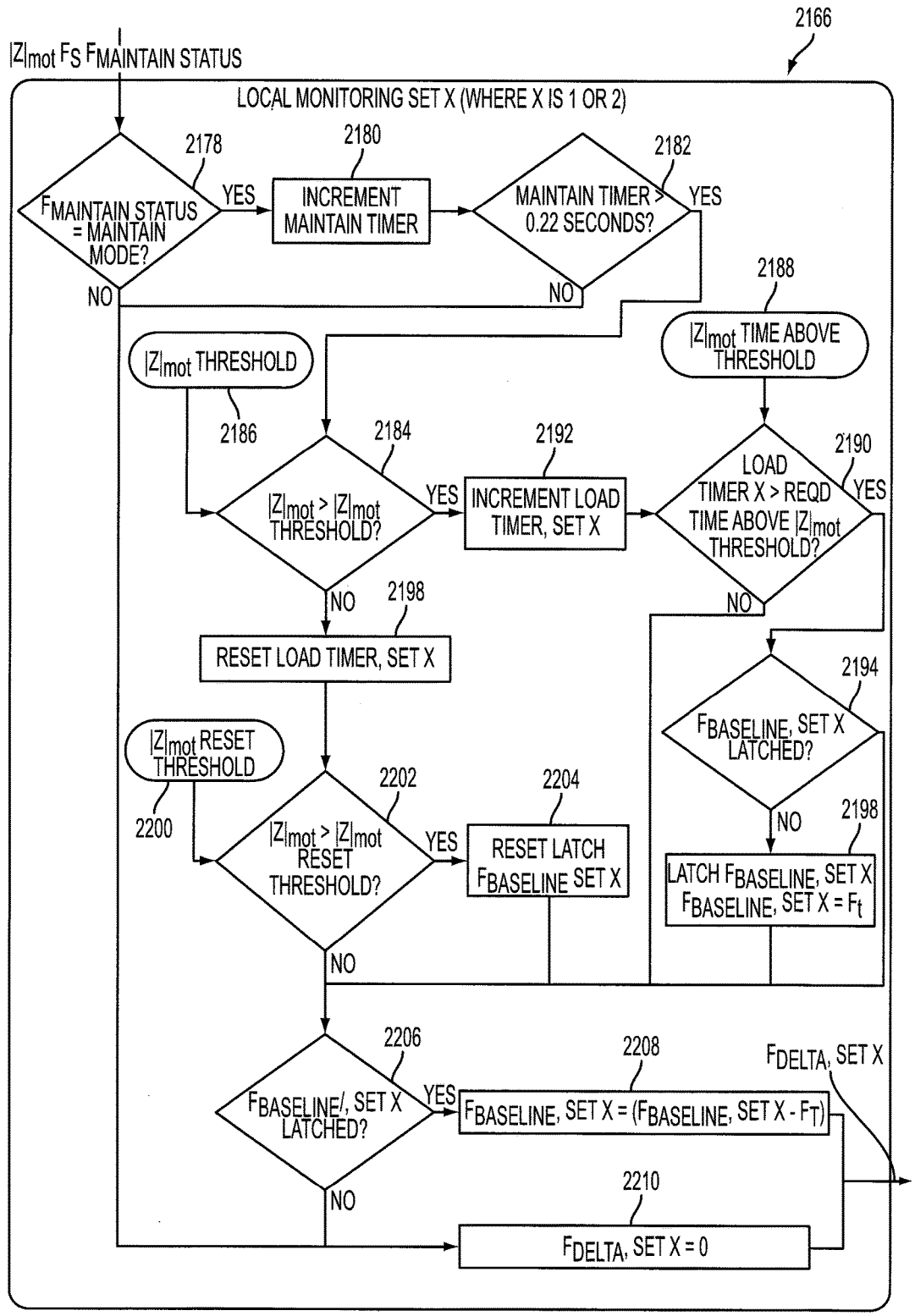
FIG. 58 is a logic flow diagram of one form of a load monitoring algorithm that may be implemented in one form of a generator.

FIG. 58 is a logic flow diagram of one form of a load monitoring algorithm 2166 that may be implemented in one form of a generator. The load monitoring algorithm 2166 may take as input a local ultrasonic impedance ($|Z|_{mot}$), a local resonant frequency ($F_t$) and the state of the maintain status flag ($F_{Maintain\ Status}$). At 2178, the generator may determine whether the maintain status flag is set. If not, then the frequency delta ($F_{delta}$) may be set to zero at 2210. In certain forms, setting the frequency delta to zero may effectively disable load monitoring. If the maintain status flag is set, a maintain timer 2180 may be incremented at 2180. At 2182, the generator may determine whether the maintain timer has reached the threshold time period for blip dissipation has been met. If not, the frequency delta may be set to zero at 2210. If yes, the generator may determine at 2184 whether the received local ultrasonic impedance is greater than a threshold impedance 2186. If yes, a load timer for implementing the time above threshold impedance described above may be incremented at 2192.

At 2190, the generator may determine if the load timer is greater than the time above threshold impedance 2188. If yes, the generator may determine whether a baseline frequency latch is set at 2194. The baseline frequency latch may prevent the baseline frequency from bouncing during a jaw closure event, indicated by ultrasonic impedance. For example if the baseline frequency latch is set, it may indicate that a baseline frequency has already been taken for a given load event. If the baseline frequency latch is not set, the generator may set the latch and set the baseline frequency as the current resonant frequency of the system at 2196. At 2206, the generator may again determine whether the baseline frequency latch is set. If yes, the frequency delta may be set to the baseline frequency minus the local resonant frequency at 2208. If the baseline latch is not set, then the frequency delta may be set to zero at 2210.

Referring back to 2184, if the ultrasonic impedance is not greater than the threshold impedance, the generator may reset the load timer at 2198. At 2202, the generator may determine whether the ultrasonic impedance is less than a reset threshold impedance ($|Z|_{mot}$ Reset Threshold). If the ultrasonic impedance is less than the reset threshold impedance, the generator may reset the baseline frequency latch at 2204 and proceed to 2206, as described above. If the ultrasonic impedance is not less than the reset threshold impedance, the generator may proceed to 2206, as described above, without resetting the baseline frequency latch.

Figure 59:
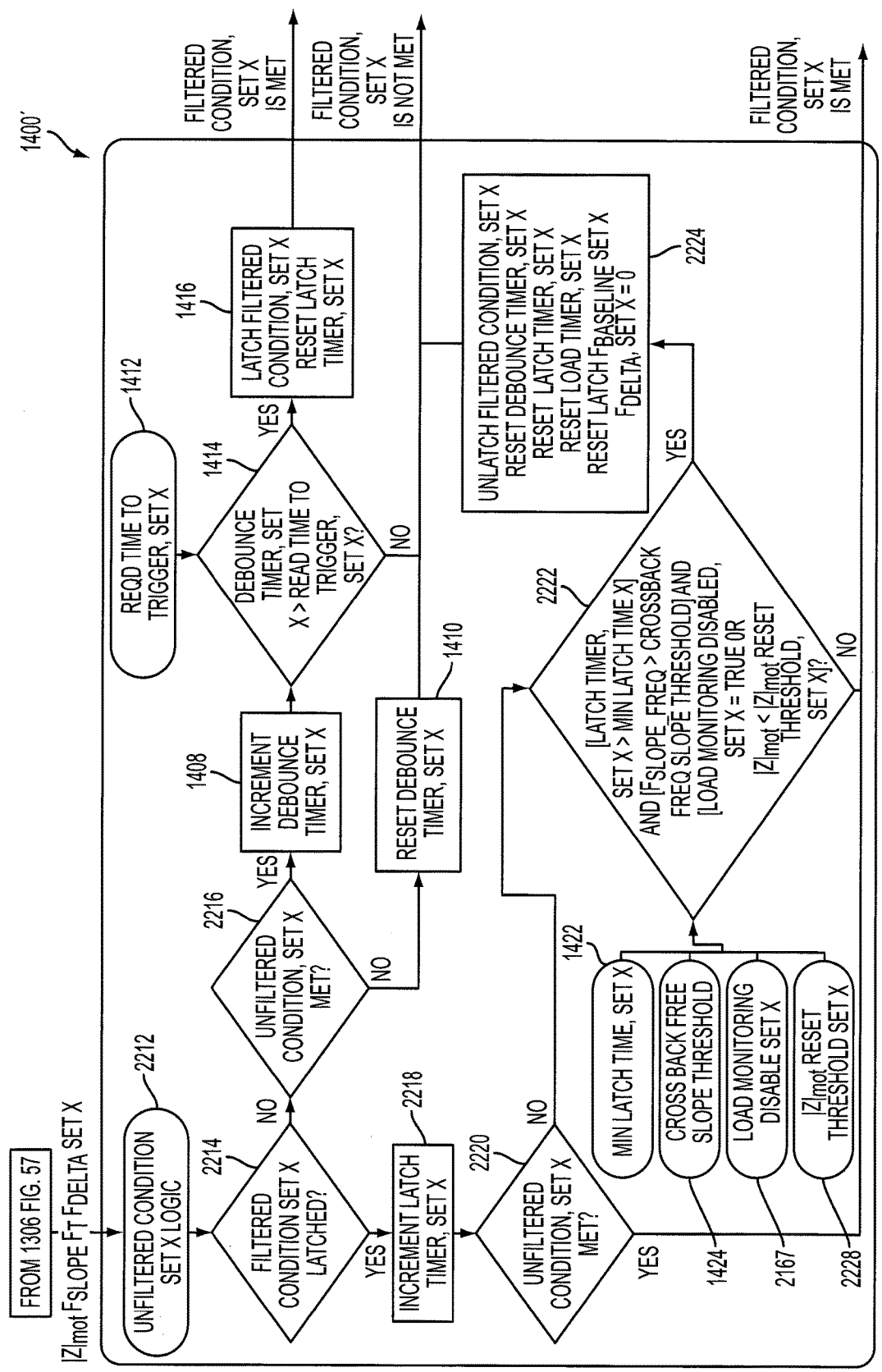
FIG. 59 is a logic flow diagram for evaluating condition sets for the signal evaluation tissue algorithm shown in FIG. 57 that may be implemented in one form of a generator.

FIG. 59 is a logic flow diagram 1400' for evaluating Condition Sets for the signal evaluation tissue algorithm 1300' shown in FIG. 57 that may be implemented in one form of a generator. At 2212, the generator may implement logic for determining if an unfiltered Condition Set is met for the evaluated Condition Set. Logic 2212 is described in more detail below with respect to FIG. 60 and may return a "true" or "false" response. At 2214, the generator may determine whether a filtered Condition Set latch is set. The filtered Condition Set latch may be set, as described below, when the filtered Condition Set is met, for example, so as to ensure that the filtered Condition Set is indicated to be set for a threshold period of time. If the filtered Condition Set latch is set, the generator may increment a latch timer at 2218 and determine whether the unfiltered Condition Set is met at 2220. If the unfiltered condition set is met, then the logic flow 1400' may return an indication that the filtered Condition Set is met.

If the unfiltered condition set is not met at 2220, the generator may evaluate whether the Condition Set is still met at 2222. For example, the generator may determine (i) whether the filtered Condition Set latch timer has exceeded a minimum latch timer 1422; and (ii) whether the frequency slope is greater than a cross-back frequency slope threshold 1424; and (iii) [whether load monitoring 2167 is disabled OR whether a load event has completed] (e.g., whether ultrasonic impedance is less than the impedance reset threshold 2228). If these conditions are met, the generator may, at 2224, release the filtered Condition Set latch; reset the debounce timer (e.g., TIMER X in FIG. 22); reset the latch timer; reset the load timer (e.g., time above impedance period), reset the baseline frequency latch; and set the frequency delta equal to zero. Logic flow 1400' may return an indication that the filtered Condition Set is not met.

Referring now back to 2214, if the filtered Condition Set latch is not set, the generator may determine if the unfiltered condition set is met at 2216 (e.g., based on the return of 2212). If not, the debounce timer may be reset at 1410 and the logic flow 1400' may return an indication that the filtered Condition Set is not met. If yes, the generator may increment the debounce timer at 1408. At 1414, the generator may determine whether the debounce timer is greater than a required time before trigger parameter 1412, as described above. If so, algorithm 1400' may proceed along the YES path, latching the filtered condition set latch at 1416 and returning an indication that the filtered Condition Set is met.

Figure 60:
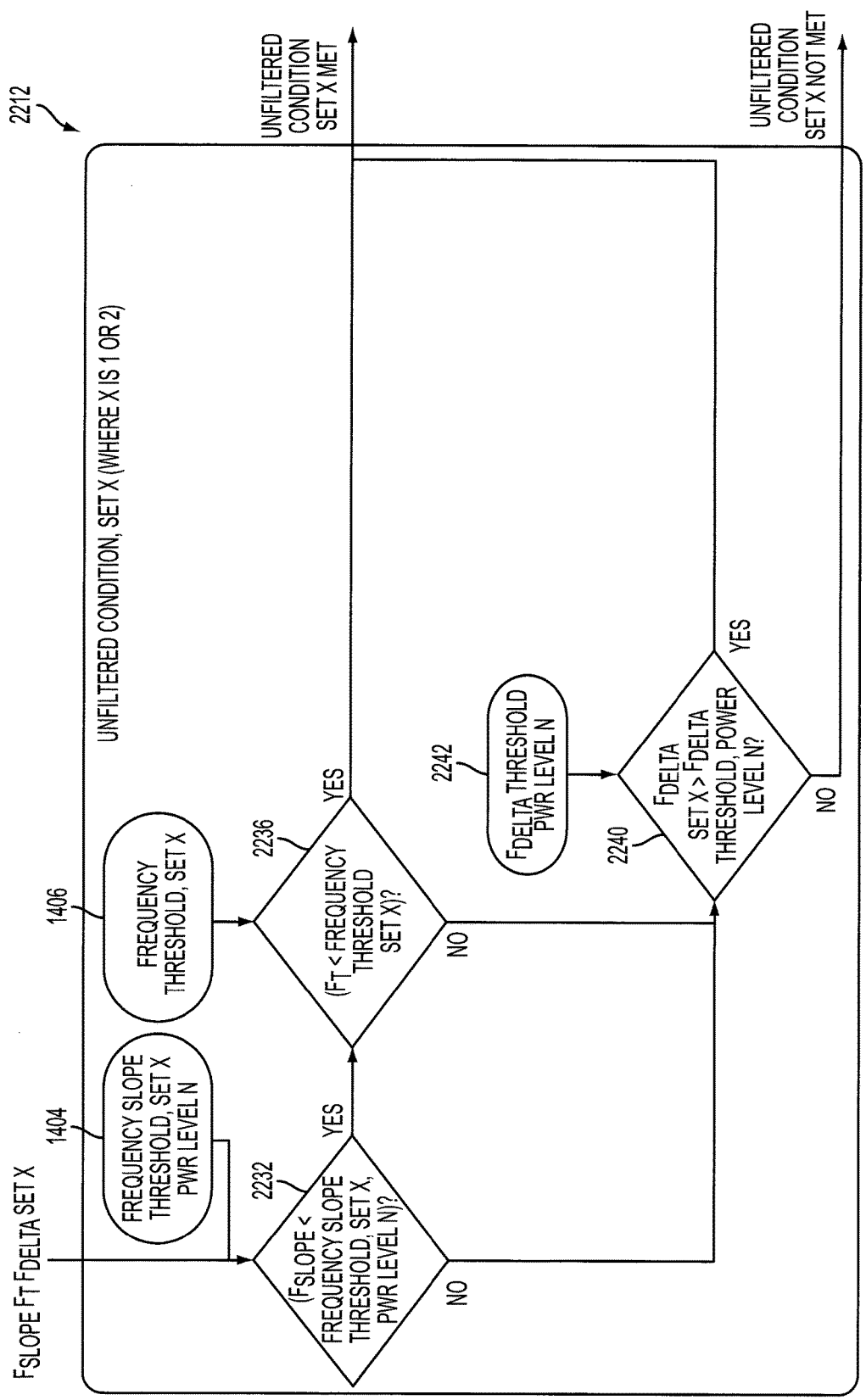
FIG. 60 is a logic flow diagram for implementing one form of the unfiltered condition set logic shown in FIG. 59 that may be implemented in one form of a generator.

FIG. 60 is a logic flow diagram for implementing one form of the unfiltered condition set logic 2212 shown in FIG. 59 that may be implemented in one form of a generator. At 2232, the generator may determine whether a local frequency slope is less than a frequency slope threshold parameter 1404. In some forms, the frequency slope threshold parameter may depend on a power level delivered by the generator, as described above. If the local frequency slope is less than the frequency slope threshold parameter 1404, the generator may, at 2236, determine whether the local resonant frequency is less than a frequency threshold parameter 1406. If so, the algorithm 2212 may return an indication that the unfiltered Condition Set is met. In some forms, the conditions 2232, 2236 may be implemented in a logical "OR" manner instead of the logical "AND" manner shown.

For example, after a determination that the local frequency slope is less than the frequency slope threshold parameter 1404, the algorithm may return an indication that the unfiltered Condition Set is met. Similarly, upon a determination that the local frequency slope is not less than the frequency slope threshold parameter 1404, the algorithm may evaluate the resonant frequency and frequency threshold parameter 1406 at 2236.

If the conditions evaluated at 2232 and 2236 are not met (in whatever logical arrangement is used), the generator may determine, at 2240, whether the difference between the baseline frequency (e.g., as set at 2196) and the local resonant frequency (e.g., the frequency delta) exceeds a baseline deviation threshold parameter 2242. If yes, the algorithm 2212 may return an indication that the unfiltered Condition Set is met. If no, the algorithm 2212 may return an indication that the unfiltered Condition Set is not met.

In certain forms, generators, such as 30, 500, 1002, and/or ultrasonic surgical instruments, such as 100, 120, 1004, may be implemented with one or more Condition Sets that utilize load events to arm Response Set triggers. For example, the generator may detect load events, as described herein. A load event may occur, for example, when the load on the ultrasonic blade experiences a change (e.g., a sudden or rapid change). Physical conditions that may cause a load change include, for example, the opening and/or closing of the clamp arm, a sudden drop of the ultrasonic blade through tissue, etc. In various forms, upon detection of a load event, Response Set triggers may be armed, or capable of being triggered upon the occurrence of other conditions in the corresponding Condition Set. When no load event is detected, the Response Set triggers may be disarmed, or incapable of being triggered even upon occurrence of other conditions in the corresponding Condition Set. The existence of a load event may serve as an alternate indicator of the types of physical conditions to be detected by various Condition Sets (e.g., changes in tissue state, such as tissue separation, desiccation, etc.). Accordingly, Condition Sets that utilize load event triggers are less likely to return false positives (e.g., situations where the Condition Set is met, but the underlying physical condition is not present). As a result, Condition Sets utilizing load events may also utilize lower and more sensitive thresholds for frequency slope thresholds 1404, frequency thresholds 1406, etc.

Figure 61:
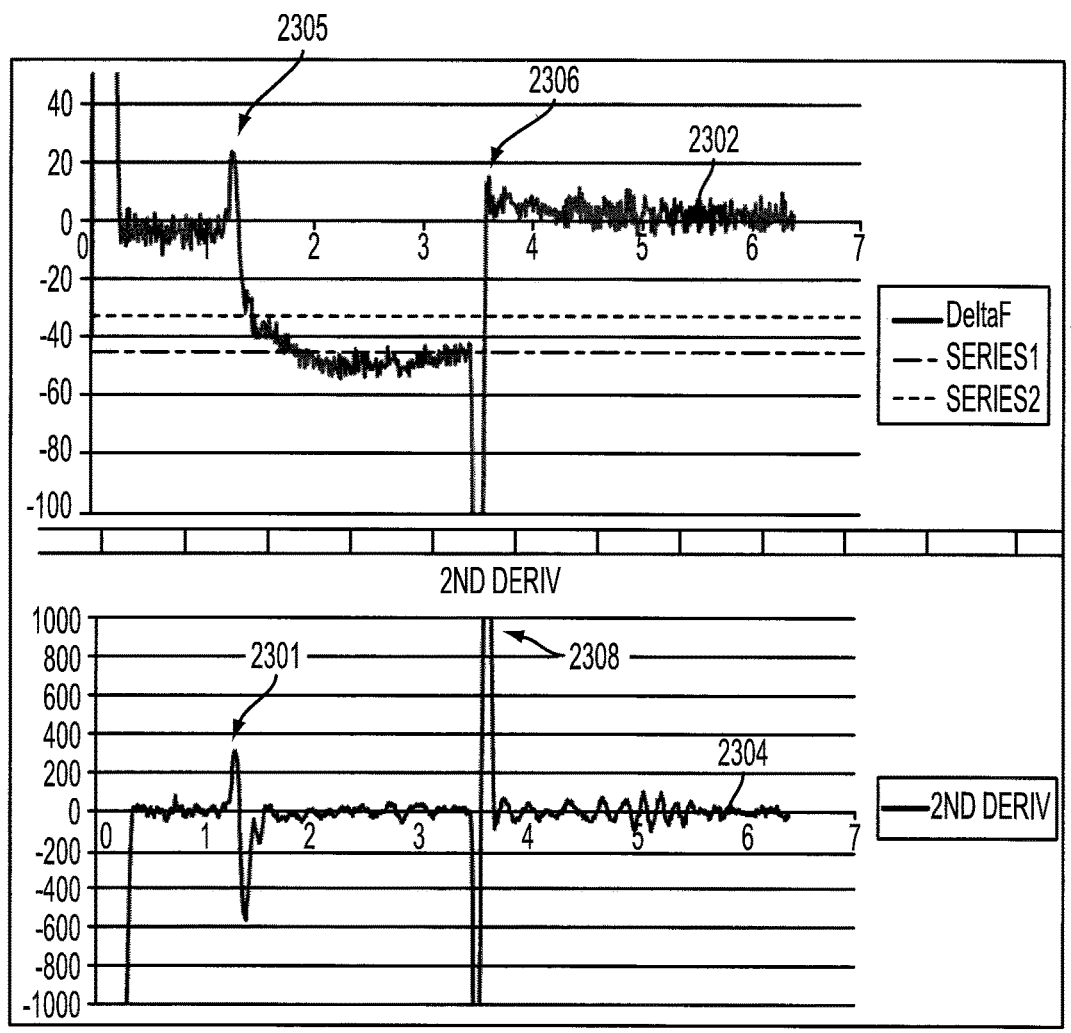
FIG. 61 is a graphical representation of a frequency slope and a second time derivative of frequency illustrating a pair of load events.

According to various forms, load events may be detected by examining changes in the frequency slope over time. FIG. 61 is a graphical representation of a frequency slope 2302 and a second time derivative of frequency 2304 for an ultrasonic blade illustrating a pair of load events. The load events are apparent in frequency slope plot 2302 at features 2305 and 2306 and in second time derivative plot 2304 at features 2307 and 2308. The blade that generated the characteristics illustrated in FIG. 61 was activated unloaded at about ½ seconds, clamped at about 1½ seconds, and unclamped at about 3½ seconds, as indicated on the horizontal axes. The clamping and unclamping may correspond to the load events indicated by 2305, 2307 and 2306, 2308. It will be appreciated that the frequency slope itself may be affected by both thermal events (e.g., changes in the temperature of the blade) and load events. This is illustrated by FIG. 61, as the frequency slope plot 2302 comprises various changes in addition to the features 2305, 2306. In contrast, the second time derivative plot 2304 is approximately constant except for dramatic changes at the features 2307, 2308.

In view of this, certain forms detect the presence of a load event by examining changes in frequency slope over a rolling window. For example, a present or local frequency slope is compared to a past frequency slope offset from the local frequency slope by a window offset time. Continuing results of the comparison may be referred to as a rolling delta. The window offset time may be any suitable time and, in certain forms, may be about 100 msec. When the rolling delta exceeds a frequency slope threshold parameter, a load event may be detected. In certain forms, load events beginning when the blade is unloaded may not be considered (e.g., Response Set triggers may not be armed). For example, before examining the frequency slope over the rolling window, the generator may first detect an increase in ultrasonic impedance above an impedance threshold. (In some forms, the impedance threshold must be held for a time above impedance threshold parameter before the generator will detect a load event.) The impedance threshold may be any suitable value and, in certain forms, is between about 5 ohms and about 260 ohms, with a resolution of about 5 ohms. In one example form, the impedance threshold is about 100 ohms. The increase in ultrasonic impedance above the threshold may indicate, for example, that the clamp arm is closed, therefore, making a load event more likely.

FIG. 62 is a graphical representation of a frequency slope 2310, a second time derivative of frequency 2312, and a rolling delta 2314 demonstrating a load event. Feature 2316 of the rolling delta plot 2314 indicates that the rolling delta exceeded the frequency slope threshold parameter, thus indicating a load event. FIG. 63 is graphical representation of another form of a frequency slope 2318, a second time derivative of frequency 2320 and a rolling delta 2322 demonstrating another load event. Feature 2324 in the rolling delta plot 2322, feature 2326 in the second derivative plot 2320 and feature 2328 in the frequency slope plot 2328 indicate the load event.

FIG. 64 is a logic flow diagram for implementing one form of an algorithm 2330 applying a Condition Set including a load event trigger that may be implemented in one form of a generator. At 2332, the generator may determine whether a load event is occurring. Further examples of how the generator may determine whether a load event is occurring are provided herein with respect to FIG. 65. If no load event is occurring, the generator may continue to test for a load event at 2332. If a load event is occurring, the generator may "arm" a relevant Response Set at 2334. Arming the Response Set may comprise enabling the Response Set to be triggered when its corresponding Condition Set is met. At 2336, the generator may determine if the local ultrasonic impedance is below an impedance reset threshold parameter. The impedance reset threshold parameter may be an impedance level at which the generator concludes that the load event is concluded. If the local ultrasonic impedance is below the impedance reset threshold parameter, the generator may disarm the Response Set at 2342. If the local ultrasonic impedance is not below the impedance reset threshold, then the generator (e.g., 30, 500, 1002) may determine of the Condition Set parameters are met at 2338. If the Condition Set is met, the generator may trigger the appropriate Response Set at 2340.

Figure 65:
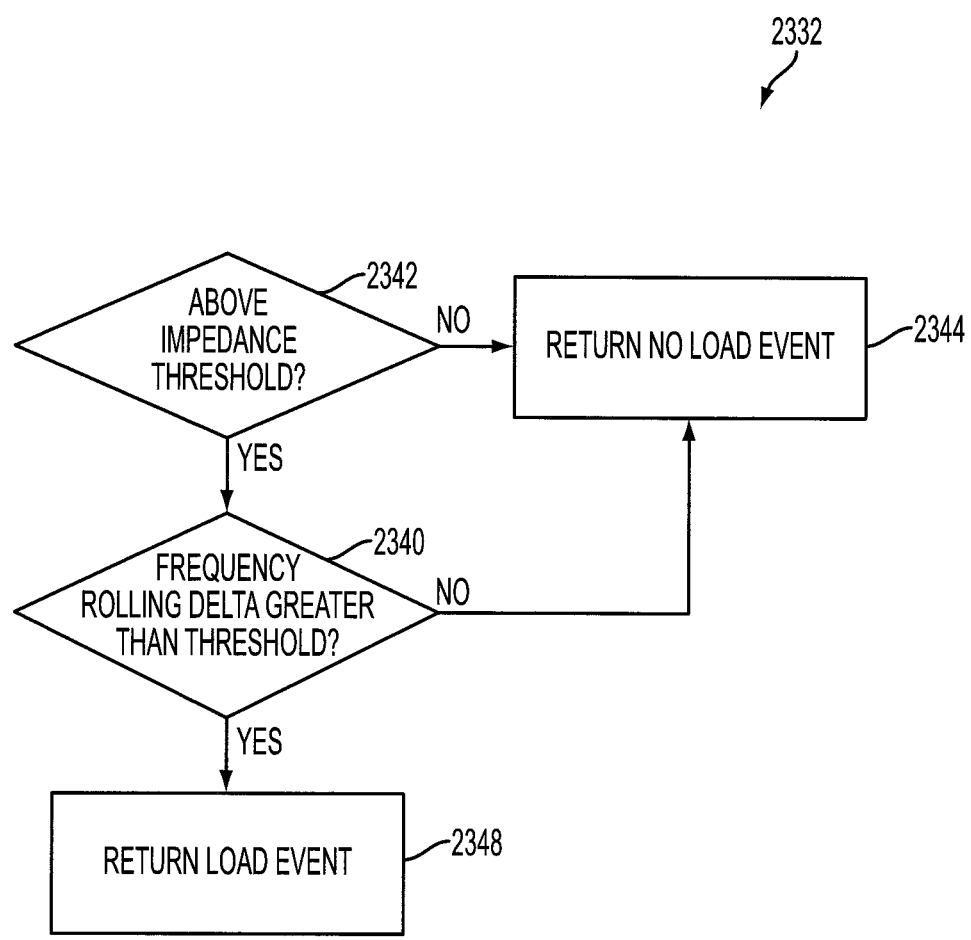
FIG. 65 is a logic flow diagram for implementing one form of logic for determining whether a load condition exists in a surgical instrument.

FIG. 65 is a logic flow diagram for implementing one form of an algorithm 2332 for determining whether a load condition exists in a surgical instrument. At 2342, the generator may determine if the local ultrasonic impedance of the ultrasonic blade/transducer system exceeds an impedance threshold. For example, ultrasonic impedance exceeds the threshold, it may indicate closure of the clamp arm. If no, the algorithm 2332 may return an indication that there is no load event at 2334. If the local ultrasonic impedance exceeds the impedance threshold, the generator may determine at 2346 whether the frequency rolling delta is greater than a frequency slope threshold parameter. If yes, the algorithm 2332 may return a load event 2348. If no, then the algorithm 2344 may return no load event.

Figure 66:
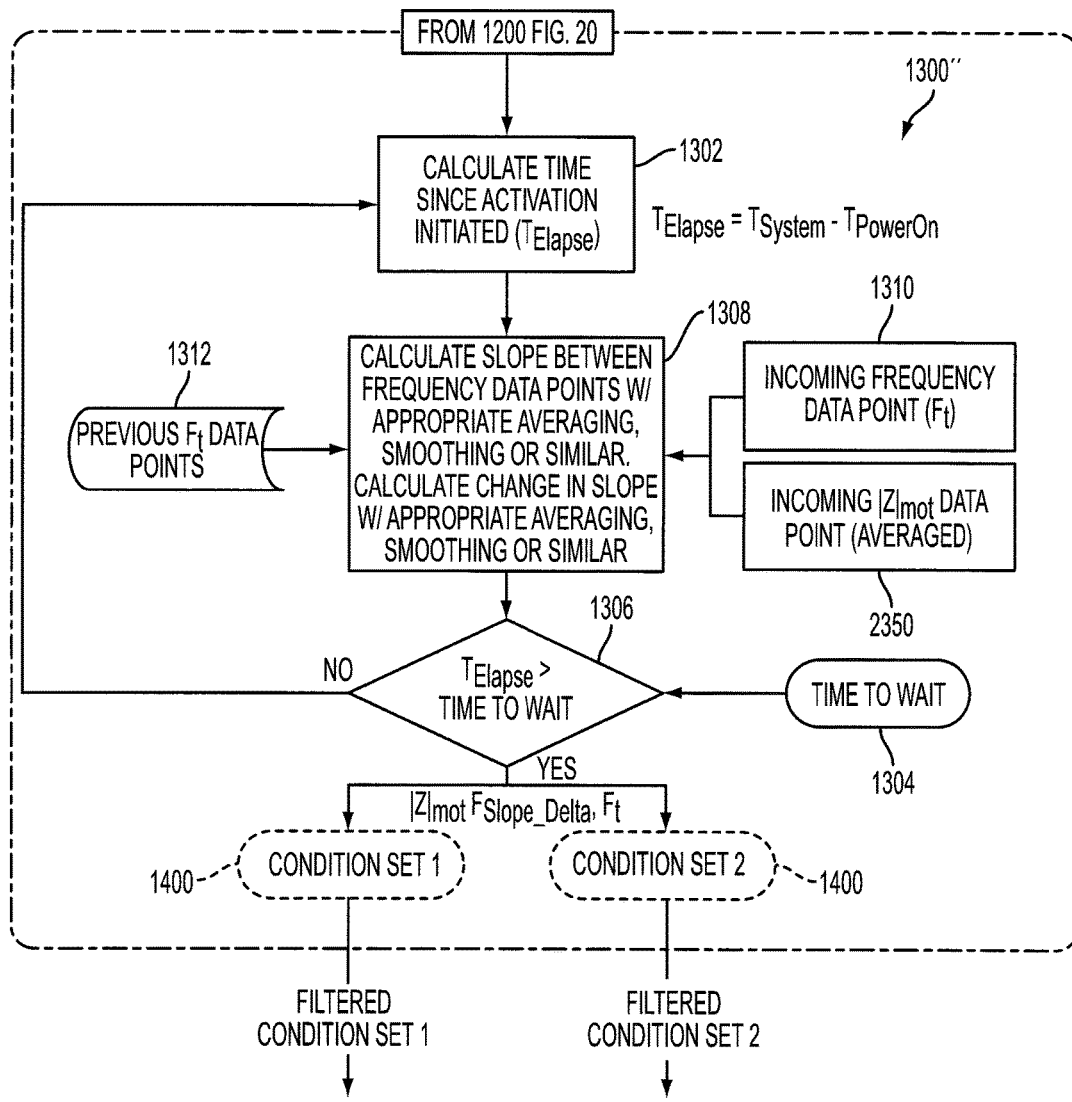
FIG. 66 is a logic flow diagram of one form of a signal evaluation tissue algorithm portion of the tissue algorithm shown in FIG. 20 considering a Condition Set utilizing a load event to arm Response Set triggers.

In various example forms, Condition Sets that utilize load events to arm Response Set triggers may be utilized in the context of the logic flow diagrams 1200, 1300, 1400 of FIGS. 20-22 described above. For example, FIG. 66 is a logic flow diagram of one form of a signal evaluation tissue algorithm portion 1300" of the tissue algorithm 1200 shown in FIG. 20 considering a Condition Set utilizing a load event to arm Response Set triggers. In various forms, the signal evaluation tissue algorithm 1300" may operate in a manner similar to that of the algorithm 1300 described above, with several differences. For example, in algorithm 1300", the Signal Evaluation/Monitoring function 1308 may be performed prior to the time to wait comparison at 1306, although it will be appreciated that these actions may be ordered in any suitable order for any of the algorithms 1300, 1300', 1300" described herein. Additionally, the Signal Evaluation/Monitoring function 1308 may also capture a local ultrasonic impedance ($|Z|_{Mot}$) and the rolling delta ($F_{slope\_delta}$), that may be passed to the various condition set evaluation algorithms 1400, as described herein. For example, the algorithm 1300 may pass as arguments the local ultrasonic impedance, the rolling delta, the local frequency slope ($F_{slope}$) and the local resonant frequency ($F_r$).

Figure 67:
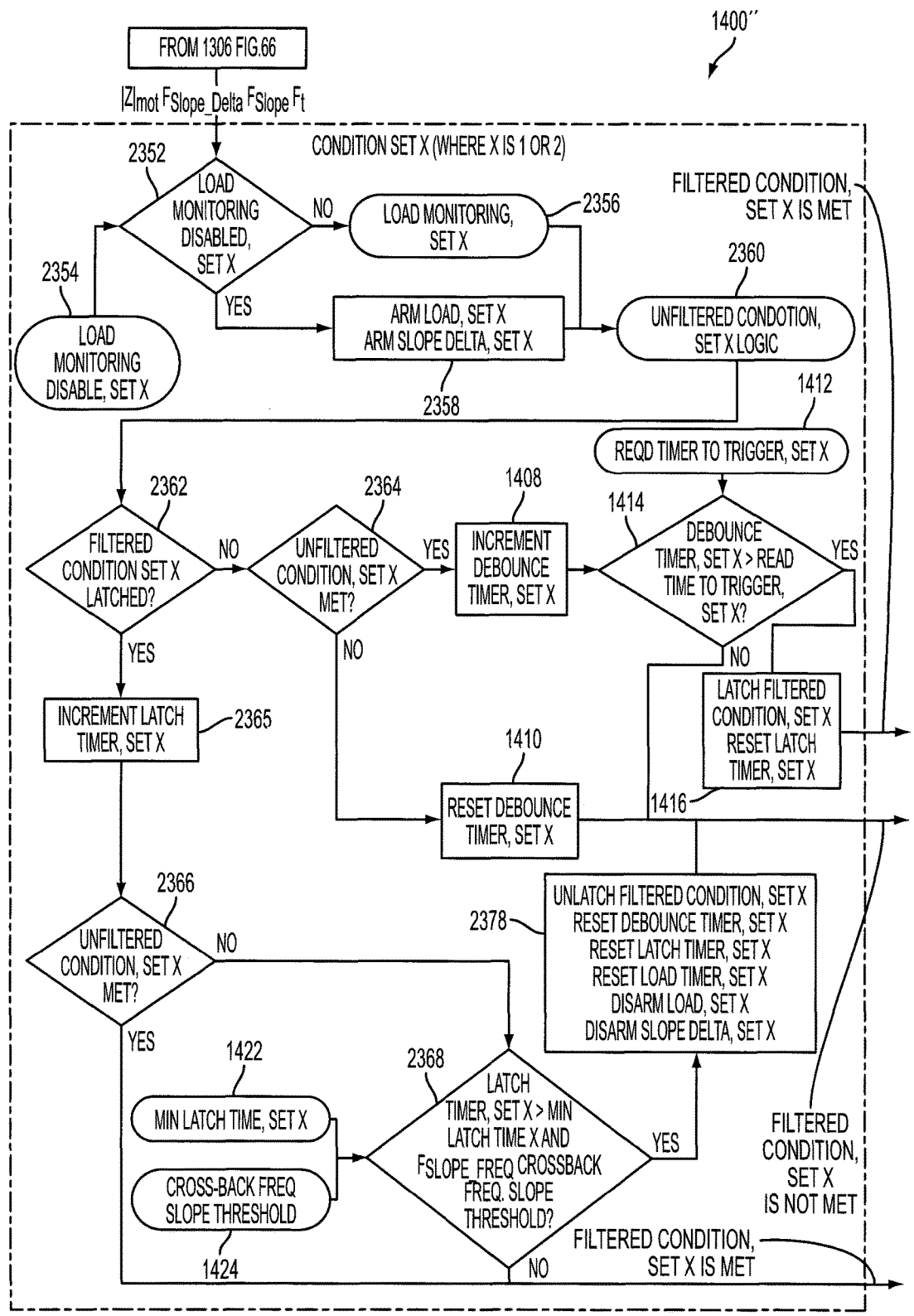
FIG. 67 is a logic flow diagram for evaluating condition sets for the signal evaluation tissue algorithm shown in FIG. 66 that may be implemented in one form of a generator.

FIG. 67 is a logic flow diagram of an algorithm 1400" for evaluating condition sets for the signal evaluation tissue algorithm 1300" shown in FIG. 66 that may be implemented in one form of a generator. At 2352, the generator may determine whether a maintain status flag 2354 is set. If not, then the Response Set corresponding to the Condition Set of the algorithm 1400" may be armed at 2358. In certain forms, arming the Response Set at 2358 may effectively disable load monitoring. If the maintain status flag 2354 is set, a load monitoring algorithm 2356 may be executed. The load monitoring algorithm 2356 may either arm, or not arm, the Response Set trigger depending on whether a load event is detected. Additional details of the load monitoring algorithm 2356 are provided below with respect to FIG. 68. At 2360, the generator may implement logic for determining if an unfiltered Condition Set is met for the evaluated Condition Set. Logic 2360 is described in more detail below with respect to FIG. 69 and may return a "true" or "false" response.

At 2368, the generator may determine whether a filtered Condition Set latch is set. The filtered Condition Set latch may be set, as described below, when the filtered Condition Set is met, for example, so as to ensure that the filtered Condition Set is indicated to be set for a threshold period of time. If the filtered Condition Set latch is set, the generator may increment a latch timer at 2365 and determine whether the unfiltered Condition Set is met at 2366. If the unfiltered condition set is met, then the logic flow 1400" may return an indication that the filtered Condition Set is met.

If the unfiltered condition set is not met at 2366, the generator may evaluate the whether the Condition Set is still met at 2368. For example, the generator may determine (i) whether the filtered Condition Set latch timer has exceeded a minimum latch timer 1422; and (ii) whether the frequency slope is greater than a cross-back frequency slope threshold 1424. If these conditions are met, the generator may, at 2378, release the filtered Condition Set latch; reset the debounce timer (e.g., TIMER X in FIG. 22); reset the latch timer; reset the load timer (e.g., time above impedance period), and disarm the Response Set trigger. Logic flow 1400" may return an indication that the filtered Condition Set is not met.

Referring now back to 2362, if the filtered Condition Set latch is not set, the generator may determine if the unfiltered condition set is met at 2364 (e.g., based on the return of 2360). If not, the debounce timer may be reset at 1410 and the logic flow 1400" may return an indication that the filtered Condition Set is not met. If yes, the generator may increment the debounce timer at 1408. At 1414, the generator may determine whether the debounce timer is greater than a required time before trigger parameter 1412, as described above. If so, algorithm 1400" may proceed along the YES path, latching the filtered condition set latch at 1416 and returning an indication that the filtered Condition Set is met.

Figure 68:
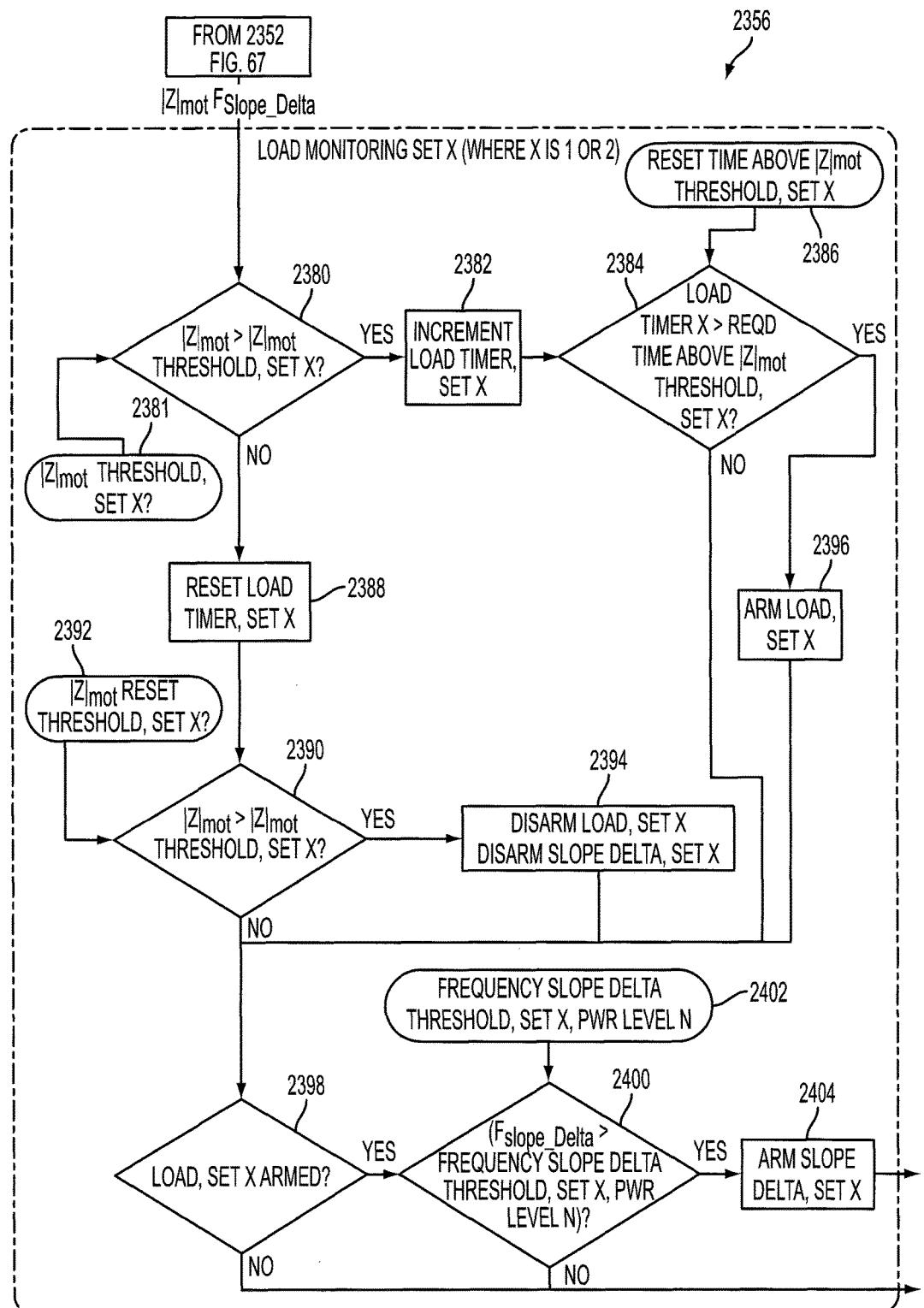
FIG. 68 is a logic flow diagram of one form of a load monitoring algorithm that may be implemented in one form of a generator, as shown in FIG. 67.

FIG. 68 is a logic flow diagram of one form of a load monitoring algorithm 2356 that may be implemented in one form of a generator, as shown in FIG. 67. The load monitoring algorithm 2356 may receive as input the local ultrasonic impedance ($|Z|_{Mot}$) and the rolling delta ($F_{slope\_delta}$). As output, the algorithm 2356 may either arm, or not arm, the relevant Response Set. At 2380, the generator may determine if the ultrasonic impedance exceeds the impedance threshold 2381. If so, the generator may increment a load timer at 2382. The load timer may act to debounce the local ultrasonic impedance. For example, the generator may not consider the ultrasonic impedance to be higher than the threshold 2381 unless it is higher than the threshold for a predetermine number of ticks of the timer.

At 2384, the generator may determine whether the load timer is greater than a required time above threshold parameter 2386. If yes, the generator may arm the load trigger at 2396 and proceed to 2398. For example, the load trigger may be armed when a load is indicated by the ultrasonic impedance. If no at 2384, the generator may proceed directly to 2398 without arming the load trigger. At 2398, the generator may determine whether the load trigger is armed. If no, the load set monitoring algorithm 2356 may return with the both the load trigger and the Response Set trigger unarmed. If yes, the generator may determine at 2400 whether the rolling delta exceeds the frequency slop threshold parameter 2402. If no, then the algorithm 2356 may return with the load trigger set and the Response Set trigger unarmed. If yes, then the Response Set trigger may be armed at 2404 and the algorithm 2356 may return. Referring back to 2380, if the ultrasonic impedance is not above the impedance threshold, the generator may reset the load timer at 2388. At 2390, the generator may determine whether the ultrasonic impedance is less than an impedance reset threshold parameter 2392. If yes, then the generator may disarm the Response Set trigger and load trigger at 2394. If no, the generator may proceed to 2398 as described above.

Figure 69:
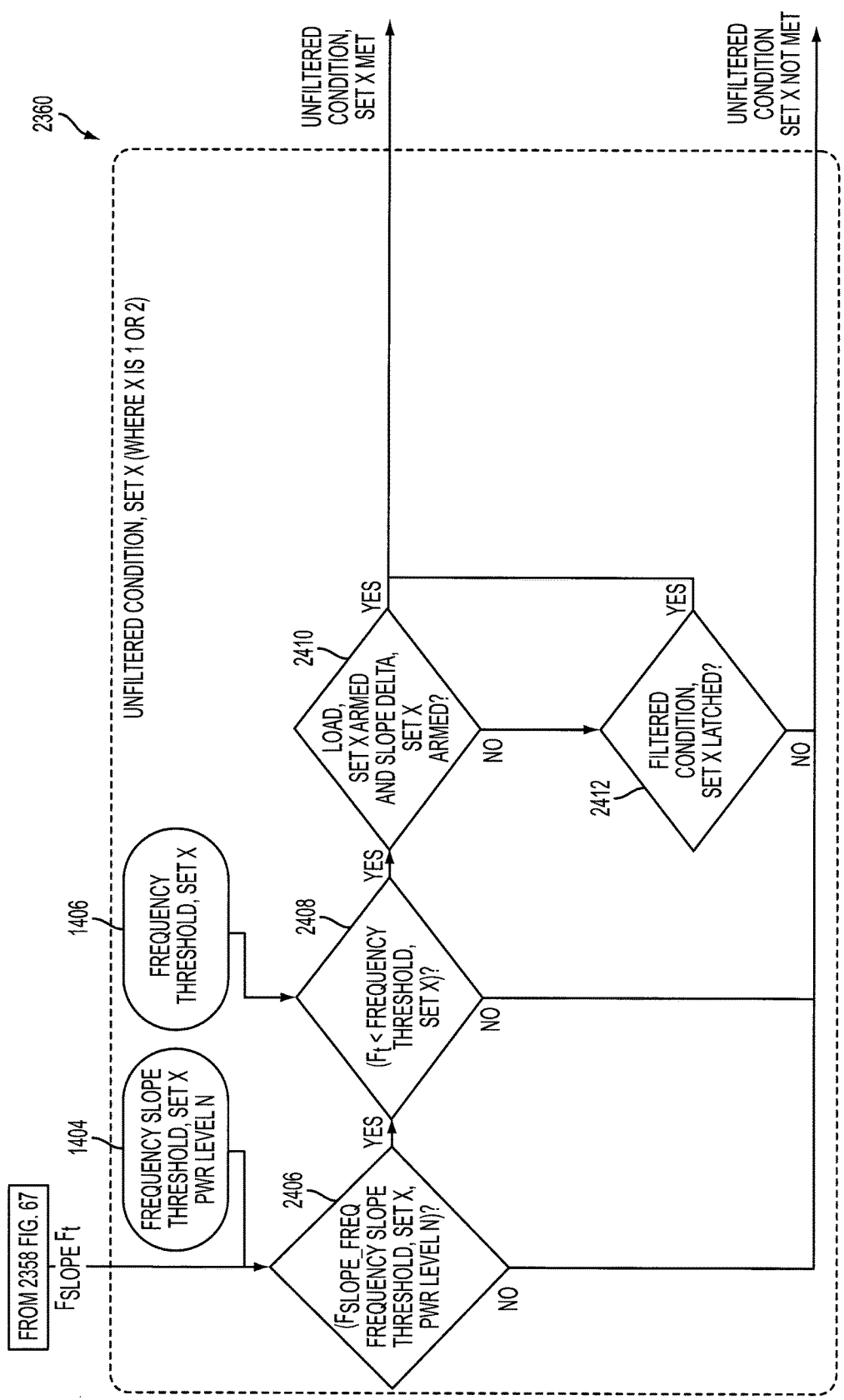
FIG. 69 is a logic flow diagram of one form of an unfiltered condition set logic shown in FIG. 67 that may be implemented by one form of a generator.

FIG. 69 is a logic flow diagram of one form of an unfiltered condition set logic 2360 shown in FIG. 67 that may be implemented by one form of a generator. At 2406, the generator may determine whether a local frequency slope is less than a frequency slope threshold parameter 1404. In some forms, the frequency slope threshold parameter may depend on a power level delivered by the generator, as described above. If the local frequency slope is less than the frequency slope threshold parameter 1404, the generator may, at 2408, determine whether the local resonant frequency is less than a frequency threshold parameter 1406. If yes, the generator may determine at 2410 whether the load trigger and the Response Set trigger are armed. If yes, the algorithm 2360 may return an indication that the unfiltered Condition Set is met. If no, the generator may determine whether the filtered Condition Set is latch is set at 2412. If yes, the algorithm 2360 may return an indication that the unfiltered Condition Set is met. If no at any one of 2406, 2408 or 2412, the algorithm 2360 may return an indication that the unfiltered Condition Set is not met.

In some forms, the conditions 2406 and 2408 may be implemented in a logical "OR" manner instead of the logical "AND" manner shown. For example, after a determination that the local frequency slope is less than the frequency slope threshold parameter 1404, the algorithm 2360 may jump directly to 2410. Similarly, upon a determination that the local frequency slope is not less than the frequency slope threshold parameter 1404, the algorithm may evaluate the resonant frequency and frequency threshold parameter 1406 at 2408.

Various forms of algorithms 1400, 1400' and 1400" for evaluating Condition Sets for the signal evaluation tissue algorithms 1300, 1300', 1300" are described. It will be appreciated that any number of Condition Set evaluation algorithms may be implemented with any of the signal evaluation tissue algorithms 1300, 1300', 1300" described herein. For example, in certain forms, the generator may implement a Condition Set evaluation algorithm 1400, as described herein above, in conjunction with a Condition Set evaluation algorithm 1400" utilizing a load event trigger. Any suitable combination of algorithms 1300, 1300', 1300", 1400, 1400', 1400" may be used.

In some example forms of the ultrasonic surgical instrument and generator, current is maintained so as to be relatively constant. This may establish a substantially constant displacement for the ultrasonic blade that, in turn, establishes a substantially constant rate of tissue-effecting activity. In some forms, the current is maintained, even over changing mechanical loads, where the mechanical load is reflected by the ultrasonic impedance. To achieve this, differences in mechanical load may be compensated for substantially by modulating applied voltage.

As described herein, to operate efficiently (e.g., minimize waste heat at the transducer), the surgical instrument (e.g., blade and transducer combination) may be driven at or near the system's resonant frequency. The frequency of the system may be determined via a phase difference between the current and voltage signals. As described herein, the resonant frequency of the system changes with thermal changes. For example, the additional of thermal energy (e.g., heat) results in a softening of the blade and/or other system components, thereby changing the system's resonant frequency. Accordingly, the generator, in some example forms, implements two control loops. A first loop maintains a substantially constant current across varying loads, while a second control loop tracks the system resonant frequency and modifies the driving electrical signals accordingly.

As described herein, various algorithms for use with ultrasonic surgical instruments approximate physical conditions of the instrument (e.g., the ultrasonic blade thereof) based on the electrical signals provided to the instrument. For example, with respect to FIGS. 58 and 65, closure of the clamp arm is determined by monitoring ultrasonic impedance. It will be appreciated, however, that in any of the forms described herein, closure of the clamp arm may be alternatively determined in any suitable manner, for example, from any suitable electrical signal provided to the instrument and/or derivations thereof. In some example forms where current is kept substantially constant, the value of the voltage signal is proportional to ultrasonic impedance. Therefore, the various ultrasonic impedance thresholds described herein may alternately be implemented as voltage thresholds. Similarly, where current is substantially constant, power or energy delivered to the blade will also be proportional to ultrasonic impedance and corresponding changes in power, energy, changes in voltage, power or energy with respect to time, etc., may also indicate clamp arm closure. Also, as illustrated herein, when the clamp arm initially closes, the temperature of the ultrasonic blade may drop as it comes into contact with cool tissue. Accordingly, blade closure may alternately be detected by monitoring for a drop in blade temperature, indicated either by a rise in the resonant frequency of the blade and/or one of the other methods described herein. Also, in some forms, closure of the clamp arm may be determined based on detecting activation of a closure trigger and/or closure control. Various forms may detect clamp arm closure utilizing combinations of some or all of the electrical signal properties described.

Also, for example, load events are described herein, for example, with respect to FIG. 65. In FIG. 65 and the associated description load events are detected based on a frequency rolling delta. Various other qualities of the electrical signals provided to the instrument may also be used to indicate a load event. For example, the physical changes indicated by the frequency rolling delta may also be indicated by the voltage signal, a change in the voltage signal with respect to time, the ultrasonic impedance including the slope thereof, a second derivative of frequency, current, changes in current with respect to time, etc. Additionally, changes in the temperature of the blade, as described herein, are determined based on detecting changes in the frequency slope. Additional electrical signal properties that may vary based on blade temperature may include, for example, the slope of the power and/or energy provided to the blade.

According to various forms, an ultrasonic instrument, such as the instruments 100, 120, 1004 may be driven according to a control algorithm that involves driving the instrument sequentially at different power levels. For example, when the ultrasonic surgical instrument is activated, it may be driven at a first power level. For example, a generator (e.g., generators 30, 500, 1002 and/or an internal generator) may provide a drive signal at a first power level. After the expiration of a first period, the generator may provide a second drive signal at a second power level less than the first power level. In some applications, the first, higher power level may serve to separate the inner muscle layer of a vessel from the adventilia layer, as described herein.

Figure 70:
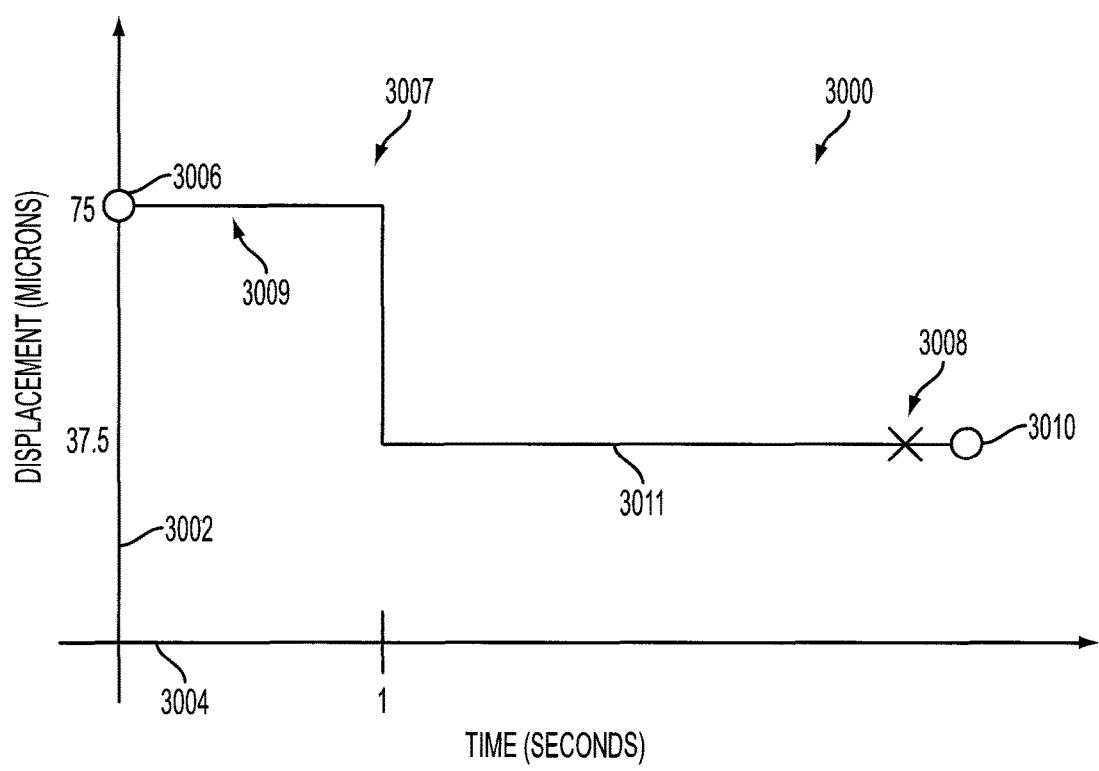
FIG. 70 is a chart illustrating a power or displacement plot for one example implementation of the algorithm of FIG. 71.
Figure 71:
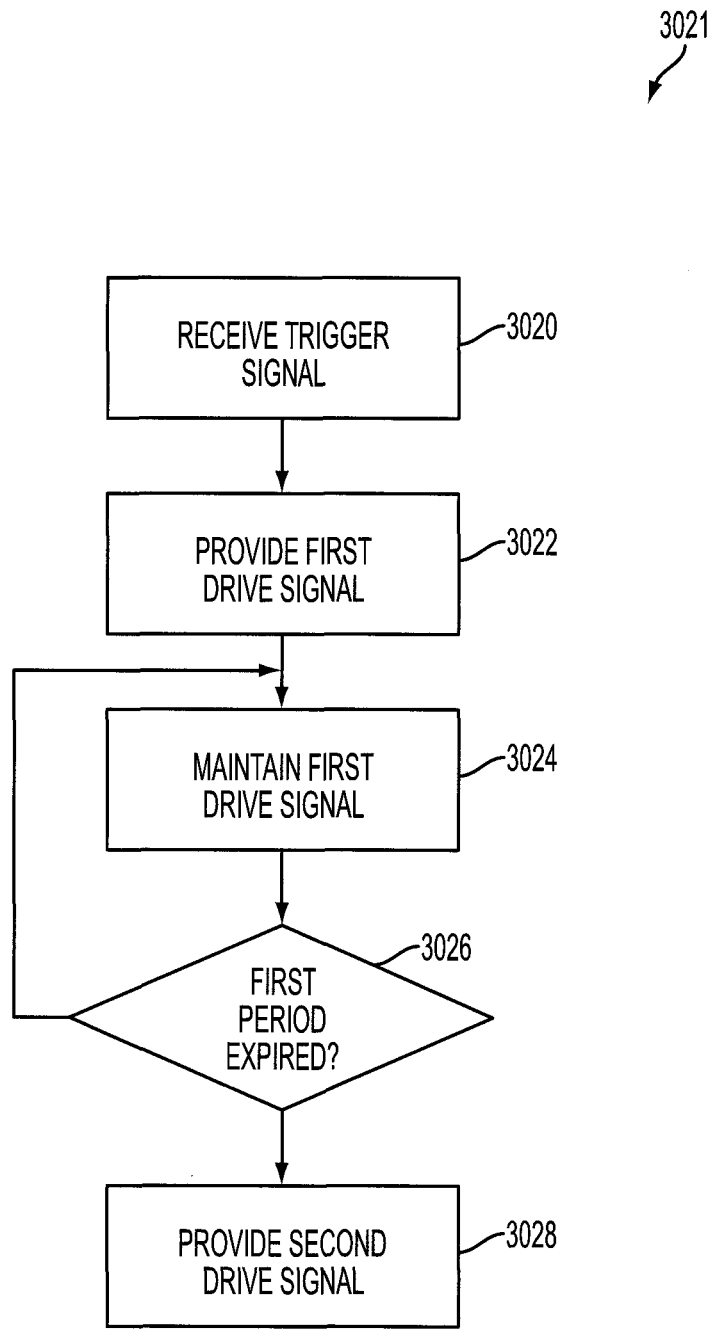
FIG. 71 is a logic flow diagram of one form of an algorithm for driving an ultrasonic instrument sequentially at two power levels.

FIG. 71 is a logic flow diagram of one form of an algorithm 3021 for driving an ultrasonic instrument sequentially at two power levels. FIG. 70 is a chart illustrating a power or displacement plot for one example implementation of the algorithm of FIG. 71. The algorithm 3021 may be implemented by a generator, such as 30, 500, 1002 and/or an internal generator, to drive an ultrasonic instrument such as 100, 120, 1004. In FIG. 70, vertical axis 3002 corresponds to a displacement of the end effector blade. The horizontal axis 3004 corresponds to time in seconds. The algorithm 3021 is described herein as implemented by a generator, such as one of generators 30, 500, 1002 herein, it will be appreciated that the algorithm 3021 may alternately be implemented by an instrument, such as 100, 120, 1004 (e.g., by a control circuit 2009 thereof).

At 3020, the generator may receive a trigger signal provided by a clinician. The trigger signal may be provided in any suitable manner. For example, in some forms, the clinician provides the trigger signal utilizing a button or other input device on the instrument itself (e.g., buttons 312a, 1036a, 1036b, 1036c, footswitches 434, 1020, etc.).

At 3022, the generator may activate the instrument by providing a first drive signal. Referring to FIG. 70, activation of the instrument is indicated at 3006. The first drive signal corresponds to a first level of power provided to the end effector of the instrument. At 3024, the generator maintains the first drive signal for a first period. The end effector displacement corresponding to the first drive signal is indicated in FIG. 70 at 3009. As illustrated in the example of FIG. 70, first power level corresponds to an end effector displacement of between 60 and 120 microns, such as about 75 microns. The first power level may be selected to separate the inner muscle layer of a vessel from the adventilia layer and/or to provide other tissue effects tending to improve the dissection and/or sealing process. In some forms, the first drive signal may also provide off-resonance, as described herein, to further aid in the separation of the inner muscle layer of a vessel from the adventilia layer The generator determines whether the first period has expired at 3026. The first period may be measured in any suitable manner. For example, in some forms, the first period is a set time period that expires after a predetermined amount of time has passed since the activation of the instrument. This is the case in the example shown in FIG. 70, wherein the first period is one second. Also, in some forms, the first period expires when a particular tissue change of state occurs. Any of the changes in tissue state described herein may indicate the end of the first period and, for example, any of the algorithms described herein for detecting a change in tissue condition may be utilized. For example, in some forms, the end of the first period may be indicated by a change in the impedance of the transducer.

When the first period expires, the generator provides a second drive signal at a second power level at 3028. In the example of FIG. 70, the transition from the first to the second drive signal is indicated at 3007. The end effector displacement at the second drive signal is indicated in FIG. 70 to be between about 20 and 60 microns, such as about 37.5 microns. Although the second drive signal is indicated in FIG. 70 to be a continuous signal, it will be appreciated that, in some forms, the second drive signal is a pulsed drive signal, for example, as described herein. The second drive signal may be provided to the instrument until any suitable endpoint. For example, referring to FIG. 70, the completion of tissue dissection is indicated at 3008. Deactivation of the instrument is indicated at 3010. In some forms, tissue dissection may be detecting using any of the algorithms for detecting tissue state changes described herein. In some forms, the generator may automatically deactivate the instrument either at dissection point 3008 and/or thereafter (e.g., a predetermined time period thereafter).

Figure 72:
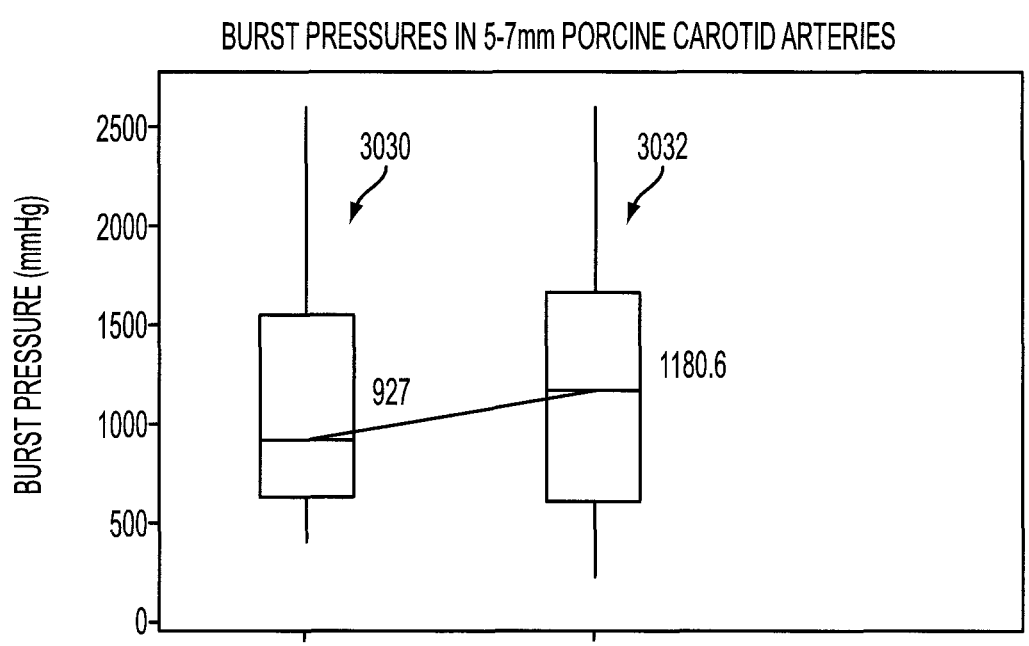
FIG. 72 is a chart illustrating burst pressures obtained with a surgical instrument operated according to the algorithm of FIG. 71 and operated by activating the instrument at a single power level.
Figure 73:
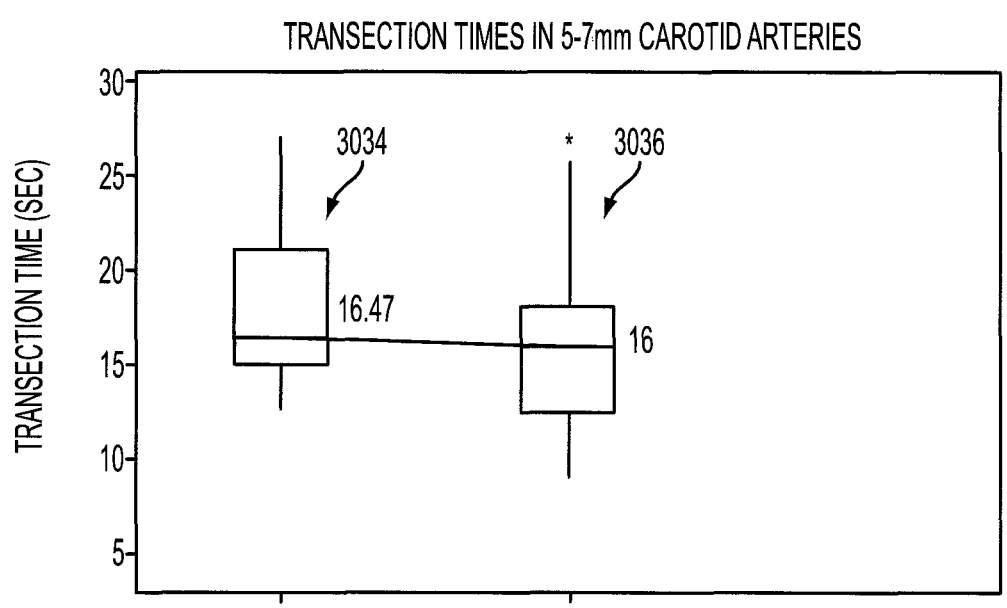
FIG. 73 is a chart illustrating transection times obtained for the trials indicated in FIG. 72.

The algorithm 3021 may improve the performance of the instrument relative to simply activating the instrument at a single power level. FIG. 72 is a chart illustrating burst pressures obtained with a surgical instrument similar to the instrument 1004 operated according to the algorithm of FIG. 71 (3030) and operated by activating the instrument 1004 at a single power level (3032). In the example of FIG. 72, plot 3032 corresponds to the instrument 1004 activated at a single power level corresponding to the second power level of the algorithm 3021. Both the trials for the algorithm 3021 and those at the single power level were conducted on 5-7 mm porcine ceratoid arteries. As can be seen, the algorithm 3012 lead to higher burst pressures, which may correspond to higher quality seals and transections. FIG. 73 is a chart illustrating transection times obtained for the trials indicated in FIG. 72. As illustrated, the algorithm 3021 may provide superior transection times.

Figure 74:
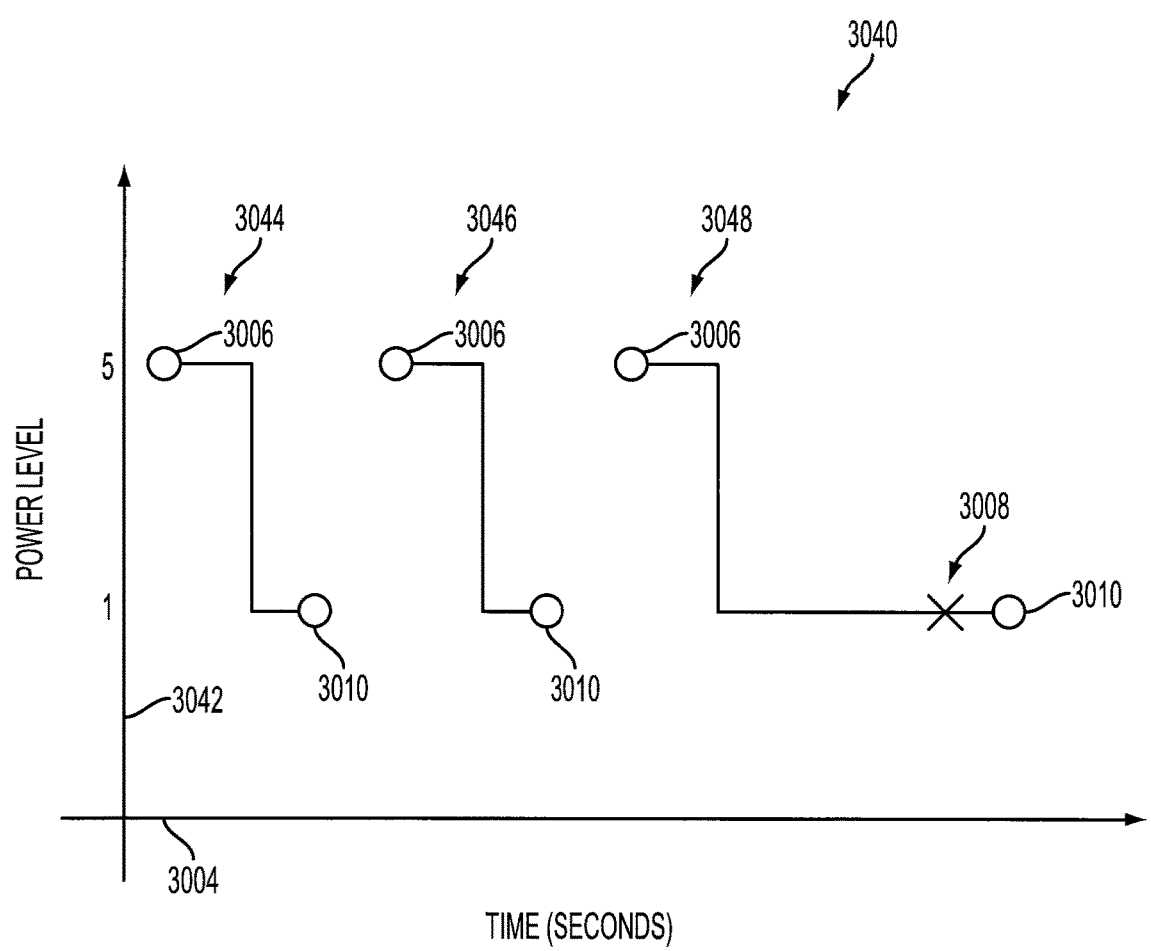
FIG. 74 is a chart illustrating a drive signal pattern according to one form of the algorithm of FIG. 71.

In use, the algorithm 3021 has a potential for misuse by clinicians. For example, FIG. 74 is a chart 3040 illustrating a drive signal pattern according to one form of the algorithm 3021. In FIG. 74, the vertical axis 3042 corresponds to a power level provided and the horizontal axis 3004 corresponds to time. The first and second power levels are indicated on the axis 3042 as "5" and "1," respectively. For example, when implemented on the GEN 11 generator available from Ethicon Endo-Surgery, Inc. of Cincinnati, Ohio, "5" may correspond to power level "5" and "1" may correspond to power level "1." As illustrated, the clinician has activated (3006) and deactivated (3010) the instrument several times in succession without completing tissue transection. As illustrated, the clinician deactivated the instrument near the beginning of the second (lower power) drive signal in order to reactivate the instrument and reestablish the first (higher power) drive signal. It will be appreciated that this type of use may prevent the algorithm 3021 from operating as designed. In some forms, the algorithm 3021 may be modified to implement a rest time between a deactivation 3010 and a subsequent activation 3006.

Figure 75:
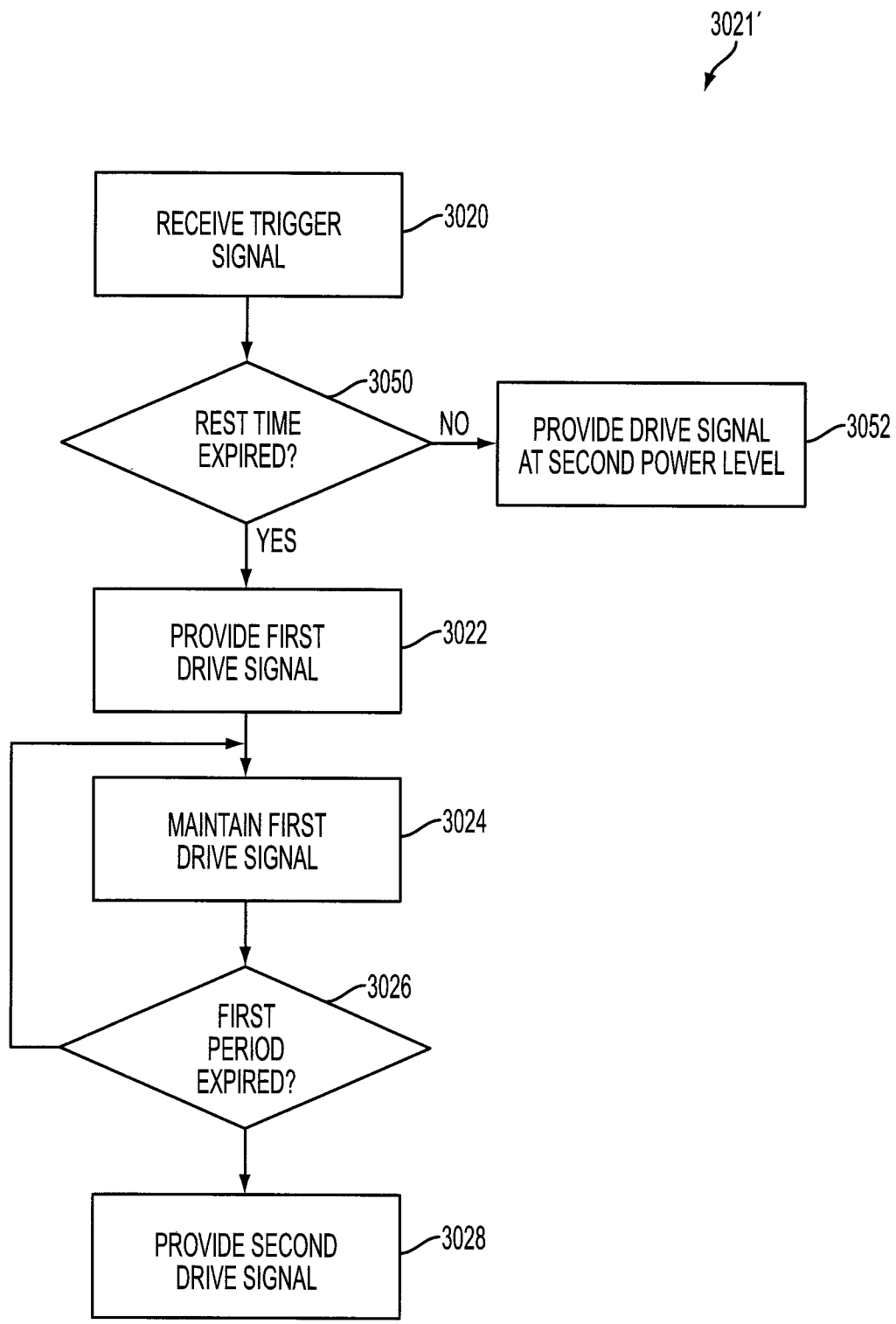
FIG. 75 is a logic flow diagram of another form of the algorithm of FIG. 71 implementing a rest time between a deactivation of the instrument and a subsequent activation.

FIG. 75 is a logic flow diagram of another form of the algorithm 3021' implementing a rest time between a deactivation of the instrument and a subsequent activation. The algorithm 3021' may be implemented by a generator, such as 30, 500, 1002 and/or an internal generator, to drive an ultrasonic instrument such as 100, 120, 1004. After receiving the trigger signal at 3020, the generator may determine at 3050 if a rest time has passed since a most recent activation of the instrument. In various forms, the rest time is selected to correspond to an amount of time that would allow the ultrasonic blade and/or tissue to return to a rest state. In one example form, the rest time is four seconds. If the rest time has passed, then the algorithm 3021' may proceed to actions 3022, 3024, 3026 and/or 3028 as described herein above. If the rest time has not passed at 3050, then the generator may, at 3052, provide the instrument with a drive signal at the second power level (e.g., the lower of the power levels of the algorithm 3021'). In this way, if the rest period has not passed since a previous deactivation, the algorithm 3021' may continue at the point where it left off at the deactivation.

Figure 76:
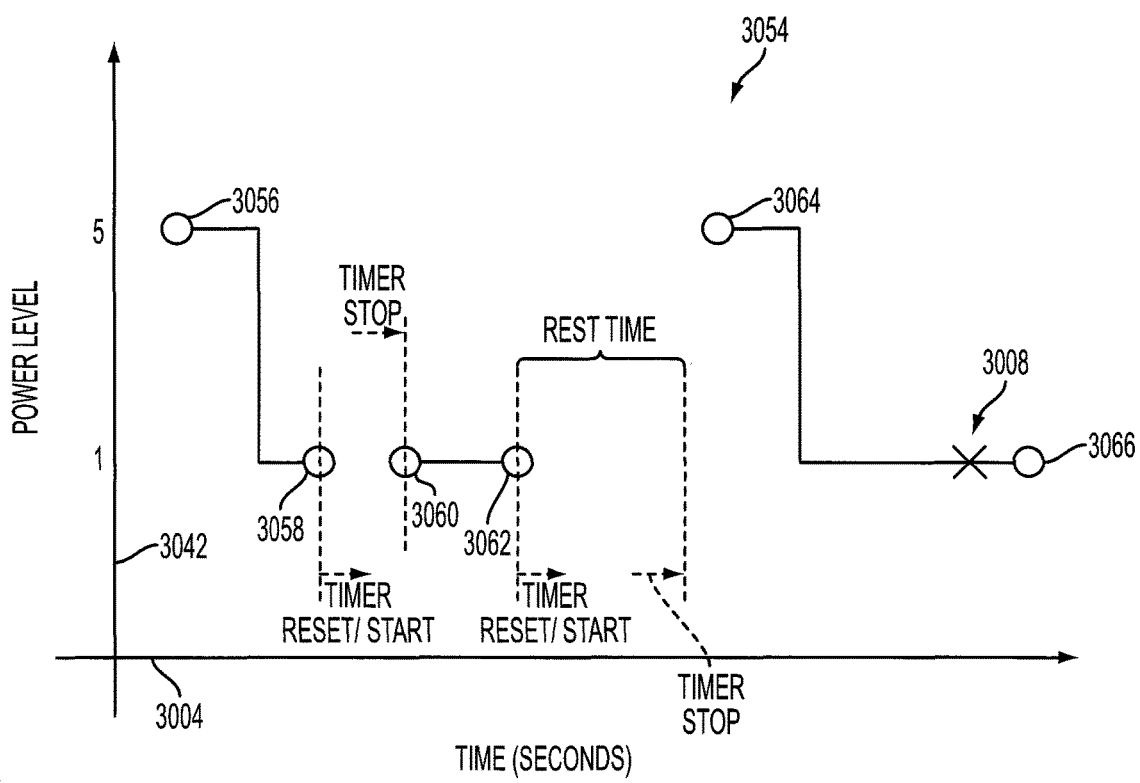
FIG. 76 is a chart illustrating a drive signal pattern according to one form of the algorithm of FIG. 75.

FIG. 76 is a chart illustrating a drive signal pattern according to one form of the algorithm 3021'. The clinician may activate the instrument at 3056. When the second drive signal is provided, the clinician deactivates the instrument at 3058. For example, the deactivation 3058 may occur before tissue sealing and transection is complete. At 3660, the clinician reactivates the instrument, for example by generating a trigger signal as described herein above. As illustrated, however, the rest time did not pass before the reactivation at 3660. Accordingly, the generator, at 3660, provides a drive signal at the second power level. After the deactivation at 3062, however, the rest time did pass before the reactivation at 3064. Accordingly, the generator provides a drive signal at the first power level and the algorithm 3021' proceeds as shown in FIG. 70.

In various forms, the algorithm 3021' may be implemented utilizing an alternate logic condition in place of the rest time. For example, instead of determining whether the rest time has expired at 3050, the generator may determine whether the alternate logic condition has been met. The alternate logic condition may be any suitable condition including, for example, an indicator of a state of the instrument and/or tissue being acted upon. In some forms, the logic condition may be, or be related to, a temperature of the end effector. For example, the alternate logic condition may be based on the resonant frequency of the ultrasonic drive system and end effector, as indicated by the frequency of the drive signal. If the frequency is above a threshold value (indicating that the temperature of the end effector temperature is below a threshold value), then the algorithm 3021' may proceed to actions 3022, 3024, 3026, 3028 as described. The frequency of the drive frequency may be measured in any way including, for example, those described herein above with respect to FIG. 21 above. In another example, the alternate logic condition may be based on the impedance of the ultrasonic transducer, which may serve as another proxy for end effector temperature, as described herein above with respect to FIGS. 10-13. Also, in some forms, the temperature of the end effector may be measured by a temperature probe at the end effector, such at the temperature probe 3070 positioned at the end effector 1026 of FIG. 16A.

Figure 77:
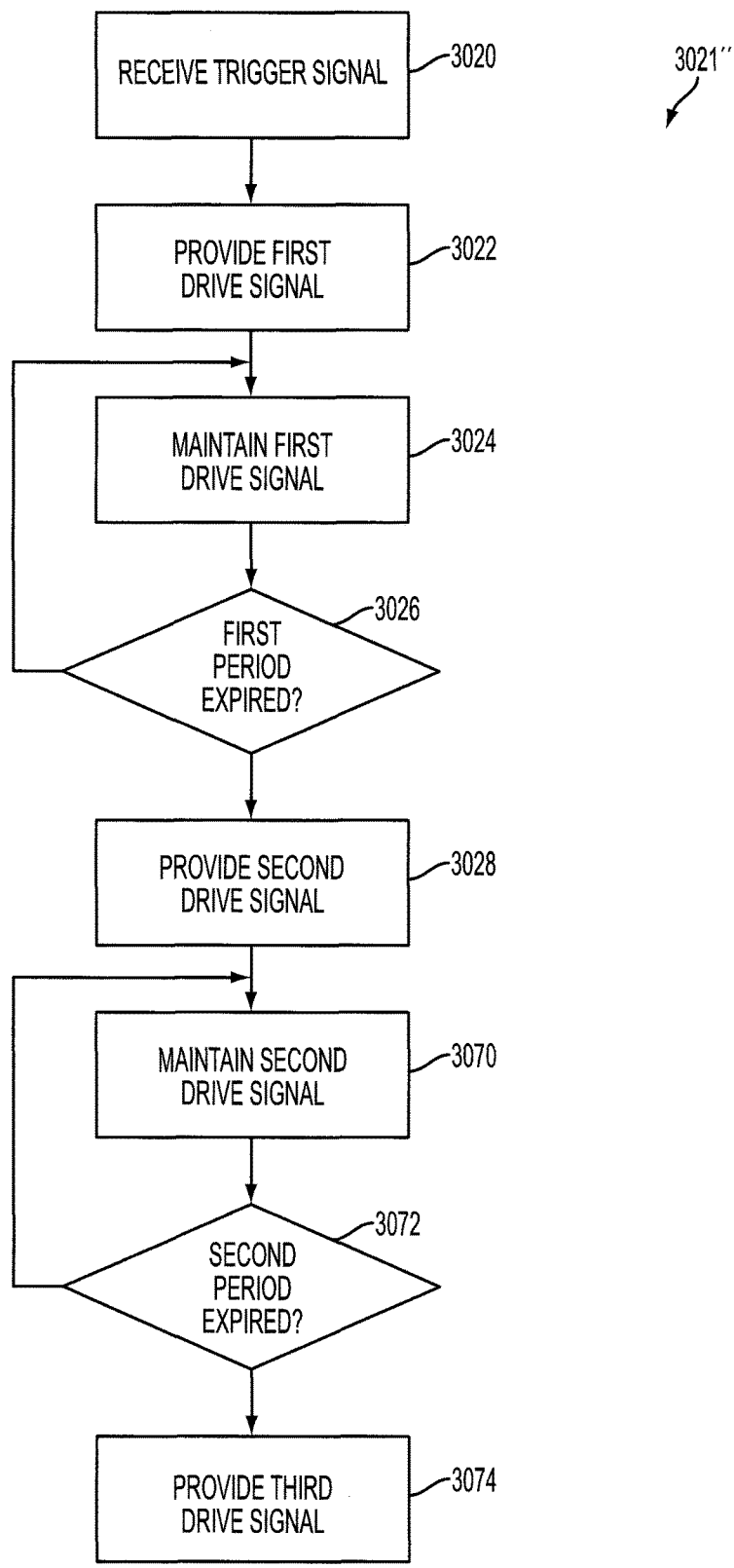
FIG. 77 is a logic flow diagram of another form of the algorithm of FIG. 71 implementing a third drive signal.
Figure 78:
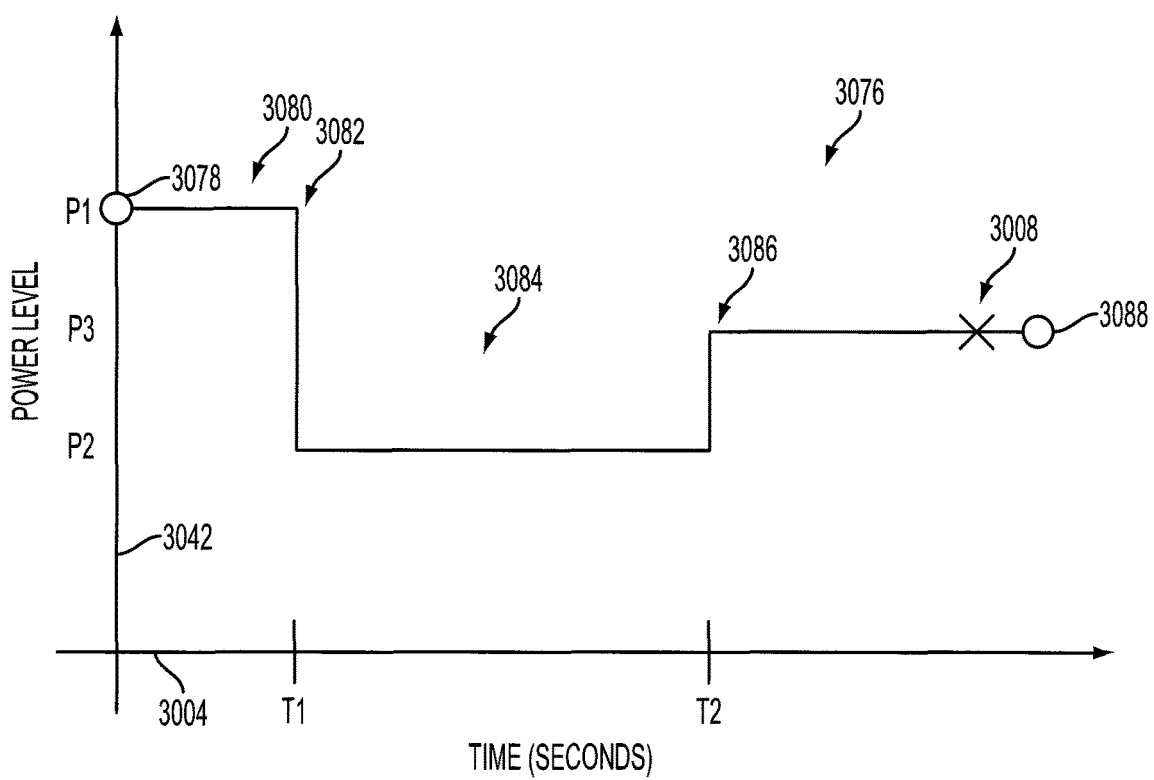
FIG. 78 is a chart illustrating burst pressures obtained with a surgical instrument operated according to the algorithm of FIG. 71 versus the surgical instrument operated according to the algorithm of FIG. 77.

FIG. 77 is a logic flow diagram of another form of the algorithm 3021" implementing a third drive signal. The algorithm 3021" may be implemented by a generator, such as 30, 500, 1002 and/or an internal generator, to drive an ultrasonic instrument such as 100, 120, 1004. The generator may perform actions 3020, 3022, 3024, 3026, 3028 as described above with respect to FIG. 71. After providing the second drive signal at 3028, however, the generator may maintain the second drive signal at 3070 until the expiration of a second period at 3072. At the expiration of the second time period, the generator may provide a third drive signal at 3074. The third drive signal is at a third power that may be greater than the second power and less than the first power. For example, in one example form, the second power level is 45% of the first power level. The third point level may be, for example 100%, 75%, etc. of the first power level. The first and second periods may be, for example, 1.5 seconds and twelve seconds, respectively. It will be appreciated that the algorithm 3021" may be implemented with a rest time period, for example, as the algorithm 3021'. For example, the actions 3070, 3072 and 3074 may be performed after action 3028 as illustrated in FIG. 75

Figure 79:
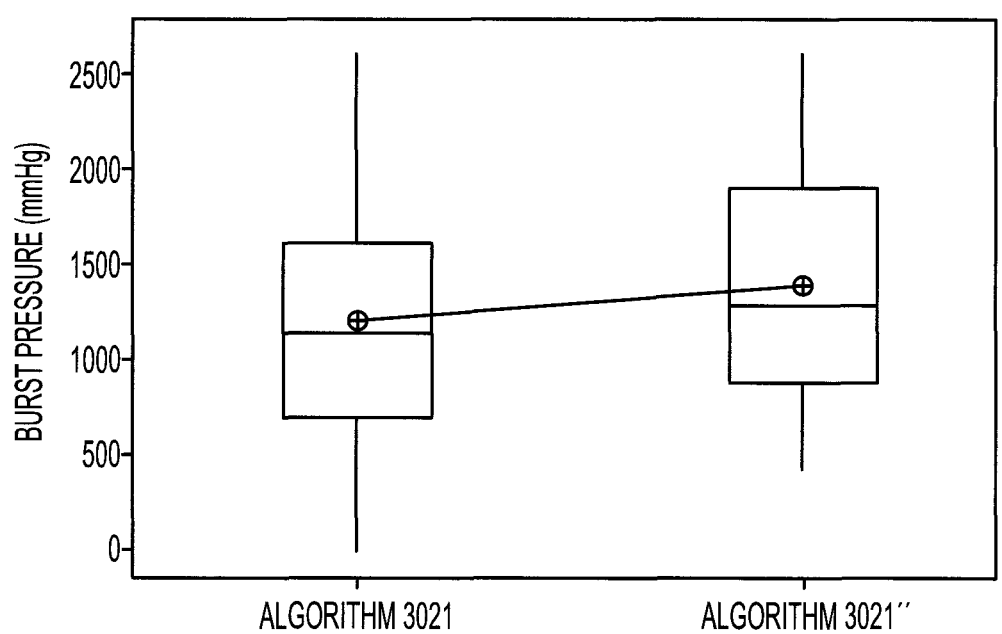
FIG. 79 is a chart illustrating burst pressures obtained with a surgical instrument similar to the instrument operated according to the algorithm of FIG. 71 versus the surgical instrument operated according to the algorithm of FIG. 78.
Figure 80:
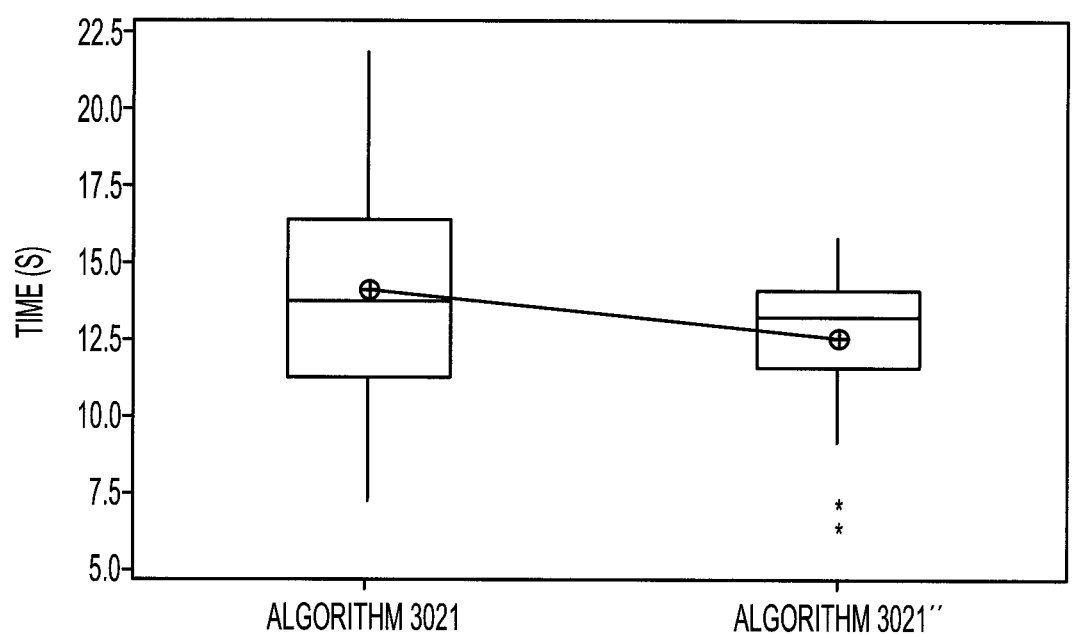
FIG. 80 is a chart illustrating transection times obtained for the trials indicated in FIG. 79.

In various forms, the algorithm 3021" may lead to higher burst pressures and shorted transection times relative to the algorithm 3021 illustrated in FIG. 71. For example, FIG. 79 is a chart illustrating burst pressures obtained with a surgical instrument similar to the instrument 1004 operated according to the algorithm 3021 versus the surgical instrument operated according to the algorithm 3021". As illustrated, the burst pressure for the algorithm 3021" are higher than with the algorithm 3021. Similarly, FIG. 80 is a chart illustrating transection times obtained for the trials indicated in FIG. 79. As illustrated, transection times for the algorithm 3021" are lower than for the algorithm 3021. Also, in some forms where the algorithm 3021" is implemented in a conjunction with another algorithm for providing feedback (e.g., a response set) upon detecting a change in tissue state (e.g., a condition set), providing the third, higher power drive signal may increase the effective of the algorithms described herein for detecting a change in tissue state.

In some forms, the algorithms 3021, 3021', 3021" may be implemented in conjunction with various other algorithms described herein. For example, any of the algorithms 3021, 3021', 3021" may be implemented in conjunction with a condition set and/or response set based on a measured characteristic of the instrument and/or tissue acted upon by the instrument. For example, the algorithms 3021, 3021', 3021" may be implemented with one of the algorithms described herein above with respect to FIGS. 15A-15C, FIGS. 20-22, FIGS. 57-60, etc. When a condition set indicates a tissue condition, the corresponding response set may be executed on top of the algorithms 3021, 3021', 3021". For example, when a triggered condition set calls for feedback, the feedback may be provided while the algorithm 3021, 3021', 3021" continues. Also, for example, when a triggered condition set calls for a change to the drive signal, the generator may deviate from the algorithm 3021, 3021', 3021" in accordance with the triggered response set.

Figure 81:
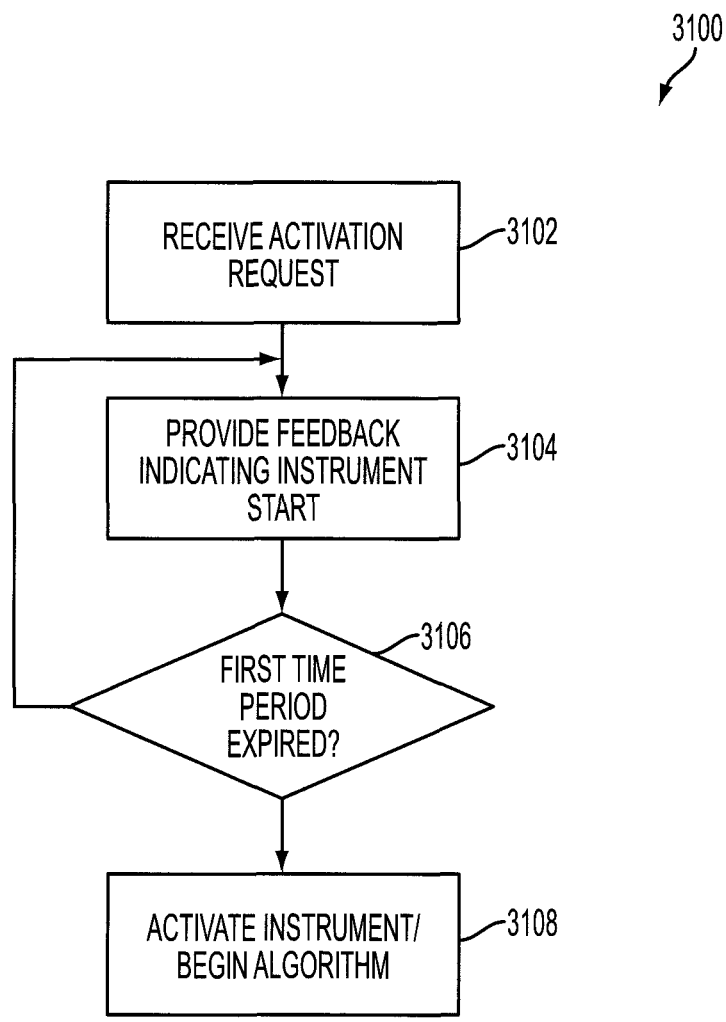
FIG. 81 is a logic flow diagram of one form of an algorithm implementing an initial clamping period.

FIG. 81 is a logic flow diagram of one form of an algorithm 3100 implementing an initial clamping period. The algorithm 3100 may be implemented by a generator, such as 30, 500, 1002 and/or an internal generator, to drive an ultrasonic instrument such as 100, 120, 1004. At 3102, the generated may receive an activation request, for example, as described herein above with respect to the activation request 3020. At 3104, the generator may provide feedback indicating that the instrument has been activated. The feedback may be audible, visual and/or tactile feedback as described herein. When the feedback is provided, however, the instrument is not yet activated. In this way, the algorithm 3100 may provide time for the end effector to compress tissue prior to activating the instrument so as to increase the efficacy of transection and sealing. At 3106, the end effector may determine whether a first time period has expired. The first time period may be, for example, a few seconds. When the first time period has expired, the generator may activate the instrument and begin executing a control algorithm. The control algorithm may be any suitable algorithm including, for example, any of the algorithms 3021, 3021', 3201". For example, referring to FIG. 71, actions 3104, 3106 would be performed after receiving the trigger signal 3020. Action 3022 would be performed to correspond to 3108.

Figure 82:
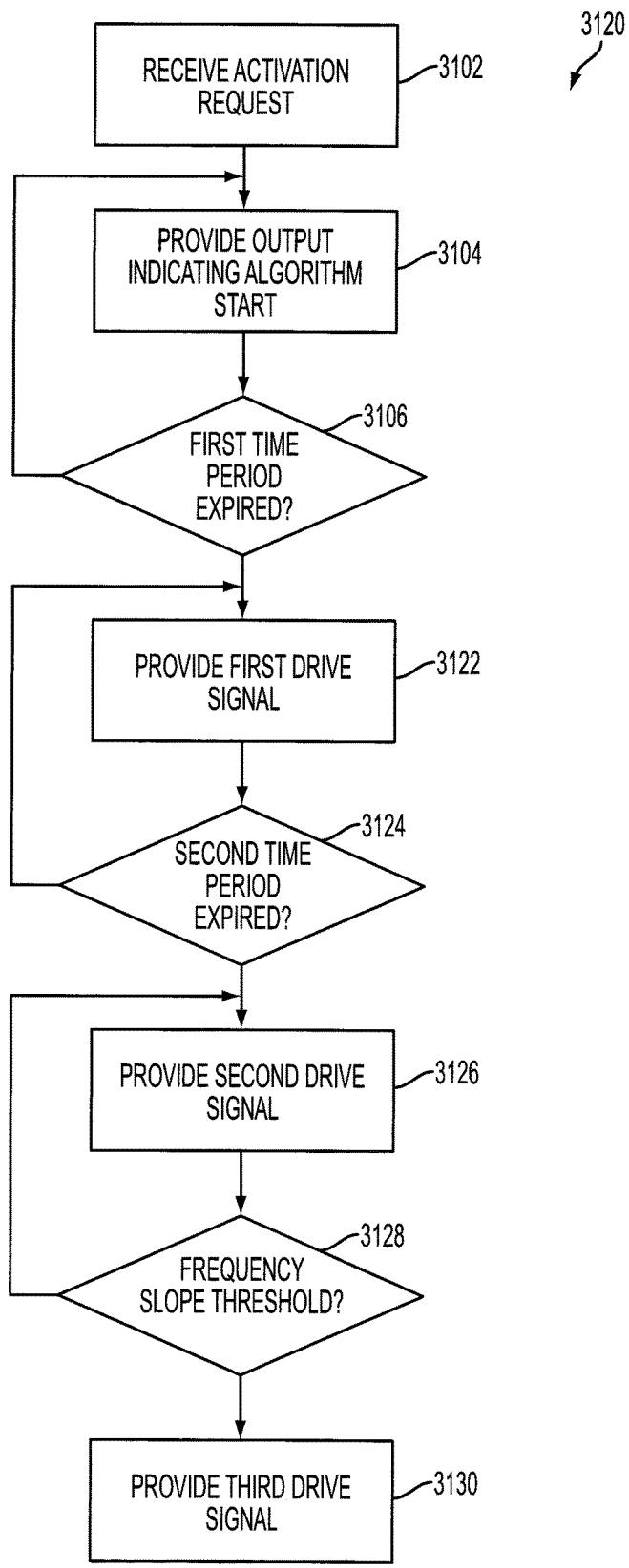
FIG. 82 is a logic flow diagram of another form of an algorithm implementing an initial clamping period.

FIG. 82 is a logic flow diagram of another form of an algorithm 3120 implementing an initial clamping period. The algorithm 3021" may be implemented by a generator, such as 30, 500, 1002 and/or an internal generator, to drive an ultrasonic instrument such as 100, 120, 1004. For example, the algorithm 3120 may implement the initial clamping period in conjunction with a step function, such as the step function described herein above with respect to FIGS. 6-8. Referring again to FIG. 82, the generator may perform actions 3102, 3104, and 3106 as described herein with respect to FIG. 81. At 3122, the generator may provide a first drive signal 3122 at a first level. The first level may correspond to a current, a power, an end effector displacement, etc. When a second time period has expired at 3124, the generator provides a second drive signal at 3126. The second drive signal corresponds to a current, power and or end effector displacement at a level higher than that of the first level. The second drive signal may be maintained until the generator detects a change in tissue state such as, for example, a drop in the frequency slope below a threshold frequency slop at 3128. Upon the occurrence of such an event, the generator may provide a third drive signal at 3130. The third drive signal may be maintained, for example, until an additional change in the state of the tissue (e.g., transection), for example, as determined by an algorithm, such as those described above with respect to FIGS. 15A-15C, FIGS. 20-22, FIGS. 57-60, etc.

Figure 83:
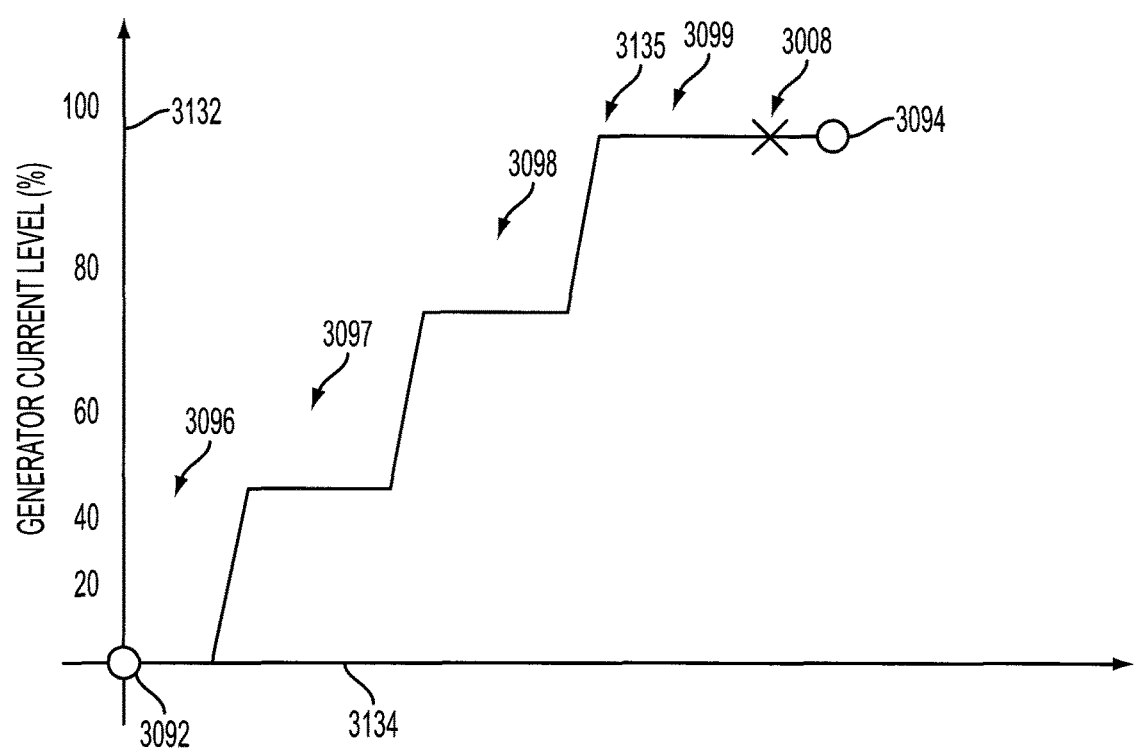
FIG. 83 is a chart illustrating a drive signal pattern according to the algorithm of FIG. 82.

FIG. 83 is a chart illustrating a drive signal pattern according to the algorithm 3120. The vertical axis 3132 corresponds to drive signal current while the horizontal axis 3134 corresponds to time. The activation signal is received at 3092. The first time period is represented by 3096. The second time period with the first drive signal is indicated at 3097. The second drive signal is provided at 3098 until the frequency slope threshold is met at 3135, upon which the third drive signal is indicated by 3099. Transection is indicated at 3008, and deactivation at 3094.

As described above, any of the algorithms described herein including, 3021, 3021', 3021", 3100, 3120, etc., may be implemented in conjunction with an algorithm for implementing a condition set and response set. The condition set, for example, may be true based on the presence or absence of a particular state of the ultrasonic instrument and/or tissue acted upon by the ultrasonic instrument. The response set may define actions to be taken by the instrument and/or the generator upon the condition set being true. In some forms, various condition sets may be estimated utilizing one or more multi-variable models. Examples of multi-variable models may include, for example, neural network models, genetic algorithm models, classification tree algorithm models, recursive Bayesian models, etc.

Figure 84:
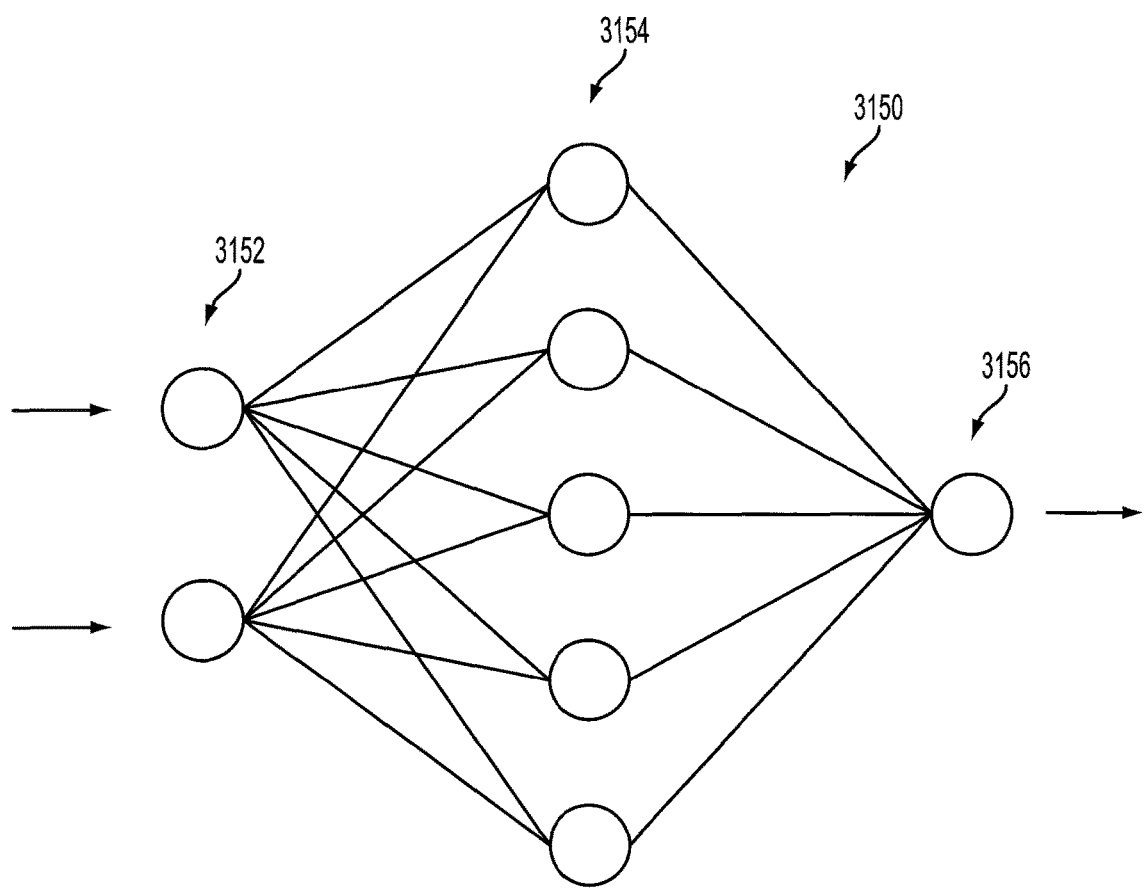
FIG. 84 is a diagram showing an example neural network.

One suitable type of multi-variable model comprises a neural network. Neural networks may be effective for recognizing complex patterns in input variables, which may make them well suited to detect condition sets based on tissue state (e.g., whether transection has occurred, whether sealing has occurred, etc.). FIG. 84 is a diagram showing an example neural network 3150. The neural network 3150 comprises a group of interconnected nodes 3152, 3154, 3156 referred to as neurons. Connections between different neurons indicate how data is passed through the network. Input neurons 3152 are assigned values from input data (e.g., various parameters of the surgical instrument, the drive signal, etc.). In various forms, the input variables are scaled to values between zero and one. The values of the input neurons 3152 (e.g., the input variables) are then utilized to calculate values of various hidden neurons 3154, which are, in turn, used to find the value of one or more output neurons 3156. The value of the output neuron 3156 may trigger (or not trigger) a response set such as, for example, feedback and/or changes to the drive signal. In practice, the number of respective input nodes 3153, hidden nodes 3154 and output nodes 3156 may vary, sometimes considerably, from what is shown in FIG. 84. In various forms, a neural network is operated on a data cycle. During each cycle, input values are provided to the input neurons 3152 and output values are taken at the output node 3156.

Neural networks may be fully connected, as shown in FIG. 84, meaning that each input neuron 3152 is connected to each hidden neuron 3154. Some forms may utilize a neural network that is not fully connected. For example not all of the input nodes may be connected to each hidden neuron 3154. Values for the hidden nodes 3154 may be determined according to an activation function. In various forms, the outputs of the activation function range from 0 to 1. For example, the output function may be selected to generate outputs between 0 and 1 or, in some forms, results of the output function may be scaled. In some forms, it is advantageous to select functions that are continuous and differentiable. This may facilitate training of the neural network. For example, back-propagation training utilizing a gradient method may require computing partial derivatives of the output function, which may be simplified when the optimization functions are continuous and differentiable. One example of such a function that may be utilized as the activation functions is the sigmoid function, as indicated by Equation (8) below:

$$x = \omega_1 \xi_1 + \omega_2 \xi_2 + \omega_3 \xi_3 + \ldots + \theta \quad (8)$$

In Equation (8), $\xi$ corresponds to the values of the input neurons, $\omega$ corresponds to the weights given to each input, $\theta$ corresponds to a constant. When the neural network is fully connected, the values of all input neurons are passed to all hidden neurons, meaning the activation function for each hidden neuron will include a ξ term corresponding to each input node. The weights given to each input (ω) may be unique for each hidden neuron and/or each input value. The constant θ may also be unique for each hidden neuron 3154. The results at each node may be given by Equations (9) and (10) below:

$$\sigma(x) = \frac{1}{1+e^{-x}} \quad (9)$$

Figure 85:
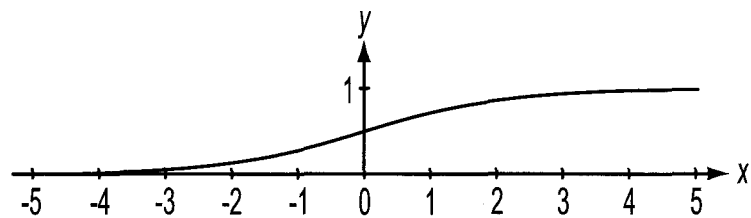
FIG. 85 is a plot of an example portion of an activation function for hidden neurons and/or output neuron(s) of a neural network.

FIG. 85 is a plot of one example implementation of Equation (9), demonstrating that the function is continuous and differentiable.

$$O=\sigma(x) \quad (10)$$

Figure 86:
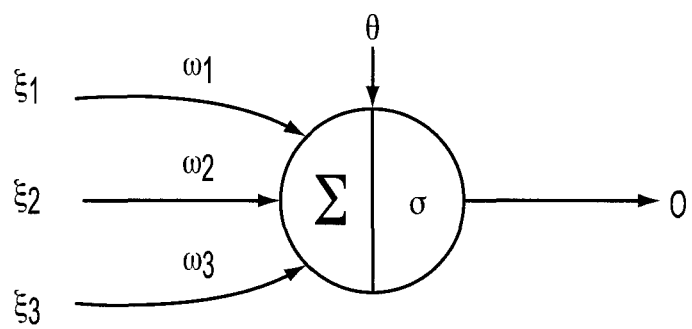
FIG. 86 is a diagram indicating an example activation function for hidden neurons and/or output neuron(s) of a neural network.

The output of the sigmoid function is illustrated in FIG. 86. For example, the output (O) may be calculated from the weighted sum of the input neurons plus theta (e.g., Equation (8)) applied to Equation (9).

In various forms, each hidden neuron has I inputs, which is equal to the number of inputs to the neural network. If there are J hidden neurons 3154, then there are I×J unique values for omega (ω) and J unique values for theta (θ). In some forms, the output neuron(s) 3156 may utilize the same activation equation. Accordingly, there may be J×K unique omega (ω) values connecting the hidden neurons 3154 to the output neuron 3156, where K is the number of output neurons, and K unique values of theta (A) for the output node(s) 3156.

The output of the neural network may indicate the truth of falsity of a condition set comprising one or more conditions of the ultrasonic surgical instrument, tissue acted upon by the surgical instrument, or some combination thereof. For example, a neural network may be used to model a condition set indicating whether to provide feedback indicating tissue transection at or near the separation point. For example, in some forms, the output of the neural network may indicate whether 80% transection has been achieved. Any suitable number or type of neurons 3152, 3154, 3156 may be used. For example, the neural network 3150 may comprise twelve input neurons 3152, (I=12), four hidden neurons (J=4), and one output neuron (K=1). The data cycle may be 10 milliseconds. Accordingly, values for the 12 inputs may be fed into the network 3150, and results calculated, every 10 milliseconds.

Input variables (e.g., variables corresponding to the input nodes 3152) may comprise any variables that could, in some circumstances, affect the value of an output node 3156. The example input variables described below may be utilized in a neural network, such as 3154, having an output node or nodes corresponding to any suitable ultrasonic instrument-related value such as, for example, 80% transection. It will be appreciated that the input variables described herein may also be used any other suitable type of model including, for example, genetic algorithm models, classification tree algorithm models, recursive Bayesian models, etc.

In some forms, input variables corresponding to input nodes 3152 include variables describing the operation of the surgical system during the treatment of tissue. A tissue treatment, for example, may begin when the surgical system is activated on tissue. Example tissue treatment input variables are described below:

An elapsed time since activation input variable may represent a time since the activation of the instrument (e.g., at the beginning of a tissue treatment). Time may be measured in any suitable increments including, for example, 10 milliseconds (0.010 seconds) beginning at instrument activation (e.g., 0.00 seconds). In some forms, the elapsed time since activation is measured and stored by the generator.

Different variables may be utilized to describe the operation of the ultrasonic transducer or hand piece including, for example, a voltage drop across the transducer, a current drawn by the transducer, and an impedance of the transducer. Values for these and similar variables may be captured and stored (e.g., by the generator) at any suitable interval. For example, voltage current and/or impedance values may be captured at an interval equal to the data cycle of the neural network 3150.

Additional input variables describe different permutations of voltage, current and/or impedance of the transducer over predetermined time periods. For example, averages of voltage, current or impedance may be taken over the entire activation period (e.g., described by the elapsed time since activation). Also, in some forms, averages of voltage, current or impedance are taken over a predetermined number of prior samples. For example, an average impedance may be taken across the last A impedance samples, where A may be equal to 10. Power, energy and various other values derivable from voltage, current and/or impedance may also be calculated as stand-alone input variables or in different permutations. For example, total energy is used as an input variable in some forms. Total energy may indicate a sum of energy delivered to the ultrasonic system since activation. This may be derived, for example, by multiplying a summation of power by time throughout the activation. An impedance curve or shape indicates changes in impedance since activation. In some forms, a spline fit or other smoothing function may be applied to the impedance curve. Application of a smoothing function may accentuate inflection points, the presence or position of which may be utilized as input variables. For example, the impedance curve, in some forms, may experience a sudden drop as cutting occurs. Various example input variables, such as the impedance curve, are described as a curve or array of values. Such variables may be input to the neural network 3150 or similar model in any suitable form including, for example, by taking an area under the curve, taking one or more peak values, taking an average or running average of the curve, etc. In some forms, integrals, peaks, averages, etc. of various curves may be bounded, for example, to exclude transient effects from activation. Additional variables may include, for example, a total energy (e.g., since activation), a total change in impedance (e.g., since activation), etc.

Various input variables are based on the resonant frequency of the surgical system (e.g., transducer, waveguide and blade). The resonant frequency of the surgical system may be manifested in the frequency of the drive signal. For example, as described herein, the generator may be tuned to drive the surgical system (e.g., provide a drive signal) at the system's resonant system. In some forms, the resonant frequency itself (e.g., a current or instantaneous resonant frequency) may be an input variable. Resonant frequency may be sampled at any suitable interval such as, for example, at the data cycle of the neural network or other model. Another example resonant frequency variable describes a change in the resonant frequency over the course of tissue treatment. For example, the change in resonant frequency may be set equal to a difference between a current resonant frequency value and a frequency value at the activation and/or at a set point after the activation (e.g., 0.5 seconds after activation). Yet another resonant frequency variable describes a frequency derivative dF/dt, or an instantaneous slope of the resonant frequency. An additional resonant frequency variable may be derived by taking an average of frequency derivative values. One example average includes all frequency derivative values since activation and/or frequency derivative values over a predetermined period such as, for example, the past 10 data cycles of the neural network 3150. In some forms, multiple average frequency derivative variables may be used, with each variable calculated over a different period (e.g., a different number of past data cycles of the neural network 3150 or other model). Various different permutations of the resonant frequency variables described herein may also be used. One example resonant frequency variable describes a maximum average frequency derivative calculated over a preceding A average dFdt values, where A may correspond to a number of data cycles of the neural network 3150 or other model. For example, A may be equal to 10. Another example input variable is a phase margin. The phase margin describes a difference in phase between the drive signal and the displacement of the blade. The phase margin may be measured in any suitable manner for example, as described in commonly-owned U.S. Pat. No. 6,678,621, entitled "Output Displacement Control Using Phase Margin In An Ultrasonic Hand Piece," which is incorporated herein by reference in its entirety.

In various forms, the neural network 3150 or other model receives input variables having values that describe a specific surgical system (e.g., system-specific variables). System-specific variables may describe properties any component or group of components of a surgical system including, for example, a hand piece, a blade, a waveguide, an end effector, a clamp arm, a clamp pad, etc. In this way, system-specific variables may serve to provide a "fingerprint" of each surgical system. Different system-specific variables may be measured and utilized in various ways. For example, system-specific variables may be used in both the training and execution of the neural network 3150 or other model.

Some system-specific variables describe properties of the surgical system, or components thereof, that can be physically measured. System length describes the length of the surgical system (e.g., the waveguide and blade thereof). Example system lengths include 23 cm, 36 cm and 45 cm. In some forms, separate neural networks 3150 may be trained and utilized for systems having different lengths, however, this may be avoided by utilizing system length as an input variable.

Some system-specific input variables describe properties of the ultrasonic blade. For example, an individual blade gain describes a ratio of an increase or decrease in displacement from a transducer to the tip of a blade (e.g., the blade gain may describe the combination of a blade and a wave guide). The gain of any given ultrasonic blade may be determined by the physical properties of the blade itself including, for example, discontinuities in the diameter of the blade. Different blades manufactured to the same specifications may have slightly different blade gains, for example, due to manufacturing tolerances. For example, the gain for one suitable blade may be 3.5±0.2. In various forms, blade gain is measured during the manufacturing and/or testing of the surgical system. For example, a laser vibrometer or other suitable instrument may be utilized to measure the displacement of the blade when driven by a generator and hand piece with known gains.

Another blade-specific variable is the natural resonant frequency of the blade. This may also be referred to as the quiescent resonant frequency. The natural resonance frequency is a function of the physical properties of the blade. In various forms, natural resonant frequency is measured during manufacturing or testing of a blade (or associated system), for example utilizing an impulse excitation or ping test. According to a ping test, sound waves or vibrations over a range of frequencies are provided to the (usually unloaded) blade. The frequency at which the blade is caused to resonate is noted. For example, a microphone or other audio sensor may be used to record the response of the blade to pings of various frequencies. The frequency content of the measured values may be analyzed to identify resonance. Yet another blade-specific variable is the Q factor for the blade. The Q factor describes the bandwidth of the blade relative to its center frequency. In other words, the Q factor describes how tightly packed the frequency spectrum of the blade is around the resonant frequency. Q factor may be measured, for example, utilizing commonly available spectrum analyzer equipment, for example, during manufacture or testing of a blade or associated system.

An additional blade-specific variable is the blade length. For example, due to manufacturing tolerances, not every blade of the same design will have the same length. Exact blade lengths may be measured using any suitable measurement technique or equipment including, for example, micrometers, optical systems, coordinate measurement machines, etc. Blade deflection describes the degree that the blade deflects when in contact with the clamp arm. The degree of blade deflection may be measured, for example, utilizing a non-contact laser displacement instrument, a dial indicator, or any other suitable instrument. Various acoustic properties of blades may also be utilized as blade-specific input variables. A Poisson's ratio for different blades may be measured utilizing strain gauges to measure transverse and axial strain and/or may be derived from the blade material. The speed of sound in different blades may also be measured and/or derived from blade materials. Other acoustic properties that are potential input variables include the phase velocity, density, compressibility or stiffness, bulk modulus, etc. For example, many acoustic properties of blades, clamp pads, etc. are provided by the material manufacturers.

Additional blade-specific variables include a surface coefficient of friction and a projected sealing surface. The surface coefficient of friction may be relevant to models of tissue effect because the coefficient of surface friction may relate to the power delivered to tissue, for example, according to Equation (11) below:

$$\text{Power} = \mu \times 2\pi * d * f * N \tag{11}$$

In Equation (11), $\mu$ is the coefficient of surface friction (e.g., dynamic friction); f is the frequency of the drive signal (e.g., the resonant frequency of the system); N is the normal force; and d is the displacement of the blade. The coefficient of surface friction may be measured in any suitable manner. For example, the blade may be mounted to a turn table and rotated while a known normal force is applied. In some forms, Equation (11) above also considers the projected sealing surface, as indicated by Equation (12) below:

$$\text{Power density} = (\mu \times 2\pi * d * f * N)/SS \tag{12}$$

In Equation (12), SS is the projected sealing surface. The projected sealing surface may be estimated, for example, based on the geometric configuration of the blade. For example, the blade length, width and curvature may be relevant. A related example input variable is blade clock. For example, in some forms the blade is curved. A blade clock describes an angular direction of blade curvature about the longitudinal axis.

In various forms, the way in which a surgical system acts on tissue depends on the way that the clamp arm and blade engage the tissue. This may, in turn, depend on various system-specific dimensions other properties. For example, various system-specific variables describe the interrelationship between the blade, the clamp arm and the clamp pad. One such example input variable is the clamping force provided between the blade and the clamp arm. For example, the clamping force may correspond to $F_T$, described herein above with respect to Equation (1). Clamping force may be measured in any suitable manner. For example, with reference to the surgical system 19 shown with respect to FIGS. 1-3, the clamp arm 56 may be secured in an open position (e.g., not in contact with the blade 79). A force transducer may be secured to the clamp arm 56, for example, at a midpoint between the pivot point and the distal-most end of the clamp arm 56. Then the handle 68 may be actuated to close the clamp arm 56 against the blade 79. The force transducer may measure the force provided. In some forms, the trigger position may be monitored to derive an input variable expressing the clamp force versus trigger position. In some forms, the maximum force is used. In some forms, clamping force is measured with the clamp arm secured in on-open positions. For example, a pressure sensor, such as those available from TEKSCAN, may be placed between the blade and clamp arm.

Figure 93:
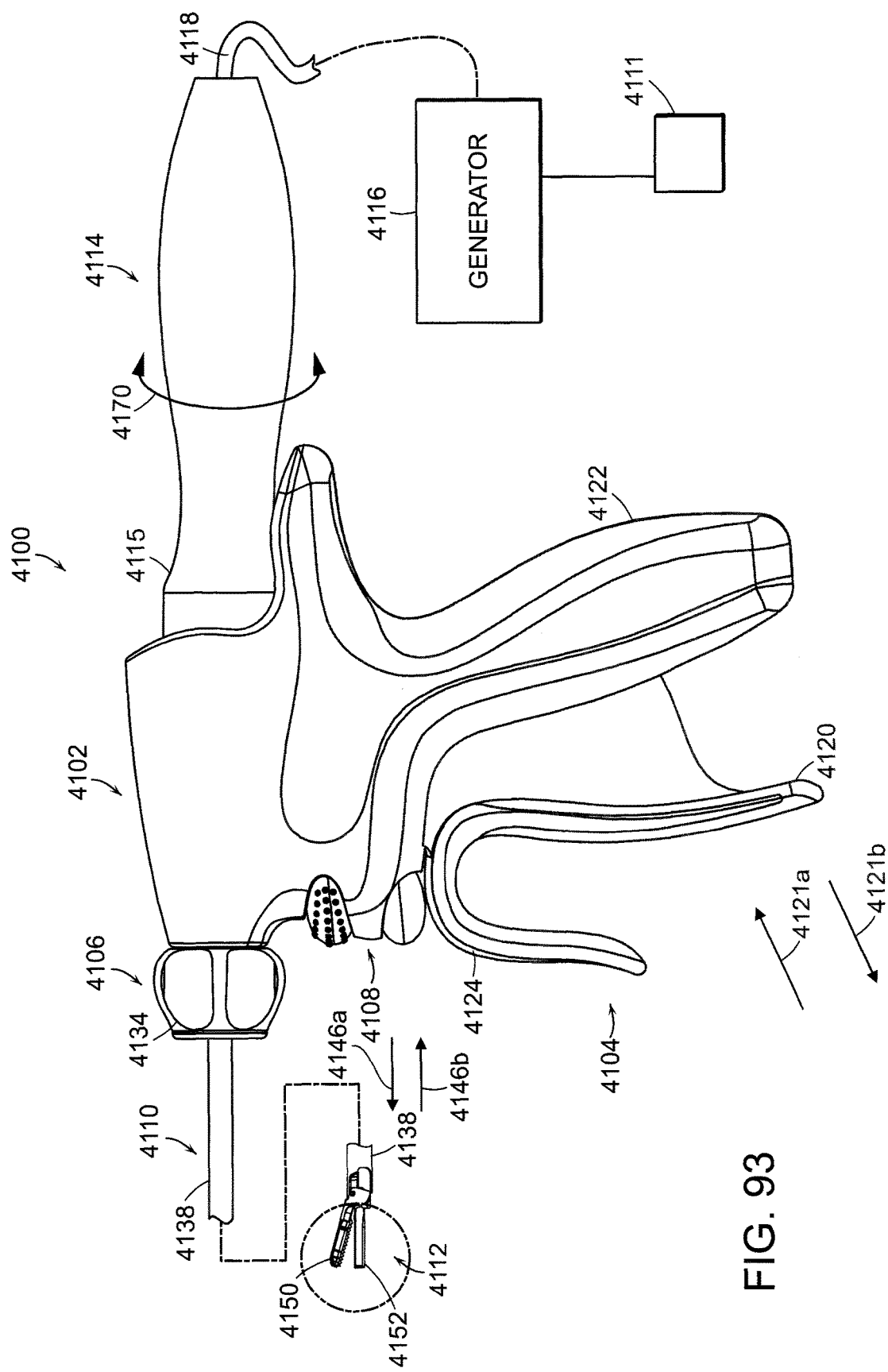
FIG. 93 is a side view of one form of an ultrasonic surgical instrument configuration comprising a rotatable electrical connection according to various forms described herein.
Figure 95:
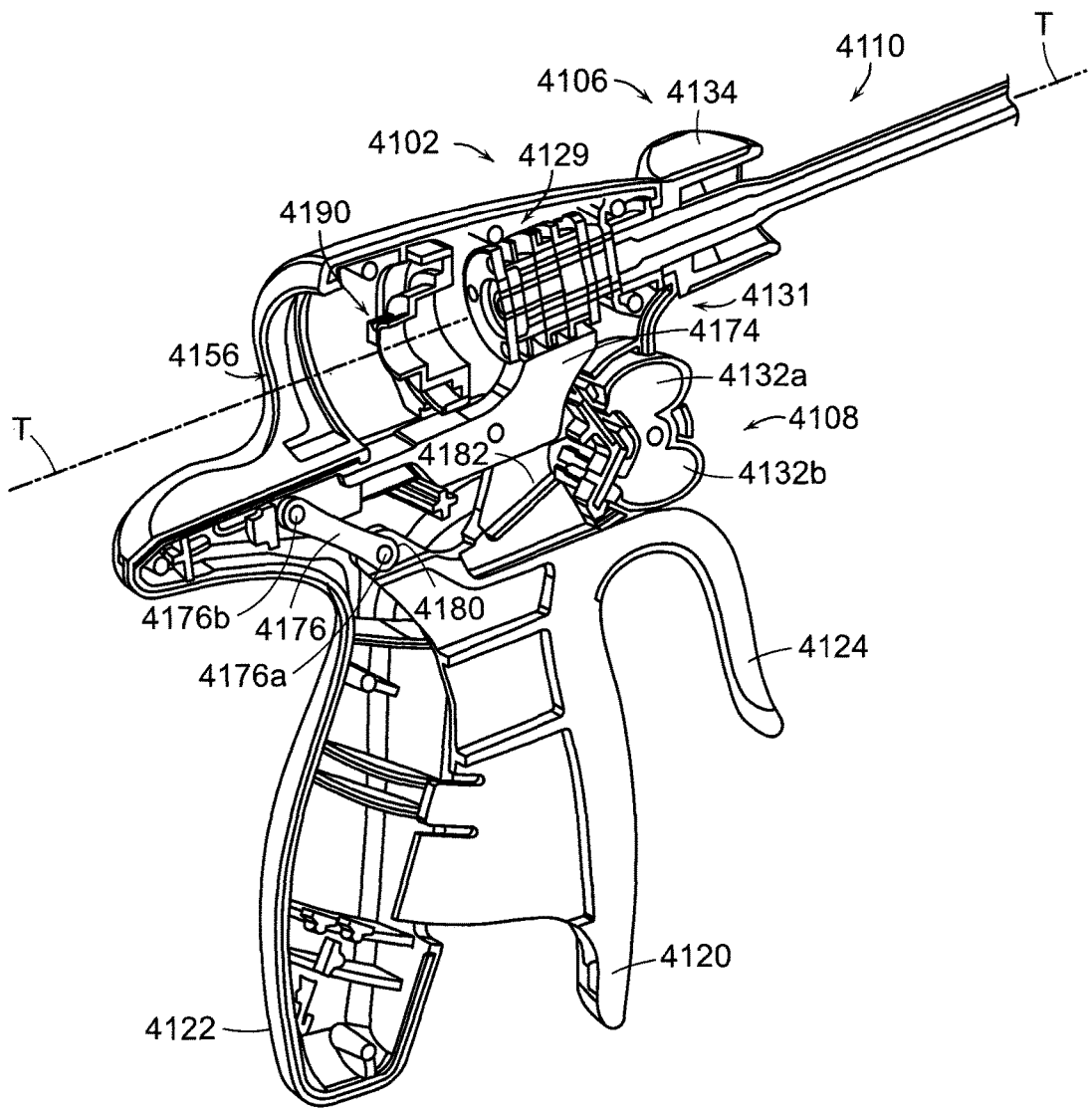
FIG. 95 illustrates a cross-section of a handle assembly of an ultrasonic surgical instrument comprising a rotatable electrical connection according to various forms described herein.
Figure 105:
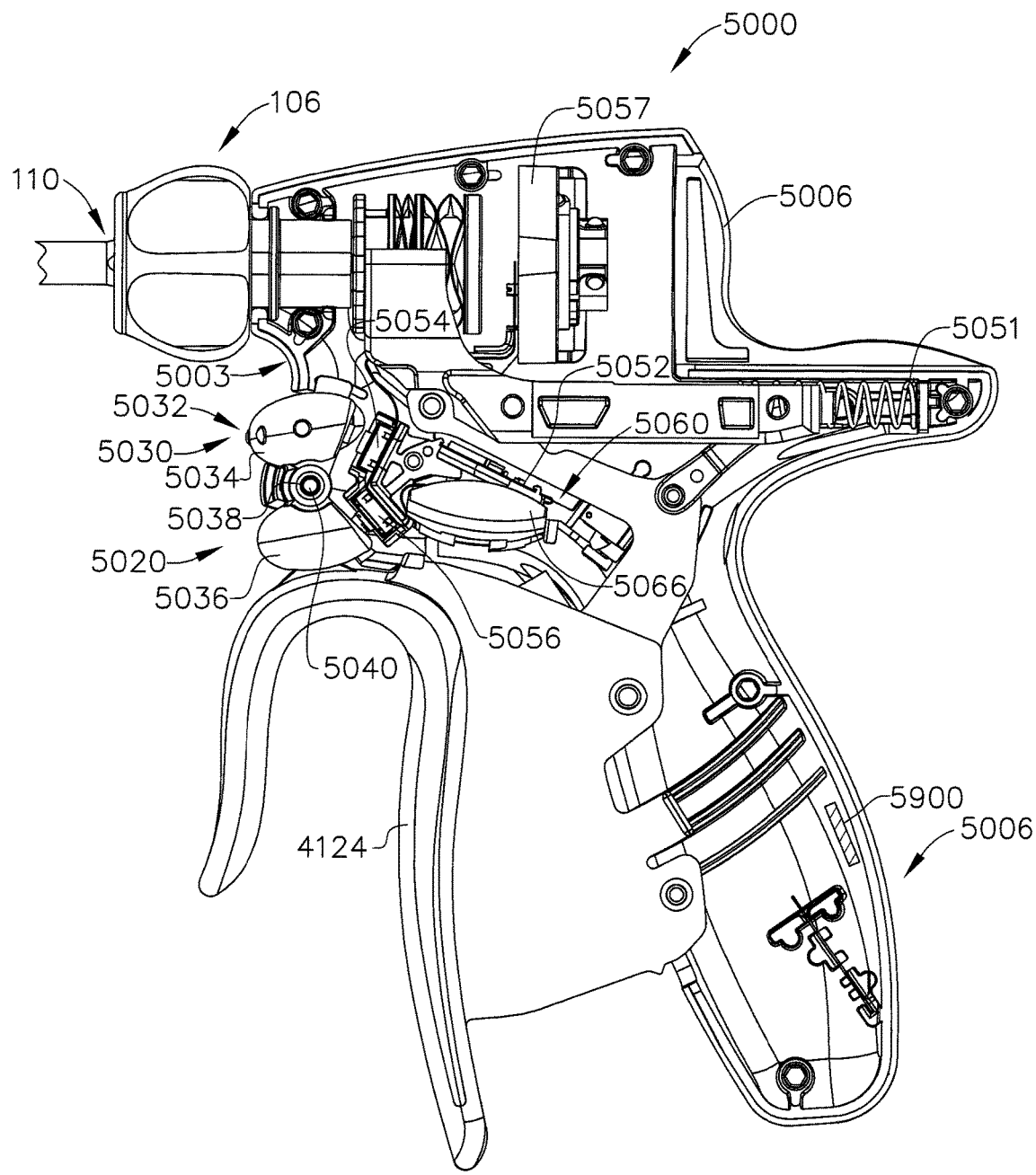
FIG. 105 is another left side view of the ultrasonic handle assembly of FIG. 104 with a left handle housing segment removed according to various forms described herein.

Similar variables include a trigger displacement, a trigger force, and a tube sub-assembly spring force. The trigger displacement is the distance that the trigger 34, 4120 (FIG. 93) is pivoted to close the clamp arm against the blade. The displacement of the trigger may correspond to degree to which a spring is displaced to close the clamp arm. For example, a spring 5051 is shown in FIG. 105. Referring now to FIGS. 93, 95 and 105, although the spring 5051 is not specifically illustrated in FIG. 95, it will be appreciated that the spring 5051 or a similar spring, may be coupled to the yoke 4174 of FIG. 95 and to the handle 4122 in a manner similar to that shown in FIG. 105. As described with respect to FIGS. 93 and 95, proximal motion of the trigger 4120 leads to distal motion of the yoke 4174 and reciprocating tubular actuating member 4138 to close the clamp arm 4150 and blade 4152. As the yoke 4174 moves distally, it may expand the spring 5051. Accordingly, the displacement of the trigger (e.g., trigger 4120) indicates the expansion of the spring (e.g., 5051) and, therefore, may serve as a proxy for clamp force. Trigger force (e.g., the force required to be provided to the trigger) may also be used as an input variable. Trigger displacement and force may be measured in any suitable manner. In some forms, a tube sub-assembly force may also be measured and used as an input variable. For example, referring again to FIG. 95, the tube sub-assembly force represents the force provided to the clamp arm 4150 and blade 4152 by the reciprocating actuating member 138. The various displacements and forces described herein may be measured in any suitable manner utilizing any suitable equipment including, for example, vision measurement systems, strain gauges, dial indicators, etc.

Other suitable clamping-related variables relate to a pressure profile. The pressure profile describes a distribution of pressure along the blade and clamp arm when the clamp arm is closed. A clamping profile may be measured in any suitable manner. For example, a pressure sensor, such as a sensor available from TEKSCAN, may be placed between the blade and the clamp arm. The clamp arm may then be closed (e.g., utilizing trigger 34 and/or trigger 4120 described herein) and the resulting force (and/or force distribution) is measured. In some forms, clamping forces may be taken over less than the entire length of the clamp arm. For example, clamping force at a particular position on the clamp arm or blade (e.g., at a proximal portion of the clamp arm) may be utilized as an input variable to the neural network 3150 or other suitable model.

Various other clamping-related input variables comprise a clamp arm deflection, a clamp arm position or ride, a jaw angle at full open trigger, and pad height. Clamp arm deflection is a measure of the degree of deflection in the clamp arm when closed against the blade. A clamp arm position or ride, also referred to as a jaw angle at full open trigger, describes a distance or angle between the clamp arm and the blade. For example, the jaw angle at full open trigger may be measured utilizing a vision system, an optical comparator, a protractor, etc. A pad height may describe a thickness of the clamp arm pad. These values may be measured in any suitable manner. For example, a vision system may be utilized to capture images of the blade and derive clamp arm deflections, etc. Also, various mechanical or optical range finding techniques may be used to measure specific dimensions. Additional clamping-related variables may describe properties of the pad (e.g., clamp pad 58). Examples of such parameters may include, a pad lot number, dimensions of the pad, a material distribution of the pad, a material hardness of the pad, thermal properties of the pad, as well as average values for these or similar values over a production lot.

In some forms, system-specific variables are assigned values based on measurements made during test procedures. For example, some input variables are determined during a system burn-in. One form of a burn-in is described herein above, with respect to FIGS. 26-28. A burn-in may be performed under known (and repeatable) conditions such as, for example, with the instrument in air, fully clamped, and dry (e.g., nothing between the clamp arm and blade). In some forms, a frequency slope during burn-in may serve as an input variable along with similar values such as, for example, power, energy, voltage, a rate of power change (dPower/dt); a rate of energy change (dEnergy/dt); a rate of change in voltage (dV/dt); a rate of change in current (dI/dt); a rate of change in frequency (df/dt); a rate of change in impedance (dZ/dt), peak impedance, etc. In some forms, when the burn-in is performed in air (e.g., with the blade against the pad), the variables described above may remain relatively constant throughout the burn-in. If the variables change, however, the frequency slope or other variable may be taken at a predetermined time after actuation, averaged or otherwise mathematically combined over all or portion of the burn-in cycle, etc.

In some forms, a frequency slope or other value is taken under burn-in conditions with the generator power set across different power levels. For example, a frequency slope or other measurement may be taken with the generator set at a first power and a second frequency slope or other measurement may be taken with the generator set at a second power level. In some forms, the burn-in may be performed with a tissue (e.g., porcine tissue) or a tissue surrogate (sponge material, etc.) positioned between the clamp arm and the blade. In some forms, the frequency slope and related variables may change as the tissue surrogate is transected. For example, the frequency slope may be taken at various different points in the burn-in cycle, averaged over all or a portion of the burn-in cycle, etc. Another test-related variable is the number of burn-in cycles that are performed. For example, in some forms, multiple burn-in cycles may be performed, for example, if there is a problem with the instrument or with the test procedure at the first burn-in.

After performing a burn-in, various other characteristics of the surgical system may be measured (and used as input variables). For example, the burn-in may create an indentation on the clamp pad corresponding to the blade. Analysis of the indentation may yield a burn-in depth (e.g., the depth of the indentation). The depth may be measured with any suitable device. In some forms, the burn-in depth may be measured with a vision system, laser range finder and/or other mechanical or optical measurement tool. In some forms, the burn-in depth is taken at various points on the clamp pad to indicate a burn-in depth distribution (e.g., a contact profile). Also, in some forms, a point of clamp arm contact may also be derived from the indentation. For example, the deepest portion of the indentation may correspond to the point of first contact.

Still other system-specific input variables are measured in a free state. A free state may be recreated with the clamp not in contact with the blade, and the blade running in air. Variables measured in a free state may include power consumption, device impedance, frequency slopes across different power levels, blade impedance at different power levels, current, voltage and impedance of the hand piece, etc. In various forms, system and environment-related variables may be measured during a pre-run. For example, various surgical systems are configured to require a pre-run test prior to operation on tissue. This may serve, for example, to ensure that the surgical system has been properly assembled. During the pre-run test, however, various system-specific variable values may be captured including, for example, voltage, current, impedance, resonant frequency and permutations thereof, for example, as described herein.

Additional system-specific variables relate to the temperature response of the blade and/or clamp arm. For example, a clamp arm temperature response describes the way that a particular clamp arm heats when exposed to a heat influx. The temperature of a clamp arm may be measured, for example, with an infrared thermometer. A clamp arm temperature response may be expressed as a number of degrees of heating in temperature per watt of heat influx. Similarly, a clamp arm temperature cooling curve may be a measure of how a given blade cools in room temperature air per unit time, for example, expressed in degrees per unit time. Similar input variables may be based on the blade including, for example, a blade temperature response and a blade cooling curve. Another example temperature response variable comprises a blade impedance versus temperature. This may be a measure of an acoustic impedance of the blade (e.g., as expressed by an electrical impedance of the transducer) as a function of temperature. Since a change in blade temperature may cause a change in frequency, the components securing the blade and waveguide within the shaft may not be necessary be at exact nodal points (e.g., positions on the waveguide with zero transverse displacement). Accordingly, when the components are not at the exact nodal points, they may cause acoustic impedance in the system when in air. Measuring how this changes and resulting changes in frequency may make it possible to model not only blade temperature, but also how far back on the blade (e.g., toward the handle) the blade temperature has changed. The respective temperature responses and/or cooling curves may be used as inputs to the neural network 3150 in any suitable manner. For example, the slope of the respective curves, a knee value where the slope changes, or any other suitable value may be selected.

Other example, system-specific variables comprise the age of the production line on which a system was produced and a transverse frequency measured within the blade, for example, at a burn-in. For example, production machinery may change over its lifetime, causing blades and other components produced at different point in the production machinery lifecycle to behave differently. Transverse frequencies describe vibrations in the blade that are in a direction orthogonal to that of the shaft and may be measured, for example, utilizing a vector signal analyzer or spectrum analyzer, such as the N9030A PXA Signal Analyzer available from AGILENT TECHNOLOGIES. Transverse frequencies may be measured in any suitable conditions including, for example, in a predetermined condition set such as a burn-in or free state.

Various input variables for the neural network 3150 may be based on the hand piece or transducer used by the surgical system to treat tissue. Examples of such variables may include an impedance of the transducer, as described above, a resonant frequency of the hand piece, a current set point of the hand piece, etc. The resonant frequency of a hand piece describes the resonant frequency of the hand piece independent of the waveguide or blade. For example, the resonant frequency of the hand piece may be measured at the time of manufacture. The current set point for a hand piece describes a level of current that is to be provided to a particular hand piece to provide a predetermined displacement. For example, different hand pieces may have different current set points based on different manufacturing tolerances. The current set point, resonant frequency, and other variable values describing a hand piece may be stored, for example, at an electrically erasable programmable read only memory (EEPROM) or other storage device associated with the hand piece. For example, the generator may interrogate the hand piece to retrieve hand piece-specific variables. In some forms, utilizing hand piece-specific variables may provide additional clarity to various other system-specific variables measured during manufacturing and/or testing. For example, when the system is utilized by a clinician, a different and often newer hand piece may be utilized. Hand piece specific variables may correct for this.

It will be appreciated that the neural network 3150 may utilize any of the input variables described herein above. In some forms, the neural network 3150 may be evaluated utilizing matrix algebra. For example, four matrices maybe used. A 1×I input matrix (O_i) may include (e.g., scaled) values for the I input neurons. An I×J hidden neuron omega matrix (W_ij) comprises omega ($\omega$) values used to calculate values of hidden neurons 3154. A J×K output neuron omega matrix (W_jk) comprises omega ($\omega$) values used to calculate the values of output neuron or neurons 3156. A 1×J hidden neuron constant matrix (O_j) comprises constant $\theta$ values for the hidden neurons 3154. A 1×K output neuron constant matrix (O_k) comprises constant $\theta$ values for the output neuron(s) 3156. For any given cycle, the output of the neural network may be calculated by evaluating the matrices as indicated by Equations (13)-(16) below:

$$x\_j = O\_i * W\_ij + O\_j \qquad (13)$$

The result of Equation (13), x_j, may be the weighted sums of the input neuron values for each hidden neuron 3154. Matrix x_j may be processed element-by-element through an equation, such as Equation (14) below, resulting in a matrix of equal size, O_j.

$$O\_j = (1 + \exp(-x\_j))\char`\^(-1 * Z) \qquad (14)$$

The result of Equation (14), O_j may be the values for each of the hidden neurons 3154. In Equation (12), Z corresponds to an matrix of ones having a size K×J.

$$x\_k = O\_j * W\_jk + O\_k \quad (15)$$

The result of Equation (15), x_k, may be the weighted sums of the hidden neuron values for each output neuron 3156. Matrix x_k is processed element-by-element through an equation, e.g., Equation (16), resulting in a matrix of equal size, O_k.

$$O\_k = (1 + \exp(-x\_k))^{\wedge}(-1*Z1) \quad (16)$$

The result of Equation (16), O_k, may be the output of the neural network. In Equation (15), Z1 may be a matrix of ones having a size K×1.

Figure 87:
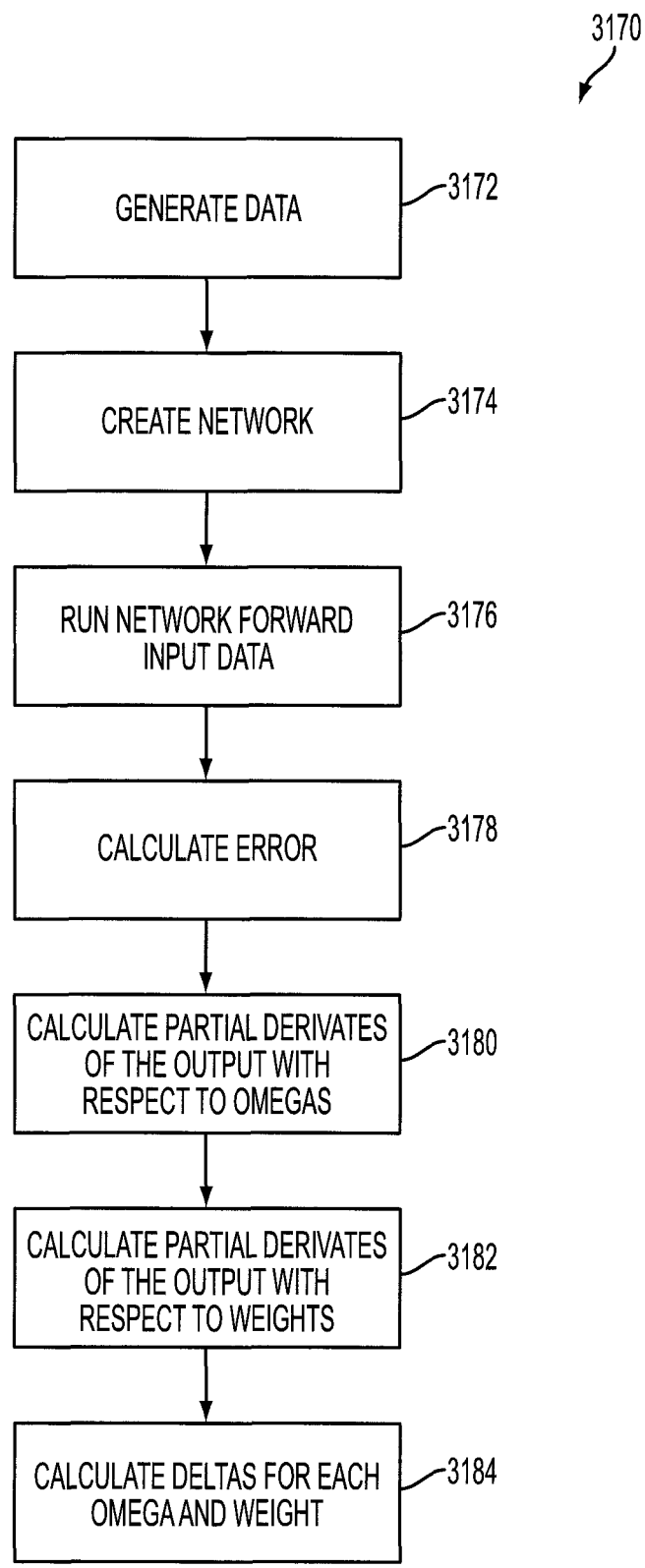
FIG. 87 is a logic flow diagram of one form of an algorithm for training a neural network, such as the neural network of FIG. 86, utilizing back-propagation.

The neural network may be trained in any suitable manner. For example, in some forms, the neural network may be trained utilizing back-propagation. During back-propagation training, the data flow of the neural network is reversed. For example, values for error versus actual output are used to modify individual weight and constant parameters. FIG. 87 is a logic flow diagram of one form of an algorithm for training a neural network, such as the neural network 3150, utilizing back-propagation. At 3172, relevant data sets may be generated. In some forms, separate data sets are generated for training and testing to ensure that actual pattern recognition is taking place instead of the network merely learning the data files being used for training Each data set may comprise, for example, all of the necessary inputs (for example, see TABLE 8). Each data set may also comprise actual values describing the state of the instrument and/or tissue corresponding to each set of input values, which represent the value modeled by the neural network. For example, in some forms, the actual values may comprise transection data, which may indicate whether the tissue has reached a threshold level of transection (e.g., 80% transection) upon any given set of input values. Neural networks trained in this manner may provide an output indicating tissue has or has not reached the threshold level of transection. It will be appreciated that any suitable value may be used including, for example, any other suitable level of transection, complete transection, tissue sealing, etc. Whether any given sample has reached 80% or any other suitable threshold transection state may be determined, in some forms, based on the amount tissue along the length of the cut that is transected. For example, transection may not occur all at once and, instead, may occur from front-to-back, back-to-from or middle out. Whether any given tissue sample is, transected to the threshold value may be determined according to any suitable method. For example, in some forms, a video camera may record a cut and a user may visually determine whether a transection is complete to the threshold value. Also, in some embodiments, an optical (e.g., laser) positioning sensor may be utilized to measure a position of the clamp arm relative to the blade. The inclination of the clamp arm relative to the blade may indicate the degree of transection.

At 3174, the neural network may be created. For example, the values for the weights and constants of the various neurons 3154, 3156 maybe randomly initialized (e.g., utilizing the MATLAB "rand" function, which generates a uniform distribution). In some forms, a value range of −2.5 to 2.5 may be utilized as these values tend to result in outputs in the range of 0-1 when processed by a sigmoid activation function. At 3176, the network 3150 may be run forward on the input data to generate a predicted output (or outputs if there are multiple output nodes). At 3178, an error may be calculated. The error is a difference between the predicted output from 3176 and the actual value of the tissue or instrument property, as described herein. In various forms, the output or outputs may be denoted as binary numbers where one (1) corresponds to the existence or truth of the condition and zero (0) corresponds to the non-existence or falsity of the condition. For example, when the condition is 80% transection, the output should be 1 when the tissue is 80% transected and 0 when the tissue is not (yet) 80% transected. In some forms, the condition may be considered true when the output of the neural network 3150 exceeds a threshold value (e.g., 0.85).

At 3180, the weights for each node are evaluated. For example, for each weight a partial derivative is found of the output or error (E) with respect to the weight (omega ($\omega$)). This may be represented as $\delta E / \delta \, \omega_{ij}$ for connections between the input layer 3152 and the hidden layer 3154 and as $\delta E / \delta \, \omega_{jk}$ for connections between the hidden layer 3154 and the output layer 3156. At 3182, the constants for each node are evaluated. For example, for each constant, a partial derivative is found of the output or error (E) with respect to the constant $\theta$. This may be represented as $\delta E / \delta \, \theta_i$ for connections between the input layer 3152 and the hidden layer 3154 and to $\delta E / \delta \, \theta_j$ for connections between the hidden layer 3154 and output layer 3156. At 3184, deltas may be calculated for each weight and constant. The deltas may found by multiplying each partial derivative by a gradient constant, $\eta$. In some forms, a value of 0.1 may be used for $\eta$. The deltas may then be added to the original values of each weight and constant. Actions 3176, 3178, 3180, 3182, and 3184 may be repeated for subsequent cycles of the input data. In some form, the network 3150, once trained, may be tested. For example, the network 3150 may be tested, as described herein, on a testing data set distinct from the training data set. In various forms, a neural network or other multi-variable model may be pre-trained. Resulting model parameters (e.g., network configuration, values for weights and constants, etc.) may be determined and stored at a generator and/or instrument. The values may be utilized to execute the model during use.

Figure 88:
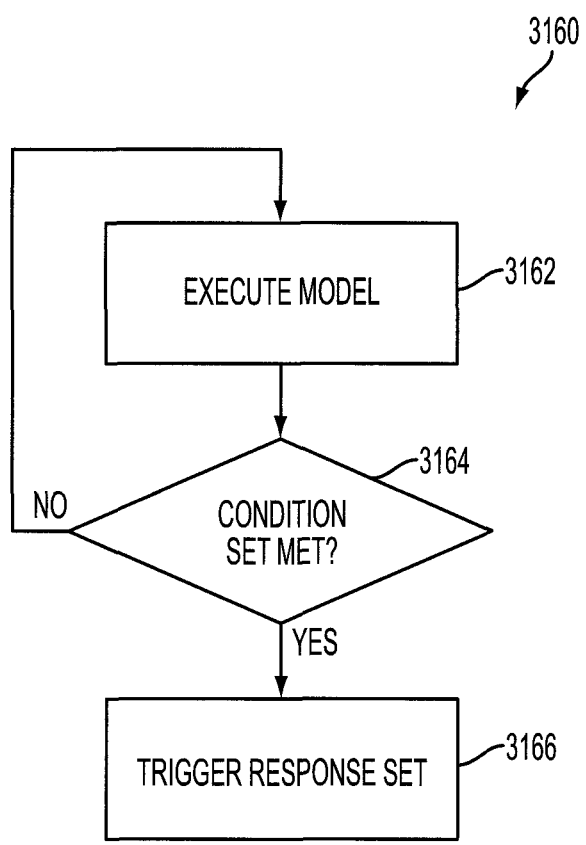
FIG. 88 is a logic flow diagram of one form of an algorithm for detecting a condition set for an ultrasonic instrument utilizing a multi-variable model.

FIG. 88 is a logic flow diagram of one form of an algorithm 3160 for detecting a condition set for an ultrasonic instrument utilizing a multi-variable model, such as the neural network 3150 described herein. As with the other instrument control algorithms described herein, the algorithm 3160 is described as being executed by a generator, such as generators 30, 50, 1002 described herein, but in some forms may be executed by an instrument itself. Also, although a neural network is described herein, it will be appreciated that the algorithm 3160 may be executed utilizing any suitable type of model including, for example, genetic algorithm models, classification tree algorithm models, recursive Bayesian models, etc. At 3162, the generator may execute the multi-variable model. Executing the multi-variable model may comprise providing input values to the model, processing the input values, and generating an output. For example, a process for executing an example neural network is described herein above in conjunction with Equations (11)-(14). At 3164, the generator may determine whether the modeled condition set is met. In the example above, this may involve determining whether 80% transection has been achieved (e.g., whether the value of the output node 3156 has exceeded a threshold value. If not, the model may continue to execute at 3162. If so, the trigger response associated with the condition set may be triggered at 3166. The response set may include any suitable actions including, for example, providing feedback indicating the truth of the condition set, modifying a drive signal for the instrument, etc.

Although a neural networks, such as the network 3150 are described herein, it will be appreciated that any other suitable type of multi-variable model may be utilized in addition to or instead of a neural network including, for example, genetic algorithm models, classification tree algorithm models, recursive Bayesian models, etc. For example, a recursive Bayesian model models the probability of an output event occurring (e.g., a threshold transection state), where the probably is equal to zero at the beginning of the transection (e.g., t=0) and continually increases with each time step. The amount of increase in the probability is based on whether certain criteria are met. The criteria may represent threshold values of different input variables. For example, if "frequency slope<threshold 1" is true, it may increase the probability by a certain amount for each time step at which it is true. If "frequency delta<threshold 2" is true, it could increase the probability by an additional amount, where the sum of increases due to different criteria at each time step indicates the increase in probability at the time. When the probability reaches a threshold value (e.g., 0.85), the recursive Bayesian model may indicate that the modeled condition is true.

Another type of suitable multi-variable model is a classification or decision tree. A classification or decision tree comprises a plurality of binary decisions arranged according to a hierarchy tree structure For example, in some embodiments, the generator may first determine if a frequency slope characterizing a drive signal provided to a surgical instrument is less than a threshold If not, then the change in frequency may be measured against a second threshold. If the change in frequency is less than the threshold, then the generator may provide feedback indicating the end of the transection. If the change in frequency is greater than the threshold, then the generator may not provide feedback. Referring back to the initial decision, if the frequency slop is less than the first threshold, then the generator may determine if a required time before trigger is greater than a threshold. The required time before trigger may refer to a threshold amount of time after the frequency slope is met before the generator provides feedback indicating the end of the transection. For example, this may correct for bounciness in the frequency slope signal. If the required time before trigger has passed, then the generator provides feedback indicating the end of the transection. If not, then no feedback is provided.

Figure 89:
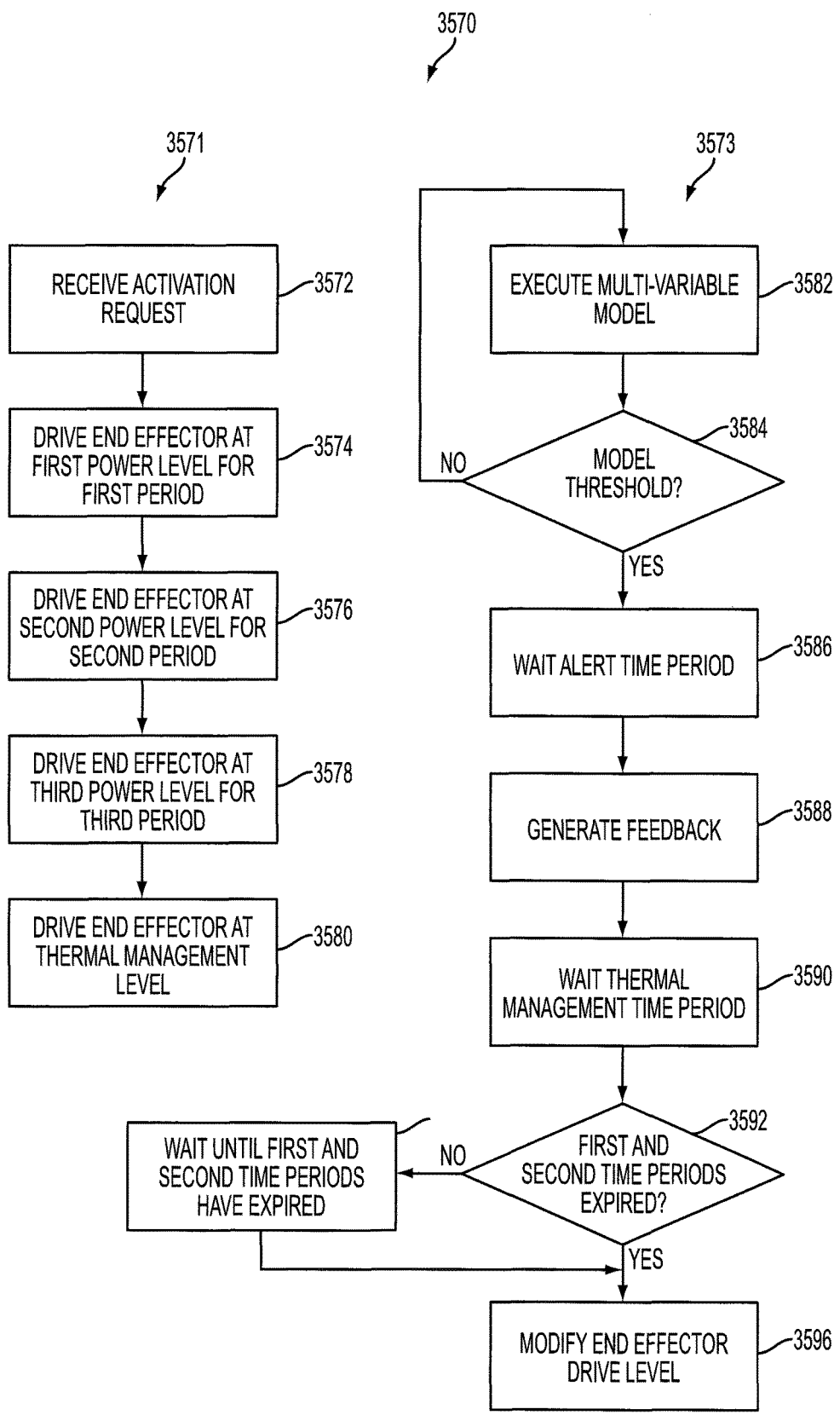
FIG. 89 is a logic flow diagram showing one form of an algorithm utilizing a multi-variable model such as, for example, the neural network described herein.

FIG. 89 is a logic flow diagram showing one form of an algorithm 3570 utilizing a multi-variable model such as, for example, the neural network 3150 or other model described herein. The algorithm 3570 is described as being executed by a generator, such as generators 30, 50, 1002 described herein, but in some forms may be executed by an instrument itself. The algorithm 3570 comprises two action threads 3571, 3573 which may execute concurrently. For example, a control thread 3571 may comprise actions for controlling the ultrasonic surgical instrument. In this way, the control thread 3571 may be similar to the algorithms 3021, 3021', 3021", 3100, 3120, described herein. A condition thread 3573 may be similar to the condition monitoring algorithms described herein with respect to FIGS. 15A-15C, FIGS. 20-22, FIGS. 57-60, etc.

Referring first to thread 3571, that control thread may be similar to the algorithm 3021" of FIG. 77. For example, at 3572, the generator may receive an activation request, similar to the activation request at 3020 described herein above. At 3574, the generator may drive the end effector at a first power level for a first period, for example, by providing a first drive signal at the first power level. At 3576, after the expiration of the first period, the generator may drive the end effector at a second power level for a second period, wherein the second power level is less than the first power level. This may be accomplished, for example, by providing a second drive signal at the second power level. At the expiration of the second period, at 3578, the generator may drive the end effector at a third level for a third period at a third power, for example, by providing a third drive signal at the third power level. The third power level may be greater than the second power level and less than the first drive level or, in some forms, may be equal to the first power level. At 3580, the generator may drive the end effector at a thermal management level, either at the expiration of the third period or as indicated by the condition thread 3573 as described herein. According to the thermal management level or stage, the generator may reduce the power provided to the end effector so as to slow down the rate of excess heat production. For example, in one form entering the thermal management stage may entail reducing the power to a level that is 75% of the first power level. Also, in some forms, the thermal management level or stage may entail ramping and/or stepping down the power provided to the end effector.

Referring now to the condition thread 3573, the generator may, at 3582, execute a multivariable model, such as the neural network 3150 described herein or any other multi-variable model. At 3584, the generator may determine whether an output of the model meets a predetermined threshold. The threshold may indicate the truth or presence of one or more of the conditions of the modeled condition set. If not, then the generator may continue to execute the model at 3582. If yes, the generator may wait an alert time period at 3586. At an expiration of the alert time period, the generator may generate feedback (e.g., audible, visual or tactile feedback) at 3588. The feedback may indicate the truth or presence of the detected condition. At 3590, the generator may wait a thermal management time period. While waiting, the feedback initiated at 3588 may be maintained. At 3592, the generator may determine whether both the first and second time periods (see thread 3571) have expired. If so, the generator may modify the power provided to the end effector at 3596. If not, then, in some forms, the generator may wait until the first and second time periods expire, at 3594, before modifying the power provided to the end effector at 3596. For example, the generator may enter the thermal management level or stage.

Figure 90:
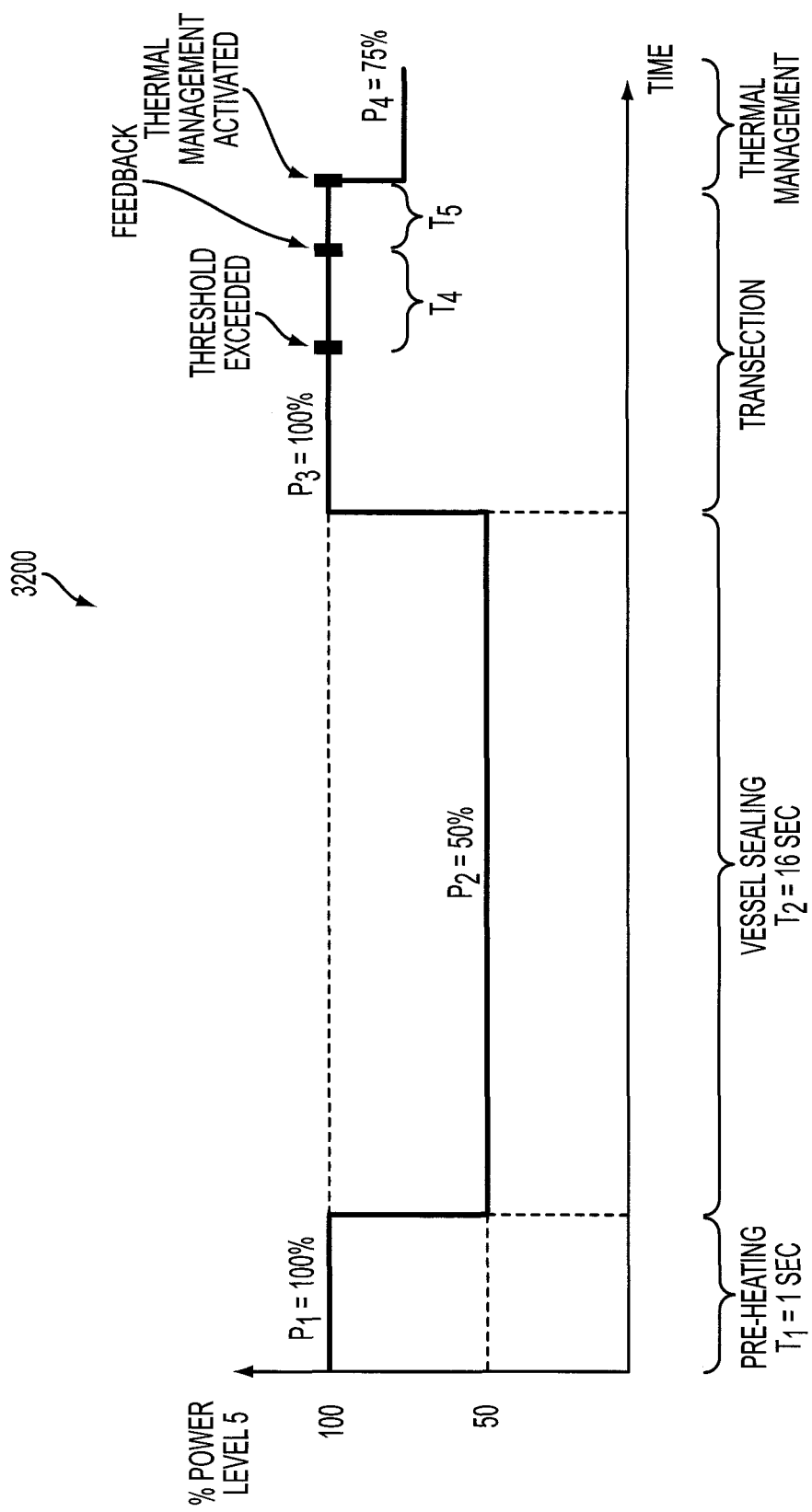
FIG. 90 is a chart illustrating a drive signal pattern of one implementation of the algorithm of FIG. 89.

FIG. 90 is a chart illustrating a drive signal pattern 3200 of one implementation of the algorithm 3170. In the example of FIG. 90, the first period is a time period of one second, the second period is a time period of sixteen seconds. The first power level is 100% of the power available from the generator (e.g., 100% of the power available at level 5 provided by the GEN 11 generator available from Ethicon Endo-Surgery, Inc. of Cincinnati, Ohio). The second power level may be 50% of the power available from the generator. The third power level may be 100% of the power available from the generator.

As illustrated, upon activation the end effector may be driven at the first power level, as indicated by 3572 (FIG. 89). The end effector is then driven at the second power level for the second period, and driven at the third power level at the expiration of the second period. The multi-variable model may return a value indicating the truth of at least one condition of the condition set at the point labeled "threshold exceeded" (see 3584 of FIG. 89). T4, as shown in FIG. 90, may correspond to the alert time period. At the expiration of the alert time period, the generator may provide the feedback descried above with respect to 3588 of FIG. 89. T5, as shown, may correspond to the thermal management time period. At its expiration, because the first and second time period is expired (3194), the generator may modify the end effector drive level (3196) as shown by the point labeled "thermal management activated." For example, the generator may provide a drive signal at a power level that is lower than or equal to the first power level and greater than the second power level (e.g., 75% of the power available from the generator).

Figure 91:
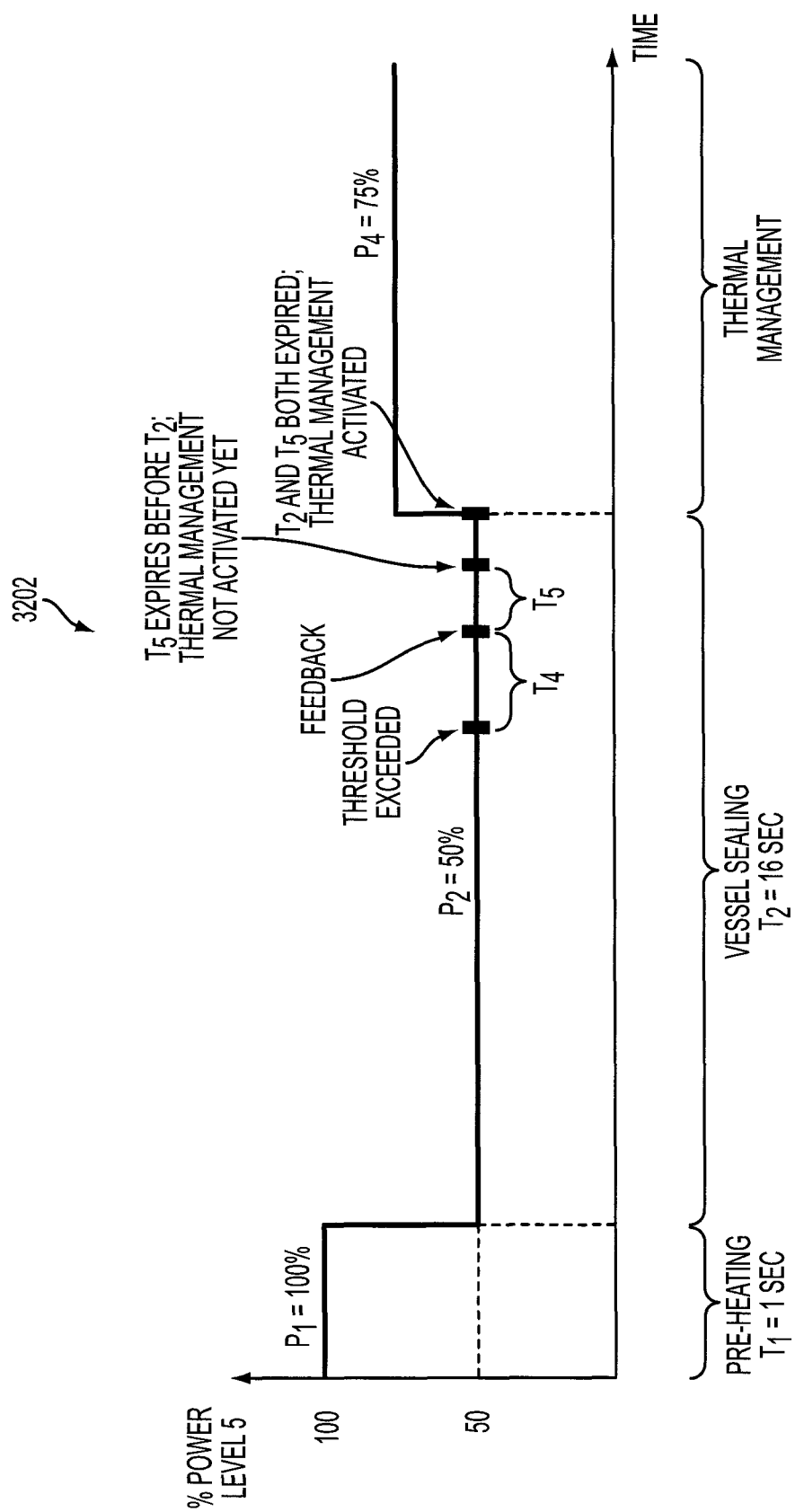
FIG. 91 is a chart illustrating a drive signal pattern of another implementation of the algorithm of FIG. 89.

FIG. 91 is a chart illustrating a drive signal pattern 3202 of another implementation of the algorithm 3570. In the example of FIG. 91, the time periods and power levels are the same as illustrated with respect to FIG. 90. Upon activation, the end effector may be driven at the first power, as indicated by 3572. At the expiration of the first period, the end effector is driven at the second power level for the second period. In FIG. 91, however, the multi-variable model returns a value indicate the truth of at least one condition of the condition set at the point labeled threshold exceeded before the expiration of the second time period, at the point labeled "threshold exceeded." As indicated at FIG. 89, the generator may wait the alert time period and then initiate the feedback of 3588 at the point labeled "feedback." At the expiration of the thermal management time period (3190), the second period is still not expired. Accordingly, the generator waits until the end of the second period (3194) and then modifies the end effector drive level, for example, by implementing the example thermal management level of 75% of the power available from the generator.

Figure 92:
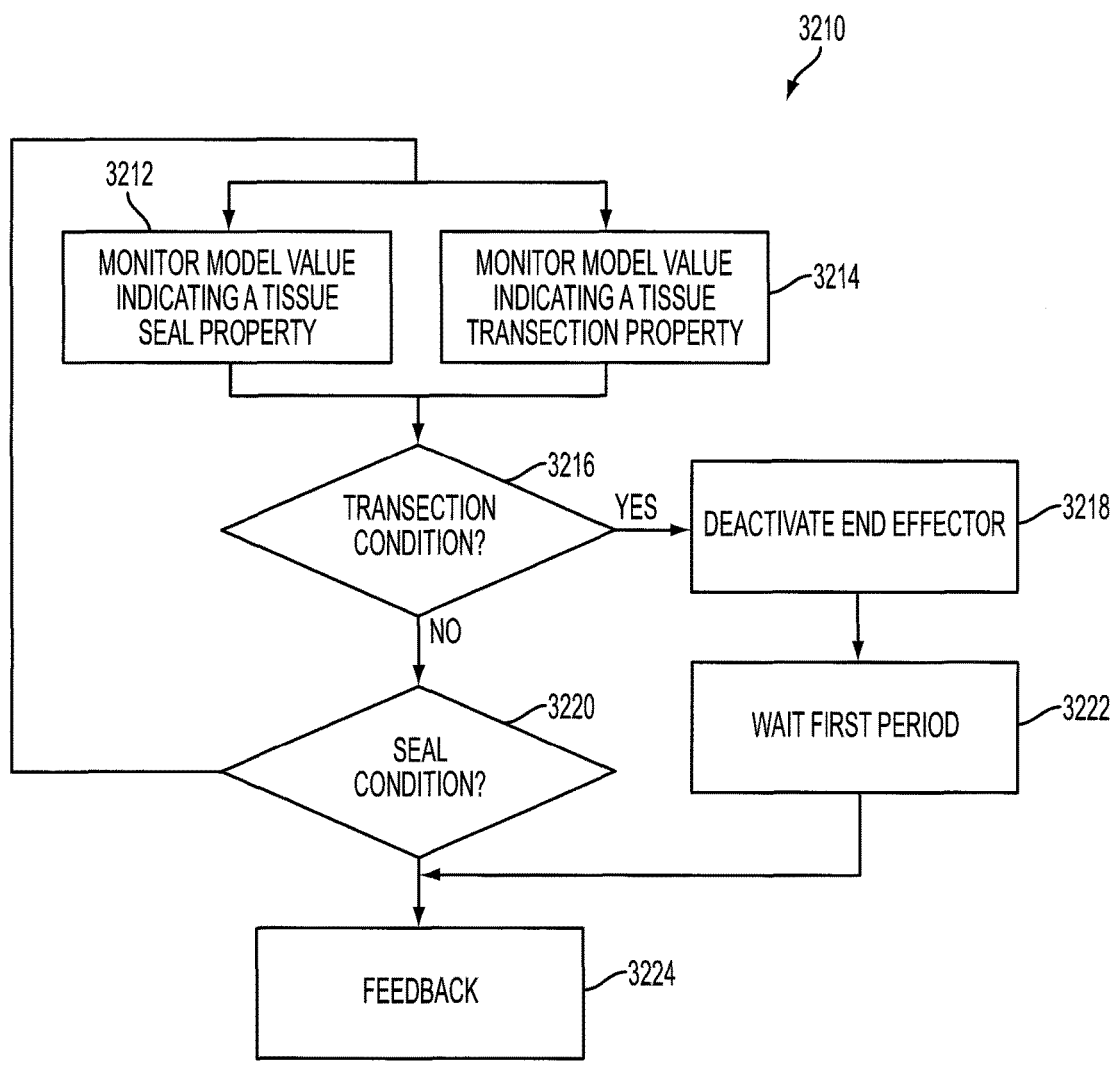
FIG. 92 is a logic flow diagram showing one form of an algorithm for utilizing a multi-variable model to monitor a condition set comprising multiple conditions.

FIG. 92 is a logic flow diagram showing one form of an algorithm 3210 for utilizing a multi-variable model to monitor a condition set comprising multiple conditions. The algorithm 3210 is described as being executed by a generator, such as one of the generators 30, 50, 1002 described herein, but in some forms may be executed by an instrument itself. In the example form shown in FIG. 92, the condition set monitored by the multi-variable model comprises two conditions, a condition indicating the presence or absence of tissue seal and a condition indicating the presence or absence of tissue transection. The tissue transection may be complete tissue transection and/or partial transection (e.g., 80% transection, as described herein). At 3212 and 3214, the generator may monitor model values indicating the truth or falsity of the tissue seal and tissue transection conditions. In some forms, both the tissue seal and tissue transection conditions may be monitored by the same model. For example, the neural network 3150 described herein may be generated and trained with two output nodes 3156. Also, in some forms, the generator implements separate models, with distinct models for each condition.

If the transection condition is met at 3216, it may indicate that transection has occurred, or is set to occur, before sealing. As this may be an undesirable occurrence, the generator may deactivate the surgical instrument at 3528 to prevent transection from occurring before sealing. At 3222, the generator may wait a first period. Waiting the first period, for example, may allow the tissue to complete sealing either before transection occurs and/or before the clinician is provided with an indication to open the end effector to release the tissue. The first period may be a predetermined time period or, in various forms, may be based on the seal condition output of the model. At the expiration of the first period, the generator may provide feedback indicating the end of the seal and transect operation at 3224. Alternatively, after the expiration of the first period, the generator may apply an amount of energy for a second period and then subsequently deactivate the instrument and provide feedback indicating the end of the seal and transect operation. If the transection condition is not met at 3216, it may indicate that transection is not set to occur before sealing. The generator may then determine at 3220 whether the seal condition is true. If not, the generator may return to the monitoring actions 3212, 3210. If the seal condition is set to occur, the generator may generate the feedback at 3224. In some forms, if the instrument is still activated at 3224, the generator may deactivate the instrument and/or deactivate the instrument after a delay period.

Various algorithms herein are described herein as being executed by a generator. It will be appreciated, however, that in certain example forms, all or a part of these algorithms may be performed by internal logic 2009 of a surgical instrument (FIG. 16A). Also, various algorithms described herein above utilize various thresholds and flags such as, for example, a threshold impedance, a time above impedance period, a baseline deviation threshold parameter frequency, a time above frequency delta period, a load monitoring flag, a maintain status flag, etc. Such thresholds, flags, etc., may be stored at any suitable location including, for example, a generator and/or at an EEPROM or other storage device included with the surgical instrument.

Multi-function capabilities of many ultrasonic surgical instruments challenge the ability of a user to comfortably access and operate the multiple functions and controls of the instrument. This includes, for example, the ability to comfortably actuate the jaws of a clamping mechanism and activate hand control buttons/switches, sometimes simultaneously. As such, various user interface controls may be desirable. One user interface design to control functions of the ultrasonic surgical instrument may include a rotation mechanism between two portions of the device requiring a rotatable electrical connection. Rotatable electrical connections may fail over time, requiring costly repairs or replacement of associated instrument components that may otherwise have valuable operation life remaining. Accordingly, there is a need to extend the operational life of various ultrasonic surgical instruments by providing alternate solutions to costly repairs and premature component replacements.

Ultrasonic surgical instruments, including both hollow core and solid core instruments, are used for the safe and effective treatment of many medical conditions. Ultrasonic surgical instruments, and particularly solid core ultrasonic surgical instruments, are advantageous because they may be used to cut and/or coagulate tissue using energy in the form of mechanical vibrations transmitted to a surgical end effector at ultrasonic frequencies. Ultrasonic vibrations, when transmitted to tissue at suitable energy levels and using a suitable end effector, may be used to cut, dissect, coagulate, elevate or separate tissue. Ultrasonic surgical instruments utilizing solid core technology are particularly advantageous because of the amount of ultrasonic energy that may be transmitted from the ultrasonic transducer, through an ultrasonic transmission waveguide, to the surgical end effector. Such instruments may be used for open procedures or minimally invasive procedures, such as endoscopic or laparoscopic procedures, where the end effector is passed through a trocar to reach the surgical site.

Activating or exciting the end effector (e.g., cutting blade, ball coagulator) of such instruments at ultrasonic frequencies induces longitudinal vibratory movement that generates localized heat within adjacent tissue, facilitating both cutting and coagulating. Because of the nature of ultrasonic surgical instruments, a particular ultrasonically actuated end effector may be designed to perform numerous functions, including, for example, cutting and coagulating.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are designed to resonate at the same frequency as the transducer. When an end effector is attached to a transducer the overall system frequency may be the same frequency as the transducer itself. The transducer and the end effector may be designed to resonate at two different frequencies and when joined or coupled may resonate at a third frequency. In some forms, the zero-to-peak amplitude of the longitudinal ultrasonic vibration at the tip, d, of the end effector behave as a simple sinusoid at the resonant frequency as given by:

$$d = A \sin(\omega t) \qquad (17)$$

where: $\omega$=the radian frequency which equals $2\pi$ times the cyclic frequency, f; and A=the zero-to-peak amplitude. The longitudinal excursion is described by a as the peak-to-peak (p-t-p) amplitude, which may be twice the amplitude of the sine wave or 2 A.

Various forms of ultrasonic surgical instruments described herein comprise a first structure and a second structure where the second structure is rotatable relative to the first structure. In some forms, electrical communication between the first structure and the second structure may be provided through a rotatable electrical connection. In one form, the first structure comprises an ultrasonic hand piece comprising an ultrasonic transducer, which in many designs, may be used to rotate a shaft extending distally from the hand piece. Rotation of the hand piece may include rotation relative to a second structure, such as a handle assembly or another component of the instrument in which electrical coupling is required. For example, in one form, the second structure may comprise a user interface. According to one form, the user interface may be engaged by the user to provide operation instructions or signals between the hand piece, power generator, or another component of the ultrasonic surgical system. In one form, instructions or signals provided at the user interface may be electrically coupled through the rotatable electrical connection to provide signals that may be used to control or provide information related to an operation associated with the ultrasonic surgical instrument. In one form, the user interface may comprise buttons, switches, knobs, or other various interfaces known in the art. In one form, the rotatable electrical connection may electrically couple an end effector that is rotatable relative to another component of the instrument, such as a hand piece or handle assembly, to provide electrical communication therebetween.

Figure 94:
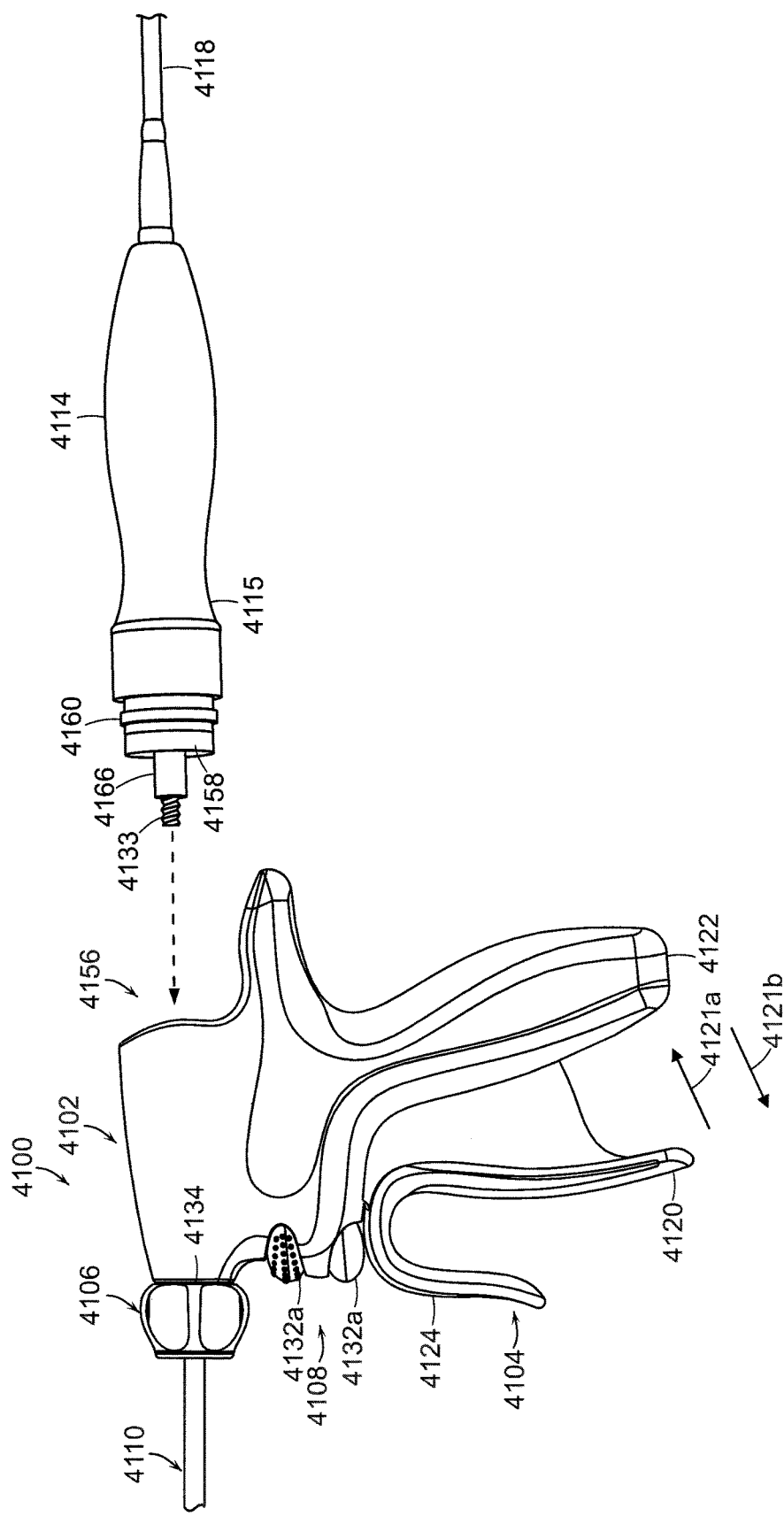
FIG. 94 is a side view of the ultrasonic surgical instrument configuration of FIG. 93 showing the handle assembly and hand piece prior to insertion of the hand piece into the handle assembly according to various forms described herein.

FIGS. 93-94 illustrate one form of an ultrasonic surgical instrument 4100. The ultrasonic surgical instrument 4100 may be employed in various surgical procedures including endoscopic or traditional open surgical procedures. In one form, the ultrasonic surgical instrument 4100 comprises a handle assembly 4102, an elongated endoscopic shaft assembly 4110, and an ultrasonic hand piece 4114 comprising an ultrasonic transducer assembly. The handle assembly 4102 comprises a trigger assembly 4104, a distal rotation assembly 4106, and a switch assembly 4108. The ultrasonic hand piece 4114 is electrically coupled to a generator 4116 via a cable 4118. The elongated endoscopic shaft assembly 4110 comprises an end effector assembly 4112, which comprises elements to dissect tissue or mutually grasp, cut, and coagulate vessels and/or tissue, and actuating elements to actuate the end effector assembly 4112. Although FIGS. 93-94 depict an end effector assembly 4112 for use in connection with endoscopic surgical procedures, the ultrasonic surgical instrument 4100 may be employed in more traditional open surgical procedures. For the purposes herein, the ultrasonic surgical instrument 4100 is described in terms of an endoscopic instrument; however, it is contemplated that an open version of the ultrasonic surgical instrument 4100 also may include the same or similar operating components and features as described herein. Additional embodiments of similar ultrasonic surgical instruments are disclosed in commonly-owned U.S. Patent Application Publication No. 2009/0105750, which is incorporated herein by reference in its entirety.

The ultrasonic transducer of the ultrasonic hand piece 4114 converts an electrical signal from a power source, such as the ultrasonic signal generator 4116 or battery (not shown), into mechanical energy that results in primarily a standing acoustic wave of longitudinal vibratory motion of the transducer and the blade 4152 portion of the end effector assembly 4112 at ultrasonic frequencies. As shown in FIG. 94, the handle assembly 4102 is adapted to receive the ultrasonic hand piece 4114 at the proximal end through a proximal opening 4156. In one form, in order for the ultrasonic hand piece to deliver energy to the end effector assembly 4112, which may include a clamp arm 4150 movably opposed to a blade 4152, components of the hand piece 4114 must be acoustically coupled to the blade 4152. In one form, for example, the ultrasonic hand piece 4114 comprises a longitudinally projecting attachment post comprising a waveguide coupling, which is illustrated as a threaded stud 4133 in FIG. 94, at a distal end of the hand piece 4114 for acoustically coupling the ultrasonic hand piece 4114 to the waveguide 4128 (see FIG. 95). The ultrasonic hand piece 4114 may mechanically engage the elongated endoscopic shaft assembly 4110 and portions of the end effector assembly 4112. For example, referring to FIG. 94, in one form, the ultrasonic transmission waveguide 4128 comprises a longitudinally extending attachment post 4129 at a proximal end 4131 of the waveguide 4128 to couple to the surface 4166 of the ultrasonic hand piece 4114 by a threaded connection, such as the stud 4133. That is, the ultrasonic transmission waveguide 4128 and the ultrasonic hand piece 4114 may mechanically couple via a threaded connection therebetween to threadably engage and acoustically couple the ultrasonic transmission waveguide 4128 and the ultrasonic hand piece 4114. In one form, when the ultrasonic hand piece 4114 is inserted through the proximal opening 4156, the ultrasonic hand piece 4114 may be secured to the waveguide 4128 with a torque wrench. In other forms, the distal waveguide coupling may be snapped onto the proximal end of the ultrasonic transmission waveguide 4128. The ultrasonic hand piece 4114 also comprises a distal rim portion 4158 with a circumferential ridge 4160 configured to engage the handle 4102 through the proximal opening 4156. As described in more detail below, the distal rim portion 4158 may comprise one or more electrical contacts configured to electrically couple to the handle assembly 4102, for example, to receive electrical control operation instructions from the user via the handle assembly 4102.

In one form, the handle assembly 4102 comprises a trigger 4120 and a fixed handle 4122. The fixed handle 4122 may be integrally associated with the handle assembly 4102 and the trigger 4120 may be movable relative to the fixed handle 4122. The trigger 4120 is movable in direction 4121*a* toward the fixed handle 4122 when the user applies a squeezing force against the trigger 4120. The trigger 4120 may be biased in the direction 4121*b* such that the trigger 4120 is caused to move in direction 4121*b* when the user releases the squeezing force against the trigger 4120. The example trigger 4120 also includes a trigger hook 4124 extension to provide an additional interface portion from which the trigger 4120 may be operated.

FIG. 95 shows a cross-section of the handle assembly according to various forms. The handle assembly 4102 comprises a trigger 4120 movable in directions 4121*a* and 4121*b* with respect to a fixed trigger 4122. The trigger 4120 is coupled to a linkage mechanism to translate the rotational motion of the trigger 4120 in directions 4121*a* and 4121*b* to the linear motion of a reciprocating tubular actuating member 4138 in along the longitudinal axis "T". The trigger 4120 comprises a first set of flanges 4182 with openings formed therein to receive a first yoke pin 4176*a*. The first yoke pin 4176*a* is also located through a set of openings formed at the distal end of the yoke 4174. The trigger 4120 also comprises a second set of flanges 4180 to receive a first end 4176*a* of a link 4176. As the trigger 4120 is pivotally rotated, the yoke 4174 translates horizontally along longitudinal axis "T". Thus, referring to FIG. 93, when the trigger 4120 is squeezed in direction 4121*a* the reciprocating tubular actuating member 4138 moves in direction 4146*a* to close the jaw elements comprising the clamp arm 4150 and blade 4152 of the end effector assembly 4112. When released, the trigger 4120 may be biased to move in direction 4121B when the squeezing force is released. Accordingly, the yoke 4174 and the reciprocating tubular actuating member 4138 move in direction 4146*b* to open the jaws of the end effector assembly 4112. In some embodiments a spring 5051 (FIG. 105) is coupled between the yoke 4174 and the handle assembly 4102. The spring 5051 biases the trigger 4120 to the open position shown in FIG. 95.

Further to the above, the distal rotation assembly 4106 may be located at a distal end of the handle assembly 4102 when the ultrasonic hand piece 4114 is received for and mechanically and acoustically coupled to the handle assembly 4102. In one form, the distal rotation assembly 4106 comprises a ring or collar shaped knob 4134. The distal rotation knob 4134 is configured to mechanically or frictionally engaged with the ultrasonic hand piece 4114. As previously discussed, the ultrasonic hand piece 4114 is mechanically engaged to the elongated endoscopic shaft assembly 4110. Thus, rotating the rotation knob 4134 rotates the ultrasonic hand piece 4114 and the elongated endoscopic shaft assembly 4110 in the same direction 4170.

In various forms, the ultrasonic surgical instrument 4100 may comprise on or more user interfaces to provide electrical control instructions to control the operation of the instrument 4100. For example, in one form, a user may employ a footswitch 4111 to activate power delivery to the ultrasonic hand piece 4114. In some forms, the ultrasonic surgical instrument 4100 comprises one or more electrical power setting switches to activate the ultrasonic hand piece 4114 and/or to set one or more power settings for the ultrasonic hand piece 4114. FIGS. 93-95 illustrate handle assemblies 4102 comprising a switch assembly 4108. The switch assembly 4108 may comprise a user interface associated with a toggle or rocker switch 4132*a*, 4132*b*, for example. In one form, the switch assembly 4108 may be at least partially associated with the handle assembly 4102 and may be implemented as a MIN/MAX rocker-style or "toggle" switch. In one position, the MIN/MAX rocker-style switch (or "toggle" style) buttons 4132*a*, 4132*b* may create an easily accessible location for power activation. For example, the user also may operate a first projecting knob 4132*a* to set the power to a first level (e.g., MAX) and may operate the second projecting knob 4132*b* to set the power to a second level (e.g., MIN). The toggle switch 4132*a*, 4132*b* may be coupled to the generator 4116 to control the operation of the instrument, such as activation or power delivery to the ultrasonic hand piece 4114. Accordingly, in various forms, the toggle switch 4132*a*, 4132*b* and the generator 4116 may be electrically coupled through a rotatable connection. For example, in certain forms, the surgical instrument 4100 may comprise a rotatable electrical connection allowing the electrical power control operations provided at the handle assembly 4102 to electrically communicate with the generator 4116 via the ultrasonic hand piece 4114. The toggle switch 4132*a*, 4132*b* may comprise a control selector and/or an activation switch electrically coupled to a circuit board, e.g., a printed circuit board, flex circuit, rigid-flex circuit, or other suitable configuration. In one form, the switch assembly 4108 comprises a toggle switch having a first electrical contact portion 4132*a* and a second electrical contact portion 4132*b* configured for modulating the power setting of the ultrasonic hand piece 4114 between a minimum power level (e.g., MIN) and maximum power level (e.g., MAX). The toggle switch may be electrically coupled to a handle portion of a circuit, which may include, for example, a flex circuit configured to electrically couple to the generator 4116 via a rotatable connection through the hand piece 4114 to control the activation of the ultrasonic hand piece 4114. In various forms, the switch assembly 4108 comprises one or more electrical power setting switches to activate the ultrasonic hand piece 4114 to set one or more power settings for the ultrasonic hand piece 4114.

As those having skill in the art will appreciate, a generator 4116 may provide activation power to the ultrasonic hand piece 4114 via cable 4118, for example. As described above, the handle assembly 4102 may be conveniently used to provide electrical power control instructions to the generator 4116 to control power delivery to the ultrasonic hand piece 4114, for example, through one or more switches associated with the switch assembly 4108. For example, in operation, the one or more switches 4108 may be configured for electrical communication with the generator 4116 to control electrical power delivery and/or electrical power operation features of the ultrasonic surgical instrument 4100. It is to be appreciated that in at least one form, the generator 4116 may be internal to the hand piece 4114.

As introduced above, the ultrasonic hand piece 4114 may be configured to rotate relative to the handle assembly 4102 or component thereof via the distal rotation knob 4134, to rotate the ultrasonic transmission waveguide 4128 and locate the end effector assembly 4112 in the proper orientation during a surgical procedure. Accordingly, in various forms, the ultrasonic hand piece 4114 may be electrically coupled at one or more points to the electrical power control operations provided by the handle assembly 4102. For example, in certain forms, the surgical instrument may comprise a rotatable electrical connection allowing the electrical power control operations provided by the handle assembly 4102 to electrically communicate with the generator 4116 via the ultrasonic hand piece 4114. That is, in one form, the handle assembly 4102 and the ultrasonic hand piece 4114 are electrically coupled via a rotatable electrical connection of a connector module 4190.

Figure 96:
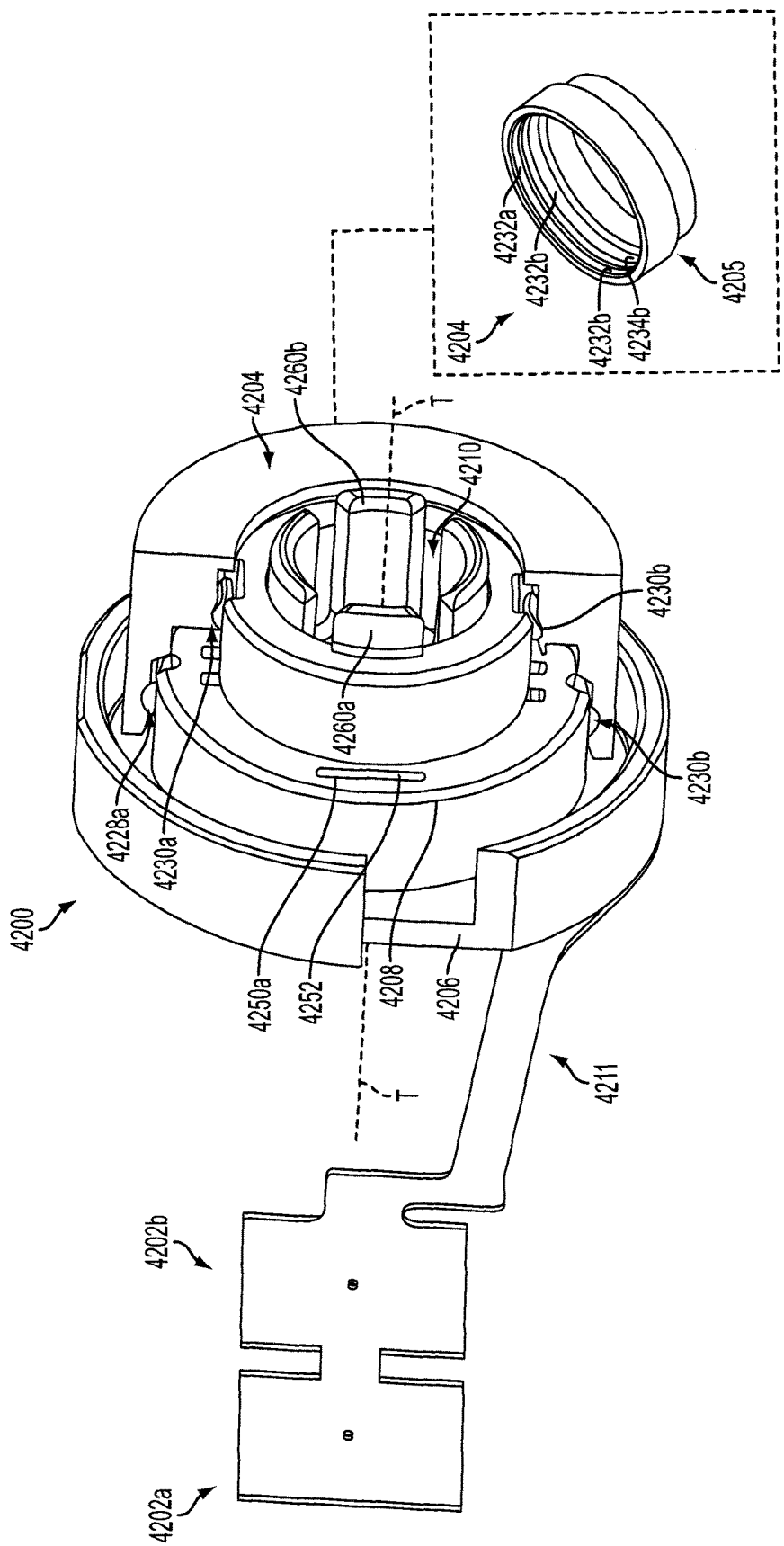
FIG. 96 is a perspective view of a connector module of an ultrasonic surgical instrument coupled to a flex circuit and a hand piece according to various forms describe herein.

FIG. 96 illustrates a connector module 4200 according to various forms. The connector module 4200 is shown coupled to a flex circuit 4202 and a distal portion 4204 of a hand piece 4114, which is also shown in an isolated view in the hatched box. The connector module 4200 comprises a housing 4206 and a rotation coupling 4208. Although not shown, the connector module 4200 and ultrasonic hand piece 4114 may be positioned within the opening 4156 the handle assembly 4102 such that the ultrasonic hand piece 4114 or waveguide 4128 is positioned within a central bore 4210 defined by the housing 4206 and a distal portion 4204 of the hand piece is thereby received and engaged by the connector module 4200. As described above, the ultrasonic hand piece 4114 may mechanically and acoustically couple to the waveguide 4128, which may be structured to operably couple to an end effector assembly 4112. The ultrasonic hand piece 4114 may also be rotatable relative to the housing 4206 of the connector module 4200, which may provide a rotatable electrical connection between the ultrasonic hand piece 4114 and a control or user interface circuit comprising a user interface, such as the switch assembly 4108 operatively associated with the flex circuit 4202.

In the illustrated form, the control or user interface circuit comprises the flex circuit 4202. For example, the rotatable electrical connection may comprise an electrical communication or conductive path along which electrical control operating instructions or signals provided by a user at a user interface, e.g., via the switch assembly 4108, may be electrically coupled to the generator 4116, e.g., via the ultrasonic hand piece 4114. Accordingly, the electrical control operating instructions or signals may be received by the generator 4116, which may respond by altering power delivery to the ultrasonic hand piece 4114 to control the operation of the instrument 4100. Further to the above, the switch assembly 4108 may comprise or be electrically coupled to the flex circuit 4202, which in turn may be configured to provide an electro-mechanical interface between the switches 4132a, 4132b and the generator 4116 via the hand piece 4114. For example, the flex circuit 4202 may comprise one or more switch points 4202a, 4202b configured for mechanical actuation via the toggle switches 4132a, 4132b. In one form, the flex circuit 4202 may comprise electrical contact switches, such as dome switches, that may be depressed to provide an electrical signal to the generator 4116. The flex circuit 4202 may comprise one or more conductors, such as conductive pathways, shown generally as 4211, which may be provided by wires, traces, or other conductive pathways as is known to those in the art. The conductive pathways may electrically couple to one or more switch conductors or ring conductors 4212, 4214, as shown in the exploded view of the connector module 4200 in FIG. 97. The flex circuit 4202 may couple to the ring conductors 4212, 4214 via one or more conductive leads 4216, 4218 or tabs of the respective delivery ring conductors 4212, 4214 (described below). It is to be appreciated that while switch conductors are generally referred to herein as ring conductors 4212, 4214 that define generally arcuate structures or bodies that may comprise one or more conductive paths, in various forms, the switch conductors may comprise other structures such as arcuate tracks, for example.

The connector module 4200 comprises an outer ring conductor 4212 and an inner ring conductor 4214. The outer ring conductor 4212 and the inner ring conductor 4214 each define a generally open-ended O-shaped structure and are configured for relative rotation with respect to the hand piece 4114. Each of the outer and inner ring conductors 4212, 4214 may further comprise a conductive connection, e.g., a lead 4216, 4218, that may be electrically coupled to the flex circuit 4202 via one or more conductive pathways 4211, thereby providing a conductive path to the connector module 4200 for rotatable electrical communication to the generator 4116 via the hand piece 4114. Accordingly, a control circuit may be established wherein the connector module 4200 provides a rotatable electrical connection between the user interface, e.g., switch assembly 4108, and the hand piece 4114.

Figure 97:
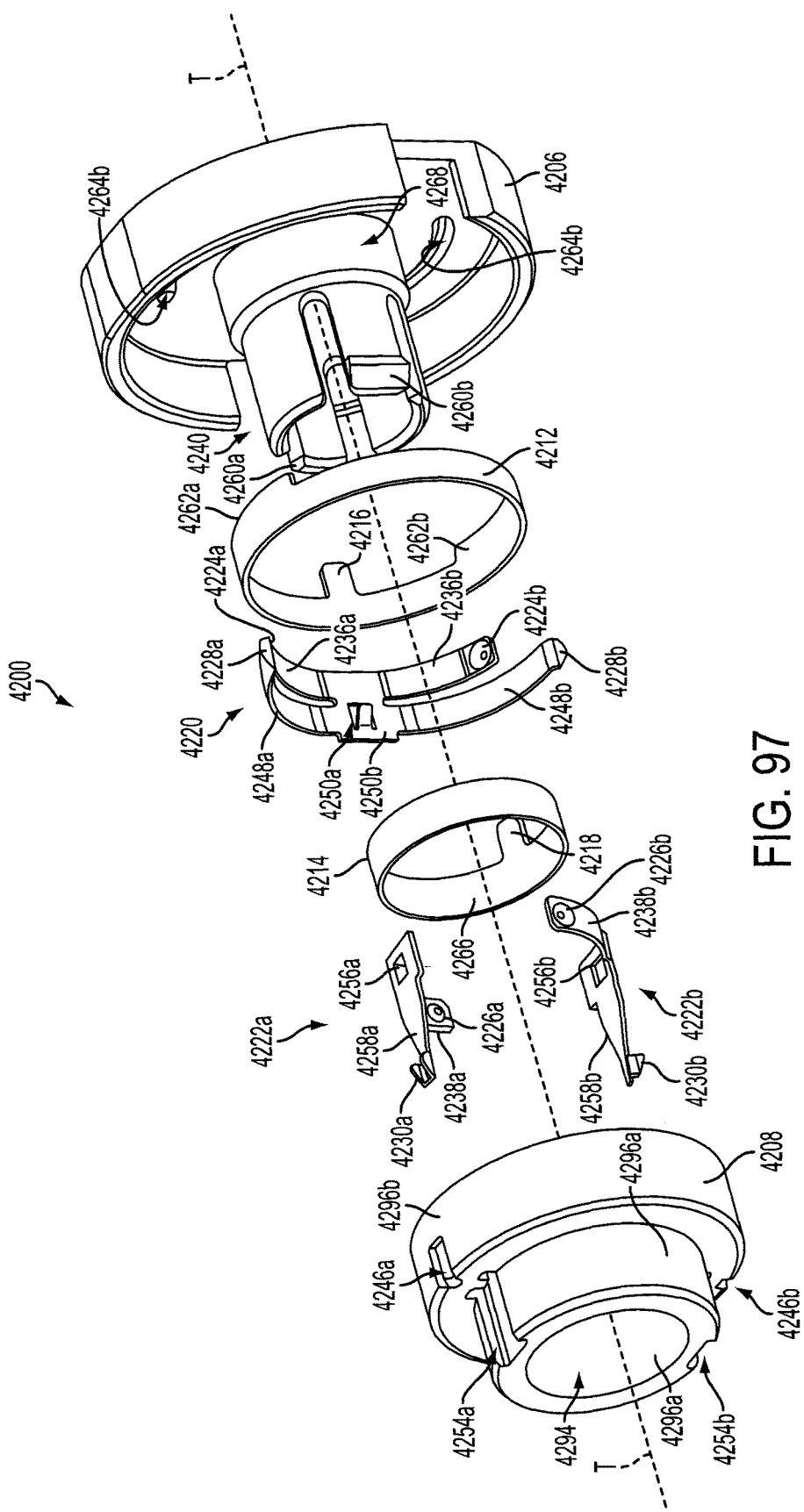
FIG. 97 is an exploded view of the connector module shown in FIG. 96 according to various forms described herein.

Referring generally to FIG. 97, in various forms, one or more links 4220, 4222a, 4222b may be positioned to be movable relative to and/or along a portion of a ring conductor 4212, 4214 comprising a conductive path. For example, a link 4220, 4222a, 4222b may be rotationally coupled to the ultrasonic hand piece 4114 when the hand piece 4114 is received within the opening 4156 to engage the connector module 4200. The rotation of the ultrasonic hand piece 4114 in direction 4170 (see FIG. 93) may produce a corresponding rotation of the link 4220, 4222a, 4222b about the longitudinal axis "T" with respect to a corresponding ring conductor 4212, 4214 between a first position and a second position. The link 4220, 4222a, 4222b may comprise one or more conductor contacts 4224a, 4224b, 4226a, 4226b positioned to electrically couple to the corresponding ring conductor 4212, 4214 when the link 4220, 4222a, 4222b is in the first position and the second position. The link 4220, 4222a, 4222b may further comprise one or more hand piece coupling contacts 4228a, 4228b, 4230a, 4230b configured to electrically couple to a distal surface 4232a, 4232b, 4234a, 4234b of the distal portion 4204 of the ultrasonic hand piece 4114 when the link 4220, 4222a, 4222b is in the first position and the second position.

Further to the above, in various forms, the links 4220, 4220a, 4220a may be rotatable relative to a respective ring conductor 4212, 4214. The ring conductor contacts 4224a, 4224b, 4226a, 4226b may be positioned to rotate about or along a surface of the ring conductors 4212, 4214 when the hand piece 4114 rotates with relative to the housing 4206. In one form, the ring conductors 4212, 4214 comprise arcuate surfaces or tracks about which the ring conductor contacts 4224a, 4224b, 4226a, 4226b may rotationally contact through an arcuate rotation extending from or between a first position and a second position. For example, in some forms, the ring conductor contacts 4224a, 4224b, 4226a, 4226b may comprise pressure contacts configured for pressure contact with a respective ring conductor 4212, 4214 along an arcuate conductive path. In one form, one or more links 4220, 4222a, 4222b comprise a tensioning member, such as a spring arm 4236a, 4236b, 4238a, 4238b, to tension or bias one or more ring conductor contacts 4224a, 4224b, 4226a, 4226b toward a ring conductor 4212, 4214 to maintain electrical coupling with respect to the ring conductor 4212, 4214 when the link 4220, 4222a, 4222b rotates relative to the ring conductor 4212, 4214. In certain forms, the ring conductor contacts 4224a, 4224b, 4226a, 4226b may be biased against an inner or outer surface of the ring conductor 4212, 4214 such that the ring conductor may electrically couple the link 4220, 4222a, 4222b with the ring conductor 4212, 4214 along one or more portions of an arcuate motion associated with the ultrasonic hand piece and/or a corresponding link 4220, 4222a, 4222b. In other forms, for example, the link 4212, 4214 may comprise a ring conductor contact 4224a, 4224b, 4226a, 4226b that may be engageable with the ring conductor 4212, 4214 along a conductive path via a hooked or looped portion about or around the ring conductor 4212, 4214.

Figure 98:
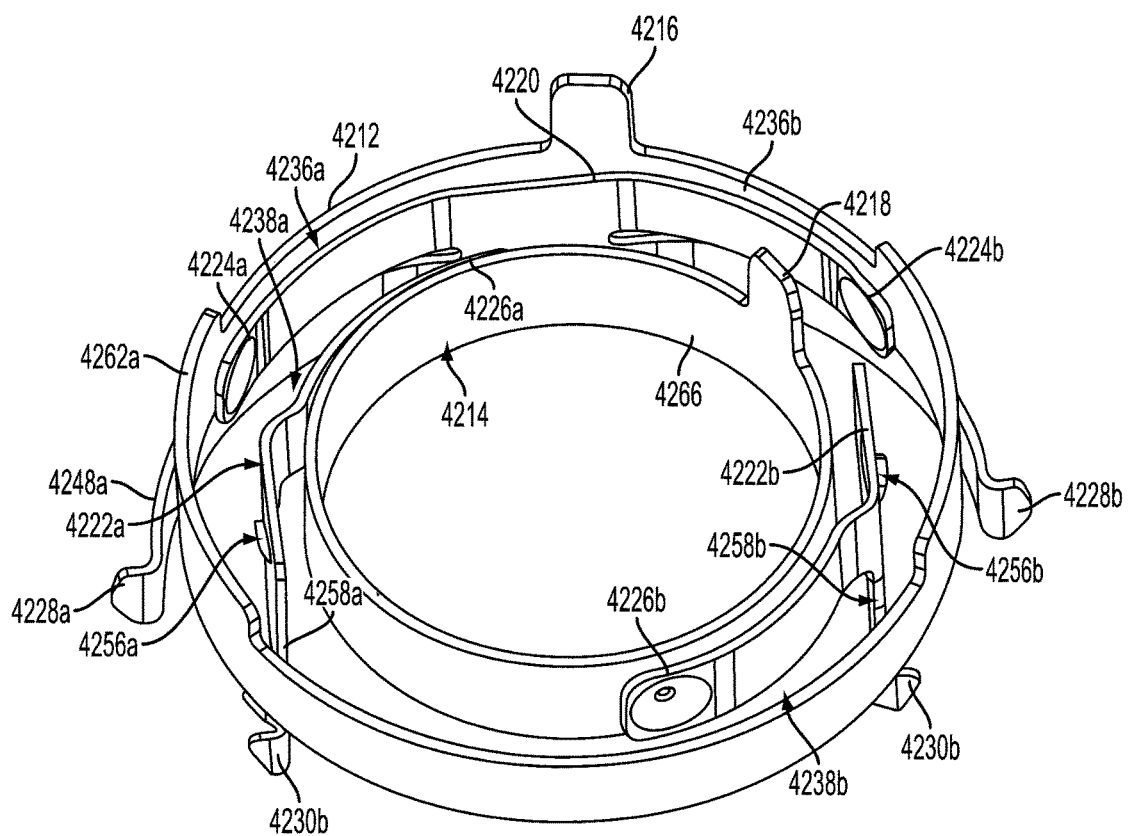
FIG. 98 is a perspective view of an arrangement of inner and outer rings and corresponding links of a connector module according to various forms described herein.

Referring to FIG. 98, showing an operational arrangement of the links 4220, 4222a, 4222b and corresponding ring conductor 4212, 4214, the connector module may comprise an outer ring conductor 4212 and an inner ring conductor 4214. In various forms, each ring conductor 4212, 4214 may also define a conductive path along an arcuate portion of the ring conductor 4212, 4214. An outer link 4220 may be provided that is configured for rotation relative to or about the outer ring conductor 4212. An inner link 4222a, 4222b may similarly be configured for rotation relative to or about the inner ring conductor 4214. For example, the outer ring conductor 4212 and the inner ring conductor 4214 may comprises conductive leads 4216, 4218 configured to electrically connect to the flex circuit 4202 through slots 4242, 4244 defined in the housing 4206. In one form, the conductive leads 4216, 4218 may at least partially retain the outer ring conductor 4212 and the inner ring conductor 4214 to allow relative rotation with respect to the links 4220, 4222a, 4222b. Each link 4220, 4222a, 4222b may comprise one or more conductor contacts 4224a, 4224b, 4226a, 4226b positioned to electrically couple to a corresponding ring conductor 4212, 4214 when the link 4220, 4222a, 4222b is in the first position and the second position. Each link 4220, 4222a, 422b may comprise one or more hand piece coupling contacts 4228a, 4228b, 4230a, 4230b configured to electrically couple to a distal surface 4232a, 4232b, 4234a, 4234b of the distal portion 4204 of the ultrasonic hand piece 4114. For example, the ring conductor contacts 4224a, 4224b, 4226a, 4226b may be rotated about the longitudinal axis between a first position and a second position such that the ring conductor contacts 4224a, 4224b, 4226a, 4226b maintain electrical contact with the corresponding ring conductor 4212, 4214 through the rotation.

The outer link may comprise a pair of ring conductor contacts 4224a, 4224b that may be coupled to spring arms 4236a, 4236b to bias the contacts 4224a, 4224b toward an inner surface of the outer ring 4212. In one form, the inner link 4214 comprises a pair of ring conductor contacts 4226a, 4226b attached to spring arms 4238a, 4238b structured to bias the contacts 4226a, 4226b toward an outer surface of the inner ring 4214. The inner link 4222a, 4222b comprises a first portion 4222a and second portion 4222b, however, in certain forms, the inner link 4222a, 4222b may comprise a unitary structure. For example, the inner link 4222a, 4222b may comprise a conductive or non-conductive body portion extending between the pair of ring conductor contacts 4226a, 4226b.

Figure 99:
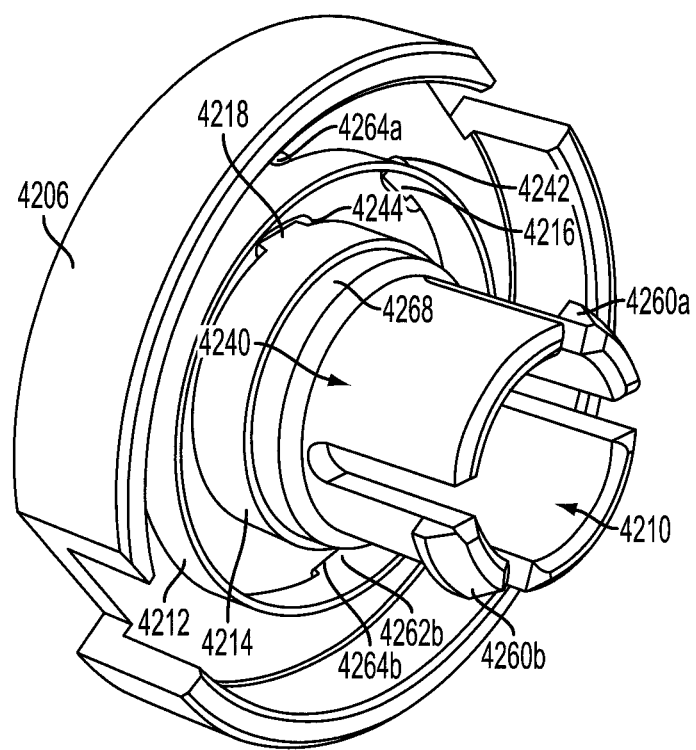
FIG. 99 is a perspective view of a first ring conductor and a second ring conductor positioned in a housing of a connector module according to various forms described herein.

As introduced above, in various forms, a connector module 4202 comprises one or more links 4220, 4222a, 4222b positioned to rotate relative to a handle assembly, a housing 4206, a user interface 4108, a trigger 4120, and or a conductive path associated with a ring conductor 4212, 4214 (see FIGS. 94, 98-99). According to various forms, the links 4220, 4222a, 4222b comprise one or more hand piece coupling contacts 4228a, 4228b, 4230a, 4230b structured to engage and electrically couple to the distal portion 4204 of ultrasonic hand piece 4114 (FIG. 96). In one form, the hand piece coupling contacts 4228a, 4228b, 4230a, 4230b may comprise an engagement member structured to engage the distal portion 4204 of ultrasonic hand piece 4114 to at least partially rotationally couple the respective link 4220, 4222a, 4222b to the ultrasonic hand piece 4114.

In one form, the outer link 4220 comprises a pair of outer hand piece coupling contacts 4228a, 4228b electrically coupled with the pair of outer ring contacts 4224a, 4224b to provide an electrical conductive path from the distal portion of the hand piece to the outer ring conductor 4212. Each of the pair of hand piece coupling contacts 4228a, 4228b is structured to extend through a respective slot 4246a, 4246b defined in the rotation coupling 4210. As explained in more detail below, the rotation coupling 4210 may be configured to couple with the rotation of the ultrasonic hand piece 4114. For example, in various forms, the rotation coupling 4210 is configured to provide a rotatable framework to couple the rotation of the ultrasonic hand piece 4114 to the links 4220, 4222a, 4222b.

Figure 100:
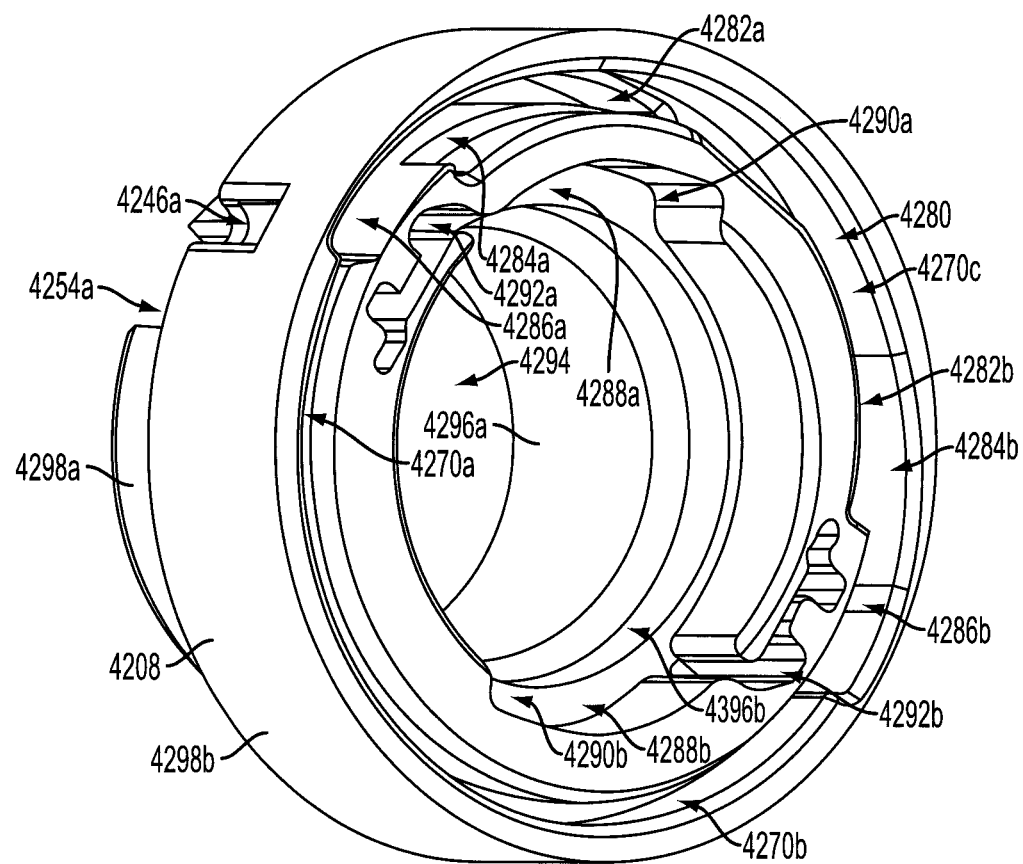
FIG. 100 is a perspective view of a distal side of a rotation coupling having inner and outer ring conductors and corresponding links positioned within recessed portions of the rotation coupling according to various forms described herein.

The pair of hand piece coupling contacts 4228, 4228b illustrated in FIG. 98 comprise curved extensions structured to engage and electrically couple to one or more electrical contacts disposed along a first distal surface 4232a, 4232b of the of the ultrasonic hand piece 4114. As illustrated, the curved extensions of the pair of outer hand piece coupling contacts 4228a, 4228b may operate to at least partially assist in coupling the rotation of the ultrasonic hand piece 4114 to effect a corresponding rotation to the outer link 4220. For example, the curved extensions may comprise an engagement member comprising an edge structured to frictionally engage the first distal surface 4232a, 4232b or be positionable within a groove or edge defined in the first distal surface 4232a, 4232b to rotationally couple the ultrasonic hand piece 4114 and the rotation coupling 4210. In certain forms, the outer hand piece coupling contacts 4228a, 4228b extend from tensioning members or spring arms 4248a, 4248b configured to bias or tension the outer hand piece coupling contacts 4228a, 4228b outward of the longitudinal axis "T" and/or toward the first distal surface 4232a, 4232b. In one form, the outer link 4220 comprises one or more tabs 4250a, 4250b, such as projections or clips, structured to retain the link 4220. For example, first tab 4250a may be received in slot 4252 defined in the rotation coupling 4208 and a second tab 4250b may clip to and/or be compressible against a portion of the rotation coupling 4208 to retain a position or orientation of the link 4220 (FIG. 100).

In one form, the inner link 4222a, 4222b comprises a pair of inner hand piece coupling contacts 4230a, 4230b electrically coupled to the pair of inner ring conductor contacts 4226a, 4226b to provide an electrical conductive path from the ultrasonic hand piece 4114 to the inner ring conductor 4214. The pair of outer hand piece coupling contacts 4230a, 4230b are each structured to extend through a slot 4254a, 4254b defined in the rotation coupling 4210 and comprise curved extensions defining edges structured to engage and electrically couple to one or more electrical contacts disposed along a second distal surface 4234a, 4234b of the distal portion 4204 of the ultrasonic hand piece 4114. As illustrated, the curved extensions may operate to at least partially assist in coupling the rotation of the ultrasonic hand piece 4114 (FIG. 96) to effect a corresponding rotation to the inner link 4222a, 4222b. For example, the curved extensions may comprise engagement members structured to frictionally engage the second distal surface 4234a, 4234b or be positionable within a groove or edge defined in the second distal surface 4234a, 4234b to rotationally couple with the rotation of the ultrasonic hand piece 4114. In various forms, the inner hand piece coupling contacts 4230a, 4230b extend from tensioning members comprising spring arms 4258a, 4258b configured to provide a bias or tension the hand piece coupling contacts 4230a, 4230b outward of the longitudinal axis "T" and/or toward the second distal surface 4234a, 4234b of the hand piece 4114. In various forms, the inner link 4220a, 4220b further comprises one or more tabs 4256a, 4256b to retain the link in a desired orientation. For example, the inner link 4220a, 4220b may comprise a first tab 4256a and second tab 4256b. The first and second tabs 4256a, 4256b may be configured to be received in a slot defined in the rotation coupling 4210 or clip to and/or compress against a portion of the rotation coupling 4210 (not shown).

In various forms, the distal portion 4204 of the ultrasonic hand piece 4114 may comprise one or more distal contact surfaces 4232a, 4232b, 4234a, 4234b, shown generally in the hatched isolation window of FIG. 96. The distal contact surfaces 4232a, 4232b, 4234a, 4234b may provide electrical contacts or contact points that may electrically couple to the ring conductors 4212, 4214 via links 4220, 4222a, 4222b. In some forms, electrically coupling the hand piece 4114 with the ring conductors 4212, 4214 may complete an electrical circuit comprising a user interface circuit, such as the flex circuit 4202, and the generator 4116, as described above.

In one form, the hand piece 4114 may comprise distal contact surfaces 4232a, 4232b, 4234a, 4234b disposed on or within a distal rim 4205 positioned along the distal portion 4204 of the hand piece 4114. The distal rim 4205 may define one or grooves defining the distal contact surfaces 4232a, 4232b, 4234a, 4234b comprising one or more electrical contacts or contact surfaces. The contact surfaces may comprise, for example, gold plating or other suitable conductive electrical contact material known in the art. In one form, this distal rim 4205 may define longitudinal or circumferential grooves dimensioned to complement or receive a hand piece coupling contact 4228a, 4228b, 4230a, 4230b. For example the distal rim 4205 may define one or more grooves along the distal contact surfaces 4232a, 4232b, 4234a, 4234b to fittably engage a respective hand piece coupling contact 4228a, 4228b, 4230a, 4230b such that the distal contact surfaces 4232a, 4232b, 4234a, 4234b and respective hand piece coupling contacts 4228a, 4228b, 4230a, 4230b may frictionally, electrically, and rotationally coupled when the connector module 4200 receives the hand piece 4114. In one form, the distal contact surfaces 4232a, 4232b, 4234a, 4234b and the respective hand piece coupling contacts 4228a, 4228b, 4230a, 4230b may couple in a male-female or lock-and-key relationship. In certain forms, the distal contact surfaces 4232a, 4232b, 4234a, 4234b comprise on or more circumferential ridges extending about an inner circumference of the distal rim 4205 to electrically couple with respective hand piece coupling contacts 4228a, 4228b, 4230a, 4230b along all or part of the circumferential ridges. In various forms, the distal contact surfaces 4232a, 4232b, 4234a, 4234b comprise gold plated circumferential electrical contacts disposed on the circumferential ridges within the inner surface of the distal rim 4205, as shown in FIG. 96.

The distal contact surfaces 4232a, 4232b, 4234a, 4234b may be electrically coupled to the generator 4116 via leads extending through the hand piece 4114 and wire 4118 to communicating electrical control signals from the user interface, e.g., the switch assembly 4108, to control an operation of the ultrasonic surgical instrument 4100. Accordingly, in one form, the flex circuit 4202 may be configured to interface with the switches 4132a, 4132b and to provide electrical signals along the conductive pathways 4211 to the conductive leads 4216, 4218, which in turn provide electrical connection to the links 4220, 4222a, 4222b via the ring conductors 4212, 4214, which in turn electrically couple, via the hand piece coupling contacts 4228a, 4228b, 4230a, 4230b, to distal contact surfaces 4232a, 4232b, 4234a, 4234b disposed at the distal portion of the ultrasonic hand piece 4114 to provide a conductive path to the generator 4116 via the ultrasonic hand piece 4114 a cable 4118.

According to various forms, the connector module 4202 comprises a spindle 4240. The spindle may extend from the housing 606 along the longitudinal axis "T" and may define a central bore 4210 along the longitudinal axis "T" dimensioned to receive a length of the hand piece 4114 and/or waveguide 4128 therethrough. As shown in FIGS. 96-97, the spindle extends proximally from the housing 4206 along the longitudinal axis "T". The rotation coupling 4208 is rotatably mounted on the spindle 4240 for rotation about the longitudinal axis "T" with relative to the housing 4206. In certain forms, the spindle 4240 comprises one or more retaining structures 4260a, 4260b structured to retain and therefore limit the longitudinal excursion of the rotation coupling 4208.

FIG. 99 illustrates the ring conductors 4212, 4214 mounted to or otherwise positioned with respect to the housing 4206 such the hand piece 4114 may rotate relative to the ring conductors 4212, 4214. One or more portions of the ring conductors 4212, 4214 may extend through slots defined in the housing 4206 to provide an anchorage with respect to the housing 4206. As describe above, the ring conductors 4212, 4214 may comprise leads 4216, 4218 extending through slots 4242, 4244 defined in the housing. As shown in FIG. 97 and FIG. 99, the outer ring conductor 4212 includes two tabs 4262a, 4262b dimensioned to be received within two retention slots 4264a, 4264b defined in the housing 4206. In various forms, the ring conductors 4212, 4214 and/or housing may comprise additional positioning features such as hooks, latches, clips, or adhesives, for example, that may be used to position the ring conductors 4212, 4214 proximate to the housing 4206 to allow relative rotation between the ultrasonic hand piece 4114 and the ring conductors 4212, 4214. In FIG. 99, the inner ring conductor 4214 comprises an inner circumference 4266 (see FIG. 97) configured to fittably engage a surface 4268 extending from the housing 4206. In one form, the inner ring conductor 4212 may be frictionally and/or adhered with an adhesive to the surface 4268.

FIG. 100 illustrates a perspective view of a distal portion of the rotation coupling 4210 having therein positioned inner and outer ring conductors 4212, 4214 and corresponding inner and outer links 4220, 4222a, 4222b. The rotation coupling 4210 comprises a plurality of internal slots configured to receive and therein retain the inner and outer links 4220, 4222a, 4222b. It is to be appreciated that various forms may comprise other slot configuration than shown in FIG. 100. For example, in various forms, the rotation coupling may contain positioning extensions to position the links. In one form, one or more portions of the links 4220, 4222a, 4222b may be adhered to the rotation coupling by an adhesive. In the illustrated form, the rotation coupling comprises an outer slot 4270a, 4270b, 4270c for receiving the outer ring conductor 4212. The outer slot 4270a, 4270b, 4270c may be dimensioned to allow relative rotation between the rotation coupling 4210 and the outer ring conductor 4212. The rotation coupling 4210 may further define slot 4280 for receiving the outer link 4220. Slot 4280 is positioned inward toward the longitudinal axis "T" (see FIG. 96) with respect to outer slot 4270a, 4270b, 4270c. Slot 4280 comprises spring arm slots 4282a, 4282b dimensioned for receiving spring arms 4236a, 4248a and 4236b, 4248b, respectively. Adjacent to the spring arm slots 4282a, 4282b, slot 4280 defines slots 4284a, 4284b, which are dimensioned to receive outer ring conductor contacts 4224a, 4224b, respectively. Slot 4280 further defines slots 4286a, 4286b, which are dimensioned to receive the outer hand piece coupling contacts 4228*a*, 4228*b* and extend proximally to slots 4246*a*, 4246*b* (slot 4246*b* is shown in FIG. 96). The rotation coupling 4210 may further define slot 4296*b* for receiving the inner ring conductor 4214 and slot 4281 for receiving the inner link 4222*a*, 4222*b*. Slot 4281 is positioned inward toward the longitudinal axis "T" (see FIG. 96) with respect to spring arm slots 4288*a*, 4288*b* and is dimensioned to receive spring arms 4238*a*, 4238*b*, respectively. Adjacent to one end of each spring arm slots 4288*a*, 4288*b*, the rotation coupling defines an inner ring contact slot 4290*a*, 4290*b* for receiving the inner ring contacts 4226*a*, 4226*b*, respectively. Adjacent to the other end of each spring arm slots 4288*a*, 4288*b*, the rotation coupling defines slots 4292*a*, 4292*b*, which are dimensioned to receive inner hand piece coupling contacts 4230*a*, 4230*b*, respectively, and respectively extend proximally to slots 4254*a*, 4254*b* (slot 4254*b* is shown in FIG. 96).

The rotation coupling further defines a bore 4294 dimensioned to be mounted about the spindle 4240. A proximal inner circumferential surface 4296*a* of the rotation coupling defines a portion of the bore 4294 that comprises a decreased diameter relative to a more distal inner circumferential surface that defines slot 4296*b*. The decreased diameter of the proximal inner circumferential surface defining slot 4296*a* may reduce rotational friction about the spindle 4240 and may provide additional space for components, such as ring conductors 4212, 4214 and links 4220, 4222*a*, 4222*b*, to be positioned about the spindle 4240 within the rotational coupling 4210. The rotational coupling 4210 further includes a proximal outer circumferential surface 4298*a* comprising a decreased diameter relative to a distal outer circumferential surface 4298*b*. The decreased diameter of the distal outer circumferential surface 4298*a* may provide additional space for components, such as ring conductors 4212, 4214 and links 4220, 4222*a*, 4222*b*, to be positioned about the spindle 4240 within the rotational coupling 4210. It is to be appreciated that additional ring conductors and links may be provided to, for example, provide additional rotatable electrical connections.

Figure 101:
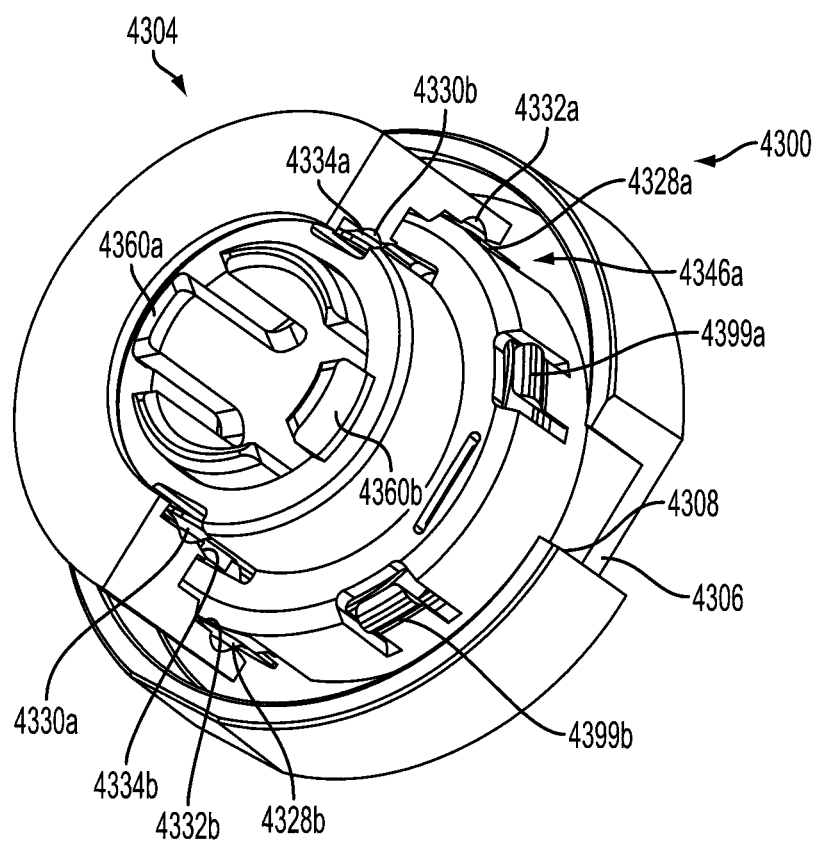
FIG. 101 is a perspective view of a connector module coupled to a distal end of a hand piece according to various forms described herein.
Figure 102:
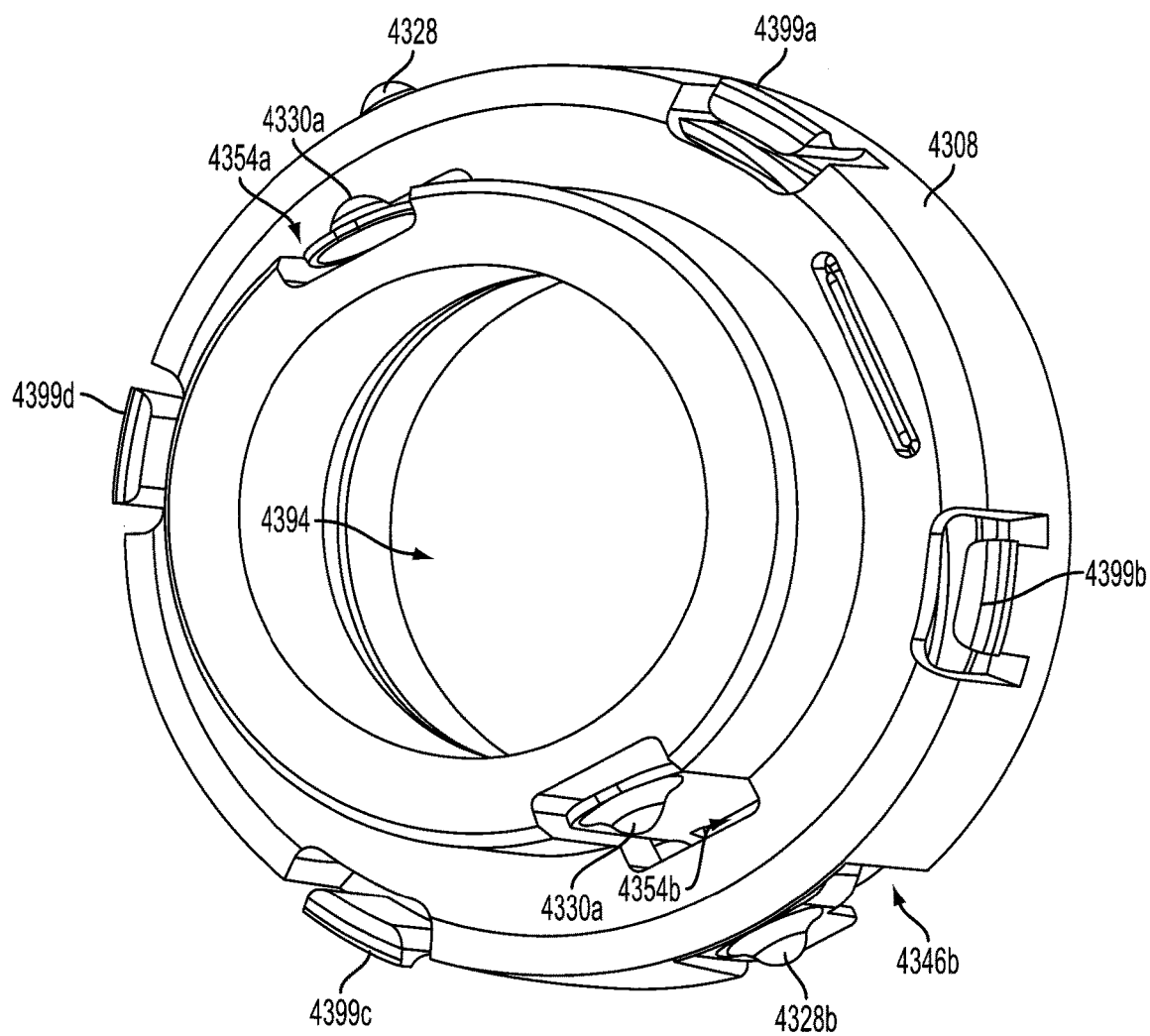
FIG. 102 is a proximal view of inner and outer ring conductors and corresponding links positioned in a rotation coupling according to various forms described herein.
Figure 103:
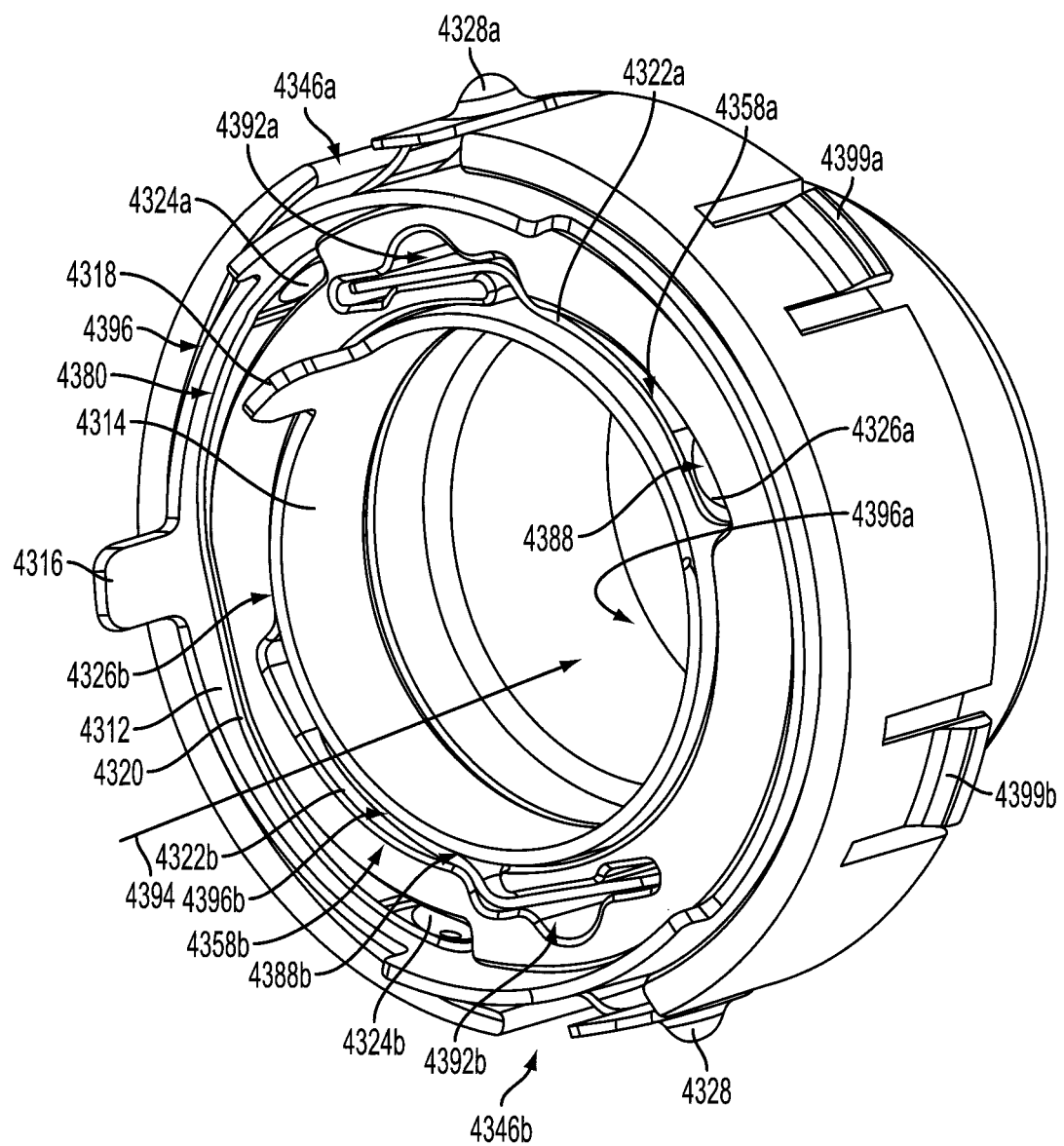
FIG. 103 is a perspective view of a distal side of a rotation coupling having inner and outer ring conductors and corresponding links positioned within recessed portions of the rotation coupling according to various forms described herein.

FIGS. 101-103 illustrate a connector module 4300 according to various forms. In one form, the connector module may find use in ultrasonic surgical instruments similar to that described above with respect to FIGS. 96-99. Therefore, for brevity, similar features and may be identified by similar numbers and may not be described in similar detail. However, it is to be understood that the various features may find similar use and share similar descriptions as those presented above with respect to connector module 4190 and connector module 4200 and ultrasonic surgical instrument 4100. For example, the connector module 4300 may be coupled to a circuit associated with a user interface, which may be similar to flex circuit 4202. The connector module 4300 may also couple to a distal portion 4304 of an ultrasonic hand piece (see FIGS. 93-94). The connector module 4300 comprises a housing 4306 and a rotation coupling 4308 and may be positionable within a handle assembly (e.g., handle assembly 4102 shown in FIGS. 93-95). As described above, the ultrasonic hand piece may mechanically and acoustically couple to a waveguide, which may be structured to operably couple to an end effector assembly. The ultrasonic hand piece may also be rotatable relative to the connector module housing 4306, which may provide a rotatable electrical connection between the ultrasonic hand piece and the user interface. The connector module 4300 may include a spindle 4340 extending generally proximally from the housing 4306 along a longitudinal axis. The rotation coupling 4308 may be rotatably mounted on the spindle 4340 for rotation thereabout with respect to the housing 4306. The spindle 4340 includes one or more retaining structures 4360*a*, 4360*b* structured to retain and therefore limit the longitudinal excursion of the rotation coupling 4308.

The switch assembly 4300 includes a pair of outer hand piece coupling contacts 4328, 4328*b* comprising pressure contacts structured to electrically couple to one or more electrical contacts disposed along a first distal surface 4332*a*, 4332*b* of the of the ultrasonic hand piece. The outer hand piece coupling contacts 4328*a*, 4328*b* may extend from tensioning members or spring arms 4348*a*, 4348*b* (see FIG. 103) configured to bias or tension the outer hand piece coupling contacts 4328*a*, 4328*b* outward of the longitudinal axis and/or toward the first distal surface 4332*a*, 4323*b*. The outer hand piece coupling contacts 4328*a*, 4328*b* may be structured to respectively extend through a slot 4346*a*, 4346*b* defined in the rotation coupling 4310 and comprise pressure contacts structured to electrically couple to one or more electrical contacts disposed along a first distal surface 4332*a*, 4332*b* of the distal portion 4304 of the ultrasonic hand piece.

In one form, the switch assembly 4300 includes a pair of inner hand piece coupling contacts 4330*a*, 4330*b* comprising pressure contacts structured to electrically couple to one or more electrical contacts disposed along a second distal surface 4334*a*, 4334*b* of the of the ultrasonic hand piece. The inner hand piece coupling contacts 4330*a*, 4330*b* may extend from tensioning members or spring arms 4358*a*, 4358*b* (see FIG. 103) configured to bias or tension the inner hand piece coupling contacts 4330*a*, 4330*b* outward of the longitudinal axis and/or toward the second distal surface 4334*a*, 4334*b*. The outer hand piece coupling contacts 4330*a*, 4330*b* may be structured to respectively extend through a slot 4354*a*, 4354*b* defined in the rotation coupling 4310 and comprise pressure contacts structured to electrically couple to one or more electrical contacts disposed along a second distal surface 4334*a*, 4334*b* of the distal portion 4304 of the ultrasonic hand piece.

As shown most clearly in FIGS. 101-102, the connector module 4300 comprises one or more engagement features 4399*a*, 4399*b*, 4399*c*, 4399*d* structured to engage the ultrasonic hand piece. The engagement features 4399*a*, 4399*b*, 4399*c*, 4399*d* may comprise one or more projections, clips, or "grippers" formed about the rotation coupling 4310. The engagement features 4399*a*, 4399*b*, 4399*c*, 4399*d* are structured to fittably engage a surface of the ultrasonic hand piece. The engagement features may comprise one or more pliable, resilient, flexible polymeric materials positioned on the rotation coupling. In one form, the engagement features 4399*a*, 4399*b*, 4399*c*, 4399*d* are dimensioned to grip a diameter of the ultrasonic instrument. For example, the engagement features 4399*a*, 4399*b*, 4399*c*, 4399*d* may define a diameter that is undersized relative to a dimension of the ultrasonic hand piece to create a friction interference fit. In various forms, the hand piece may comprise a distal portion 4304 defining a ridge or groove configured to receive a portion of the engagement features 4399*a*, 4399*b*, 4399*c*, 4399*d*. In one form, the engagement 4399*a*, 4399*b*, 4399*c*, 4399*d* may be configured to flex inward toward the longitudinal axis to receive the hand piece while providing tension outward of the longitudinal axis to rotationally couple with the hand piece when the hand piece has been received.

FIG. 103 illustrates a distal view of the rotation coupling 4310 having therein disposed inner and outer ring conductors 4312, 4314 and corresponding inner and outer links 4320, 4322a, 4322b. The inner and outer links 4320, 4322a, 4322b are rotatable relative to the outer ring conductor 4312 and an inner ring conductor 4314. The outer ring conductor 4312 and the inner ring conductor 4314 comprises conductive leads 4316, 4318 configured to electrically connect to a user interface through slots defined in the housing 4306, which may be similar to slots 4342, 4344. Each link 4320, 4322a, 4322b comprises a pair or conductor contacts 4324a, 4324b, 4326a, 4326b positioned to electrically couple to the corresponding ring conductor 4312, 4314 when the link 4320, 4322a, 4322b is in the first position and the second position and a pair of hand piece coupling contacts 4328a, 4328b, 4330a, 4330b configured to electrically couple to a distal surface 4332a, 4332b, 4334a, 4334b of the distal portion 4304 of the ultrasonic hand piece. For example, the ring conductor contacts 4324a, 4324b, 4326a, 4326b may be rotated about a longitudinal axis between a first position and a second position such that the ring conductor contacts 4324a, 4324b, 4326a, 4326b maintain electrical contact with the corresponding ring conductor 4312, 4314 through the rotation.

The outer link 4312 comprises a pair of ring conductor contacts 4324a, 4324b coupled to spring arms 4336a, 4336b structured to bias the contacts 4324a, 4324b toward an inner surface of the outer ring 4312. The pair of outer hand piece coupling contacts 4328a, 4328b electrically coupled with the pair of outer ring contacts 4324a, 4324b to provide an electrical conductive path from the distal portion 4304 of the hand piece to the outer ring. The inner link 4314 comprises a pair of ring conductor contacts 4326a, 4326b electrically coupled to the pair of hand piece coupling contacts 4320a, 4320b and are attached to spring arms 4338a, 4338b structured to bias the ring conductor contacts 4326a, 4326b toward an outer surface of the inner ring 4314. The inner link 4322a, 4322b comprises a first portion 4322a and second portion 4322b.

The rotation coupling 4310 forms a central bore 4394 defined by a proximal rotation surface 4396a and a distal slot 4396b. The rotation coupling 4310 comprises a plurality of slots dimensioned to receive the ring conductors 4312, 4314 and corresponding links 4320, 4322a, 4322b. The slot configuration shown in FIG. 103 is similar to the slot configuration shown in FIG. 100 and, for brevity, will not be described in detail. For example, the rotation coupling comprises slot 4370 to receive the outer ring conductor 4312 and slot 4396b to receive inner ring conductor 4314. The rotation coupling defines slot 4380, which is dimensioned to receive the outer link 4312. The rotation coupling also defines slot 4388a to receive the first portion of the inner link 4322a and slot 4388b to receive the second portion of the inner link 4322b. Slots 4346a, 4346b comprise circumferential window facing outward of the longitudinal axis. Slots 4392a, 4392b define outward facing arcuate grooves structure to receive the inner hand piece coupling contacts 4330a, 4320b.

Figure 104:
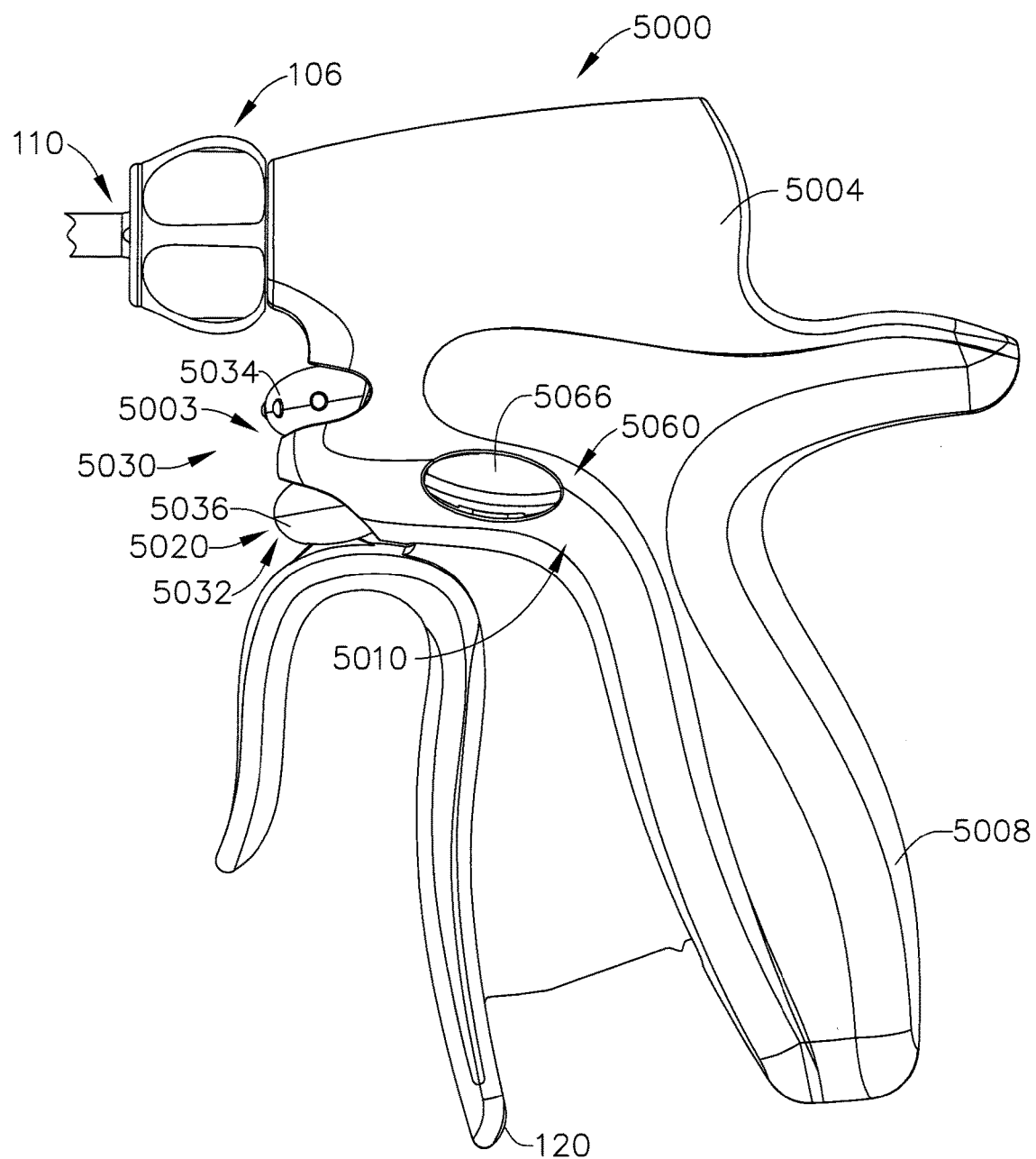
FIG. 104 is a left side elevational view of an ultrasonic handle assembly according to various forms described herein.

FIGS. 104 and 105 illustrate one form of a handle assembly 5000 that employs a unique and novel switch assembly, generally designated as 5020. In various forms, the handle assembly 5000 may be similar in design and use to other handle assemblies disclosed herein. Accordingly those features that are common to other handle assembly arrangements that have been described above will not be discussed in detail beyond that which may be necessary to understand the design and operation of handle assembly 5000.

In at least one form, the handle assembly 5000 may comprise two handle housing segments that are configured to be coupled together to form a handle housing 5002. For example, a left handle housing segment 5004 is shown in FIG. 104 and a right handle housing segment 5006 is shown in FIG. 105. The handle housing segments 5004, 5006 may each be fabricated from a plastic or other polymer material and be coupled together by fasteners such as screws, bolts, snap features, adhesive, etc. The handle housing segments 5004, 5006 cooperate to form a handle housing 5002 that has a "fixed" handle portion that may form a pistol grip 5008 that may be easily gripped and manipulated by one hand. As can be seen in FIG. 104, the left handle housing segment 5004 may be contoured in such a manner so as to establish a "thumb groove" area, generally designated as 5010. Those of ordinary skill in the art will readily appreciate that when a clinician is gripping the pistol grip 5008 in his or her right hand, for example, the clinician's thumb may be naturally located in the thumb groove area 5010. In at least one form, the right handle housing 5006 may also be formed with a similar thumb groove area (not shown), such that if the clinician is gripping the handle assembly 5000 in his or her left hand, the clinician's left thumb would naturally be located in that area.

Figure 106:
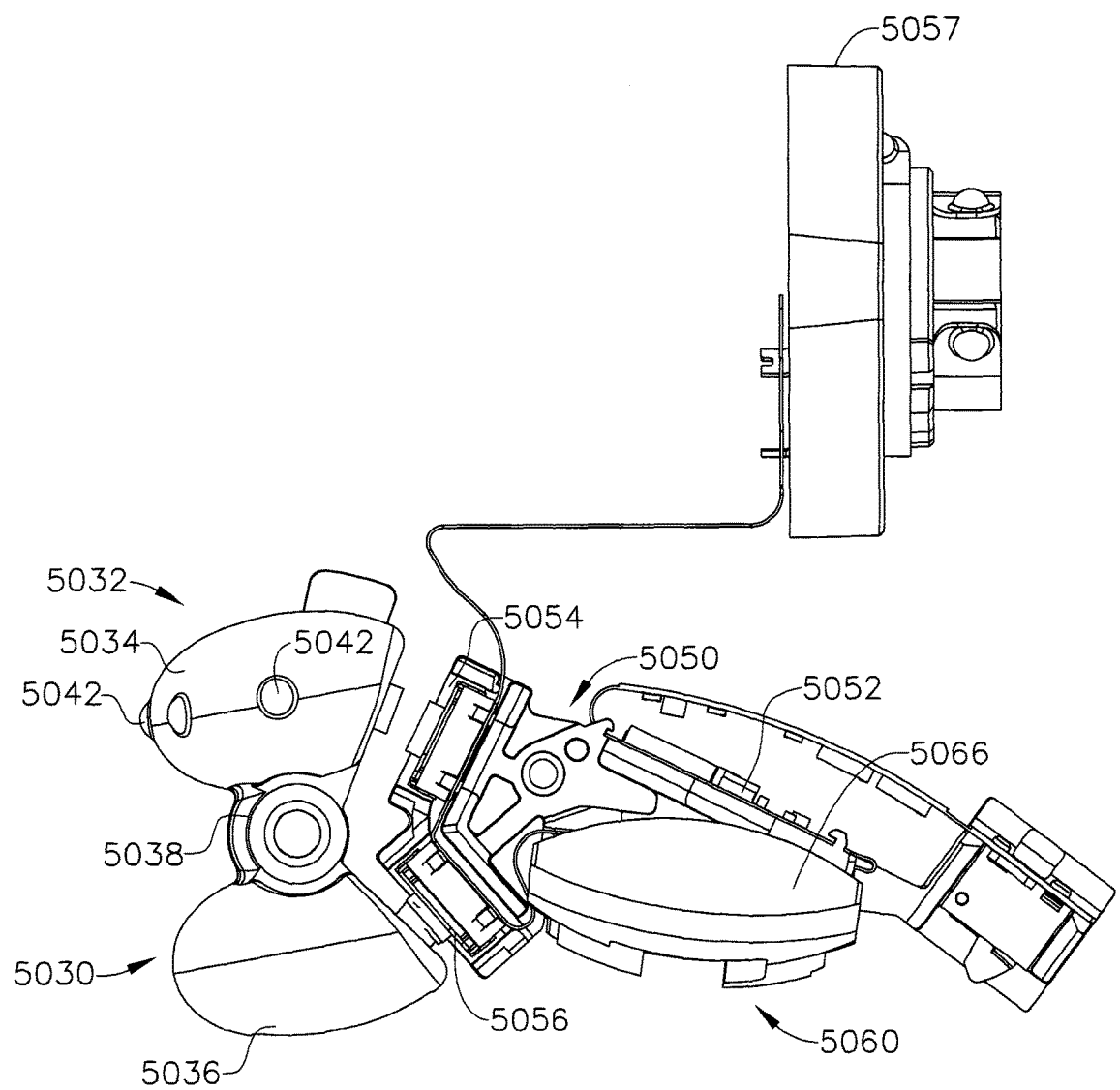
FIG. 106 is a side elevational view of a switch assembly for an ultrasonic surgical instrument according to various forms described herein.
Figure 107:
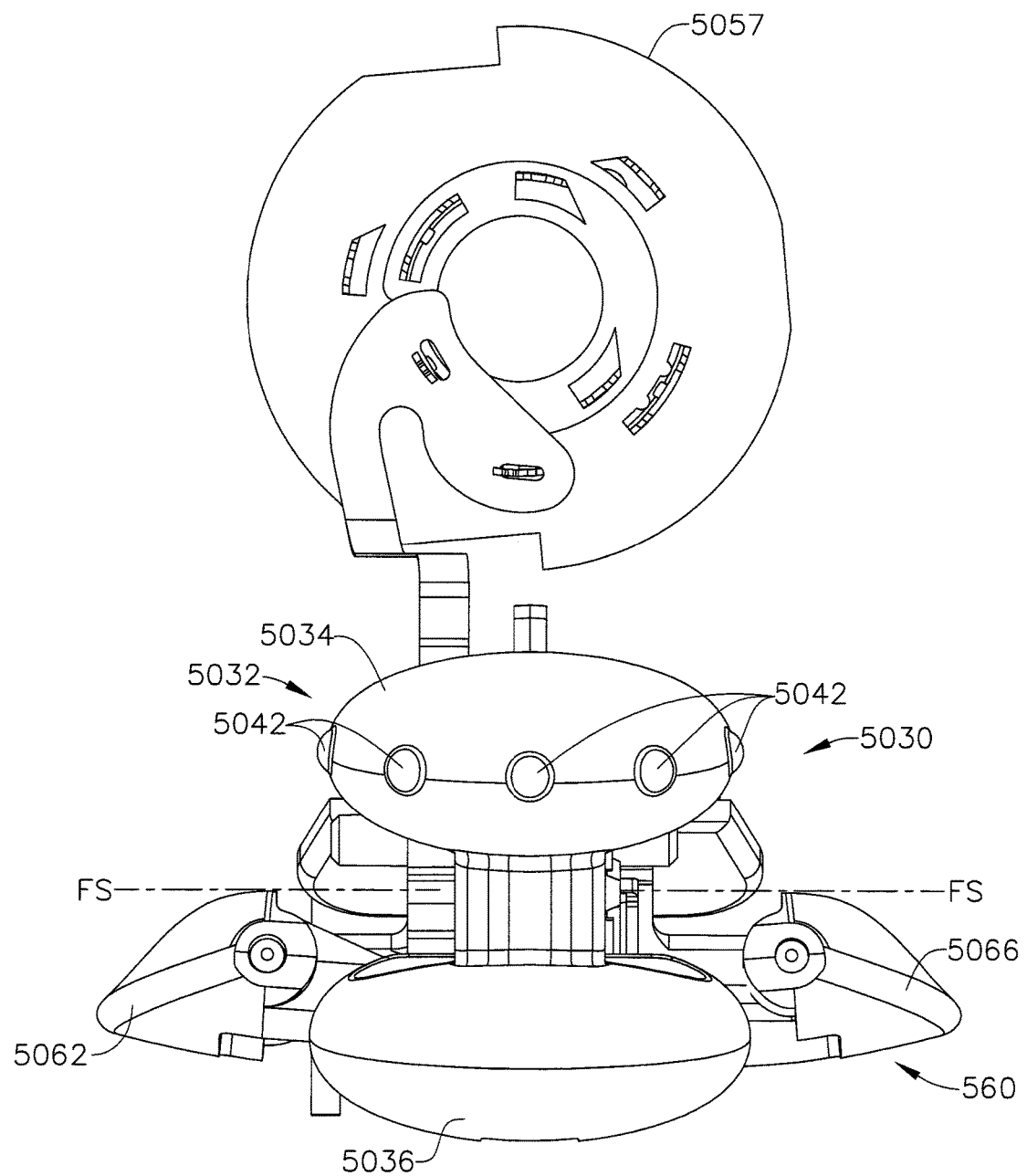
FIG. 107 is a front view of the switch assembly of FIG. 106 according to various forms described herein.

As indicated above, the handle assembly 5000 includes a switch assembly 5020 that may include a first switch arrangement 5030 and a second switch arrangement 5060. In at least one form, the first switch 5030 includes a first button assembly 5032 that is supported for pivotal travel relative to a "forward portion" 5003 of the handle housing 5002. The first button assembly 5032 may be formed from, for example, a polymer or other suitable material and include a first finger button 5034 and a second finger button 5036 that are interconnected by a journal portion 5038. The journal portion 5038 serves to pivotally support the first button assembly 5032 on a first pivot pin 5040 that extends between the left and right housing segments 5004, 5006. The first pivot pin 5040 may be molded into one of the housing segments 5004, 5006 and be received in a corresponding socket (not shown) formed in the other housing segment 5004, 5006. The first pivot pin 5040 may be attached to the handle housing segments 5004, 5006, by other means as well. The first pivot pin 5040 defines a first switch axis FS-FS about which the first button assembly 5032 may be "rocked". See FIG. 107. In at least one form, the first and second finger buttons 5034, 5036 may be provided with a somewhat "bulbous" shape as shown in FIGS. 106 and 107. In addition, to further enhance the clinician's ability to distinguish between the first finger button 5034 and second finger button 5036 without looking directly at the finger buttons 5034, 5036, one of the finger buttons may be provided with a distinguishing feature or features. For example, as shown in FIGS. 106 and 107, the first finger button 5034 has a plurality of detents 5042 or other formations formed into its perimeter.

As can be seen in FIG. 105, a switch frame 5050 is supported within the handle assembly 5002 such that it is located proximal to the first button assembly 5032 and in the portion of the housing assembly 5002 that is adjacent to the thumb groove area 5010 (FIG. 104). In one form, the switch frame 5050 is non-movable relative to the first button assembly 5032 and may be rigidly supported on stand-offs or other gusset-like support features molded into or otherwise formed on the handle housing segments 5004, 5006. The switch frame 5050 may support a circuit board 5052, e.g., a printed circuit board, flex circuit, rigid-flex circuit, or other suitable configuration that includes a first contact pad 5054 that corresponds to the first finger button 5034 and a second contact pad 5056 that corresponds to the second finger button 5036. Those of ordinary skill in the art will understand that by rocking or pivoting the first button assembly 5032 about the first switch axis FS-FS, the clinician can activate the first contact pad 5054 by pivoting the first finger button 5034 into actuation contact with the first contact pad 5054. As used herein, the term "actuation contact" may include a sufficient amount of physical contact between the finger button and the first contact pad required to initiate actuation of the contact pad (or similar contact arrangement). "Actuation contact" may also include a sufficient amount of physical proximity of the finger button relative to the contact pad (or other contact arrangement) that is sufficient to initiate actuation of the contact pad—but without any portion of the finger button actually physically touching the contact pad. The clinician can activate the second contact pad 5056 by pivoting the second finger button 5036 into actuation contact with the second contact pad 5056. Such unique and novel first switch arrangement may be easily actuated by the clinician's index finger when her or she is gripping the pistol grip portion 5008 of the handle assembly 5000. Thus, every button of the switch assembly may be easily actuated by the single hand supporting the handle assembly. As in the various forms described above, the first switch arrangement 5030 may be employed to modulate the power setting of the ultrasonic handpiece and/or to active various algorithms described herein.

In some forms, the first switch arrangement 5030 is coupled to a generator, such as any of the generators 30, 500, 1002. For example, the respective contact pads 5054, 5056 may be in electrical communication with the generator via a connector module 5057, which, in some forms, is similar to the connector module 4200 described herein above. The connector module 5057 is coupled to an internal or external generator. Signals indicating activation of the respective contact pads 5054, 5056 may cause the generator to modify the operation of the instrument 5000. For example, when the clinician selects the first finger button 5034, it may cause the generator to increase the level of power provided to the end effector. When the clinician selects the second finger button 5036, it may cause the generator to decrease the level of power provided to the end effector. In various embodiments, the generator may be configurable between a minimum power level (e.g., MIN) and maximum power level (e.g., MAX). For example, some forms of the GEN11 generator available from Ethicon Endo-Surgery, Inc. of Cincinnati Ohio provide five power levels. The finger buttons may be used to toggle the generator among the power levels. Also, in some forms, one or both of the finger buttons 5034, 5036 may be associated with an algorithm, such as those described herein. For example, when the user selects one of the buttons 5034, the generator may execute an algorithm, such as, for example, one or more of algorithms 3021, 3021', 3021", 3120, 3170 any of the algorithms described with respect to FIGS. 15A-15C, 20-22, 57-60, etc.

Figure 108:
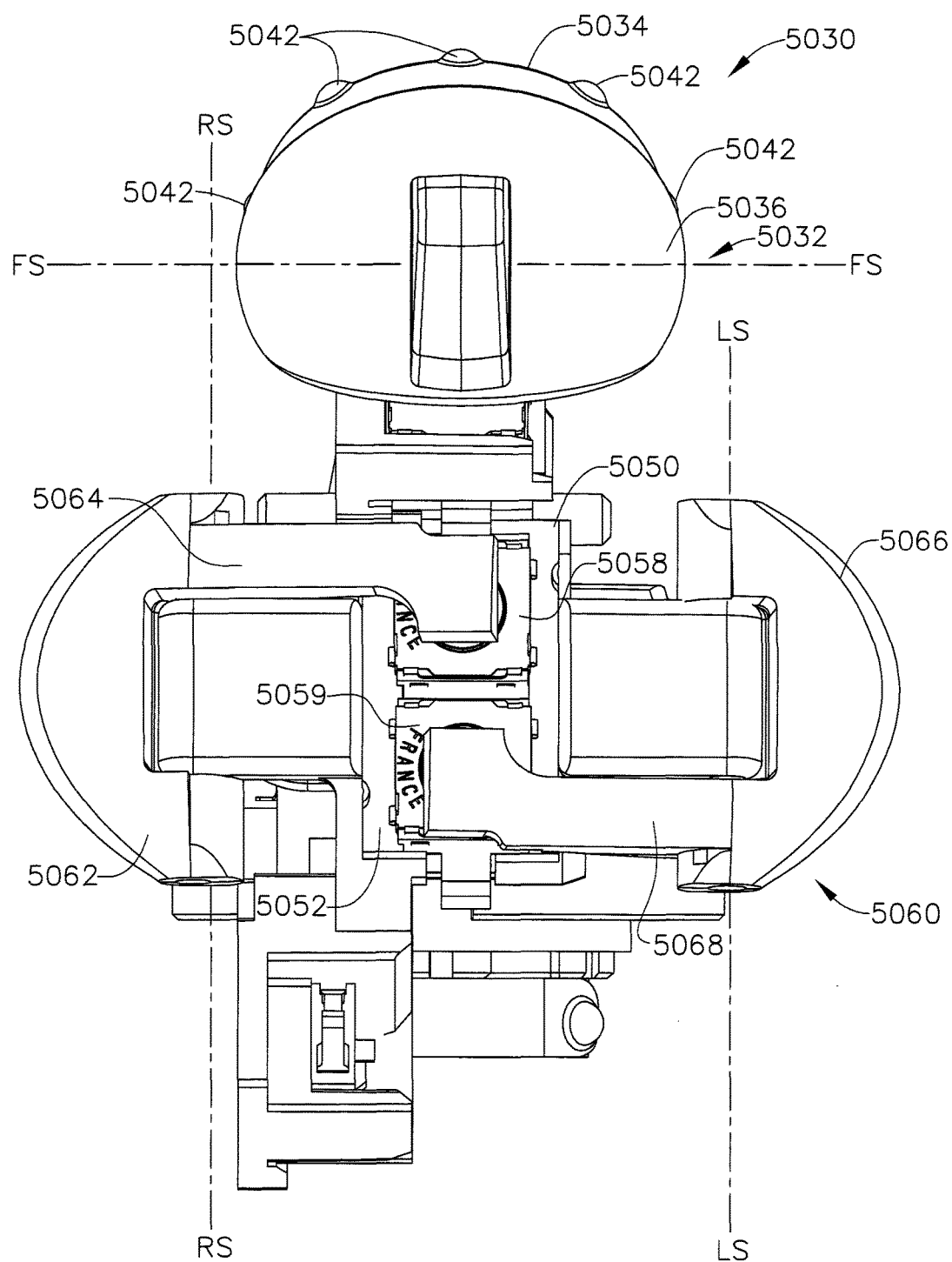
FIG. 108 is a bottom view of the switch assembly of FIGS. 106 and 107 according to various forms described herein.
Figure 109:
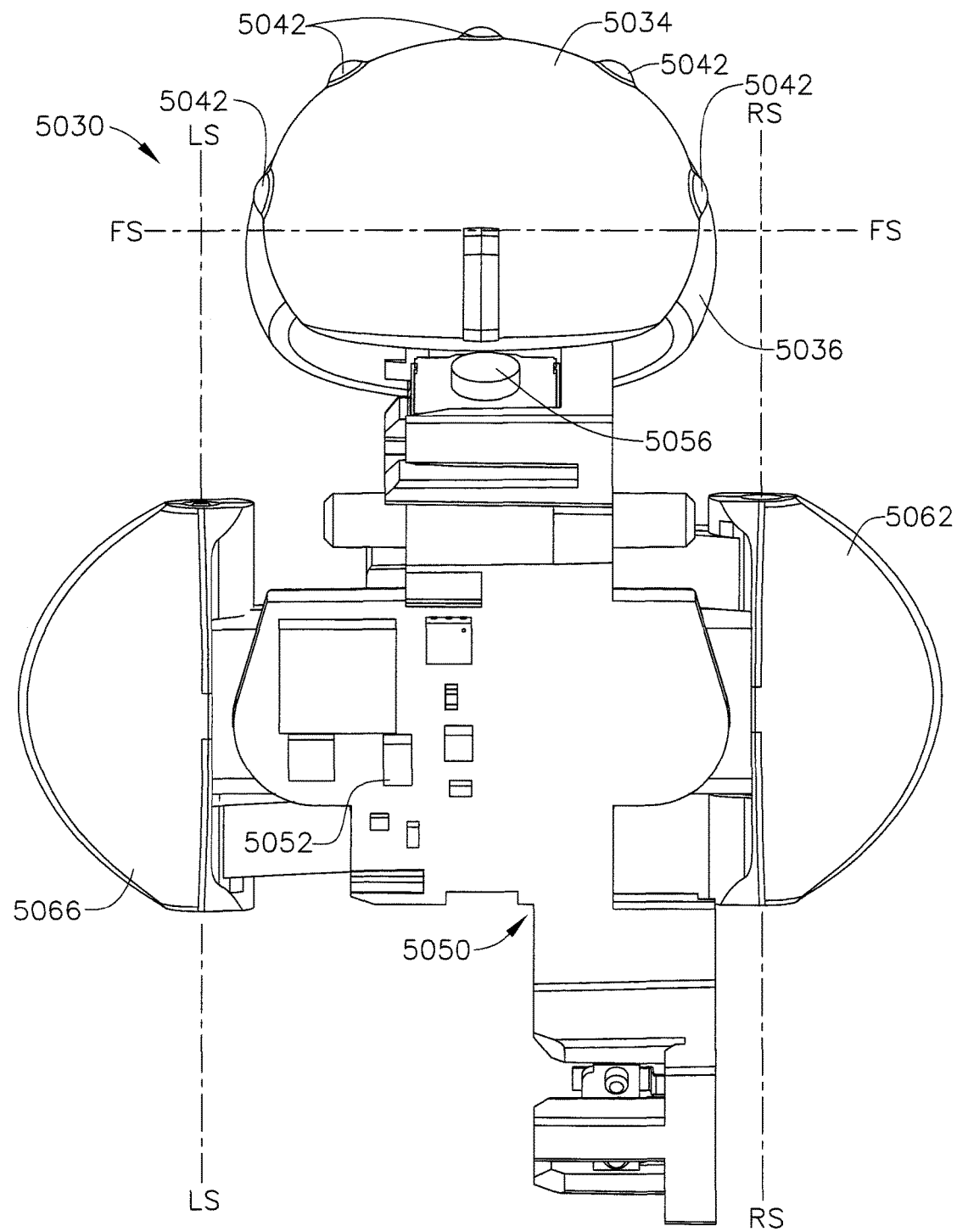
FIG. 109 is a top view of the switch assembly of FIGS. 106-109 according to various forms herein.

In various forms, the switch assembly 5020 also includes a second switch arrangement 5060. Referring to FIGS. 107-109, the second switch arrangement 5060 may include a right switch button 5062 and a left switch button 5066 that are each pivotally attached to the switch frame 5050. For example, the right switch button 5062 is pivotally attached to or pinned to the switch frame 5050 for selective pivotal travel about a right switch axis RS-RS that is substantially transverse to the first switch axis FS-FS. See FIGS. 108 and 109. Likewise, the left switch button 5066 is pivotally attached to the switch frame 5050 for selective pivotal travel about a left switch axis LS-LS. In alternative arrangements, the right and left switch buttons 5062, 5066 may be pivotally supported by the handle housing segments 5004, 5006.

In at least one form, the right and left buttons 5062 and 5066 may have a general "barrel-shape" to facilitate ease of actuation by the clinician's thumb and/or finger. This ease of actuation is further enhanced by the fact that the right and left buttons 5062, 5066 are strategically located in the general thumb groove areas associated with each handle housing segment. For example, if the clinician is holding the pistol grip 5008 in his or her right hand, the clinician may activate the right switch button 5062 by sweeping his or her right thumb down across the right switch button 5062 in a contacting sweeping motion. Similarly, if the clinician was holding the pistol grip 5008 in his or her left hand, he or she may activate the left switch button 5066 by sweeping her left thumb down across the left switch button 5066 in a contacting sweeping motion. Such unique and novel switch arrangements enable activation of the left and right switch buttons 5062, 5066 by avoiding inadvertent activation from direct inward forces to the switch buttons.

As can be seen in FIG. 108, the right switch button 5062 has a right switch arm 5064 protruding therefrom for actuating a right contact pad 5058 that comprises a portion of the circuit board 5052. Likewise, the left switch button 5062 has a left switch arm 5068 protruding therefrom for actuating a left contact pad 5059 that comprises a portion of the circuit board 5052. Thus, those of ordinary skill in the art will understand that by rocking or pivoting the right switch button 5062 about the right switch axis RS-RS, the clinician can activate the right contact pad 5058 and by rocking the left switch button 5066, the clinician can activate the left contact pad 5059. The left and right contact pads 5058, 5059 may be in electrical communication with a generator, e.g., via the connector module 5057. The generator may be programmed to modify the operation of the instrument 5000 in any suitable manner in response to the activation of one of the switch buttons 5062, 5066. For, example, in some forms one or both of the switch buttons 5062, 5066 may be associated with an algorithm, such as those described herein. For example, when the user selects one of the buttons 5034, the generator may execute an algorithm, such as, for example, one or more of algorithms 3021, 3021', 3021", 3120, 3170 any of the algorithms described with respect to FIGS. 15A-15C, 20-22, 57-60, etc. In some forms, the generator is configured to execute the same algorithm in response to activation of either of the switch buttons 5062, 5066, for example, so as to accommodate clinicians that are right or left handed.

Figure 109A:
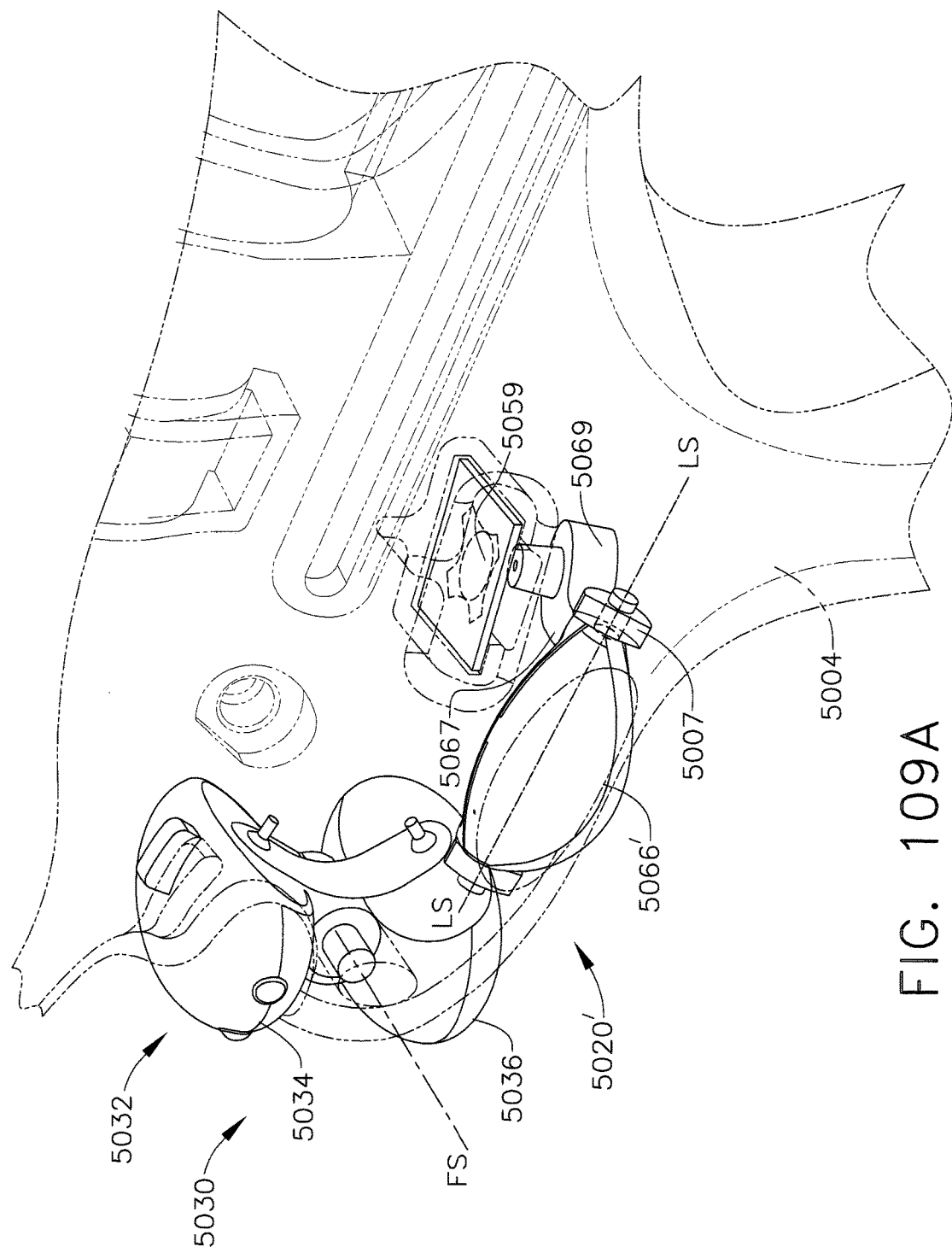
FIG. 109A is a left side view of a portion of another ultrasonic handle assembly according to various forms described herein.

FIG. 109A, illustrates a switch assembly 5020' that may include the first switch arrangement 5030 as well as a second switch arrangement 5060'. In at least one form, the second switch arrangement 5060' includes a left switch button 5066' that has a left pivot arm 5067 protruding therefrom. The left switch button 5066' may be pivotally mounted on pivot mounts 5007 or formations molded or otherwise formed in the left handle housing 5004. The left switch button 5066' may have a barrel-like shape or configuration and be selectively pivotable about a left switch axis LS-LS that may be substantially transverse to the first switch axis FS-FS. The clinician may selectively pivot the left switch button 5066' to bring an actuator portion 5069 of the left switch arm 5067 into actuation contact with a corresponding left contact pad 5059 supported within the handle assembly. In the illustrated arrangement, the second switch arrangement only includes the left switch button 5066' as described above. In alternative forms, the second switch arrangement may only include a right switch button mounted on the right side of the handle housing in the manner illustrated in FIG. 109A. Still other forms of the second switch arrangement may include both right and left switch buttons mounted in the manner illustrated in FIG. 109A.

Figure 110:
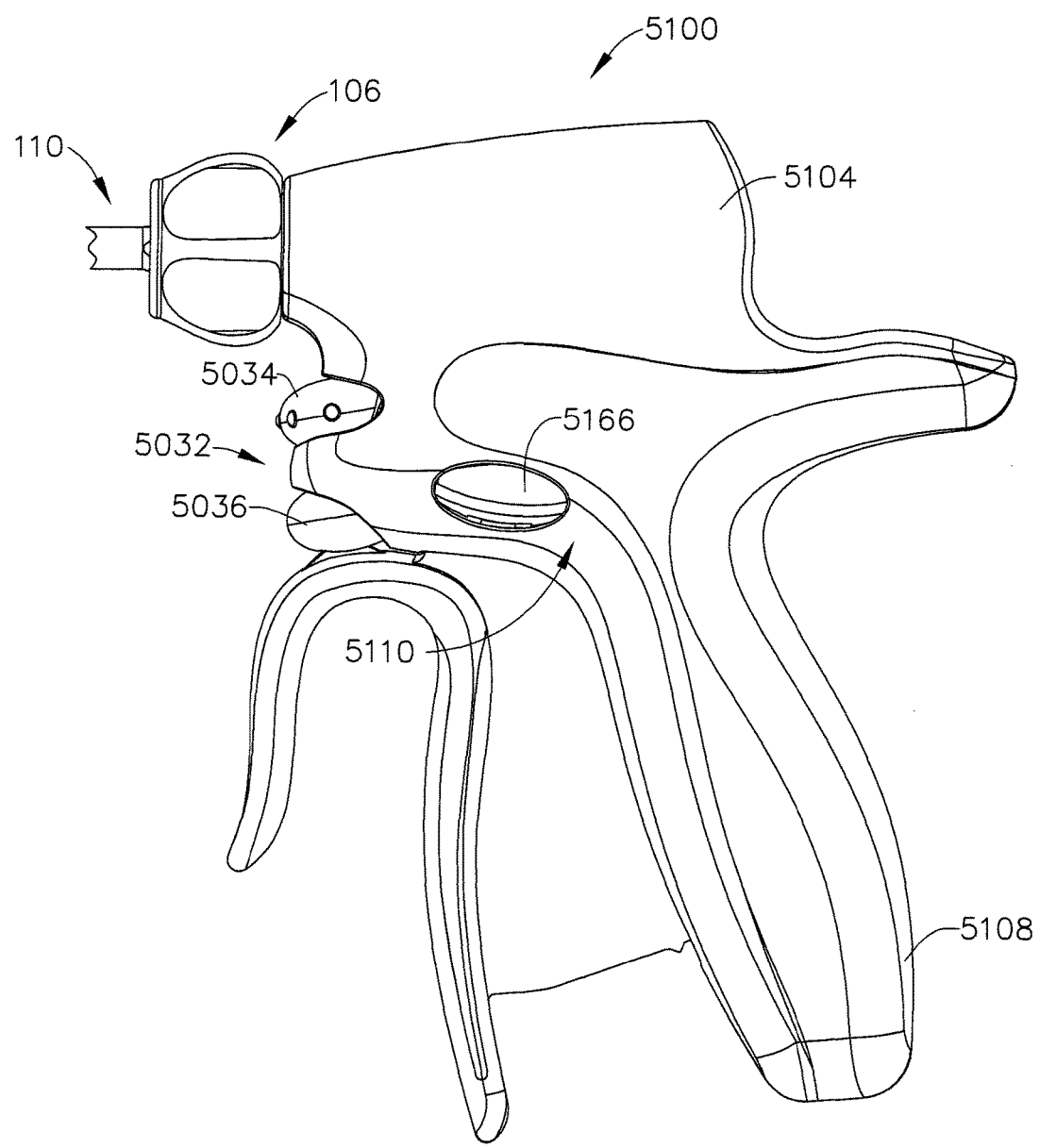
FIG. 110 is a left side elevational view of another ultrasonic handle assembly according to various forms described herein.
Figure 111:
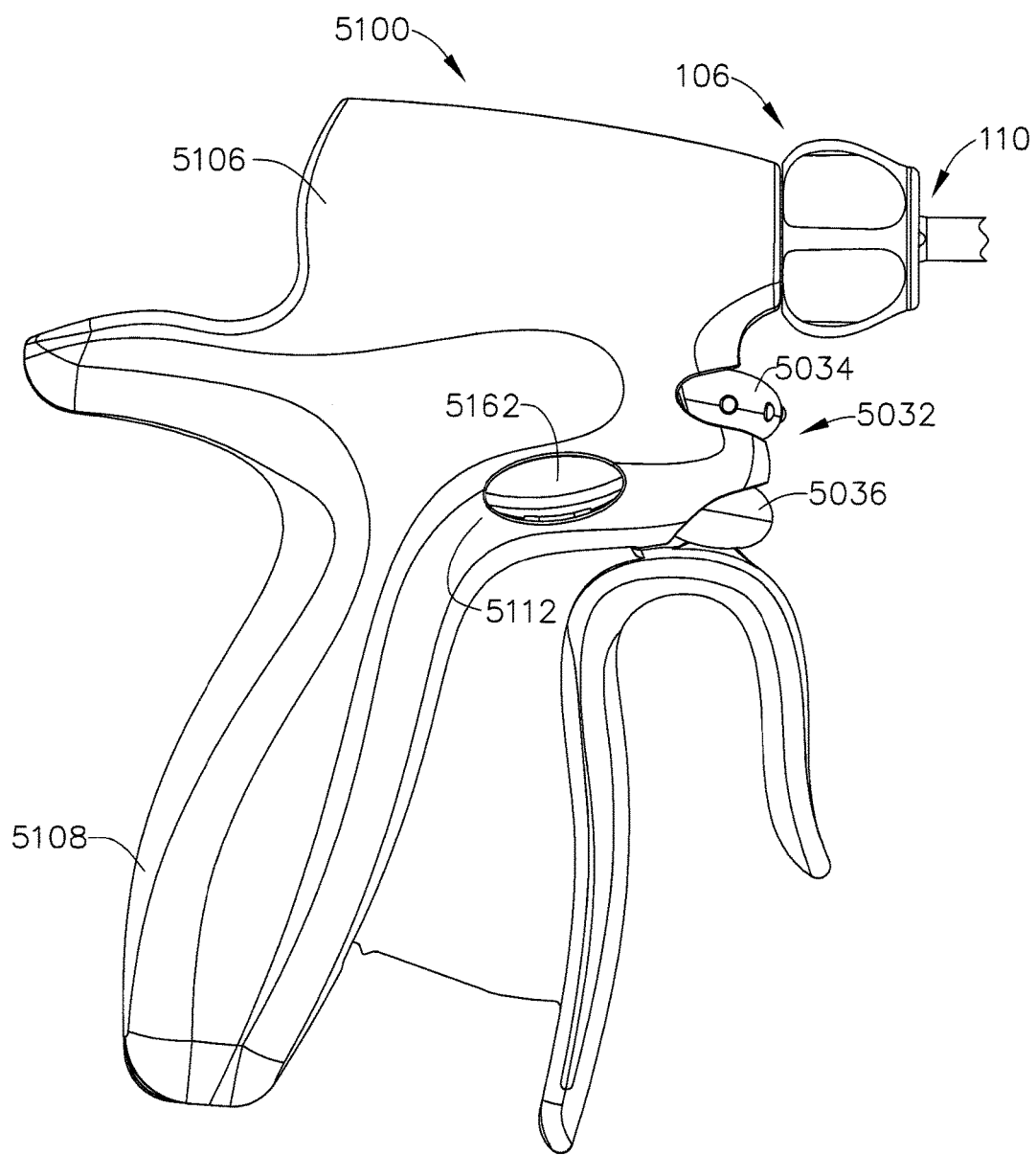
FIG. 111 is a right side elevational view of the ultrasonic handle assembly of FIG. 110 according to various forms described herein.

FIGS. 110 and 111 illustrate another form of a handle assembly 5100 that is similar to the handle assembly 5000 described above, except that the right and left switch buttons 5162, 5166 do not pivot, but instead are supported in their respective handle housing segments 5106, 5104 such that they may be depressed inwardly into contact with their respective right and left contacts (not shown). As with the handle assembly 5000 described above, however, the right and left switch buttons 5162, 5166 are located in the general thumb groove areas 5012, 5010, respectively in the manner described above to facilitate ease of operation when the clinician is gripping the pistol grip portion 5108.

Figure 112:
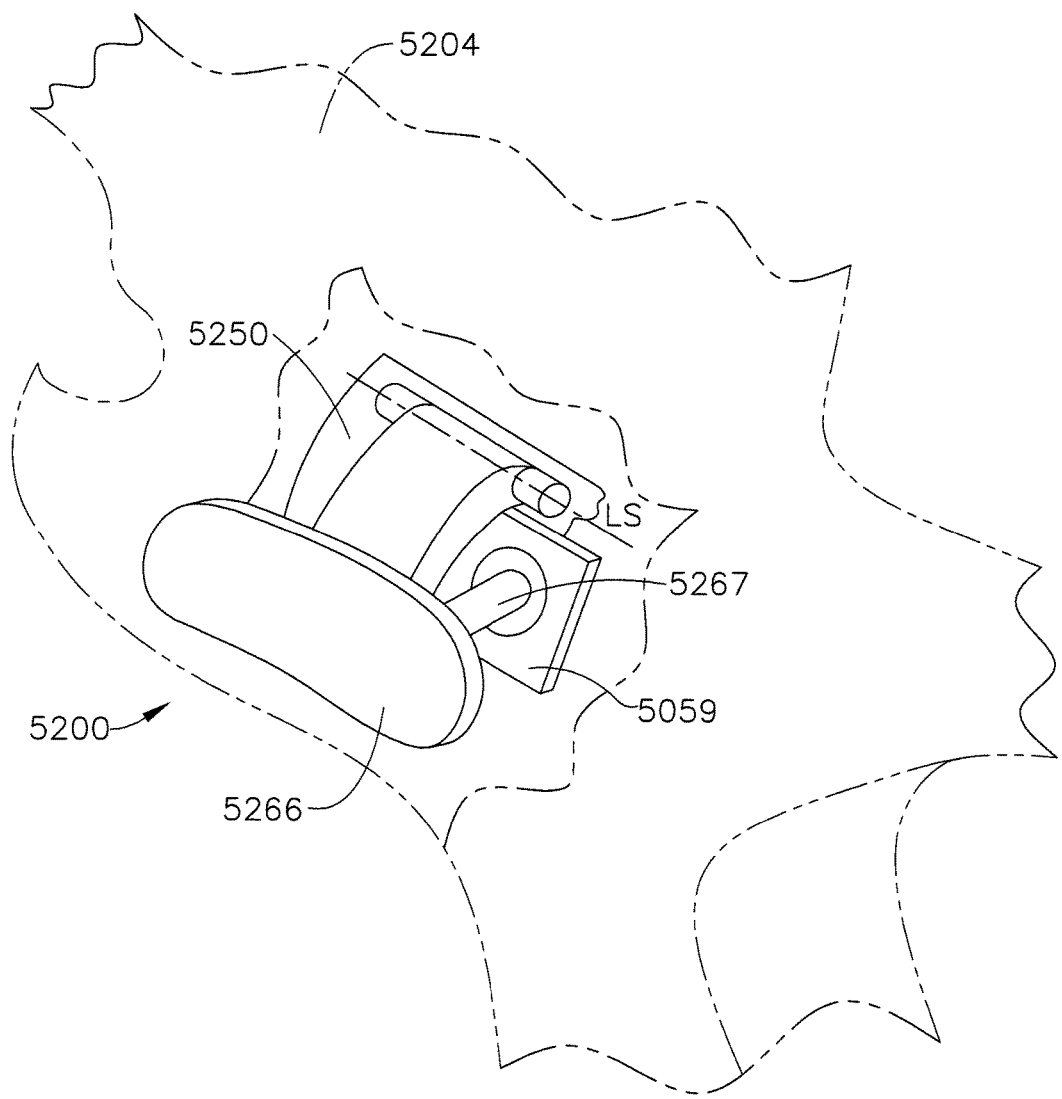
FIG. 112 is a perspective view of a portion of another ultrasonic handle assembly according to various forms described herein.

FIG. 112 illustrates a portion of a left handle housing segment 5204 of another handle assembly 5200 wherein a left side button 5266 thereof may be pivotally coupled to the switch frame 5250 as shown and be formed with a switch post 5267 that is adapted to be pivoted into actuation contact with the corresponding left contact pad 5059. The right button assembly (not shown) of the handle assembly 5200 may be similarly configured. In alternative arrangements, the right and left buttons may be pivotally coupled to their respective handle housing segments.

Figure 113:
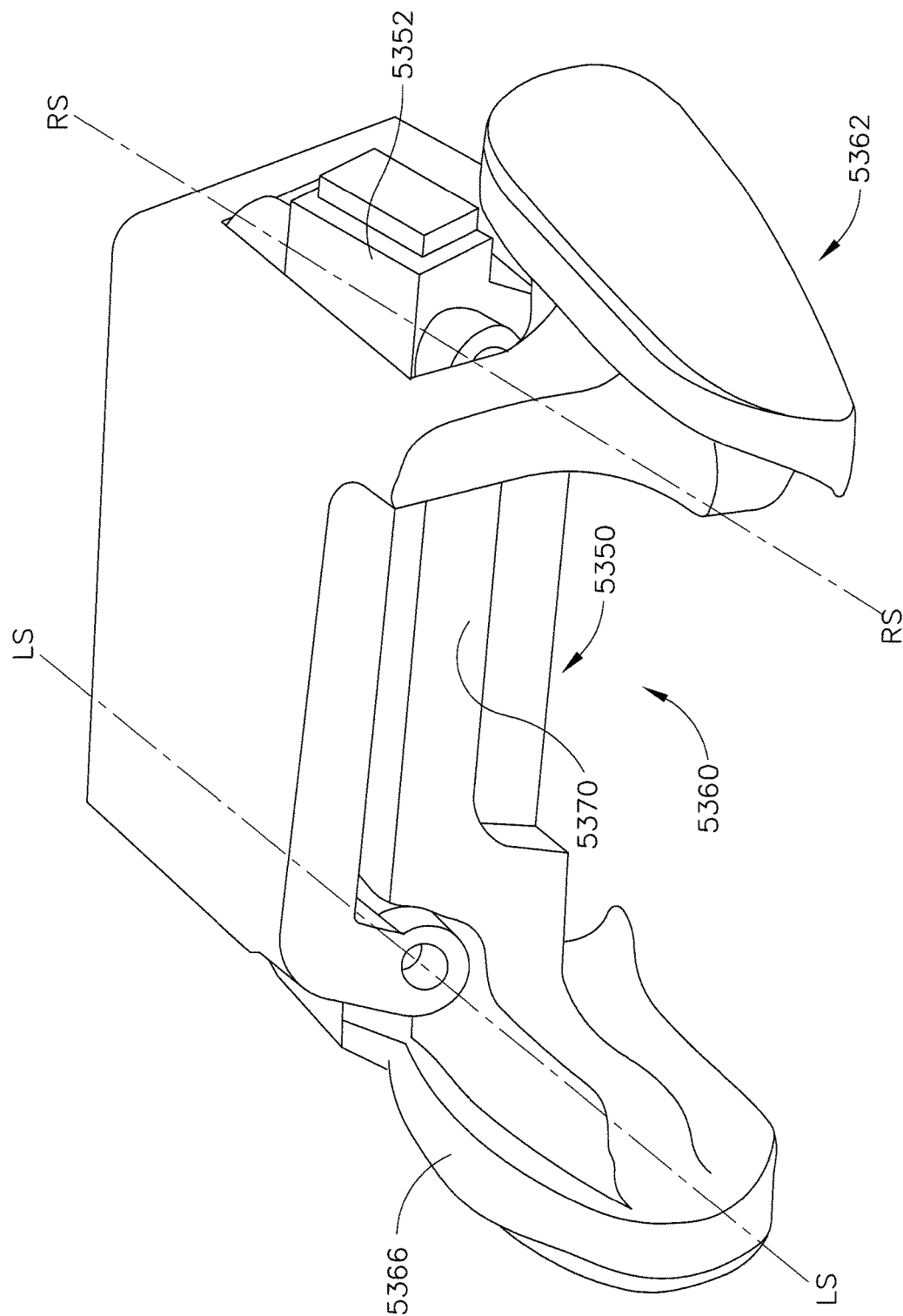
FIG. 113 is a perspective view of another second switch arrangement according to various forms described herein.
Figure 114:
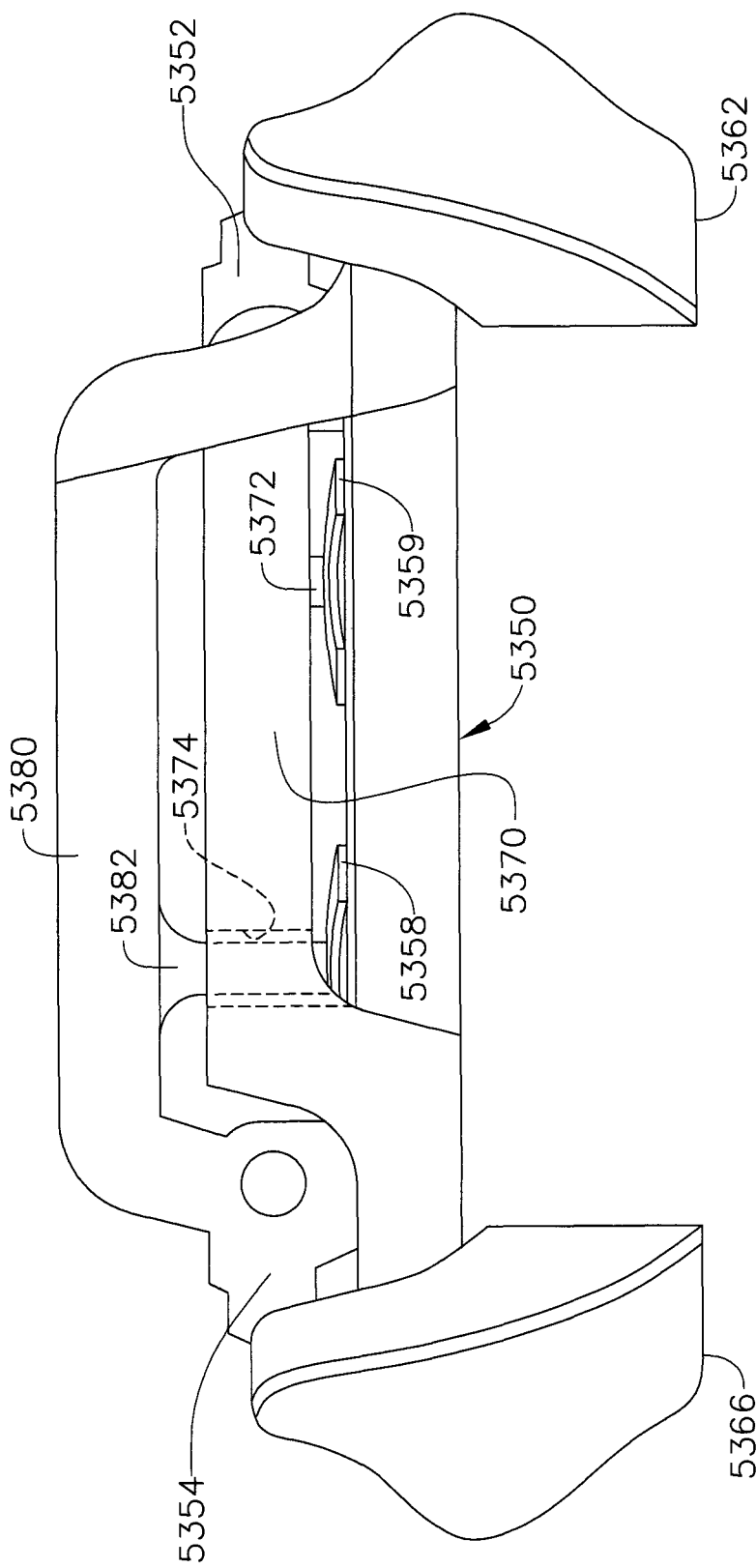
FIG. 114 is a rear elevational view of the second switch arrangement of FIG. 113 according to various forms described herein.

FIGS. 113 and 114 illustrate another form of a second switch arrangement 5360 that may be employed for example in a handle assembly 5000 described above in place of the second switch arrangement 5060. As can be seen in FIGS. 113 and 114, the second switch arrangement 5360 may include a left switch button 5366 that has a left switch arm 5370 that extends laterally above and across a switch frame 5350 which is supported within the handle assembly as was discussed above. The left switch arm 5370 is configured to be pivotally coupled to a right portion or formation 5352 of the switch frame 5350 which is adjacent to a right handle housing (not shown) of the handle assembly. The left switch arm 5370 may be pinned for example to the right portion 5352 of the switch frame 5350 to define a right switch axis RS-RS about which the left switch arm may pivot. See FIG. 113. A left actuation pin or lug 5372 extends downwardly from the left switch arm 5370 such that when clinician rocks the left switch button 5366 in a manner described above, the left actuation pin 5372 is brought into actuation contact with the corresponding left contact pad 5359 supported on the switch frame 5350.

Still referring to FIGS. 113 and 114, the second switch arrangement 5360 may further include a right switch button 5362 that has a right switch arm 5380 that extends laterally above and across the left switch arm 5370 to be pivotally coupled to a left portion or formation 5354 of the switch frame 5350 which is adjacent to a left handle housing (not shown) of the handle assembly. The right switch arm 5380 may be pinned for example to the left portion 5354 of the switch frame 5350 to define a left switch axis LS-LS about which the right switch arm 5380 may pivot. See FIG. 113. A right actuation pin or lug 5382 extends downwardly from the right switch arm 5380 through a corresponding hole 5374 in the left switch arm 5370 such that when clinician rocks the right switch button 5362 in a manner described above, the right actuation pin 5382 is brought into actuation contact with the corresponding right contact pad 5358 supported on the switch frame 5350. The right and left switch axes may be substantially parallel to each other, but laterally displaced from each other. When employed in a handle assembly that includes a first switch arrangement 5030, the right and left switch axes may each be substantially transverse to the first switch axis FS-FS of that first switch arrangement. Those or ordinary skill in the art will understand that such switch arrangement facilitates longer pivot arms or lengths which also facilitate button motion that is substantially straight down.

Figure 115:
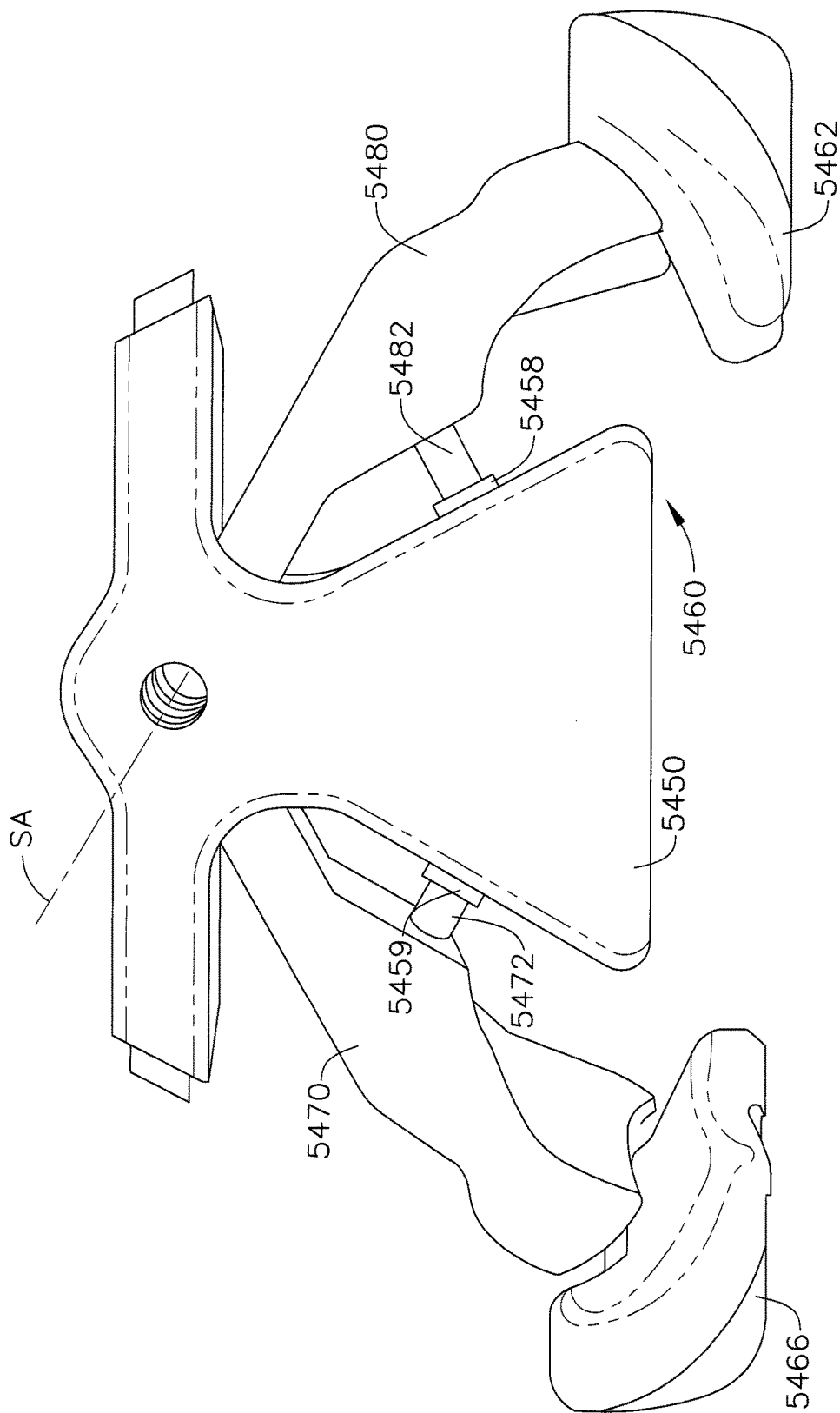
FIG. 115 is a rear elevational view of another second switch arrangement according to various forms described herein.

FIG. 115 illustrates another form of second switch arrangement 5460 that may be employed for example in a handle assembly 5000 described above in place of the second switch arrangement 5060. As can be seen in that Figure, the left and right switch buttons 5566, 5562 are configured to be pivotally coupled to a switch frame 5450 that is centrally disposed between the switch buttons 5566, 5562 and which defines a single switch axis SA. When employed in a handle assembly that includes a first switch arrangement 5030, the switch axis SA may be substantially transverse to the first switch axis FS-FS of that first switch arrangement. The switch frame 5450 may be rigidly supported within the handle housing assembly and extend between the respective right and left handle housing segments (not shown).

In at least one form, the right switch button 5462 has a right link 5480 extending therefrom which is pivotally coupled to the switch frame 5450. Likewise, the left switch button has a left link 5470 extending therefrom to be pivotally coupled to the switch frame 5460. The right and left links 5480, 5470 may be pivoted to the switch frame 5450 by a common pin (not shown) to define the switch axis SA about which the buttons 5462 and 5466 may pivot. A right actuation pin or lug 5482 extends inwardly from the right switch link 5480 such that when clinician rocks or pivots the right switch button 5462 in a manner described above, the right actuation pin 5482 is brought into actuation contact with the corresponding right contact pad 5458 supported on the switch frame 5450. Likewise, a left actuation pin or lug 5472 extends inwardly from the left switch link 5470 such that when the clinician rocks or pivots the left switch button 5466 in a manner described above, the left actuation pin 5472 is brought into actuation contact with the corresponding left contact pad 5459 on the switch frame 5450. Each of the switch arms 5470 and 5480 may be biased into unactuated positions by corresponding springs or biasing arrangements (not shown) positioned, for example, between switch link 5470, 5480 and the frame 5450.

Figure 116:
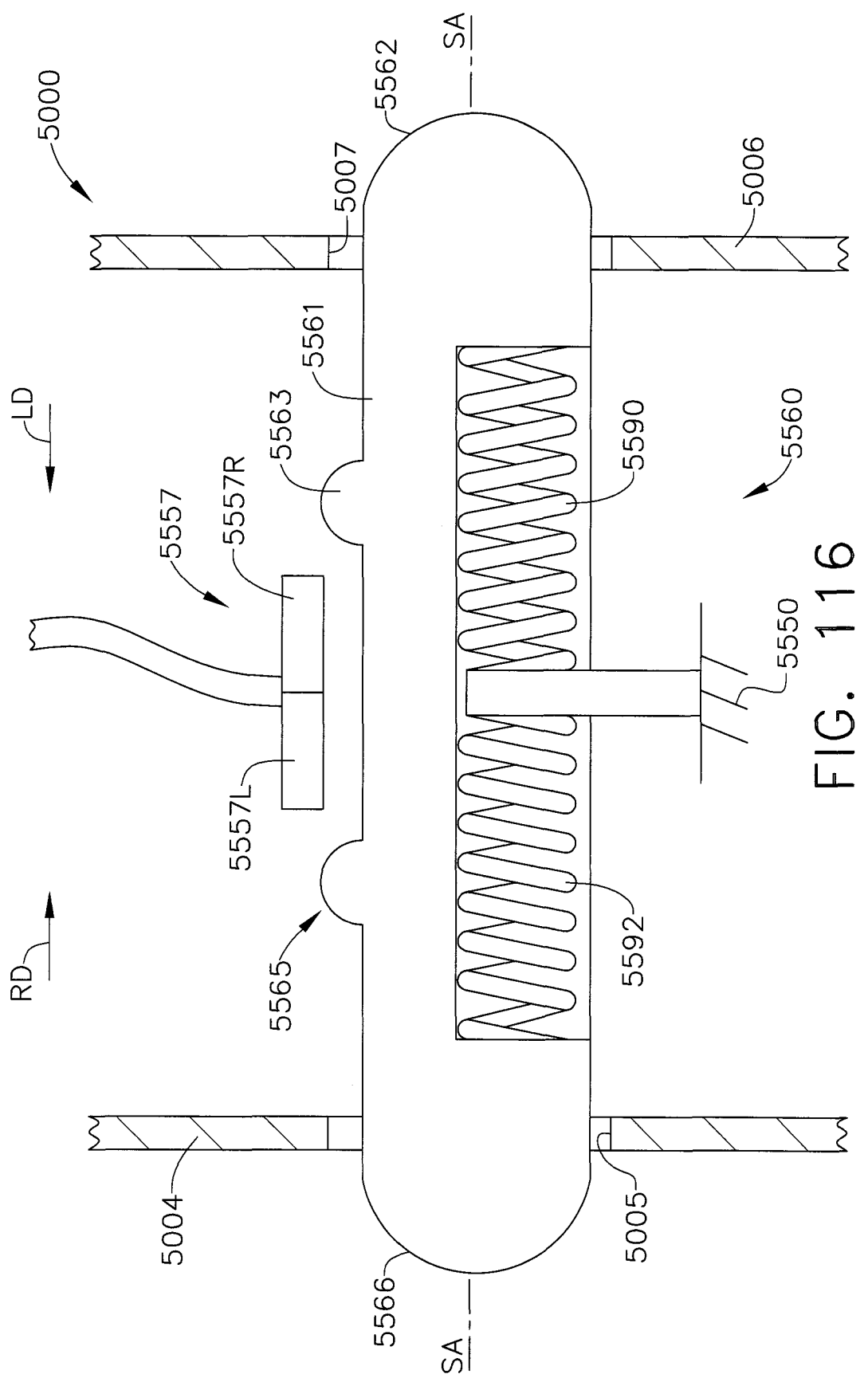
FIG. 116 is a top view of a portion of a second switch arrangement and handle assembly according to various forms describe herein.

FIG. 116 illustrates another form of second switch arrangement 5560 that may be employed for example in a handle assembly 5000 described above in place of the second switch arrangement 5060. As can be seen in that Figure, the second switch arrangement 5560 employs a single second switch actuator 5561 that extends between the right handle housing portion 5006 and the left handle housing portion 5004 such that a right end thereof forms the right switch button 5562 and the left end thereof forms the left switch button 5566. The second switch actuator 5561 slidably extends through corresponding openings 5005 and 5007 in the left and right handle housing segments 5004, 5006 such that the second actuator 5561 may be selectively axially displaceable along a switch axis SA-SA. When employed in a handle assembly 5000 that includes a first switch arrangement 5030, the switch axis SA-SA may be substantially parallel to the first switch FS-FS axis of that first switch arrangement.

A right biasing member 5590 and a left biasing member 5592 may be positioned within the second switch actuator 5561 and configured to cooperate with a centrally disposed portion of the switch frame 5550 to keep the second switch actuator 5561 centrally disposed in an unactuated position as shown in FIG. 116. A switch contact assembly 5557 may be centrally located between a right actuator member or protrusion 5563 attached to or formed on the second actuator 5561 and a left actuator member or protrusion 5565 formed on the second actuator 5561. The switch contact assembly 5557 may, for example, have a right portion 5557R that corresponds to the right actuator 5563 and a left portion 5557L that corresponds to the left actuator member 5565. Thus, by depressing the right switch button 5562 inwardly, the second switch actuator 5561 will move laterally in the left direction "LD" to bring the right actuator 5563 into actuation contact with the right portion 5557R of the switch contact assembly 5557. Likewise, by depressing the left switch button 5566 inwardly, the second switch actuator 5561 will move laterally in the right direction "RD" to bring the left actuator 5565 into actuation contact with the left portion 5557L of the switch contact assembly 5557.

FIGS. 117-120 depict in somewhat diagrammatic form a switch assembly 5620 that may be employed in connection with the various ultrasonic handle assemblies disclosed herein. In at least one form, the switch assembly 5620 includes a single button assembly 5632 that may be located, for example, where the first button assembly 5032 is positioned in the handle assembly 5000 as was described in detail above. For example, the button assembly 5632 may include a button carriage arm 5633 that has an actuator button 5634 formed thereon that may actuatable by the clinician's index finger when the clinician is gripping the pistol portion of the corresponding handle assembly.

In at least one form, the button carriage arm 5633 may include a pair of pivot pins 5637, 5639 that are movably received within an elongate slot 5671 in a switch housing 5670 that is operably supported within the handle housing. The button pivot pins 5637, 5639 facilitate axial movement of the button carriage arm 5633 (FIG. 118) as well as rotational or pivotal movement of the button carriage arm 5633 relative to the switch housing 5670 (FIGS. 119 and 120). As can be seen in FIGS. 117-120, the elongate slot 5671 opens into a three-way actuator opening 5673 that has a right end 5675 that corresponds to a right switch 5658, a left end 5677 that corresponds to a left switch 5659 and a central end 5679 that corresponds to a central switch 5654. As can be seen in FIG. 117, the button carriage arm 5633 may include a left switch actuator portion 5690, a central switch actuator portion 5692 and a right switch actuator portion 5694. In addition, a right spring 5680 and a left spring 5682 may be provided between the button carriage arm 5633 and the handle housing 5002 to keep the button carriage arm 5633 in a central and neutral position (FIG. 117) when it is unactuated.

Operation of the switch assembly 5620 may be understood from reference to FIGS. 118-120. FIG. 118 illustrates actuation of the central switch 5654 by depressing the actuator button 5634 inwardly as represented by arrow "D". As the actuator button 5634 is depressed, the button carriage arm 5633 moves axially along or relative to the elongate slot 5671 in the switch housing 5670 to bring the central switch actuator portion 5692 into actuation contact with the central switch 5654. FIG. 119 illustrates actuation of the right switch 5658 by pivoting the actuator button 5634 in the direction represented by the arrow labeled "MIN" which brings the right switch actuator portion 5694 into actuation contact with the right switch 5658. FIG. 120 illustrates actuation of the left switch 5659 by pivoting the actuator button 5634 in the direction represented by the "MAX" arrow which brings the left switch actuator portion 5690 into actuation contact with the left switch 5659. The respective switches 5654, 5658, 5659 may be in electrical communication with a generator, for example, via a connector module 5057, as described herein above. The generator may be programmed to perform any suitable action with respect to the instrument 500 in response to activation of one of the switches 5654, 5658, 5659. For example, in some forms, switches 5658 and 5659 perform a function similar to that of the finger buttons 5034, 5036 described above. For example, activating one of the buttons 5658, 5659 may cause the generator to increase the power provided to the end effector while activating the other button 5658, 5659 may cause the generator to decrease the power provided to the end effector. Also, responsive to any one or more of the buttons 5654, 5658, 5659, the generator may be configured to an algorithm, such as, for example, one or more of algorithms 3021, 3021', 3021", 3120, 3170 any of the algorithms described with respect to FIGS. 15A-15C, 20-22, 57-60, etc.

Different clinicians often have different techniques for using ultrasonic surgical instruments and systems as described herein. For example, some clinicians routinely activate an ultrasonic surgical instrument without fully closing the clamp arm against the blade. Although some clinicians believe that this technique improves system performance, in practice it often does not and has the potential to damage tissue, for example, by requiring longer transection times and sometimes causing transection and/or coagulation to be compromised.

In various forms, this and other problems may be addressed by configuring a surgical instrument with a closure switch indicating when the clamp arm is fully closed. The generator may be configured to refrain from activating the surgical instrument until or unless the closure switch indicates that the clamp arm is fully closed. Referring now to FIGS. 95 and 105, some forms of the closure switch are positioned in the handle 4122 (FIG. 95). For example, both FIGS. 95 and 105 illustrate an optional closure switch 5900 positioned on an inside, proximal portion of the handle 4122 (FIG. 95) and one or more of the handle housing segments 5004, 5006 (FIG. 105).

The switch 5900 may be positioned such that the trigger 4124 contacts the switch 5900 at its proximal-most position. For example, the switch 5900 may be positioned at an end of the stroke of the trigger 4124 (e.g., in the direction of arrow 4121a in FIG. 93). In this way, the trigger 4124 may contact the switch 5900 when the trigger 4124 is pulled proximally to close the clamp arm against the blade. In various forms, the switch 5900 may be positioned anywhere were it will be activated when the end effector is closed (e.g., the clamp arm is pivoted towards the blade). For example, the switch 5900 may be positioned distal of the yoke 4174 and/or reciprocating tubular actuating member 4138, so as to be activated when one or the other of those components translates distally to close the end effector. The switch 5900 may be in electrical communication with the generator, such as generator 30, 50, 1002, for example, via the connector module 5057 and/or 4200 and hand piece, as described herein. In various forms, the generator is programmed not to activate the surgical instrument unless the switch 5900 is also activated. For example, if the generator receives an activation request from one or more of the switches described herein, it may respond to the activation request only if the switch 5900 is activated to indicate that the clamp arm is closed.

Figure 121:
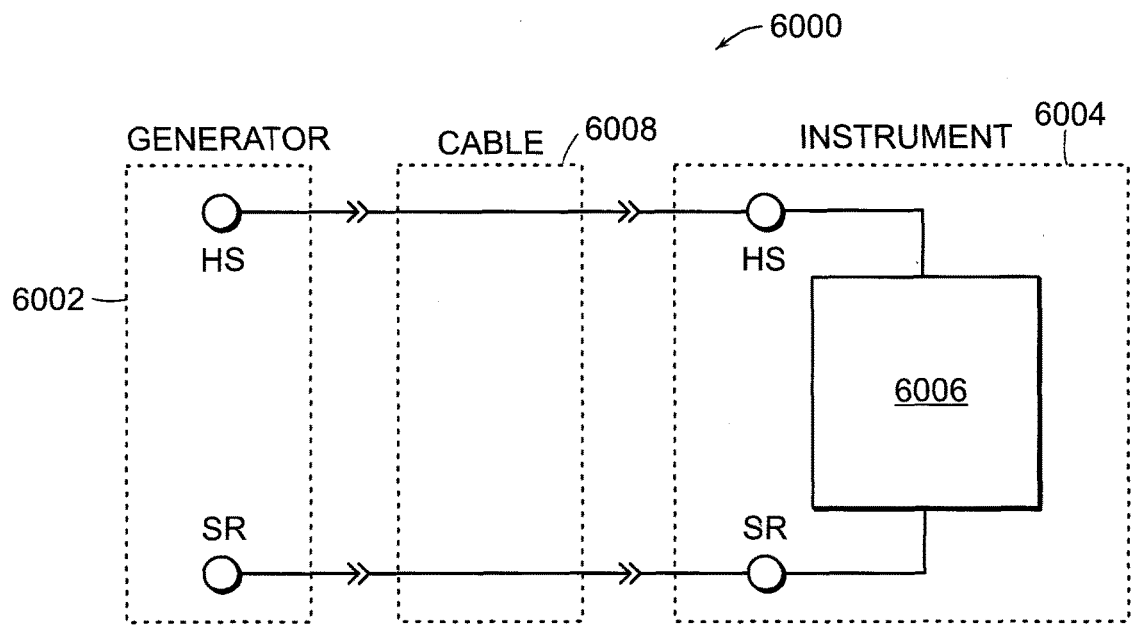
FIG. 121 illustrates a block diagram of a system depicting a generator coupled to a medical instrument and a circuit.

FIG. 121 illustrates a block diagram of a system 6000 depicting a generator 6002 coupled to a medical instrument 6004 and a circuit 6006. The generator 6002 may be coupled directly to the instrument 6004 or may be coupled through a cable 6008. The circuit 6006 may be connected to the generator 6002 to receive an encoded transmission frame of bits from a signal conditioning circuit 2002 (e.g., from generator 1002 terminals HS and SR (FIG. 19) via a pair of conductive elements HS/SR). In various forms, the generator 6002 is functionally equivalent to the generator 2002 and has been described in connection with FIG. 19. Therefore, for conciseness and clarity, the description of the generator 2002, 6002 will not be repeated here. Nevertheless, it will be appreciated that other generators may be employed in the system 6000. Also, although some aspects of the disclosed serial protocols may be described hereinbelow in connection with various circuits and systems, it will be appreciated that any scope of the present disclosure is intended to encompass any and all methods for generating signals over a transmission frame in accordance with the protocol timing diagrams disclosed in FIGS. 123-128.

The encoded transmission frame, which is described in detail hereinbelow in connection with FIGS. 123-127, is a repetitive, bidirectional communication signal, where an encoded frame is repeatedly transmitted by the generator 6002. The frame comprises a series of bits that simultaneously encode input/output (I/O) information on a single bit by modulating both the amplitude of the bit and the pulse width of the bit. The input bits are encoded such that information regarding the state of the circuit 6006 is communicated to the generator 6002 simultaneously with output bits encoded with information from the generator 6002 regarding how to set the outputs of the circuit 6006 and, accordingly, the output states of the instrument 6004. In various forms described herein, the generator 6002 modulates or sets the width of the pulses (time) to communicate information from the generator 6002 to the circuit 6006 on how to set the outputs of the circuit 6006. In various forms described herein, the circuit 6006 modulates or sets the height (amplitude) of the pulses to communicate information about the state of the circuit to the generator 6002. Furthermore, in one form, the circuit 6006 may be parasitically powered from the bidirectional communication signal includes no other power source. In other forms, the circuit 6006 may be powered from other power sources. In other forms, the circuit 6006 may be both parasitically powered from the bidirectional communication signal and other power sources.

The instrument 6004 comprises a circuit 6006, which may include at least one switch that, in conjunction with the generator 6002, supports activation switch inputs and instrument EEPROMs. The circuit 6006 may be provided within the instrument (as shown above with respect to data circuits 2006, 2007. In some embodiments, the circuit 6006 may be positioned on the hand piece, such as hand piece 1014 and may provide the generator with hand piece specific data such as, for example, a current set point, a gain, etc. The instruments 6004 provides various I/O capabilities and may employ a plurality of switch inputs, analog inputs as well as discrete outputs, analog outputs. In order to implement the functionality of the plurality of switch inputs and outputs, the circuit 6006 communicates with the generator 6002 using a novel serial communication protocol, the timing diagrams of which are illustrated in connection with FIGS. 122-127. The circuit 6006 is configured to short circuit the HS-SR electrical conductive elements electrically coupling the generator 6002 and the instrument 6004. Short circuiting the HS-SR lines enables the circuit 6006 to set the transmission frame start and stop pulses, which also may be referred to as start/stop bits. In addition to setting the frame length, short circuiting the HS-SR lines enables the generator 6002 to conduct a loop calibration where the generator 6002 measures the loop resistance for each frame being transmitted.

Forms of the generator 6002 may enable communication with one or more circuits 6006 contained in the instrument 6004. In certain forms, the circuit 6006 may generally be any circuit for transmitting and/or receiving data. In one form, for example, the circuit 6006 may store information pertaining to the particular surgical instrument 6004 with which it is associated. Such information may include, for example, a model number, a serial number, a number of operations in which the surgical instrument has been used, and/or any other type of information. Additionally or alternatively, any type of information may be communicated to circuit 6006 for storage therein. Such information may comprise, for example, an updated number of operations in which the instrument 6004 has been used and/or dates and/or times of its usage. In certain forms, the circuit 6006 may transmit data acquired by one or more sensors (e.g., an instrument-based temperature sensor). In certain forms, the circuit 6006 may receive data from the generator 6002 and provide an indication to a user (e.g., an LED, power switch information, and audible and/or visible indication) based on the received data.

In certain forms, the circuit 6006 may be configured such that communication between instrument 6004 and the generator 6002 can be effected without the need to provide additional conductors for this purpose (e.g., dedicated conductors of a cable connecting a hand piece to the generator 6002). In one form, for example, information may be communicated to and from the circuit using a 1-wire bus communication scheme implemented on existing cabling, such as one of the conductors used to transmit interrogation signals from the signal conditioning circuit to the circuit 6006 in the instrument. In this way, design changes or modifications to the instrument 6004 that might otherwise be necessary are minimized or reduced. Moreover, because different types of communications can be implemented over a common physical channel (either with or without frequency-band separation), the presence of the circuit 6004 may be "invisible" to the generators that do not have the requisite data reading functionality, thus enabling backward compatibility of the instrument 6004.

The generator 6002 may exchange information with the circuit 6006 that is specific to a surgical device integral with, or configured for use with, the cable 6008 and may comprise, for example, a model number, a serial number, a number of operations in which the surgical device has been used, and/or any other type of information. Information may also be communicated from the generator 6002 to the circuit 6006 for storage therein. In one form, the circuit 6006 need not be located on or in the instrument 6004, but may be disposed in an adaptor for interfacing a specific instrument 6004 type or model with the generator 6002.

Figure 122:
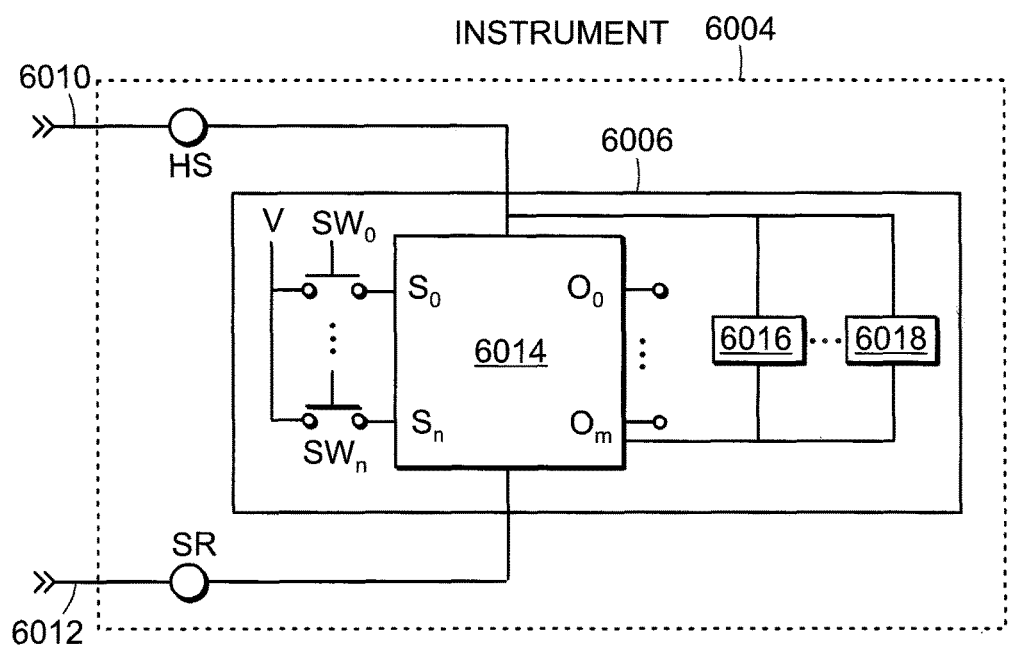
FIG. 122 illustrates a block diagram of a circuit within an instrument.

FIG. 122 illustrates a block diagram of the circuit 6006 within the instrument 6004. The circuit 6006 may be connected to the generator to receive an interrogation signal via a pair conductive pair of conductive elements 6010, 6012. The circuit 6006 may comprise multiple branches. A first branch comprises a controller 6014, a second branch comprises a data circuit 6016, and additional branches may comprise additional data circuits 6018 or other circuits, sensors, switches, indicators (audible, tactile, visual). The controller 6014, the data circuits 6018, and/or other circuits may be parasitically powered by the energy in the frame bits.

In other forms, the controller 6014, the data circuits 6018, and/or other circuits may be powered from other power sources. In other forms, the controller 6014, the data circuits 6018, and/or other circuits may be both parasitically powered from the bidirectional communication signal and other power sources.

The controller 6014 may be an application specific integrated circuit (ASIC), a microcontroller comprising a processor and memory, a digital signal processing circuit, a programmable logic device, field programmable gate array, discrete circuit, and the like. The controller comprises a plurality of inputs $S_0$ to $S_n$, where n is a suitable integer. As illustrated in FIG. 122, the plurality of inputs $S_0$ to $S_n$ are coupled to a plurality of switches $SW_0$ to $SW_n$, where n is any suitable integer. The switches $SW_0$ to $SW_n$ provide inputs to the controller 6014 to control functions associated with the instruments 6004. The controller 6014 communicates the states of the switches $SW_0$ to $SW_n$ to the generator 6002 via a serial protocol in accordance with the present disclosure.

The controller 6014 also comprises a plurality of outputs $O_0$ to $O_m$, where m is any suitable integer, and may be the same as n. The outputs $O_0$ to $O_m$ are driven by the controller 6014 to control functions associated with the instrument 6004 in accordance with information communicated by the generator 6002.

In various forms, the circuit 6006 also may comprise one or more data circuits 6016, 6018 that communicate over a 1-wire protocol. In certain forms, the data circuits 6016, 6018 include storage elements that may be a single-wire bus device (e.g., a single-wire protocol EEPROM), or other single-wire protocol or local interconnect network (LIN) protocol device. In one form, for example, the data storage element 302 may comprise a single wire EEPROM. The data storage element is one example of a circuit element that may be contained in the data circuits 6016, 6018. The data circuit may additionally or alternatively comprise one or more other circuit elements or components capable of transmitting or receiving data. Such circuit elements or components may be configured to, for example, transmit data acquired by one or more sensors (e.g., an instrument-based temperature sensor) and/or receive data from the generator 6002 and provide an indication to a user (e.g., an LED indication or other visible indication) based on the received data.

During operation, the generator 6002 and the circuit 6006 communicate over a robust, flexible, highly noise-immune communications protocol according to the present disclosure. The protocol is used over the two instrument conductive elements 6010, 6012 (HS, HSR) to allow the generator 6002 to communicate up to 8 or more discrete inputs and outputs to the instrument 6004, while coexisting on the same lines as the 1-Wire EEPROM (e.g., data circuits 6016, 6018) communications, and maintaining backward compatibility with existing legacy circuits. The protocol comprises a frame that is repeatedly transmitted. The frame comprises overhead pulses (bits) such as start/stop and header pulses and simultaneously encoded information pulses (bits) that encode both input and output information into a single pulse (bit) by modulating both the amplitude and width (pulse duration) of each information pulse.

Figure 123:
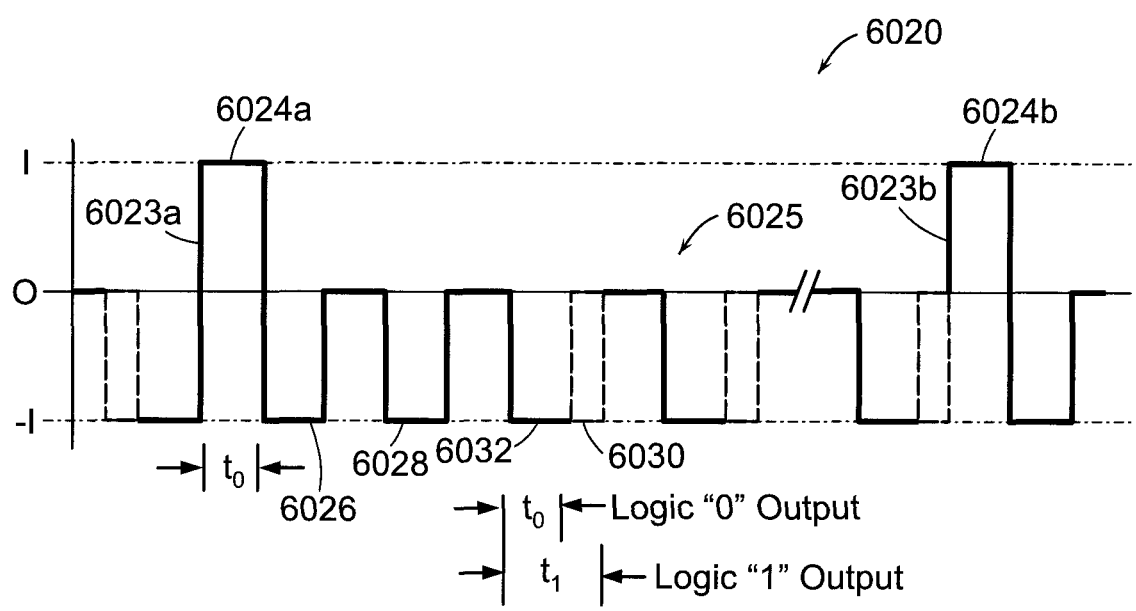
FIG. 123 illustrates a timing diagram of current pulses in a transmission frame of a serial protocol at a generator output.
Figure 124:
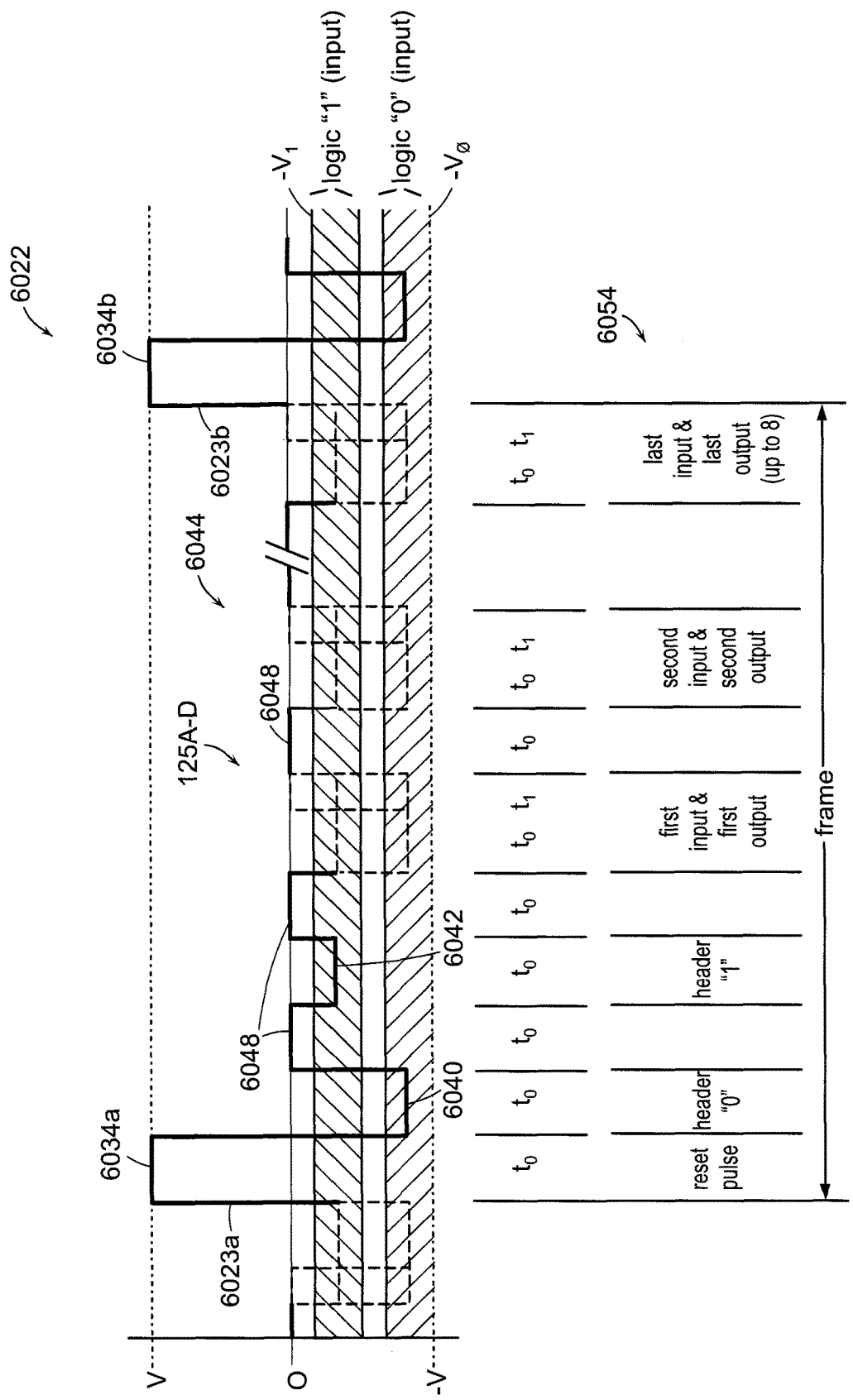
FIG. 124 illustrates a timing diagram of voltage pulses in a transmission frame of a serial protocol at a circuit output.

One form of such a protocol is illustrated in connection with FIGS. 123 and 124, where FIG. 123 shows a timing diagram 6020 of current pulses in a frame of a serial protocol at the generator 6002 output and FIG. 124 shows a timing diagram 6022 of voltage pulses in a frame of the serial protocol at the circuit 6014 output. Turning first to FIG. 123 whose description should be read in conjunction with FIG. 122, the timing diagram 6020 shows an output signal from the generator 6002 to the controller 6014 in the form of current pulses. The current limit (rails) may be selected in accordance with the specific generator 6002/instrument 6006 combination. In one form, for example, the current rails are +15 mA and −15 mA. A frame begins and ends on the rising edges 6023a, 6023b of start/stop pulses 6024a, 6024b generated by the controller 6014 by applying a short circuit across the rails HS-SR. The frame begins on the rising edge 6023a of the start pulse 6024a and ends on the rising edge 6023b of the stop pulse 6024b. The current signal pulses swing from the negative rail −I to the positive rail +I though a zero crossover during the transmission of the start pulse 6024a from the generator 6002 to the controller 6014. After the start pulse 6024 is generated, the header pulses 6026, 6028 and encoded I/O information pulses 6025 are transmitted. After the last encoded information pulse 6025 is transmitted the rising edge 6023b of the stop pulse 6024b signals the end of the current frame. The next frame is then initiated and the process repeats. In one aspect, the frame bits other than the start/stop pulses 6024a, 6024b swing from 0 to the negative rail −I. In other aspects, some of the frame bits following the start pulse 6024a swing between the positive and negative rails +I, −I. The latter aspect is discussed hereinbelow in connection with FIG. 128.

The frame information pulses are simultaneously encoded both in regards to width and amplitude. The width of the start/stop pulses 6204a, 6024b is $t_o$. The current pulses following the start pulse 6024a are header pulses represent header pulses 6026, 6028 and also have a pulse width $t_0$. In the context of encoding output pulses carrying information from the generator 6002 to the instrument 6004, the information pulses 6025 are encode as a logic "1" output pulse 6030 by increasing the pulse to width to $t_1$ whereas a logic "0" output pulse 6032 may have the same pulse width $t_0$ as the start pulse 6024 the header pulses 6026, 6028. Output logic "1" maps to the output active state, where the instrument 6004 is drawing power from the generator 6002. As previously discussed, a frame is initiated with the rising edge 6023a of the start current pulse 6024 by short circuiting the first conductive element 6010 (HS) to the second conductive element 6012 (SR), which are the power and signal lines connecting the generator 6002 with the instrument 6004.

FIG. 124 shows the timing diagram 6022 of voltage pulses +/−V through a zero crossover. The timing diagram 6022 shows I/O information pulses simultaneously encoded with input information from the controller 6014 to the generator 6002 (inputs) and output information from the generator 6002 to the controller 6014 (output). Besides the start pulse 6034a the serial communication occurs between zero and the negative side of the signal. As shown, a logic "1" input voltage signal $-V_1$ is negative but more positive than a logic "0" input voltage signal $-V_0$. Input logic "1" maps to a switch ($SW_0$-$SW_n$) closed state.

With reference now to the timing diagrams 6020, 6022 shown in FIGS. 123, 124 in conjunction with the circuit 6006 shown in FIG. 122, a frame is initiated at the rising edge 6023a of the a start pulse 6034a and ends at the rising edge of the stop pulse 6023b. In between, the frame comprises two header pulses 6040, 6042 transmitted after the start pulse 6024a and a plurality of simultaneously encoded I/O information pulses 6044. In one form, bits 6048 between the header pulses 6042, 6042 and information pulses 6044 return to zero and have a pulse width of $t_0$. In other forms, as described hereinbelow, in connection with FIG. 128, bits between the header pulses 6042, 6042 and information pulses 6044 return to either one of the positive or negative rails in alternating fashion. It will be appreciated that one benefit of such a configuration is exploitation of additional parasitic power from the frame signals to power the circuit 6066.

The information pulses 6044 are encoded to carry information about both input and output. Accordingly, each information pulse 6044 defines a first logic state associated with an input from the instrument 6004 to the generator 6002 as well as a second logic state associated with an output from the generator 6002 to the instrument 6002. The simultaneous encoding of I/O signals is discussed in more detail in connection with FIGS. 125A-D, where the four logic states of an encoded I/O bit are depicted separately for clarity of disclosure.

With reference back to FIG. 124, the header pulse 6040 represents an input logic "0" and header pulse 6042 represents an input logic "1". The header pulses 6040, 6042 can be used by the generator 6002 for presence detection and to identify the circuit 6006 type. The generator 6002 may use specific ADC values read for either or both of the header pulses 6040, 6042, or start bit 6084 to calibrate the ADC ranges for the input pulses within the current frame. The generator 6002 will determine the number of inputs and outputs used by the specific instrument 6004 by reading parameters from the EEPROM 6016, 6018.

The number of I/O pulses per frame may be the greater of the number of used inputs or outputs for a given instrument 6004 or may be a fixed number. Although the maximum number of both inputs and outputs is a predetermined number, for example 8 (16 total), unused inputs and outputs for a given instrument 6004 may or may not be implemented or pinned out. Unused inputs (if there are more outputs than inputs) can be set by the circuit 6006 to logic "0". Unused outputs can be set by the generator 6002 to logic state "0" or "1" as appropriate, to optimize either polling speed or energy transfer to the circuit 6006. The circuit 6006 will store energy from the negative pulses to power both its own circuitry, and any output devices (e.g., LEDs, switches, power switches including transistors, feedback devices, e.g., audio, visual, tactile). EEPROM 6016, 6018 communications will occur on the positive voltage side of the signal.

Turning to the legend 6054 below the timing diagram 6022, it can be seen that each information pulse 6044 has two possible input logic states (input logic "1" and input logic "0") indicated by two negative voltage levels $-V_1$, $-V_0$, and two possible output logic states (output logic "1" and output logic "0") indicated by two pulse width $t_1$, $t_0$. Accordingly, if a switch ($SW_0$-$SW_n$) closure occurs, the next information pulse drops to the input logic "1" state $-V_1$ and if a switch ($SW_0$-$SW_n$) remains open the next information pulse drops to the input logic "0" state $-V_0$. At the same time interval, if the instrument 6004 is drawing power from the generator 6002, the output logic "1" pulse width is $t_1$, and if instrument 6004 is not drawing power from the generator 6002, the output logic "0" pulse width is $t_0$.

As indicated in the timing diagram 6022, the pulse width of the reset pulse 6034, the header pulses 6040, 6042, the output logic "0" pulses, and the return to zero pulses 6048 each have pulse widths of $t_0$. Only the output logic "1" pulses have a pulse width of $t_1$, where $t_0 < t_1$. It will be appreciated that the specific voltage levels and pulse widths illustrated herein may be selected otherwise such that $-V_1 < -V_2$ and $t_0 > t_1$. Also, the reset pulse 6034, the header pulses 6040, 6042, the output logic "0" pulses, and the return to zero pulses 6048 each may have different pulse widths.

Figure 125A:
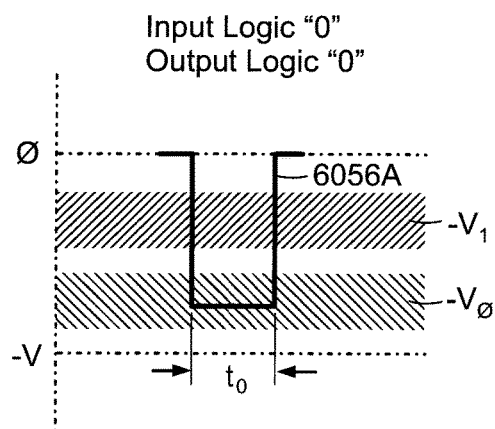
FIG. 125A illustrates a partial timing diagram of a serial protocol.
Figure 125B:
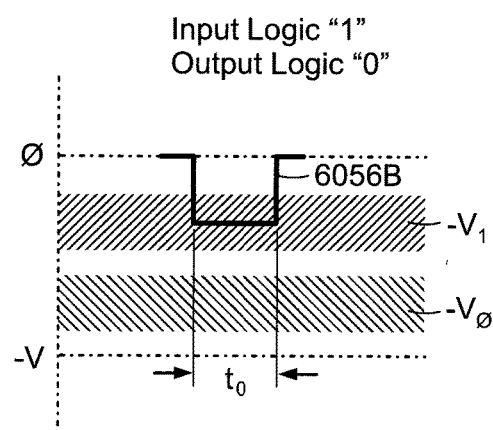
FIG. 125B illustrates a partial timing diagram of a serial protocol.
Figure 125C:
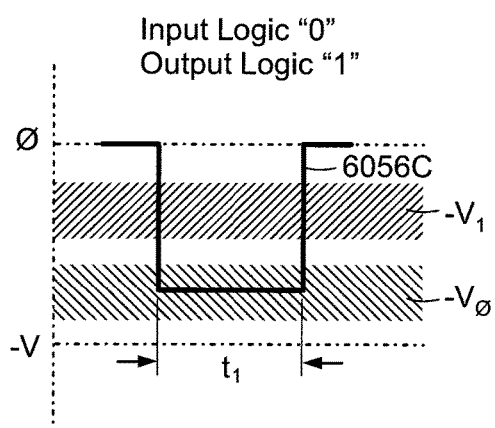
FIG. 125C illustrates a partial timing diagram of a serial protocol.
Figure 125D:
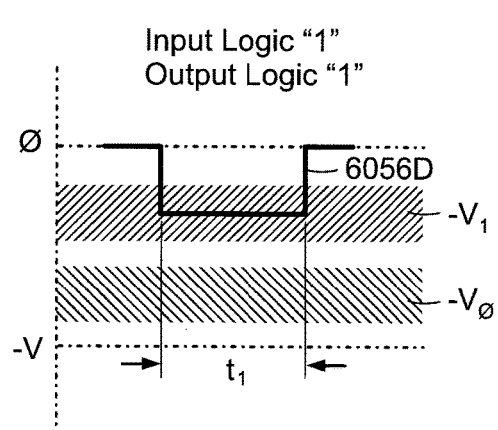
FIG. 125D illustrates a partial timing diagram of a serial protocol.

As illustrated in FIGS. 125A-D, an information pulse 6056 may be encoded in two of four I/O logic states during communication between the generator 6002 and the instrument 6004, e.g., the circuit 6006. In FIG. 125A, for example, the information pulse 6056A represents an input logic "0" and an output logic "0" because the logic voltage level is $-V_0$ and the logic current pulse width is $t_0$. In FIG. 125B, for example, the information pulse 6056B represents an input logic "1" and an output logic "0" because the logic voltage level is $-V_1$ and the logic current pulse width is $t_0$. In FIG. 125C, for example, the information pulse 6056C represents an input logic "0" and an output logic "1" because the logic voltage level is $-V_0$ and the logic current pulse width is $t_1$. In FIG. 125D, for example, the information pulse 6056D represents an input logic "1" and an output logic "1" because the logic voltage level is $-V_1$ and the logic current pulse width is $t_1$.

Figure 126:
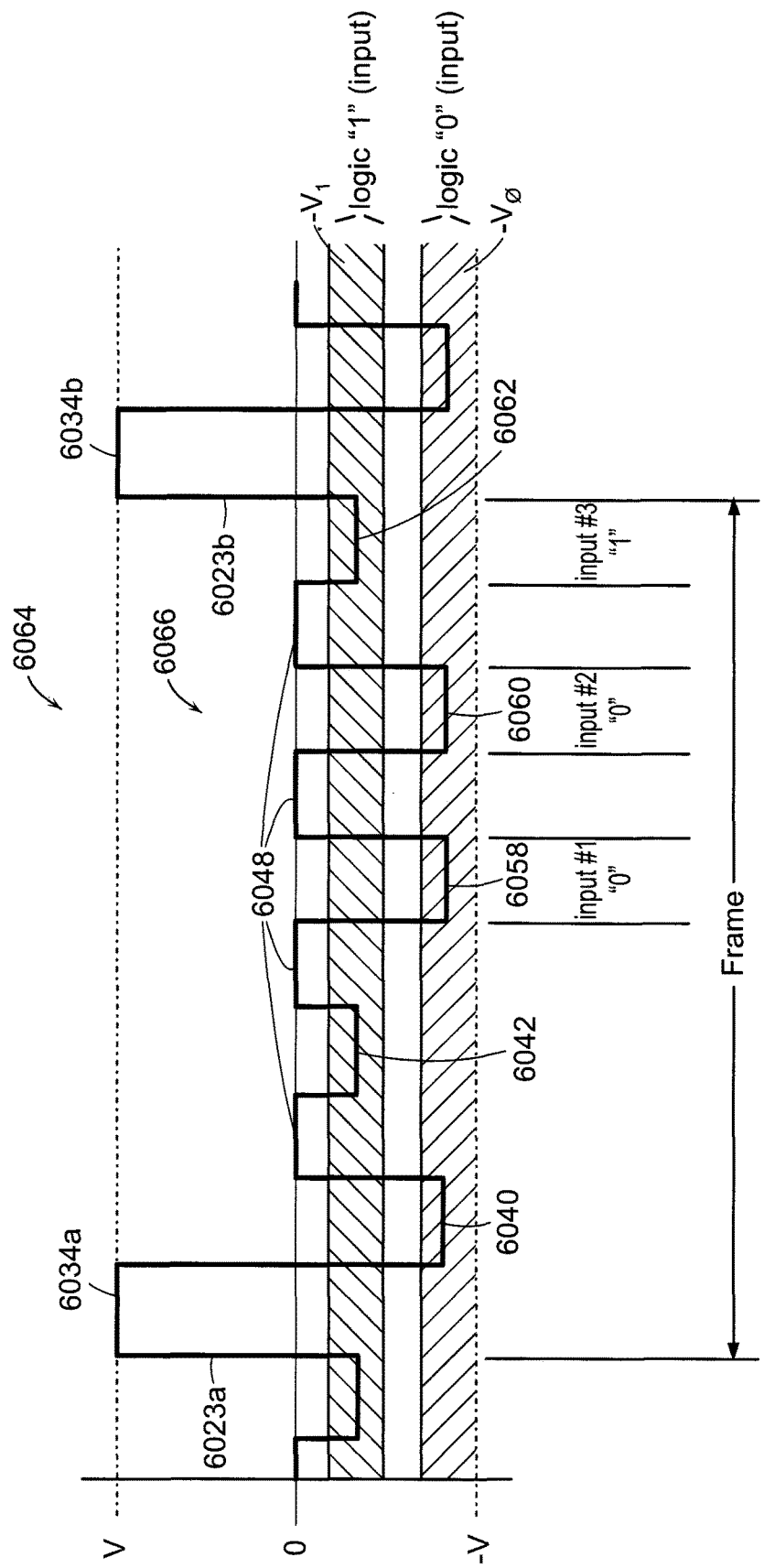
FIG. 126 illustrates one example timing diagram of a serial protocol.

FIG. 126 illustrates one example timing diagram 6064 of a serial protocol. As shown in FIG. 126, and with reference also to FIG. 122, the timing diagram 6064 represents a protocol communication signal comprising three inputs and no outputs. The inputs, referenced as $S_0$, $S_1$, and $S_2$ in FIG. 22, are coupled into controller 6014 portion of the circuit 6006. The three inputs may be associated with the state of the switches $SW_0$, $SW_1$, $SW_2$ coupled to the controller 6014, or may be associated with other types of inputs. The controller 6014 modulates the amplitude of a corresponding encoded bit to $-V_0$ or $-V_1$ based on the state (open or closed) of the switches $SW_0$, $SW_1$, $SW_2$. The frame in this example comprises a start pulse 6034a, two header pulses 6040, 6042, and three information pulses 6058, 6060, 6062 corresponding with the states of the switches $SW_0$, $SW_1$, $SW_2$, for a total of six pulses. The frame ends on the rising edge 6023b of the stop pulse 6034b.

As shown in FIG. 126, the first and second information pulses 6058, 6060 are input logic "0" indicating that the input switches $SW_0$, $SW_1$, $SW_2$ are open and the third information pulse is input logic "1" indicating that the switch $SW_2$ is closed. Since there are no outputs, there are no output pulses being encoded, thus the frame consists of six pulses, three overhead pulses (e.g., reset and header pulses 6034, 6040, 6042) and three information pulses 6058, 6060, 6062. The frame is repeatedly transmitted to inform the generator 6002 of the state of the input switches $SW_0$, $SW_1$, $SW_2$ at the instrument 6004. When a change occurs in the state of a switch $SW_0$, $SW_1$, $SW_2$, the bit associated with that switch is automatically encoded and the frame repeats.

Figure 127:
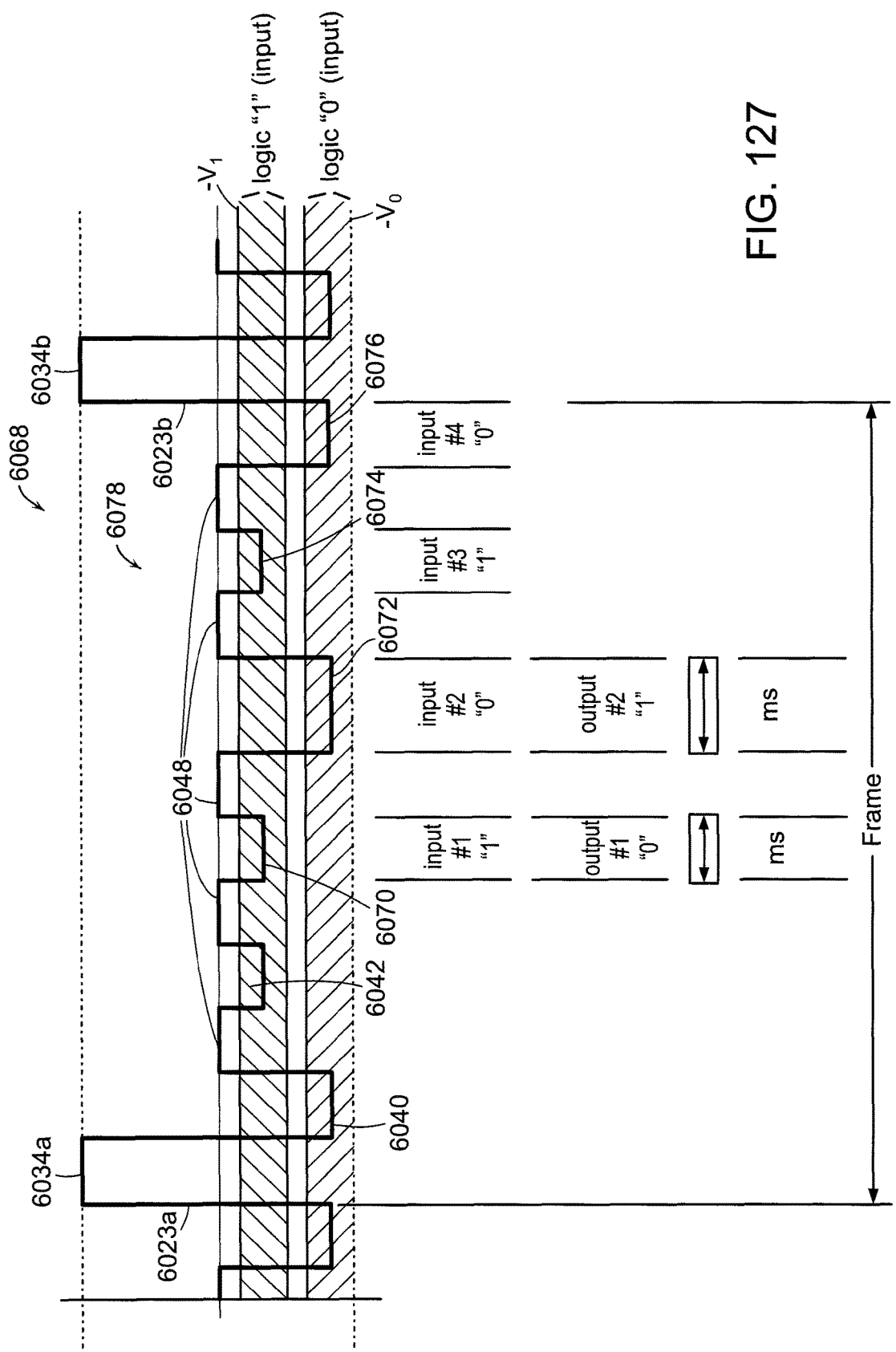
FIG. 127 illustrates one example timing diagram of a serial protocol.

FIG. 127 illustrates one example timing diagram 6068 of a serial protocol. As shown in FIG. 127, and with reference also to FIG. 122, the timing diagram 6068 represents a protocol communication signal comprising four inputs and two outputs. The inputs, referenced as $S_0$, $S_1$, $S_2$ and $S_3$ in FIG. 22, are coupled into controller 6014 portion of the circuit 6006. The outputs are associated with $O_0$ and $O_1$ of the controller 6014. The four inputs may be associated with the state of the switches $SW_0$, $SW_1$, $SW_2$, $SW_3$ coupled to the controller 6014, or may be associated with other types of inputs. The outputs $O_0$ and $O_1$ are used to control various functions of the instrument 6004 such as, for example, driving audible, visual, tactile feedback, power control, among other functions. The controller 6014 modulates the pulse height (amplitude) of corresponding encoded bits to $-V_0$ or $-V_1$ based on the state (open or closed) of the switches $SW_0$, $SW_1$, $SW_2$, $SW_3$. The generator 6002 modulates the pulse width (time) of the encoded bit based on the output control information that the generator 6002 wishes to communicate to the controller 6014. The frame in this example comprises a start pulse 6034a, two header pulses 6040, 6042, and four information pulses 6058, 6060, 6062 corresponding with the states of the switches $SW_0$, $SW_1$, $SW_2$, $SW_3$, for a total of seven pulses. The frame ends on the rising edge 6023b of the stop pulse 6034b.

As shown in FIG. 127, the controller 6014 has encoded the first information bit 6070 with both input and output information. Thus, the voltage and pulse width of the first information bit 6070 are modulated to encode the output as logic "0" and the input as logic "1". Likewise, the controller 6014 has encoded the second information bit 6072 with both input and output information. Thus, the voltage and pulse width of the second information bit 6072 are modulated to encode the output as logic "1" and the input as logic "0". Since in this example there are four inputs and only two outputs, the third and fourth bits 6074, 6076 are encoded with input information only, where the third bit 6074 is encoded as input logic "1" and the fourth bit is encoded as input logic "0". The frame is repeatedly transmitted to inform the generator 6002 of the state of the input switches $SW_0$, $SW_1$, $SW_2$, $SW_3$ at the instrument 6004 and the outputs $O_0$ and $O_1$ are driven by the controller 6014. When a change occurs in the state of a switch $SW_0$, $SW_1$, $SW_2$, $SW_3$, or the generator 6002 wants to control one of the two outputs $O_0$ and $O_1$, the bits associated therewith are automatically encoded and the frame repeats.

Figure 128:
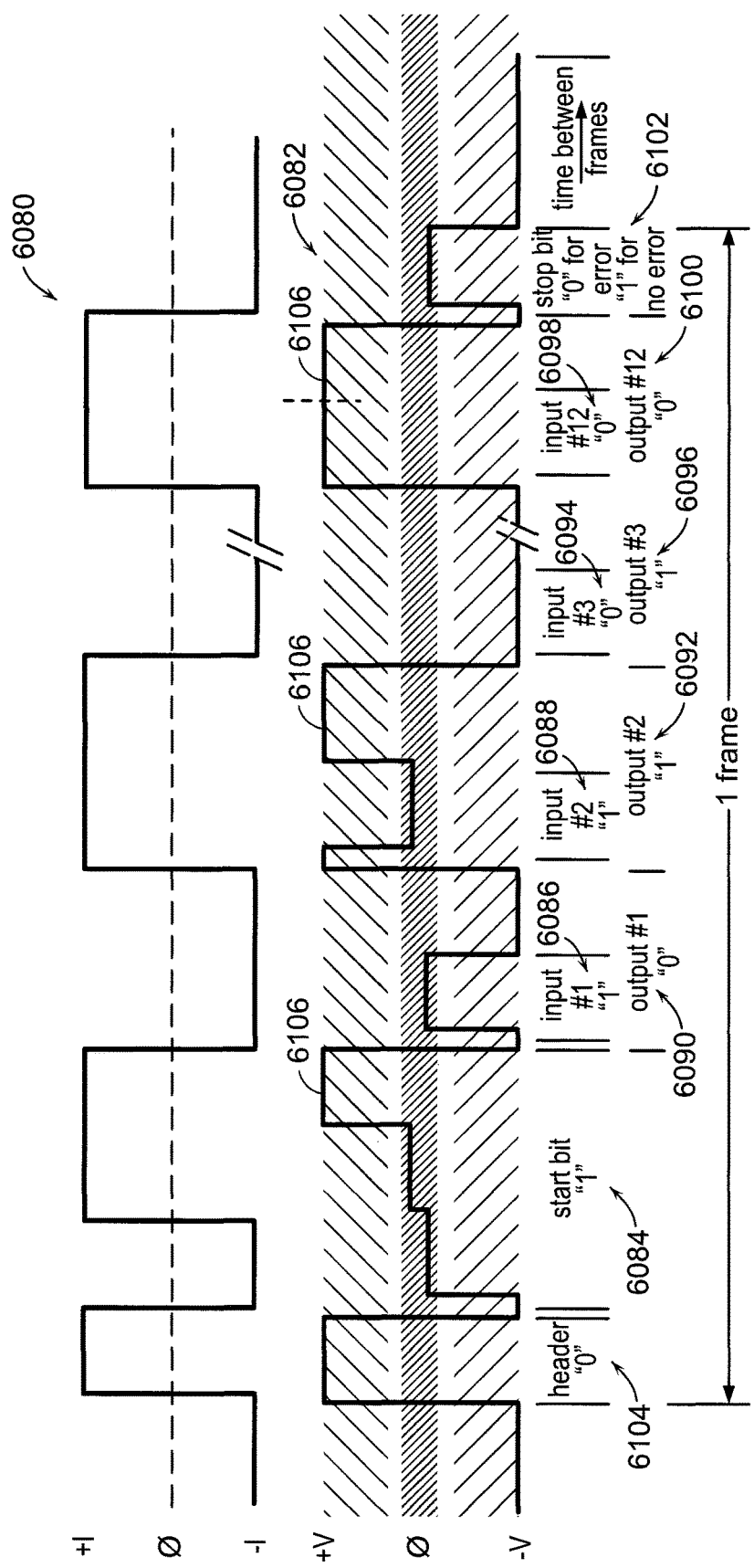
FIG. 128 illustrates example timing diagrams of a serial protocol.

FIG. 128 illustrates example timing diagrams 6080, 6083 of a serial protocol. With reference now to FIGS. 128 and 122, the top waveform is a current timing diagram 6080 as output by the generator 6002. The current signal swings from +I to −I crossing at zero. This timing diagram 6080 provides power to the circuit 6014 continuously except during the start bits 6084, input logic "1" transmission 6086, and stop bit 6102 "no error" condition. The bottom waveform 6082 is a voltage timing diagram at the circuit 6014. A header bit 6104 starts the frame followed by one start bit 6084. The 12 input bits and 12 output bits are simultaneously encoded over a single frame as discussed above, where the input logic bits are encoded by modulating the pulse amplitude and output logic bits are encoded by modulating the pulse width. The 12 information bits are then transmitted to encode 12 inputs and 12 outputs. As shown, input #1 6086 is encoded as logic "1" and output #1 6090 is encoded as logic "0". Input #2 6088 is encoded as logic "1" and output #2 6092 is encoded as logic "1". Input #3 6094 is encoded as logic "0" and output #3 6092 is encoded as logic "1". The last bit represents input #12 6098 is encoded as logic "0" and output #12 is encoded as logic "0". As indicated, every other bit 6106 returns to the positive supply rail, which provides additional parasitic power for the instrument 6004 circuit 6006.

While various details have been set forth in the foregoing description, it will be appreciated that the various aspects of the serial communication protocol for medical device may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one form," or "an form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

It is worthy to note that any reference to "one aspect," "an aspect," "one form," or "an form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

Although various forms have been described herein, many modifications, variations, substitutions, changes, and equivalents to those forms may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed forms. The following claims are intended to cover all such modification and variations.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one form, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various forms have been described herein, many modifications, variations, substitutions, changes, and equivalents to those forms may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed forms. The following claims are intended to cover all such modification and variations.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Examples

In one general aspect, a surgical instrument assembly embodying the principles of the described forms is configured to permit selective dissection, cutting, coagulation, and clamping of tissue during surgical procedures. A generator may generate at least one electrical signal, which may be monitored against a first set of logic conditions. When the first set of logic conditions is met, a first response of the generator may be triggered.

In certain forms, ultrasonic impedance of the surgical instrument is monitored. When the ultrasonic impedance of the surgical instrument exceeds a threshold impedance, a resonant frequency of the at least one electrical signal may be stored as a baseline frequency. Also, the first response of the generator may be triggered when either the first set of logic conditions is met or the resonant frequency of the at least one electrical signal differs from the baseline frequency by a baseline deviation threshold.

In certain forms, load events at an end effector of the surgical instrument may be monitored. The first response of the generator may be triggered when the first set of logic conditions is met and a load event is detected.

In accordance with one general form, there is provided a switch assembly for an ultrasonic surgical instrument that includes a handle housing that is configured to be supported in one hand. In at least one form, the switch assembly comprises a first switch arrangement that is operably supported on a forward portion of the handle housing and is selectively movable relative to at least one first switch contact. The switch assembly further comprises a second switch arrangement that may comprise at least one of a right switch button and a left switch button. The right switch button may be movably supported on a right side of the handle housing and be selectively movable relative to at least one right switch contact supported by the handle housing. The left switch button may be movably supported on a left side of the handle housing and be selectively movable relative to at least one left switch contact supported by the handle housing. The first and second switch arrangements may be configured to be selectively operated by a single hand supporting the handle housing.

In accordance with at least one other general form, there is provided an ultrasonic surgical instrument. In at least one form, the ultrasonic surgical instrument comprises a generator for generating ultrasonic signals and a handle assembly that includes a handle housing that is configured to be operably supported in one hand. The instrument may further comprise a switch assembly that includes a first switch arrangement that is operably supported on a forward portion of the handle housing and is selectively movable relative to at least one first switch contact that communicates with the generator. The switch assembly may further include a second switch arrangement that comprises at least one of a right switch button and a left switch button. The right switch button may be movably supported on a right side of the handle housing and be selectively movable relative to at least one right switch contact that is supported by the handle housing. The at least one right switch contact may communicate with the generator. The left switch button may be movably supported on a left side of the handle housing and be selectively movable relative to at least one left switch contact that is supported by the handle housing and may operably communicate with the generator. The first and second switch arrangements may be configured to be selectively operated by a single hand supporting the handle housing.

In accordance with still another general form, there is provided a switch assembly for an ultrasonic surgical instrument that includes a handle housing that is configured to be supported in one hand. In at least one form, the switch assembly comprises a button assembly that is movably supported by the handle housing for selective axial and pivotal travel relative to a right switch contact, a central switch contact and a left switch contact such that axial movement of the button assembly in a first direction causes the button assembly to actuate the central switch contact and pivotal movement of the button assembly in a first pivotal direction causes the button assembly to actuate the left switch contact and pivotal movement of the button assembly in a second pivotal direction causes the button assembly to actuate the right switch contact.

According to various forms, the connector module may be a modular component that may be provided as an accessory with the ultrasonic surgical instrument or components thereof but not attached thereto or may be used to repair, replace, or retrofit ultrasonic surgical instruments. In certain forms, however, the connector module may be associated with the handle assembly or the ultrasonic transducer. In one form, the connector module may comprise an assembly that may be easily removed and/or replaced by a user. The connector module may also comprise removable features allowing the user to, for example, remove and/or replace rotation couplings, switch conductors, or links. Accordingly, in certain forms, one or more connector modules may be included in a kit. The kit may comprise various rotation couplings configured for adaptable use with one or more ultrasonic transducers or hand pieces. The kit may include connector modules, rotation couplings, or housings comprising various configurations of user interfaces that may require one, two, or more conductive paths.

In one aspect, the present disclosure is directed to an ultrasonic surgical instrument. The ultrasonic instrument may comprise an end effector, a waveguide extending proximally from the end effector along a longitudinal axis, and a connector module for receiving an ultrasonic hand piece. The connector module may comprise a housing defining a spindle extending along the longitudinal axis, a coupling positioned on the spindle and rotatable relative to the housing, a first conductor mechanically coupled to the housing and extending at least partially around the longitudinal axis, and a first link rotatable about the longitudinal axis relative to the first conductor between a first position and a second position. The first link may comprise a first contact positioned to electrically contact the first conductor when the first link is in the first position and the second position and a second contact electrically coupled to the first contact and positioned to electrically contact the ultrasonic hand piece when the first link is in the first position and the second position.

In one aspect, the first and second conductors each comprise a conductive lead configured to electrically couple to a user interface configured for receiving power control signals from a user. The ultrasonic hand piece may be adapted to electrically couple to a generator and rotationally couple to the first and second links when received by the connector module. The connector module may be configured to electrically couple the user interface circuit and the generator via the ultrasonic hand piece when the first and second links are in respective first and second positions. In one aspect, the user interface comprises a toggle switch operatively coupled to a handle assembly and the connector module is secured to the handle assembly. The ultrasonic hand piece may be rotatable relative to the handle assembly when received by the connector module. In one aspect, the housing electrically isolates the first and second conductors with respect to each other.

Various aspects of the subject matter described herein are directed to an apparatus, comprising a circuit configured to transmit a signal as a serial protocol over a pair of electrical conductors. The serial protocol may be defined as a series of pulses distributed over at least one transmission frame. At least one pulse in the transmission frame is simultaneously encoded by modulating an amplitude of the pulse to represent one of two first logic states and modulating a width of the pulse to represent one of two second logic states.

Various aspects of the subject matter described herein are directed to an instrument, comprising a circuit configured to transmit a signal as a serial protocol over a pair of electrical conductors. The serial protocol may be defined as a series of pulses distributed over at least one transmission frame. At least one pulse in the transmission frame may be simultaneously encoded by modulating an amplitude of the pulse to represent one of two first logic states and modulating a width of the pulse to represent one of two second logic states. The instrument may also comprise an output device coupled to an output of the circuit; and an input device coupled to an input of the circuit.

Various aspects of the subject matter described herein are directed to a generator, comprising a conditioning circuit configured to communicate to an instrument over a two wire interface. The generator may comprises a control circuit configured to transmit a signal as a serial protocol over a pair of electrical conductors. The serial protocol may be defined as a series of pulses distributed over at least one transmission frame. At least one pulse in the transmission frame is simultaneously encoded by modulating an amplitude of the pulse to represent one of two first logic states and modulating a width of the pulse to represent one of two second logic states. The generator may also comprise an energy circuit configured to drive the instrument.

Various aspects are directed to methods of driving an end effector coupled to an ultrasonic drive system of an ultrasonic surgical instrument. A trigger signal may be received. In response to the trigger signal, a first drive signal may be provided to the ultrasonic drive system to drive the end effector at a first power level. The first drive signal may be maintained for a first period. At the end of the first period a second drive signal may be provided to the ultrasonic drive system to drive the end effector at a second power level less than the first power level.

In another aspect, after receiving a trigger signal, a surgical system generates feedback indicating that the ultrasonic surgical instrument is activated while maintaining the ultrasonic instrument in a deactivated state. At an end of the threshold time period, the ultrasonic surgical instrument is activated by providing a drive signal to the ultrasonic drive system to drive the end effector.

In another aspect, the ultrasonic surgical instrument is activated by generating a drive signal provided to the ultrasonic drive system to drive the end effector. A plurality of input variables may be applied to a multi-variable model to generate a multi-variable model output, where the multi-variable model output corresponds to an effect of the ultrasonic instrument on tissue. The plurality of input variables may comprise at least one variable describing the drive signal and at least one variable describing a property of the ultrasonic surgical instrument. When the multi-variable model output reaches a threshold value, feedback may be generated indicating a corresponding state of at least one of the ultrasonic surgical instrument and tissue acted upon by the ultrasonic surgical instrument.

In another aspect, in response to a trigger signal, a first drive signal at a first power level is provided to the ultrasonic drive system to drive the end effector. The first drive signal is maintained at the first level for a first period. A second drive signal is provided to the ultrasonic drive system to drive the end effector at a second power level less than the first power level. A plurality of input variables may be applied to a multi-variable model to generate a multi-variable model output. The multi-variable model output may correspond to an effect of the ultrasonic instrument on tissue, and the plurality of variables may comprise at least one variable describing the drive signal and at least one variable describing a property of the ultrasonic surgical instrument. After the multi-variable model output exceeds a threshold value for a threshold time period, a first response may be triggered.

While several forms have been illustrated and described, it is not the intention of the applicant to restrict or limit the scope of the appended claims to such detail. Numerous variations, changes, and substitutions will occur to those skilled in the art without departing from the scope of the invention. Moreover, the structure of each element associated with the described forms can be alternatively described as a means for providing the function performed by the element. Accordingly, it is intended that the described forms be limited only by the scope of the appended claims.

Reference throughout the specification to "various forms," "some forms," "one form," or "an form" means that a particular feature, structure, or characteristic described in connection with the form is included in at least one form. Thus, appearances of the phrases "in various forms," "in some forms," "in one form," or "in an form" in places throughout the specification are not necessarily all referring to the same form. Furthermore, the particular features, structures, or characteristics may be combined in any suitable manner in one or more forms. Thus, the particular features, structures, or characteristics illustrated or described in connection with one form may be combined, in whole or in part, with the features structures, or characteristics of one or more other forms without limitation.

We claim:

1. A method of driving an end effector coupled to an ultrasonic drive system of a surgical instrument, the method comprising:
   providing, by a generator configured to drive the surgical instrument, a first electrical signal to an ultrasonic transducer acoustically coupled to the end effector;
   detecting, by the generator, that an impedance of the ultrasonic transducer exceeds a threshold impedance;
   storing, by the generator, a first local resonant frequency of the first electrical signal as a baseline resonant frequency;
   monitoring, by the generator, the first electrical signal against a first set of logic conditions comprising a first logic condition and a second logic condition, wherein the first logic condition is defined by a difference between a second local resonant frequency of the first electrical signal and the baseline resonant frequency that is greater than a baseline deviation threshold;
   determining, by the generator, that the first logic condition is met; and
   triggering, by the generator, a first response.

2. The method of claim 1, wherein, with a clamp arm of the end effector in a closed position, the impedance exceeds the threshold impedance.

3. The method of claim 1, wherein triggering the first response comprises triggering at least one response selected from the group consisting of an audible response, a visual response and a pulsing response.

4. The method of claim 1, wherein triggering the first response comprises pulsing the first electrical signal, and wherein the pulsing comprises:
   driving, by the generator, the first electrical signal to a first pulse amplitude for a first pulse time; and
   driving, by the generator, the first electrical signal to a second pulse amplitude for a second pulse time.

5. The method of claim 4, wherein the first pulse amplitude is equal to the second pulse amplitude and the first pulse time is about one minute.

6. The method of claim 1, further comprising:
   monitoring, by the generator, the first electrical signal against a second set of logic conditions;
   determining, by the generator, that the second set of logic conditions are met; and
   triggering, by the generator, a second response.

7. The method of claim 6, further comprising:
   determining, by the generator, the triggering of the first response or the second response on a hierarchical basis.

8. The method of claim 1, wherein the first set of logic conditions further comprises at least one logic condition selected from the group consisting of:
   the second logic condition defined by the second local resonant frequency that is less than a frequency threshold; and
   a third logic condition that is defined by a local resonant frequency slope that is less than a frequency slope threshold.

9. The method of claim 1, further comprising:
   before storing the first local resonant frequency of the first electrical signal as the baseline resonant frequency, determining, by the generator, that the impedance has exceeded the threshold impedance for a time above impedance period.

10. The method of claim 1, further comprising:
determining, by the generator, that the impedance is less than a reset threshold impedance; and
ceasing the first response.

11. A surgical system, comprising:
a surgical instrument, comprising:
an end effector; and
an ultrasonic transducer coupled to the end effector; and
at least one circuit configured to:
store a first resonant frequency of a drive signal provided to the ultrasonic transducer as a baseline resonant frequency after an impedance of the ultrasonic transducer exceeds a threshold impedance;
monitor the drive signal against a first set of logic conditions comprising a first logic condition and a second logic condition, wherein the first logic condition is defined by a difference between a second resonant frequency of the drive signal and the baseline resonant frequency that is greater than a baseline deviation threshold;
determine that the first logic condition is met; and
trigger a first response.

12. A method of driving an end effector coupled to an ultrasonic drive system of a surgical instrument, the method comprising:
providing, by a generator configured to drive the surgical instrument, an electrical signal to an ultrasonic transducer coupled to the end effector;
detecting, by the generator, that an impedance of the ultrasonic transducer exceeds a threshold impedance;
capturing, by the generator, a first resonant frequency of the electrical signal as a baseline resonant frequency;
detecting, by the generator, a load event at the end effector; and
monitoring, by the generator, the electrical signal against a first set of logic conditions comprising a first logic condition and a second logic condition, wherein the first logic condition is defined by a difference between a second resonant frequency of the electrical signal and the baseline resonant frequency that is greater than a baseline deviation threshold;
determining, by the generator, that the first logic condition is met; and
triggering, by the generator, a first response.

13. The method of claim 12, wherein detecting the load event comprises:
comparing a present resonant frequency slope of the electrical signal with a past resonant frequency slope of the electrical signal offset from the present resonant frequency slope by a window offset time.

14. The method of claim 13, wherein the window offset time is about 100 milliseconds.

15. The method of claim 12, wherein detecting the load event comprises:
determining, by the generator, that a present resonant frequency slope of the electrical signal differs from a past resonant frequency slope of the electrical signal by more than a frequency slope threshold.

16. The method of claim 12, further comprising:
determining, by the generator, that the impedance has exceeded the threshold impedance for a threshold time above impedance; and
wherein detecting the load event comprises:
determining, by the generator, that a present resonant frequency slope of the electrical signal differs from a past resonant frequency slope of the electrical signal by more than a frequency slope threshold.

17. The method of claim 12, further comprising:
determining, by the generator, that the impedance is below an impedance reset threshold; and
ceasing the monitoring of the electrical signal against the first set of logic conditions.

18. The method of claim 12, wherein triggering the first response comprises pulsing the electrical signal, and wherein the pulsing comprises:
driving, by the generator, the electrical signal to a first pulse amplitude for a first pulse time; and
driving, by the generator, the electrical signal to a second pulse amplitude for a second pulse time.

19. The method of claim 18, wherein the first pulse amplitude is equal to the second pulse amplitude, and wherein the first pulse time is about one minute.

20. The method of claim 12, further comprising:
monitoring, by the generator, the electrical signal against a second set of logic conditions;
determining, by the generator, that the second set of logic conditions are met; and
triggering, by the generator, a second response.

21. The method of claim 12, wherein the first set of logic conditions further comprises at least one logic condition selected from the group consisting of:
the second logic condition defined by the second resonant frequency that is less than a frequency threshold; and
a third logic condition defined by a local resonant frequency slope that is less than a frequency slope threshold.

* * * * *